(12) United States Patent
Duthie et al.

(10) Patent No.: US 9,909,114 B2
(45) Date of Patent: Mar. 6, 2018

(54) **VACCINES COMPRISING *LEISHMANIA* POLYPEPTIDES FOR THE TREATMENT AND DIAGNOSIS OF LEISHMANIASIS**

(71) Applicant: Infectious Disease Research Institute, Seattle, WA (US)

(72) Inventors: Malcolm Duthie, Seattle, WA (US); Jeff Guderian, Seattle, WA (US); Steven G. Reed, Bellevue, WA (US)

(73) Assignee: INFECTIOUS DISEASE RESEARCH INSTITUTE, Seattle, WA (US)

( * ) Notice: Subject to any disclaimer, the term of this patent is extended or adjusted under 35 U.S.C. 154(b) by 33 days.

(21) Appl. No.: 14/780,504

(22) PCT Filed: Mar. 28, 2014

(86) PCT No.: PCT/US2014/032276
§ 371 (c)(1),
(2) Date: Sep. 25, 2015

(87) PCT Pub. No.: WO2014/160987
PCT Pub. Date: Feb. 10, 2014

(65) Prior Publication Data
US 2016/0186158 A1   Jun. 30, 2016

Related U.S. Application Data

(60) Provisional application No. 61/822,545, filed on May 13, 2013, provisional application No. 61/806,368, filed on Mar. 28, 2013.

(51) Int. Cl.
*C12N 9/24* (2006.01)
*A61K 39/008* (2006.01)
*C12N 9/10* (2006.01)
*G01N 33/569* (2006.01)

(52) U.S. Cl.
CPC .......... *C12N 9/2497* (2013.01); *A61K 39/008* (2013.01); *C12N 9/1007* (2013.01); *G01N 33/56905* (2013.01); *C12Y 201/01041* (2013.01); *C12Y 302/02001* (2013.01); *G01N 2333/44* (2013.01); *G01N 2469/20* (2013.01)

(58) Field of Classification Search
None
See application file for complete search history.

(56) References Cited

U.S. PATENT DOCUMENTS

| | | | |
|---|---|---|---|
| 4,235,877 A | 11/1980 | Fullerton | |
| 4,436,727 A | 3/1984 | Ribi | |
| 4,554,101 A | 11/1985 | Hopp | |
| 4,683,195 A | 7/1987 | Mullis et al. | |
| 4,751,180 A | 6/1988 | Cousens et al. | |
| 4,816,566 A | 3/1989 | DeChiara et al. | |
| 4,866,034 A | 9/1989 | Ribi | |
| 4,877,611 A | 10/1989 | Cantrell | |
| 4,912,094 A | 3/1990 | Myers et al. | |
| 4,935,233 A | 6/1990 | Bell et al. | |
| 5,278,302 A | 1/1994 | Caruthers et al. | |
| 5,359,681 A | 10/1994 | Jorgenson et al. | |
| 5,399,363 A | 3/1995 | Liversidge et al. | |
| 5,411,865 A | 5/1995 | Reed | |
| 5,466,468 A | 11/1995 | Schneider et al. | |
| 5,543,158 A | 8/1996 | Gref et al. | |
| 5,641,515 A | 6/1997 | Ramtoola | |
| 5,666,153 A | 9/1997 | Copeland | |
| 5,719,263 A | 2/1998 | Reed | |
| 5,725,871 A | 3/1998 | Illum | |
| 5,756,353 A | 5/1998 | Debs | |
| 5,780,045 A | 7/1998 | McQuinn et al. | |
| 5,804,212 A | 9/1998 | Illum | |
| 5,834,592 A | 11/1998 | Reed et al. | |
| 5,856,462 A | 1/1999 | Agrawal | |
| 5,876,966 A | 3/1999 | Reed | |
| 5,912,166 A | 6/1999 | Reed et al. | |
| 5,965,142 A | 10/1999 | Dillon et al. | |
| 6,113,918 A | 9/2000 | Johnson et al. | |
| 6,355,257 B1 | 3/2002 | Johnson et al. | |
| 6,365,165 B1 | 4/2002 | Reed et al. | |
| 6,375,955 B1 | 4/2002 | Reed et al. | |
| 6,500,437 B1 | 12/2002 | Reed et al. | |
| 6,544,518 B1 | 4/2003 | Friede et al. | |
| 6,607,731 B1 | 8/2003 | Reed et al. | |
| 6,613,337 B1 | 9/2003 | Reed et al. | |
| 6,638,517 B2 | 10/2003 | Reed et al. | |
| 6,709,661 B1 | 3/2004 | Reed et al. | |
| 7,189,522 B2 | 3/2007 | Esfandiari | |
| 7,833,534 B2 | 11/2010 | Goto et al. | |

(Continued)

FOREIGN PATENT DOCUMENTS

| EP | 0468520 A2 | 1/1992 |
|---|---|---|
| EP | 0468520 A3 | 1/1992 |

(Continued)

OTHER PUBLICATIONS

US 6,008,200, 12/1999, Krieg (withdrawn)
Greenspan et al. (Nature Biotechnology 7: 936-937, 1999).*
Chothia et al. (The EMBO Journal, 1986, 5/4:823-26).*
Mikayama et al. (Nov. 1993.Proc.Natl.Acad.Sci. USA, vol. 90 : 10056-10060).*
Rudinger et al. (Jun. 1976. Peptide Hormones. Biol.Council. pp. 5-7).*
Gamboa-León et al. (May 29, 2006, e-pub Mar. 20, 2006). "Immunotherapy Against Visceral Leishmaniasis with the Nucleoside Hydrolase—DNA Vaccine of Leishmania Donovani," *Vaccine*; 24(22):4863-4873.

(Continued)

*Primary Examiner* — Jennifer E Graser
(74) *Attorney, Agent, or Firm* — Morrison & Foerster, LLP

(57) ABSTRACT

Compositions and methods for preventing, treating and detecting leishmaniasis are disclosed. The compositions generally comprise polypeptides comprising *Leishmania* antigens as well as polynucleotides encoding such polypeptides.

23 Claims, 8 Drawing Sheets

(56) References Cited

U.S. PATENT DOCUMENTS

| | | |
|---|---|---|
| 8,231,881 B2 | 7/2012 | Bhatia et al. |
| 8,410,258 B2 | 4/2013 | Goto et al. |
| 8,425,919 B2 | 4/2013 | Goto et al. |
| 8,771,710 B2 | 7/2014 | Bhatia et al. |
| 8,865,180 B2 | 10/2014 | Goto et al. |
| 8,911,746 B2 | 12/2014 | Goto et al. |
| 8,916,168 B2 | 12/2014 | Reed et al. |
| 2008/0131466 A1 | 6/2008 | Reed et al. |
| 2009/0291099 A1 | 11/2009 | Goto et al. |
| 2009/0325204 A1 | 12/2009 | Reed et al. |
| 2010/0136046 A1 | 6/2010 | Goto et al. |
| 2012/0114688 A1 | 10/2012 | Bhatia |
| 2015/0017200 A1 | 1/2015 | Bhatia et al. |

FOREIGN PATENT DOCUMENTS

| | | |
|---|---|---|
| WO | WO-91/18926 A1 | 12/1991 |
| WO | WO-94/00153 A1 | 1/1994 |
| WO | WO-95/17210 A1 | 6/1995 |
| WO | WO-95/26204 A1 | 10/1995 |
| WO | WO-96/02555 A1 | 2/1996 |
| WO | WO-96/33739 A1 | 10/1996 |
| WO | WO-98/16247 A1 | 4/1998 |
| WO | WO-99/33488 A2 | 7/1999 |
| WO | WO-99/33488 A3 | 7/1999 |
| WO | WO-99/52549 A1 | 10/1999 |
| WO | WO-00/09159 A1 | 2/2000 |
| WO | WO-00/09159 A9 | 2/2000 |
| WO | WO-2009/143006 A1 | 11/2009 |
| WO | WO-2012/064659 A1 | 5/2012 |
| WO | WO-2014/036349 A1 | 3/2014 |

OTHER PUBLICATIONS

Afonso et al., (Jan. 14, 1994) "The Adjuvant Effect of Interleukin-12 in a Vaccine Against Leishmania major," *Science* 263: 235-237.

Aguilar-Be et al., (Feb. 2005) "Cross-Protective Efficacy of a Prophylactic Leishmania donovani DNA Vaccine against Visceral and Cutaneous Murine Leishmaniasis," *Infection and Immunity* 73(2): 812-819.

Altschul, S.F. et al. (1990). "Basic Local Alignment Search Tool," *J. Mol. Biol.* 215:403-410.

Altschul, S.F. et al. (1997). "Gapped BLAST and PSI-BLAST: A New Generation of Protein Database Search Programs," *Nucleic Acids Research* 25(17):3389-3402.

Armant, M.A. et al. (Jul. 29, 2002). "Toll-Like Receptors: A Family of Pattern-Recognition Receptors in Mammals," *Genome Biology* 3(8):Reviews 3011.1-3011.6.

Basu et al., (2005) "Kinetoplastid Membrane Protein-11 DNA Vaccination Induces Complete Protection against Both Pentavalent Antimonial-Sensitive and -Resistant Strains of Leishmania donovani That Correlates with Inducible Nitric Oxide Synthase Activity and IL-4 Generation: Evidence for Mixed Th1-and Th2-Like Responses in Visceral Leishmaniasis," *The Journal of Immunology* 174: 7160-7171.

Bayés, M. et al. (Apr. 2005). "Gateways to Clinical Trials," *Methods Find Exp Clin Pharmacol* 27(3):193-219.

Bitter, G.A. et al. (1987). "Expression and Secretion Vectors for Yeast," *Methods in Enzymology* 153:516-544.

Brazolot Millan, C.L. et al. (Dec. 1998). "CpG DNA Can Induce Strong Th1 Humoral and Cell-Mediated Immune Responses Against Hepatitis B Surface Antigen in Young Mice," *Proc. Natl. Acad. Sci.* 95(26):15553-15558.

Broglie, R. et al. (1984). "Light-Regulated Expression of a Pea Ribulose-1, 5-Bisphosphate Carboxylase Small Subunit Gene in Transformed Plant Cells," *Science* 224(4651):838-843.

Chen, W. et al. (Feb. 15, 1994). "T-Cells for Tumor Therapy can be Obtained from Antigen-loaded Sponge Implants," *Cancer Research* 54:1065-1070.

Chen, L. et al. (2006). "Distinct Responses of Lung and Spleen Dendritic Cells to the TLR9 Agonist CpG Oligodeoxynucleotide," *The Journal of Immunology* 177(4):2373-2383.

Cohen, J. (Mar. 19, 1993). "Naked DNA Points Way to Vaccines," *Science* 259:1691-1692.

Colbere-Garapin, F. et al. (1981). "A New Dominant Hybrid Selective Marker for Higher Eukaryotic Cells," *J. Mol. Biol.* 150:1-14.

Coler, R.N. et al., (Aug. 2002) "Immunization with a Polyprotein Vaccine Consisting of the T-Cell Antigens Thiol-Specific Antioxidant, Leishmania major Stress-Inducible Protein 1, and Leishmania Elongation Initiation Factor Protects against Leishmaniasis," *Infection and Immunity* 70(8): 4215-4225.

Coligan, J.E. eds. et al. (1999). Current Protocols in Immunology, vol. 1, Supplement 32, John Wiley & Sons, Inc., pp. 1-10, (Table of Contents Only.).

Cooper, C.L. et al. (2005). "CPG 7909 Adjuvant Improves Hepatitis B Virus Vaccine Seroprotection in Antiretroviral-Treated HIV-Infected Adults," *AIDS* 19(14) :1473-1479.

Datta, S.K. et al. (2003). "A Subset of Toll-Like Receptor Ligands Induces Cross-Presentation by Bone Marrow-Derived Dendritic Cells," *The Journal of Immunology* 170(8):4102-4110.

Davis, H.L. et al. (1998). "CpG DNA is a Potent Enhancer of Specific Immunity in Mice Immunized with Recombinant Hepatitis B Surface Antigen," *The Journal of Immunology* 160(2):870-876.

Dayhoff, M.O. et al. (1978). "A Model of Evolutionary Change in Proteins," Chapter 22 in Atlas of Protein Sequence and Structure, *The National Biomedical Research Foundation*, Silver Spring, MD, 5(Suppl 3):345-352.

Deng, J.C. et al. (2004). "CpG Oligodeoxynucleotides Stimulate Protective Innate Immunity Against Pulmonary Klebsiella Infection," *The Journal of Immunology* 173(8):5148-5155.

El Andaloussi, A. et al. (2006). "Stimulation of TLR9 with CpG ODN Enhances Apoptosis of Glioma and Prolongs the Survival of Mice with Experimental Brain Tumors," *Glia* 54:526-535.

Engelhard, E.K. et al. (Apr. 1994). "The Insect Tracheal System: A Conduit for the Systemic Spread of Autographa Californica M Nuclear Polyhedrosis Virus," *Proc. Natl. Acad. Sci. USA* 91:3224-3227.

Engwerda et al., (1998) "Neutralization of IL-12 demonstrates the existence of discrete organ-specific phases in the control of Leishmania donovani," *European Journal of Immunology* 28: 669-680.

Fearon, D.T. et al. (Apr. 5, 1996). "The Instructive Role of Innate Immunity in the Acquired Immune Response," *Science* 272:50-54.

Feuillet, V. et al. (Aug. 15, 2006). "Involvement of Toll-Like Receptor 5 in the Recognition of Flagellated Bacteria," *Proceedings of the National Academy of Sciences* 103(33):12487-12492.

Garcia, P. et al. (1986). "Nucleotide Sequence and Expression of the Pneumococcal Autolysin Gene from its Own Promoter in *Escherichia coli*," *Gene* 43:265-272.

Ghosh et al., (Oct. 12, 2001) "Immunization with A2 protein results in a mixed Th1/Th2 and a humoral response which protects mice against Leishmania donovani infections," *Vaccine* 20(1-2): 59-66.

Gorden, K.B. et al. (2005). "Synthetic TLR Agonists Reveal Functional Differences between Human TLR7 and TLR8," *The Journal of Immunology* 174(3):1259-1268.

Gurunathan et al., (Oct. 6, 1997) "Vaccination with DNA Encoding the Immunodominant LACK Parasite Antigen Confers Protective Immunity to Mice Infected with Leishmania major," *The Journal of Experimental Medicine* 186(7):1137-1147.

Hampton, R. et al. eds. (1990). Serological Methods for Detection and Identification of Viral and Bacterial Plant Pathogens, a Laboratory Manual, APS Press, St. Paul, MN, pp. iii-v, (Table of Contents Only.).

Harlow, E. et al. (1988). Antibodies: A Laboratory Manual, Cold Spring Harbor Laboratory, New York, pp. iii-ix, (Table of Contents Only.).

Hartman, S.C. et al. (Nov. 1988). "Two Dominant-Acting Selectable Markers for Gene Transfer Studies in Mammalian Cells," *Proc. Natl. Acad. Sci. USA* 85(21):8047-8051.

Henikoff, S. et al. (Nov. 1992). "Amino Acid Substitution Matrices from Protein Blocks," *Proc. Natl. Acad. Sci. USA* 89:10915-10919.

Hein, J. (1990). "Unified Approach to Alignment and Phylogenies," *Method in Enzymology, Academic* 183:626-645.

Higgins, D.G. et al. (1989). "Fast and Sensitive Multiple Sequence Alignments on a Microcomputer," *Cabios Communications* 5(2):151-153.

(56) References Cited

OTHER PUBLICATIONS

Hobbs, S. (1991). "Genetic Engineering," in McGraw-Hill Yearbook of Science and Technology, McGraw-Hill, Inc. New York, pp. 191-196.
Horsmans, Y. et al. (2005). "Isatoribine, an Agonist of TLR7, Reduces Plasma Virus Concentration in Chronic Hepatitis C Infection," *Hepatology* 42(3):724-731.
International Preliminary Report on Patentability dated Oct. 8, 2015, for PCT Application No. PCT/US2014/032276, filed on Mar. 28, 2014, 8 pages.
International Search Report dated Nov. 11, 2014, for PCT Application No. PCT/US2014/032276, filed on Mar. 28, 2014, 5 pages.
Johansen, P. et al. (2005). "Toll-Like Receptor Ligands as Adjuvants in Allergen-Specific Immunotherapy," *Clinical and Experimental Allergy* 35:1591-1598.
Kaye et al., (Oct. 1992) "Leishmania donovani Infection in scid Mice: Lack of Tissue Response and In Vivo Macrophage Activation Correlates with Failure to Trigger Natural Killer Cell-Derived Gamma Interferon Production In Vitro," *Infection and D Immunity* 60(10): 4335-4342.
Kenney et al., (1999) "Protective Immunity Using Recombinant Human IL-12 and Alum as Adjuvants in a Primate Model of Cutaneous Leishmaniasis," *The Journal of Immunology* 163: 4481-4488.
Köhler, G. et al. (1976). "Derivation of Specific Antibody-Producing Tissue Culture and Tumor Lines by Cell Fusion," *Eur. J. Immunol.* 6:511-519.
Krieg, A.M. et al. (Apr. 6, 1995). "CpG Motifs in Bacterial DNA Trigger Direct B-Cell Activation," *Nature* 374(6522):546-549.
Kyte, J. et al. (1982). "A Simple Method for Displaying the Hydropathic Character of a Protein," *J. Mol. Biol.* 157:105-132.
Lee, J. et al. (2006). "Activation of Anti-Hepatitis C Virus Responses Via Toll-Like Receptor 7," *PNAS* 103(6):1828-1833.
Lin, W-J. et al. (Sep. 2005). "Implication of Toll-Like Receptor and Tumor Necrosis Factor α Signaling in Septic Shock," *Shock* 24(3):206-209.
Logan, J. et al. (Jun. 1984). "Adenovirus Tripartite Leader Sequence Enhances Translation of mRNAs Late After Infection," *Proc. Natl. Acad. Sci. USA* 81:3655-3659.
Lowy, I. et al., (Dec. 1980). "Isolation of Transforming DNA: Cloning the Hamster aprt Gene," *Cell* 22:817-823.
Luster, A.D. (2002). "The Role of Chemokines in Linking Innate and Adaptive Immunity," *Current Opinion in Immunology* 14:129-135.
Maddox, D.E. et al. (Oct. 1983). "Elevated Serum Levels in Human Pregnancy of a Molecule Immunochemically Similar to Eosinophil Granule Major Basic Protein," *J. Exp. Med.* 158:1211-1226.
Maratea, D. et al. (1985). "Deletion and Fusion Analysis of the Phage ΦX174 Lysis Gene E," *Gene* 40:39-46.
McCluskie, M.J. et al. (1998). "Cutting Edge: CpG DNA is a Potent Enhancer of Systemic and Mucosal Immune Responses Against Hepatitis B Surface Antigen with Intranasal Administration to Mice," *The Journal of Immunology* 161:4463-4466.
Medzhitov, R. et al. (1997). "Innate Immunity: Impact on the Adaptive Immune Response," *Current Opinion in Immunology* 9:4-9.
Medzhitov, R. (Nov. 2001). "Toll-Like Receptors and Innate Immunity," *Nature Reviews Immunology* 1:135-146.
Mendez et al., (2001) "The Potency and Durability of DNA-and Protein-Based Vaccines Against Leishmania major D Evaluated Using Low-Dose, Intradermal Challenge," *The Journal of Immunology* 166: 5122-5128.
Mosmann, T.R. et al. (1989). "TH1 and TH2 Cells: Different Patterns of Lymphokine Secretion Lead to Different Functional Properties," *Ann. Rev. Immunol.* 7:145-173.
Murphy, J.R. et al. (Nov. 1986). "Genetic Construction, Expression, and Melanoma-Selective Cytotoxicity of a Diphtheria Toxin-Related α-Melanocyte-Stimulating Hormone Fusion Protein," *Proc. Natl. Acad. Sci. USA* 83:8258-8262.

Murphy et al., (2001) "IL-10 mediates susceptibility to Leishmania donovani infection," European Journal of Immunology 31:2848-2856.
Murray et al., (Feb. 15, 1999) "Macrophage Microbicidal Mechanisms In Vivo: Reactive Nitrogen versus Oxygen Intermediates in the Killing of Intracellular Visceral Leishmania donovani," Journal of Experimental Medicine 189(4): 741-746.
Murray et al., (Nov. 2000) "Visceral Leishmaniasis in Mice Devoid of Tumor Necrosis Factor and Response to Treatment," Infection and Immunity 68(11 ): 6289-6293.
Myers, E.W. et al. (1988). "Optimal Alignments in Linear Space," *Cabios* 4(1):11-17.
Nakao, Y. et al. (2005). "Surface-Expressed TLR6 Participates in the Recognition of Diacylated Lipopeptide and Peptidoglycan in Human Cells" The Journal of Immunology 174:1566-1573.
Needleman, S.B. et al. (1970). "A General Method Applicable to the Search for Similarities in the Amino Acid Sequence of Two Proteins," *J. Mol. Biol.* 48:443-453.
Nico et al., " Adaptive Immunity against Leishmania Nucleoside Hydrolase Maps Its C-Terminal Domain as the Target of the CD4+ T Cell-Driven Protective Response"*PLoS Negl Trop Dis* 2010,4(11): e866.
Ortega, S. et al. (Jul. 1992). "Single-Step Purification on Deae-Sephacel of Recombinant Polypeptides Produced in *Escherichia coli*," Biotechnology 10(7):795-798.
Pearson, W.R. et al. (Apr. 1988). "Improved Tools for Biological Sequence Comparison," Proc. Natl Acad. Sci. USA 85:2444-2448.
Piedrafita et al., (1999) "Protective Immune Responses Induced by Vaccination with an Expression Genomic Library of Leishmania major," *The Journal of Immunology* 163: 1467-1472.
Powell, M.F. et al eds. (1995). Vaccine Design. The Subunit and Adjuvant Approach, Plenum Press, New York, pp. xvii-xxxvii (Table of Contents Only.).
Rafati et al., (2006) "Prime-boost vaccination using cysteine proteinases type I and II of Leishmania infantum confers protective immunity in murine visceral leishmaniasis," Vaccine 24: 2169-2175.
Rathore, D. et al. (Jul. 18, 2000). "Role of Cysteines in Plasmodium falciparum Circumsporozoite Protein: Interactions with Heparin can Rejuvenate Inactive Protein Mutants," PNAS 97(15):8530-8535.
Remington's Pharmaceutical Sciences, 15th Edition, 1975, Mack Publishing Company, Easton, PA, pp. 1035-1038 and 1570-1580.
Rhee et al., (Jun. 17, 2002) "Vaccination with Heat-killed Leishmania Antigen or Recombinant Leishmanial Protein and CpG Oligodeoxynucleotides Induces Long-Term Memory CD4+ and CD8+ T Cell Responses and Protection Against Leishmania major Infection," The Journal of Experimental Medicine 195(12): 1565-1573.
Rhodes, C.A. et al. (1995). "Transformation of Maize by Electroporation of Embryos," Chapter 9 in Methods in Molecular Biology, Nickoloff, J.A. ed., Humana Press Inc., Totowa, NJ, 55:121-131.
Robinson, D.F. (1971). "Comparison of Labeled Trees with Valency Three," Journal of Combinatorial Theory 11:105-119.
Sackett, D.L. et al. (1985). "Diagnosis," in Clinical Epidemiology—A Basic Science for Clinical Medicine, Little Brown and Company, pp. 106-107.
Saitou, N. et al. (1987). "The Neighbor-Joining Method: A New Method for Reconstructing Phylogenetic Trees," Molecular Biology and Evolution 4:406-425.
Salem, M.L. et al. (2006, e-pub. May 2, 2006). "The Adjuvant Effects of the Toll-Like Receptor 3 Ligand Polyinosinic-Cytidylic Acid Poly (I:C) on Antigen-Specific CD8+ T Cell Responses are Partially Dependent on NK Cells with the Induction of a Beneficial Cytokine Milieu," Vaccine 24:5119-5132.
Sato, Y. et al. (Jul. 19, 1996). "Immunostimulatory DNA Sequences Necessary for Effective Intradermal Gene Immunization," Science 273:352-354.
Scharf, K-D. et al. (1994). "Heat Stress Promoters and Transcription Factors," Chapter 6 in Results and Problems in Cell Differentiation, Hennig, W. et al eds., 20:125-162.
Schirmbeck, R. et al. (2003). "Antigenic Epitopes Fused to Cationic Peptide Bound to Oligonucleotides Facilitate Toll-Like Receptor

(56) References Cited

OTHER PUBLICATIONS

9-Dependent, but CD4+ T Cell Help-Independent, Priming of CD8+ T Cells" The Journal of Immunology 171:5198-5207.
Skeiky, Y.A.W. et al. (2002). "Protective Efficacy of a Tandemly Linked, Multi-Subunit Recombinant Leishmanial Vaccine (Leish-111f) Formulated in MPL® Adjuvant," Vaccine 20:3292-3303.
Smith, T.F. et al. (1981). "Comparison of Biosequences," Advances in Applied Mathematics 2:482-489.
Sneath, P.H.A. et al. (1973). Numerical Taxonomy—The Principles and Practice of Numerical Classification, W.H. Freeman and Company, San Francisco, CA, pp. vii-ix, (Table of Contents Only.).
Soboll, G. et al. (2006, e-pub. Jul. 1, 2006). "Expression of Toll-Like Receptors (TLR) and Responsiveness to TLR Agonists by Polarized Mouse Uterine Epithelial Cells in Culture" Biology of Reproduction 75:131-139.
Stacey et al., (Aug. 1999) "Immunostimulatory DNA as an Adjuvant in Vaccination against Leishmania major," Infection and Immunity 67(8): 3719-3726.
Stager et al., (2000) "Immunization with a Recombinant Stage-Regulated Surface Protein from Leishmania donovani Induces Protection Against Visceral Leishmaniasis," The Journal of Immunology 165: 7064-7071.
Stern et al., (Jun. 1, 1988) "Role of L3T4+ and L YT-2+ Cells in Experimental Visceral Leishmaniasis," The Journal of Immunology 140(11): 3971-3977.
Stobie, L. et al. (Jul. 18, 2000). "The Role of Antigen and IL-12 in Sustaining Th1 Memory Cells in vivo: IL-12 is Required to Maintain Memory/Effector Th1 Cells Sufficient to Mediate Protection to an Infectious Parasite Challenge," PNAS 97(15):8427-8432.
Takamatsu, N. et al. (1987). "Expression of Bacterial Chloramphenicol Acetyltransferase Gene in Tobacco Plants Mediated by TMV-RNA," Embo J. 6(2):307-311.
Takeda, K. et al. (2003, e-pub. Jan. 9, 2003). "Toll-Like Receptors," Annu. Rev. Immunol.21:335-376.
Takeda, K. et al. (2005). "Toll-Like Receptors in Innate Immunity," International Immunology 17(1):1-14.
Takenaga, M. et al. (1998). "Microparticle Resins as a Potential Nasal Drug Delivery System for Insulin," Journal of Controlled Release 52:81-87.
Taylor et al., (Apr. 7, 1997) "Intracellular Antimicrobial Activity in the Absence of Interferon-y: Effect of Interleukin-12 in Experimental Visceral Leishmaniasis in Interferon-y Gene-disrupted Mice," Journal of Experimental Medicine 185(7) :1231-1239.
Tewary et al., (Jun. 15, 2005) "A Heterologous Prime-Boost Vaccination Regimen Using ORFF DNA and Recombinant ORFF Protein Confers Protective Immunity against Experimental Visceral Leishmaniasis," The Journal of Infectious Diseases 191: 2130-2137.
Tsan, M-F. et al. (Apr. 2004). "Cytokine Function of Heat Shock Proteins," Am. J. Physiol. Cell Physiol. 286:C739-C744.
Tsan, M-F. et al. (Sep. 2004). "Endogenous Ligands of Toll-Like Receptors," Journal of Leukocyte Biology 76:514-519.
Ulmer, J.B. et al. (Mar. 19, 1993). "Heterologous Protection Against Influenza by Injection of DNA Encoding a Viral Protein," Science 259:1745-1749.
Van Heeke, G. et al. (Apr. 5, 1989). "Expression of Human Asparagine Synthetase in Escherichia coli," J. Biol. Chem. 264(10):5503-5509.
Vogel, F.R. et al. (1995). "A Compendium of Vaccine Adjuvants and Excipients," Pharm. Biotechnol. 6:141-228.
Vollmer, J. et al. (Jun. 2004). "Immunopharmacology of CpG Oligodeoxynucleotides and Ribavirin," Antimicrobial Agents Chemotherapy 48(6):2314-2417.
Vollmer, J. (2005). "Progress in Drug Development of Immunostimulatory CpG Oligodeoxynucleotide Ligands for TLR9," Expert Opin. Biol. Ther. 5(5):673-682.
Walker, P.S. et al. (Jun. 1999). "Immunostimulatory Oligodeoxynucleotides Promote Protective Immunity and Provide Systemic Therapy for Leishmaniasis Via IL-12- and IFN-γ-Dependent Mechanisms," Proc. Natl. Acad. Sci. USA 96:6970-6975.
Wigler, M. et al. (May 1977). "Transfer of Purified Herpes Virus Thymidine Kinase Gene to Cultured Mouse Cells," Cell 11:223-232.
Wigler, M. et al. (Jun. 1980). "Transformation of Mammalian Cells with an Amplifiable Dominant-Acting Gene," Proc. Natl. Acad. Sci. USA 77(6):3567-3570.
Wilbur, W.J. et al. (Feb. 1983). "Rapid Similarity Searches of Nucleic Acid and Protein Data Banks," Proc. Natl. Acad. Sci. USA 80:726-730.
Wilson et al., (May 1995) "A Recombinant Leishmania chagasi Antigen That Stimulates Cellular Immune Responses in Infected Mice," Infection and Immunity 63(5): 2062-2069.
Wilson et al., (1998) "The Importance of TGF-β in Murine Visceral Leishmaniais," The Journal of Immunology 161:6148-6155.
Winter, J. et al. (1991). "The Expression of Heat Shock Protein and Cognate Genes During Plant Development," Chapter 6 in Results and Problems in Cell Differentiation, Hennig, W. et al. eds., 17:85-105.
U.S. Appl. No. 14/780,494, Internationally filed on Mar. 28, 2014, by Guderian et al. (Copy Not Attached).

* cited by examiner

Leish Polypeptide Recall Responses for IFN-γ

Figure 4  Leish Fusion Polypeptide Recall Responses for IFN-γ

US 9,909,114 B2

VACCINES COMPRISING *LEISHMANIA* POLYPEPTIDES FOR THE TREATMENT AND DIAGNOSIS OF LEISHMANIASIS

CROSS-REFERENCE TO RELATED PATENT APPLICATIONS

This application is a National Phase filing under 35 U.S.C. § 371 of International Application No. PCT/US2014/032276, filed Mar. 28, 2014, which claims the priority benefit of U.S. Provisional Application Ser. Nos. 61/806,368, filed Mar. 28, 2013, and 61/822,545, filed May 13, 2013, the entire contents of each which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 712192002900SEQLISTING.txt, date recorded: Jan. 8, 2016, size: 191 KB)

STATEMENT REGARDING FEDERALLY SPONSORED RESEARCH OR DEVELOPMENT

This invention was made with government support under Grant No. R0A1025038 awarded from the National Institute of Allergy and Infectious Disease of the National Institutes of Health. The government has certain rights in this invention.

BACKGROUND

Technical Field

The present invention relates generally to compositions and methods for preventing, treating and detecting leishmaniasis in patients. More particularly, the invention relates to compositions and methods comprising *Leishmania* antigens and fusion polypeptides, as well as polynucleotides encoding such antigens and fusion polypeptides.

Description of the Related Art

*Leishmania* organisms are obligate intracellular parasites that cause a large clinical spectrum of diseases named leishmaniasis. *Leishmania* organisms are intracellular protozoan parasites of the genus *Leishmania*. *Leishmania* organisms target host macrophages; thus causing a wide spectrum of clinical diseases in humans and domestic animals, primarily dogs. In some infections, the parasite may lie dormant for many years. In other cases, the host may develop one of a variety of forms of leishmaniasis. Leishmaniases are roughly classified into three types of diseases, cutaneous leishmaniasis (CL), mucosal leishmaniasis (ML) and visceral leishmaniasis (VL), according to the clinical manifestations.

Leishmaniasis is a serious problem in much of the world, including Brazil, China, East Africa, India and areas of the Middle East. The disease is also endemic in the Mediterranean region, including southern France, Italy, Greece, Spain, Portugal and North Africa. The number of cases of leishmaniasis has increased dramatically in the last 20 years, and millions of cases of this disease now exist worldwide. About 2 million new cases are diagnosed each year, 25% of which are visceral leishmaniasis.

Visceral leishmaniasis (VL) has been reported in 88 countries, but roughly 90% of VL cases occur in Brazil, India, Sudan, Bangladesh, and Nepal (Mendez et al. J Immunol 2001; 166(8): pp. 5122-8). The annual incidence is estimated to be approximately 500,000 cases of VL, and the population at risk is 350 million (Engwerda et al. Eur J Immunol 1998; 28(2): pp. 669-80; Squires et al. J Immunol 1989; 143(12): pp. 4244-9). Visceral leishmaniasis, generally caused by species of the *L. donovani* complex, i.e. *L. donovani* and *L. infantum* (*chagasi*). *L. donovani* is the causative agent of visceral leishmaniasis in Africa and Asia, *L. infantum/chagasi* in Mediterranean countries and in the New World (Piedrafita et al. J Immunol 1999; 163(3): pp. 1467-72). VL is a severe debilitating disease that evolves with visceral infection involving the spleen, liver and lymph nodes, which, untreated, is generally a fatal disease. Symptoms of acute visceral leishmaniasis include hepatosplenomegaly, fever, leukopenia, anemia and hypergammaglobulinemia. Active VL is generally fatal unless properly treated.

*Leishmania* parasites are transmitted by the bite of sandflies and the infecting promastigotes differentiate into and replicate as amastigotes within macrophages in the mammalian host. In common with other intracellular pathogens, cellular immune responses are critical for protection against leishmaniasis. Th1 immune responses play an important role in mediating protection against *Leishmania*, including roles for CD4+ and CD8+ T cells, IFN-γ, IL-12, TNF-α and NO, whereas inhibitory effects have been reported for IL-10 and TGF-B (Engwerda et al. Eur J Immunol 1998; 28(2): pp. 669-80; Murphy et al. Eur J Immunol. 2001; 31(10): pp. 2848-56; Murray et al. J Exp Med. 1999; 189(4): pp. 741-6; Murray et al. Infect Immun. 2000; 68(11): pp. 6289-93; Squires et al. J Immunol 1989; 143(12): pp. 4244-9 6; Taylor and Murray. J Exp Med. 1997; 185(7): pp. 1231-9; Kaye and Bancroft. Infect Immun. 1992; 60(10): pp. 4335-42; Stern et al. J Immunol. 1988; 140(11): pp. 3971-7; Wilson et al. J Immunol. 1998; 161(11): pp. 6148-55).

Immunization against leishmaniasis in animal models can be effected by delivery of antigen-encoding DNA vectors (Gurunathan et al. J Exp Med. 1997; 186(7): pp. 1137-47; Piedrafita et al. J Immunol. 1999; 163(3):1467-72; Mendez et al. J Immunol. 2001; 166(8): pp. 5122-8) or by administration of proteins formulated with Th1-inducing adjuvants including IL-12 (Afonso et al. Science. 1994; 263(5144): pp. 235-7; Stobie et al. Proc Natl Acad Sci USA. 2000; 97(15): pp. 8427-32; Kenney et al. J Immunol. 1999; 163(8): pp. 4481-8) or TLR ligands such as CpG oligonucleotides (Rhee et al. J Exp Med. 2002; 195(12): pp. 1565]73; Stacey and Blackwell. Infect Immun. 1999; 67(8): pp. 3719-26; Walker et al. Proc Nat/Acad Sci USA. 1999; 96(12): pp. 6970-5) and monophosphoryl lipid A (Coler et al. Infect Immun. 2002; 70(8): pp. 4215-25; Skeiky et al. Vaccine. 2002; 20(2728): pp. 3292-303).

In spite of some evidence that sub-unit vaccines may be effective in certain models of VL (Basu et al. J Immunol. 2005; 174(11): pp. 7160-71; Stager et al. J Immunol. 2000; 165(12): pp. 7064-71; Ghosh et al. Vaccine. 2001; 20(12): pp. 59-66; Wilson et al. Infect Immun. 1995; 63(5): pp. 2062-9; Tewary et al. J Infect Dis. 2005; 191(12): pp. 2130-7; Aguilar-Be et al. Infect Immun. 2005; 73(2): pp. 812-9. Rafati et al. Vaccine. 2006; 24(12):2169-75), progress toward defining antigen candidates effective against VL in vivo has been lacking.

Strategies employing vaccines consisting of whole organisms for preventing or treating leishmaniasis have not been effective in humans. In addition, more effective reagents are needed for accurately diagnosing leishmaniasis in patients. Accordingly, there remains a significant need for immunogenic compositions and vaccines that can effectively prevent, treat and/or diagnose leishmaniasis in humans and other mammals (e.g., canines). The present invention fulfills these needs and offers other related advantages.

BRIEF SUMMARY

The present invention provides compositions, kits and methods for preventing, treating and detecting leishmaniasis.

In one aspect, the invention provides a fusion polypeptide comprising a *Leishmania* non-specific nucleoside hydrolase (NH) polypeptide, a *Leishmania* sterol 24-c-methyltransferase (SMT) polypeptide, and a *Leishmania* polypeptide selected from the group consisting of a putative mitochondrial HSP70 (mtHSP70) polypeptide, a cysteine polypeptidease B (CpB) polypeptide, a histone H2BN (H2BN) polypeptide sequence, an A2 (A2) polypeptide, and a p21 antigen (p21) polypeptide. In some embodiments, the fusion polypeptide comprises a *Leishmania* non-specific nucleoside hydrolase (NH) polypeptide, a *Leishmania* sterol 24-c-methyltransferase (SMT) polypeptide, and one or more of a *Leishmania* polypeptide selected from the group consisting of a putative mitochondrial HSP70 (mtHSP70) polypeptide, a cysteine polypeptidease B (CpB) polypeptide, a histone H2BN (H2BN) polypeptide sequence, an A2 (A2) polypeptide, a p21 antigen (p21) polypeptide, and a putative eukaryotic initiation factor 4a (Leif) polypeptide.

In some embodiments, the fusion polypeptide comprises a *Leishmania* NH polypeptide, a *Leishmania* SMT polypeptide, a *Leishmania* H2BN polypeptide, and a *Leishmania* A2 polypeptide. In some embodiments, the fusion polypeptide comprises a *Leishmania* NH polypeptide, a *Leishmania* SMT polypeptide, a *Leishmania* mtHSP70 polypeptide, and a *Leishmania* A2 polypeptide. In some embodiments, the fusion polypeptide comprises a *Leishmania* NH polypeptide, a *Leishmania* SMT polypeptide, a *Leishmania* A2 polypeptide, and a *Leishmania* p21 polypeptide. In some embodiments, the fusion polypeptide comprises a *Leishmania* NH polypeptide, a *Leishmania* SMT polypeptide, a *Leishmania* mtHSP70 polypeptide, and a *Leishmania* p21 polypeptide. In some embodiments, the fusion polypeptide comprises a *Leishmania* NH polypeptide, a *Leishmania* SMT, and a *Leishmania* mtHSP70 polypeptide. In some embodiments, the fusion polypeptide comprises a *Leishmania* NH polypeptide, a *Leishmania* SMT polypeptide, and a *Leishmania* CpB polypeptide. In some embodiments, the fusion polypeptide comprises a *Leishmania* NH polypeptide, a *Leishmania* SMT polypeptide, and a *Leishmania* A2 polypeptide. In some embodiments, the fusion polypeptide comprises a *Leishmania* NH polypeptide, a *Leishmania* SMT polypeptide, and a *Leishmania* H2BN polypeptide. In some embodiments, the fusion polypeptide comprises a *Leishmania* NH polypeptide, a *Leishmania* SMT polypeptide, and a *Leishmania* p21 polypeptide. In some embodiments, the fusion polypeptide comprises a *Leishmania* mtHSP70 polypeptide, a *Leishmania* H2BN polypeptide, a *Leishmania* NH polypeptide, and a *Leishmania* SMT polypeptide. In some embodiments, the fusion polypeptide comprises a *Leishmania* H2BN polypeptide, a *Leishmania* p21 polypeptide, a *Leishmania* NH polypeptide, and a *Leishmania* SMT polypeptide. In some embodiments, the fusion polypeptide comprises a *Leishmania* NH polypeptide, a *Leishmania* SMT polypeptide, a *Leishmania* H2BN polypeptide, and CpB. In some embodiments, the fusion polypeptide comprises a *Leishmania* NH polypeptide, a *Leishmania* SMT polypeptide, and a *Leishmania* LeiF polypeptide.

In another aspect, the invention provides a fusion polypeptide comprising a *Leishmania* SMT polypeptide and a *Leishmania* polypeptide selected from the group consisting of a mtHSP70 polypeptide, a CpB polypeptide, a H2BN polypeptide, a A2 polypeptide, and a p21 polypeptide. In some embodiments, the fusion polypeptide comprises a *Leishmania* SMT polypeptide, a *Leishmania* CpB polypeptide, and a *Leishmania* p21 polypeptide. In some embodiments, the fusion polypeptide comprises a *Leishmania* SMT polypeptide, a *Leishmania* mtHSP70 polypeptide, and a *Leishmania* H2BN polypeptide. In some embodiments, the fusion polypeptide comprises a *Leishmania* SMT polypeptide, a *Leishmania* mtHSP70 polypeptide, and a *Leishmania* p21 polypeptide.

In some of embodiments of the polypeptides described herein, the NH polypeptide is from a *L. infantum*, a *L. donovani*, a *L. major*, a *L. mexicana*, or a *L. braziliensis*. In some embodiments, the SMT polypeptide, the mtHSP70 polypeptide, the CpB polypeptide, the H2BN polypeptide, the A2 polypeptide, the p21 polypeptide, or the LeiF polypeptide is from a *L. infantum, L. donovani*, a *L. major*, a *L. mexicana*, or a *L. braziliensis*. In some embodiments, the fusion polypeptide comprises sequences from at least two, at least three, or at least four different *Leishmania* strains.

In some embodiments, the mtHSP90 polypeptide comprises the amino acid sequence of SEQ ID NO:27, 28, 29, or 30 or a sequence having at least a 90% (e.g., 91%, 92%, 93%, 94%, 95%, 96%, 97%, 98%, or 99%) identity to SEQ ID NO:27, 28, 29, or 30.

In some embodiments, the CpB polypeptide comprises the amino acid sequence of SEQ ID NO:31 or a sequence having at least a 90% (e.g., 91%, 92%, 93%, 94%, 95%, 96%, 97%, 98%, or 99%) identity to SEQ ID NO:31.

In some embodiments, the H2BN polypeptide comprises the amino acid sequence of SEQ ID NO:32 or a sequence having at least a 90% (e.g., 91%, 92%, 93%, 94%, 95%, 96%, 97%, 98%, or 99%) identity to SEQ ID NO:32.

In some embodiments, the A2 polypeptide comprises the amino acid sequence of SEQ ID NO:33 or 37, or a sequence having at least a 90% (e.g., 91%, 92%, 93%, 94%, 95%, 96%, 97%, 98%, or 99%) identity to SEQ ID NO:33 or 37.

In some embodiments, the p21 polypeptide comprises the amino acid sequence of SEQ ID NO:34 or a sequence having at least a 90% (e.g., 91%, 92%, 93%, 94%, 95%, 96%, 97%, 98%, or 99%) identity to SEQ ID NO:34.

In some embodiments, the LeiF polypeptide comprises the amino acid sequence of SEQ ID NO:42 or a sequence having at least a 90% (e.g., 91%, 92%, 93%, 94%, 95%, 96%, 97%, 98%, or 99%) identity to SEQ ID NO:42.

In some embodiments, the NH polypeptide comprises the amino acid sequence of SEQ ID NO:35 or a sequence having at least a 90% (e.g., 91%, 92%, 93%, 94%, 95%, 96%, 97%, 98%, or 99%) identity to SEQ ID NO:35.

In some embodiments, the SMT polypeptide comprises the amino acid sequence of SEQ ID NO:36 or a sequence having at least a 90% (e.g., 91%, 92%, 93%, 94%, 95%, 96%, 97%, 98%, or 99%) identity to SEQ ID NO:36.

In another aspect, the invention provides a fusion polypeptide comprising the amino acid sequence of SEQ ID NO:2, 4, 6, 8, 10, 12, 14, 16, 18, 20, 22, 24, 26, 39, 41, 43 or 44 or a sequence having at least 90% (e.g., 91%, 92%, 93%, 94%, 95%, 96%, 97%, 98%, or 99%) identity to SEQ ID NO: 2, 4, 6, 8, 10, 12, 14, 16, 18, 20, 22, 24, 26, 39, 41, 43 or 44.

In another aspect, the invention provides an isolated polynucleotide encoding the polypeptides described herein, for example, encoding a fusion polypeptide comprising the amino acid sequence of SEQ ID NO:2, 4, 6, 8, 10, 12, 14, 16, 18, 20, 22, 24, 26, 39, 41, 43 or 44 or a sequence having at least 90% (e.g., 91%, 92%, 93%, 94%, 95%, 96%, 97%, 98%, or 99%) identity to SEQ ID NO: 2, 4, 6, 8, 10, 12, 14, 16, 18, 20, 22, 24, 26, 39, 41, 43 or 44. In some embodiments, the polynucleotide comprises a sequence of SEQ ID NO:1, 3, 5, 7, 9, 11, 13, 15, 17, 19, 21, 23, 25, 38, or 40 or a sequence having at least 90% (e.g., 91%, 92%, 93%, 94%, 95%, 96%, 97%, 98%, or 99%) identity to SEQ ID NO: 1, 3, 5, 7, 9, 11, 13, 15, 17, 19, 21, 23, 25, 38, or 40.

In another aspect, the invention provides a composition comprising a fusion polypeptide as described herein and/or a polynucleotide encoding a polypeptide as described herein, in combination with at least one immunostimulant. Many immunostimulants are known and can be used in the compositions herein, illustrative examples of which include, but are not limited to, a CpG-containing oligonucleotide, synthetic lipid A, MPLTM, 3D-MPLTM, saponins, saponin mimetics, AGPs, Toll-like receptor agonists, or a combination thereof. Other illustrative immunostimulants comprise, for example, aTLR4 agonist, a TLR7/8 agonist and/or a TLR9 agonist. Still other immunostimulants comprise, for example, imiquimod, gardiquimod and/or resiquimod.

In some embodiments, the immunostimulant has the formula:

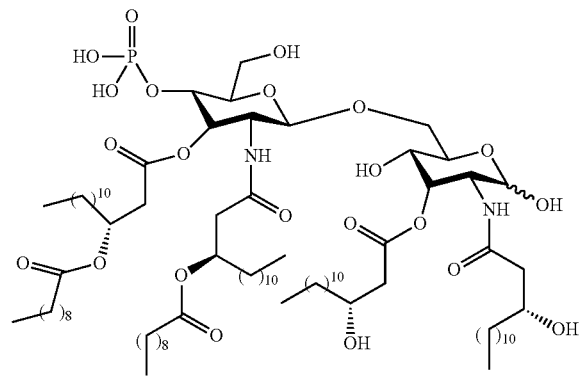

In another aspect, the invention provides a method for stimulating an immune response against *Leishmania* in a mammal comprising administering to a mammal in need thereof a composition as described herein.

In another aspect, the invention provides a method for detecting *Leishmania* infection in a biological sample, comprising: (a) contacting a biological sample with a fusion polypeptide as described herein; and (b) detecting in the biological sample the presence of antibodies that bind to the fusion polypeptide, thereby detecting *Leishmania* infection in a biological sample. Any suitable biological sample type may be analyzed by the method, illustrative examples of which may include, for example, sera, blood and saliva.

In certain embodiments of the disclosed diagnostic methods, the polypeptide is bound to a solid support. Accordingly, the present invention further provides diagnostic reagents comprising a polypeptide as described herein, immobilized on a solid support.

In another aspect, the invention provides a diagnostic kit for detecting *Leishmania* infection in a biological sample, wherein the kit comprises a polypeptide as described herein and a detection reagent. It will be understood that the kit may employ a polypeptide of the invention in any of a variety of assay formats known in the art, including, for example, a lateral flow test strip assay, a dual path platform (DPP) assay and an ELISA assay. These kits and compositions of the invention can offer valuable point of care diagnostic information. Furthermore, the kits and compositions can also be advantageously used as test-of-cure kits for monitoring the status of infection in an infected individual over time and/or in response to treatment.

It is to be understood that one, some, or all of the properties of the various embodiments described herein may be combined to form other embodiments of the present invention. These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIG. 6D shows that animals immunized with the fusion polypeptides demonstrated greater reductions in parasite burden when immunized with the fusion polypeptides (NS or NSC) compared to the individual polypeptides of the fusions (NH, SMT, or CpB).

BRIEF DESCRIPTION OF THE SEQUENCE IDENTIFIERS

Figure 1:
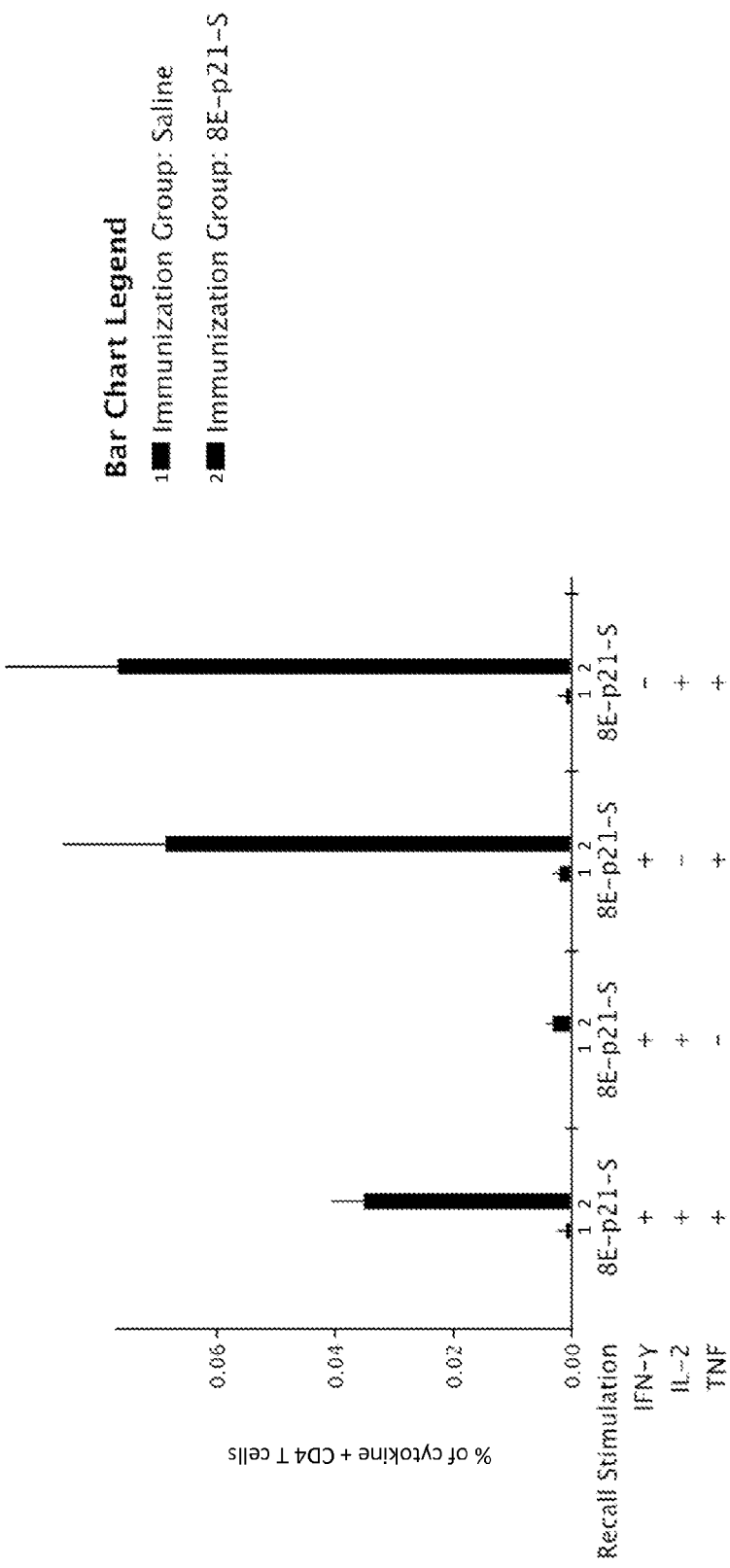
FIG. 1 shows flow cytometry analysis of spleen cell cultures from mice immunized with 821S or saline and restimulated in vitro with saline or 821S for the percentage of cells secreting IFN-γ, IL-2, or TNF. CD4 T cells that produce multiple (two or more) cytokines are termed multifunctional.

SEQ ID NO: 1 is a nucleic acid sequence encoding the NSC fusion polypeptide of SEQ ID NO: 2.

SEQ ID NO: 2 is an amino acid sequence for an NSC fusion polypeptide.

SEQ ID NO: 3 is a nucleic acid sequence encoding the NSA fusion polypeptide of SEQ ID NO: 4.

SEQ ID NO: 4 is an amino acid sequence for an NSA fusion polypeptide.

SEQ ID NO: 5 is a nucleic acid sequence encoding the NSAfl fusion polypeptide of SEQ ID NO: 6.

SEQ ID NO: 6 is an amino acid sequence for an NSAfl fusion polypeptide.

SEQ ID NO: 7 is a nucleic acid sequence encoding the HNSA fusion polypeptide of SEQ ID NO: 8.

SEQ ID NO: 8 is an amino acid sequence for a HNSA fusion polypeptide

SEQ ID NO: 9 is a nucleic acid sequence encoding the 8NSA fusion polypeptide of SEQ ID NO: 10.

SEQ ID NO: 10 is an amino acid sequence for a 8NSA fusion polypeptide.

SEQ ID NO: 11 is a nucleic acid sequence encoding the 21NSA fusion polypeptide of SEQ ID NO: 12.

SEQ ID NO: 12 is an amino acid sequence for a 21NSA fusion polypeptide.

SEQ ID NO: 13 is a nucleic acid sequence encoding the 821NS fusion polypeptide of SEQ ID NO: 14.

SEQ ID NO: 14 is an amino acid sequence for a 821NS fusion polypeptide.

SEQ ID NO: 15 is a nucleic acid sequence encoding the HNS fusion polypeptide of SEQ ID NO: 16.

SEQ ID NO: 16 is an amino acid sequence for a HNS fusion polypeptide.

SEQ ID NO: 17 is a nucleic acid sequence encoding the 8NS fusion polypeptide of SEQ ID NO: 18.

SEQ ID NO: 18 is an amino acid sequence for a 8NS fusion polypeptide.

SEQ ID NO: 19 is a nucleic acid sequence encoding the 21NS fusion polypeptide of SEQ ID NO: 20.

SEQ ID NO: 20 is an amino acid sequence for a 21NS fusion polypeptide.

SEQ ID NO: 21 is a nucleic acid sequence encoding the 21SC fusion polypeptide of SEQ ID NO: 22.

SEQ ID NO: 22 is an amino acid sequence for a 21SC fusion polypeptide.

SEQ ID NO: 23 is a nucleic acid sequence encoding the 821S fusion polypeptide of SEQ ID NO: 24.

SEQ ID NO: 24 is an amino acid sequence for a 821S fusion polypeptide.

SEQ ID NO: 25 is a nucleic acid sequence encoding the 8HS fusion polypeptide of SEQ ID NO: 26.

SEQ ID NO: 26 is an amino acid sequence for 8HS fusion polypeptide.

SEQ ID NO: 27 is an amino acid sequence of a carboxy-terminal fragment of the putative mitochondrial HSP70 polypeptide (designated 8E or 8 herein) from *Leishmania infantum* or *donovani*. The 8E carboxy-terminal fragment comprises amino acids 509 to 660 of the putative mitochondrial HSP70 polypeptide.

SEQ ID NO: 28 is an amino acid sequence of a carboxy-terminal fragment of the putative mitochondrial HSP70 polypeptide (designated 8E or 8 herein) from *Leishmania major*.

SEQ ID NO: 29 is an amino acid sequence of a carboxy-terminal fragment of the putative mitochondrial HSP70 polypeptide (designated 8E or 8 herein) from *Leishmania Mexicana*.

SEQ ID NO: 30 is an amino acid sequence of a carboxy-terminal fragment of the putative mitochondrial HSP70 polypeptide (designated 8E or 8 herein) from *Leishmania braziliensis*.

SEQ ID NO: 31 is an amino acid sequence of a carboxy-terminal fragment of the cysteine polypeptidease B polypeptide (designated CpB, CPB or C herein) from *Leishmania infantum*. The CpB fragment comprises amino acids 154 to 443 of the cysteine polypeptidease B polypeptide.

SEQ ID NO: 32 is an amino acid sequence of an amino terminal fragment of the histone H2BN polypeptide (designated H2BN, h2Bn, or H herein) polypeptide from *Leishmania infantum*. The H2BN amino terminal fragment comprises amino acids 1 to 46 of the histone H2BN polypeptide.

SEQ ID NO: 33 is an amino acid sequence of a mature A2 polypeptide (designated A herein) from *Leishmania donovani*. The mature A2 polypeptide comprises amino acids 23 to 236 of the A2 polypeptide.

SEQ ID NO: 34 is an amino acid sequence of a full length p21 antigen polypeptide (designated p21 or 21 herein) of *Leishamnia infantum*. The 21 polypeptide comprises amino acids 1 to 191 of the p21 antigen.

SEQ ID NO: 35 is an amino acid sequence of a full length nonspecific nucleoside hydrolase polypeptide (designated NH or H herein) from *Leishmania infantum/donovani*. The full length polypeptide comprises amino acid 1 to 314 of the nonspecific nucleoside hydrolase polypeptide.

SEQ ID NO: 36 is an amino acid sequences of a full length Sterol 24-c-methyltransferase polypeptide which lacks the N terminal Methionine (initiation codon) (designated SMT or S herein) from *Leishmania infantum*. The full length polypeptide minus the N terminal methionine comprises amino acids 2 to 353 of the full length Sterol 24-c-methyltransferase polypeptide.

SEQ ID NO: 37 is an amino acid sequence of a full length A2 polypeptide (designated Afl herein) from *Leishmania donovani*. The Afl polypeptide comprises amino acids 1 to 236 of the A2 polypeptide.

SEQ ID NO: 38 is a nucleic acid sequence encoding the 8HNS fusion polypeptide of SEQ ID NO: 39.

SEQ ID NO.: 39 is an amino acid sequence for an 8HNS fusion polypeptide.

SEQ ID NO.: 40 is a nucleic acid sequence encoding the H21NS fusion polypeptide of SEQ ID NO: 41.

SEQ ID NO.: 41 is an amino acid sequence for an H21NS fusion polypeptide.

SEQ ID NO: 42 is an amino acid sequence of a putative eukaryotic initiation factor 4a polypeptide (designate Leif or L herein) of *Leishmania major*. The Leif polypeptide comprises amino acids 1 to 226 of the putative eukaryotic initiation factor 4a polypeptide.

SEQ ID NO: 43 is an amino acid sequence of the NSL fusion polypeptide.

SEQ ID NO:44 is an amino acid sequence for the HNSC fusion polypeptide.

DETAILED DESCRIPTION

The practice of the present invention will employ, unless otherwise indicated, conventional techniques of molecular biology, recombinant DNA, and chemistry, which are within the skill of the art. Such techniques are explained fully in the literature. See, e.g., Molecular Cloning A Laboratory Manual, 2nd Ed., Sambrook et al., ed., Cold Spring Harbor Laboratory Press: (1989); DNA Cloning, Volumes I and II (D. N. Glover ed., 1985); Oligonucleotide Synthesis (M. J. Gait ed., 1984); Mullis et al., U.S. Pat. No. 4,683,195; Nucleic Acid Hybridization (B. D. Hames & S. J. Higgins eds. 1984); B. Perbal, A Practical Guide To Molecular Cloning (1984); the treatise, Methods In Enzymology (Academic Press, Inc., N.Y.); and in Ausubel et al., Current Protocols in Molecular Biology, John Wiley and Sons, Baltimore, Md. (1989).

As noted above, the present invention is generally directed to compositions and methods for preventing, treating and detecting leishmaniasis. The compositions of the invention include, for example, polypeptides including fusion polypeptides that comprise various immunogenic portions of *Leishmania* proteins, wherein the portions and variants preferably retain substantially the same or similar immunogenic properties as a corresponding full length *Leishmania* protein. Immunization strategies using compositions of the invention can be applied to the in vivo protection against, for example, *L. infantum*, *L. donovani*, and *L. major*, which are causative agents of VL in humans and dogs. The present invention also contemplates, in other embodiments, using the polypeptides including fusion polypeptides described herein in diagnostic applications, including, but not limited to, serodiagnosis and whole blood assays in patients and dogs, preferably in a format amenable to providing rapid, point of care diagnostic results, such as a lateral flow assay or a dual path platform assay.

*Leishmania* Polypeptides and Uses Therefor

In a general aspect, the present invention provides isolated *Leishmania* polypeptides, as described herein, including fusion polypeptides and compositions containing the same.

In some embodiments, the invention provides a fusion polypeptide comprising a *Leishmania* non-specific nucleoside hydrolase (NH) polypeptide or a variant thereof, a *Leishmania* sterol 24-c-methyltransferase (SMT) polypeptide or a variant thereof, and a *Leishmania* polypeptide selected from the group consisting of a putative mitochondrial HSP70 (mtHSP70) polypeptide, a cysteine polypeptidase B (CpB) polypeptide, a histone H2BN (H2BN) polypeptide, an A2 polypeptide, a p21 antigen (p21) polypeptide, and a putative eukaryotic initiation factor 4a (LeiF) polypeptide, or a variant of these polypeptides.

In some embodiments, the invention provides a fusion polypeptide comprising a *Leishmania* SMT polypeptide or a variant thereof, and a *Leishmania* polypeptide selected from the group consisting of an mtHSP70 polypeptide, a CpB polypeptide, a H2BN polypeptide, an A2 polypeptide, and a p21 polypeptide or a variant of these polypeptides.

In some embodiments, the polypeptides and fusion polypeptides of the invention can generate an immune response or an effective immune response to *Leishmania*. In some embodiments, the polypeptides and fusion polypeptides may have one or more of the following characteristics: 1) a reduction in parasite burden in immunized hosts upon experimental challenge with a *Leishmania* parasite infection either by direct innoculation of promastigotes or models of natural infection such as the bites of infected sandflies; 2) secretion of IFNγ in in vitro spleen cell cultures from mice immunized with the individual polypeptides or fusion polypeptides of the invention upon incubation with the matched fusion polypeptide or individual polypeptides of the fusion polypeptide; 3) IFNγ secretion in vitro spleen cell cultures from mice immunized with the individual polypeptides or fusion polypeptides of the invention following incubation with crude parasite; 4) generation of antigen-specific multifunctional Th1 cells, for example CD4 T cells that produce multiple cytokines indicative of a Th1 phenotype such as IFNγ, TNF and IL-2 or IFNγ and TNF; and or 5) improvement or enhancement of the immune recognition of one or more individual polypeptide(s), when presented in the context of a fusion polypeptide, as measured for example by the secretion of cytokines such γIFN, or the titer of presence of antibodies or cellular responses to the polypeptide. Methods for testing immune responses are known in the art and are described in detail in Example 2.

As used herein, the term "polypeptide" or "protein" encompasses amino acid chains of any length, including full length proteins, wherein the amino acid residues are linked by covalent bonds. A polypeptide comprising an immunogenic portion of a *Leishmania* polypeptide or protein may consist solely of an immunogenic portion, may contain two or more immunogenic portions and/or may contain additional sequences. The additional sequences may be derived from a native *Leishmania* polypeptide or protein or may be heterologous, and such heterologous sequences may (but need not) be immunogenic.

Different *Leishmania* polypeptides in the fusion polypeptides may be arranged in the fusion polypeptide in any order. For example, any particular polypeptide of the fusion polypeptide may be located towards the C-terminal end of the fusion polypeptide or the N-terminal end of the polypeptide or in the center of the fusion polypeptide (i.e., located in between at least two other polypeptides in the fusion polypeptide). Different *Leishmania* polypeptides may be linked by a linker sequence of any length.

An "isolated polypeptide" is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. One of ordinary skill in the art would appreciate that antigenic polypeptide fragments could also be obtained from those already available in the art. Polypeptides of the invention, antigenic/immunogenic fragments thereof, and other variants may be prepared using conventional recombinant and/or synthetic techniques.

The *Leishmania* polypeptide used in a fusion polypeptide of the present invention can be full length, substantially full length polypeptides, or variants thereof as described herein. Alternatively, a fusion polypeptide or composition of the invention can comprise or consist of immunogenic portions or fragments of a full length *Leishmania* polypeptide, or variants thereof.

In certain more specific embodiments, an immunogenic portion of a *Leishmania* polypeptide is a portion that is capable of eliciting an immune response (i.e., cellular and/or humoral) in a presently or previously *Leishmania*-infected patient (such as a human or a mammal (e.g., a dog)) and/or in cultures of lymph node cells or peripheral blood mononuclear cells (PBMC) isolated from presently or previously *Leishmania*-infected individuals. The cells in which a response is elicited may comprise a mixture of cell types or may contain isolated component cells (including, but not limited to, T-cells, NK cells, macrophages, monocytes and/or B cells). In a particular embodiment, immunogenic portions of a fusion polypeptide of the invention are capable of inducing T-cell proliferation and/or a predominantly Th1-type cytokine response (e.g., IL-2, IFN-γ, and/or TNF-α production by T-cells and/or NK cells, and/or IL-12 production by monocytes, macrophages and/or B cells). Immunogenic portions of the antigens described herein may generally be identified using techniques known to those of ordinary skill in the art, including the representative methods summarized in Paul, Fundamental Immunology, 5th ed., Lippincott Williams & Wilkins, 2003 and references cited therein. Such techniques include screening fusion polypeptides for the ability to react with antigen-specific antibodies, antisera and/or T cell lines or clones. As used herein, antisera and antibodies are "antigen-specific" if they specifically bind to an antigen (i.e., they react with the protein in an immunoassay, and do not react detectably with unrelated proteins). Such antisera and antibodies may be prepared as described herein and using well-known techniques.

Immunogenic portions of a *Leishmania* can be essentially any length; provided they retain one or more of the immunogenic regions that are responsible for or contribute to the in vivo protection provided against leishmaniasis by one or more fusion polypeptides of the invention, as disclosed herein. In one embodiment, the ability of an immunogenic portion to react with antigen-specific antisera may be enhanced or unchanged, relative to the native protein, or may be diminished by less than 50%, and preferably less than 20%, relative to the native protein. Illustrative portions will generally be at least 10, 15, 25, 50, 150, 200, 250, 300, or 350 amino acids in length, or more, up to and including full length *Leishmania* polypeptide.

In some embodiments, a *Leishmania* polypeptide described herein includes a mtHSP70 polypeptide, a CpB polypeptide, a H2BN polypeptide, an A2 polypeptide, a p21 polypeptide, a LeiF polypeptide, a NH polypeptide and a SMT polypeptide. In some embodiments, the *Leishmania* polypeptide or protein is from a *L. infantum*, a *L. donovani*, a *L. major*, a *L. mexicana*, or a *L. braziliensis* strain. In some embodiments, the fusion polypeptide comprises sequences from at least two, at least three, at least four different *Leishmania* strains. In some embodiments, these *Leishmania* polypeptides (including immunogenic portions) include any naturally occurring variants.

In a particular embodiment, immunogenic portions of a *Leishmania* polypeptide are those, which when used in combination, are capable of providing protection against, for example in an in vivo assay as described herein, or serodiagnosis of *Leishmania* species such as *L. donovani*, *L. major* and/or *L. infantum*, which are believed to be causative agents of VL in humans and dogs. In addition, polypeptides (including fusion polypeptides) of the invention may also be useful in blocking transmission of the causative agent of VL from dogs to humans, e.g., by reducing or eliminating the number of parasites in the blood and skin of infected dogs.

As would be recognized by the skilled artisan, a polypeptide composition of the invention may also comprise one or more polypeptides that are immunologically reactive with T cells and/or antibodies generated against a polypeptide of the invention, particularly a polypeptide having an amino acid sequence disclosed herein, or to an immunogenic fragment or variant thereof. In a specific embodiment, the polypeptide is a fusion polypeptide, as described herein.

As noted, in various embodiments of the present invention, fusion polypeptides generally comprise at least an immunogenic portion or variant of the *Leishmania* polypeptides described herein. In some instances, preferred immunogenic portions will be identified that have a level of immunogenic activity greater than that of the corresponding full-length polypeptide, e.g., having greater than about 100% or 150% or more immunogenic activity. In particular embodiments, the immunogenicity of the full-length fusion polypeptide will have additive, or greater than additive immunogenicity contributed by of each of the antigenic/immunogenic portions contained therein.

In another aspect, fusion polypeptides of the present invention may contain multiple copies of polypeptide fragments, repeats of polypeptide fragments, or multimeric polypeptide fragments, including antigenic/immunogenic fragments, such as *Leishmania* polypeptides comprising at least about 1, 2, 3, 4, 5, 6, 7, 8, 9, 10 or more contiguous fragments of a *Leishmania* polypeptide, in any order, and including all lengths of a polypeptide composition set forth herein, or those encoded by a polynucleotide sequence set forth herein.

In some embodiments, an immunogenic portion of a mtHSP70 polypeptide comprises the amino acid sequence of SEQ ID NO:27, 28, 29, or 30, or a sequence having at least 85% identity (e.g., at least 90% or at least 95%) to SEQ ID NO: 27, 28, 29, or 30. In some embodiments, an immunogenic portion of a CpB polypeptide comprises the amino acid sequence of SEQ ID NO:31, or a sequence having at least 85% identity (e.g., at least 90% or at least 95%) to SEQ ID NO:31. In some embodiments, the immunogenic portion of a H2BN comprises the amino acid sequence of SEQ ID NO: 32, or a sequence having at least 85% identity (e.g., at least 90% or at least 95%) to SEQ ID NO: 32. In some embodiments, a A2 polypeptide comprises the amino acid sequence of SEQ ID NO: 33 or 37, or a sequence having at least 85% identity (e.g., at least 90% or at least 95%) to SEQ ID NO: 33 or 37. In some embodiments, a p21 polypeptide comprises the amino acid sequence of SEQ ID NO: 34, or a sequence having at least 85% identity (e.g., at least 90% or at least 95%) to SEQ ID NO: 34. In some embodiments, a LeiF polypeptide comprises the amino acid sequence of SEQ ID NO: 42, or a sequence having at least 85% identity (e.g., at least 90% or at least 95%) to SEQ ID NO:42. In some embodiments, a NH polypeptide comprises the amino acid sequence of SEQ ID NO: 35, or a sequence having at least 85% identity (e.g., at least 90% or at least 95%) to SEQ ID NO: 35. In some embodiments, the NH polypeptide comprises the NH polypeptide sequences (e.g., an immunogenic portion of SEQ ID NO:1, 3, or 5 in US Pat. App. Pub. No. 2012/0114688 or a sequence having at least 90% or at least 95% identity thereto) as described in US Pat. App. Pub. No. 2012/0114688 which is incorporated herein by reference. In some embodiments, a SMT polypeptide comprises the amino acid sequence of SEQ ID NO: 36 or a sequence having at least 85% identity (e.g., at least 90% or at least 95%) to SEQ ID NO: 36. In some embodiments, the SMT polypeptide comprises a SMT sequence described in US Pat. App. Pub. Nos. 2009/0041798 and 2012/0114688 which are incorporated herein by reference (e.g., SEQ ID NO:7, 9, or 11 in US 2012/0114688 or a sequence having at least 90% or at least 95% identity thereto).

In some embodiments, the fusion polypeptide comprises, consists of, or consists essentially of the amino acid sequence set forth in SEQ ID NO: 2, 4, 6, 8, 10, 12, 14, 16, 18, 20, 22, 24, 26, 39, 41, 42 or 44 or a sequence having at least 85%, at least 90%, at least 95% or at least 98% identity thereto.

The fusion polypeptides described herein may contain an optional amino terminal linker comprising a methionine initiation codon and six histidine amino acids (his tag) encoded by the polynucleotides 5'-ATGCATCAC CATCAC CATCAC3' (SEQ ID NO:45) immediately 5' to the initiation methionine encoded by an ATG codon of the fusion polypeptide. For fusion polypeptides wherein the first polypeptide is the carboxy terminus of the putative mtHSP70 polypeptide (8 or 8E), the his tagged fusion polynucleotide does not comprise a 3' ATG codon prior to the first polynucleotide encoding 8E.

In yet another aspect, the present invention provides fusion polypeptides comprising one or more variants of the Leishmania polypeptide (including immunogenic portions) described herein. Polypeptide variants generally encompassed by the present invention will typically exhibit at least about 70%, 75%, 80%, 85%, 90%, 91%, 92%, 93%, 94%, 95%, 96%, 97%, 98%, or 99% or more identity (determined as described below), along its length, to a polypeptide sequence set forth herein.

In other related embodiments, a polypeptide "variant," includes polypeptides that differ from a native protein in one or more substitutions, deletions, additions and/or insertions, such that the desired immunogenicity of the variant polypeptide is not substantially diminished relative to a native polypeptide.

For example, certain variants of the invention include polypeptides of the invention that have been modified to replace one or more cysteine residues with alternative residues. Such polypeptides are referred to hereinafter as cysteine-modified polypeptides or cysteine-modified fusion polypeptides. Preferably, the modified polypeptides retain substantially the same or similar immunogenic properties as the corresponding unmodified polypeptides. In a more specific embodiment, cysteine residues are replaced with serine residues because of the similarity in the spatial arrangement of their respective side chains. However, it will be apparent to one skilled in the art that any amino acid that is incapable of interchain or intrachain disulfide bond formation can be used as a replacement for cysteine. When all or substantially all of the cysteine residues in a polypeptide or fusion polypeptide of this invention are replaced, the resulting cysteine-modified variant may be less prone to aggregation and thus easier to purify, more homogeneous, and/or obtainable in higher yields following purification.

In one embodiment, the ability of a variant to react with antigen-specific antisera may be enhanced or unchanged, relative to the native protein, or may be diminished by less than 50%, and preferably less than 20%, relative to a corresponding native or control polypeptide. In a particular embodiment, a variant of an Leishmania polypeptide is one capable of providing protection, for example in an in vivo assay as described herein, against a *Leishmania* species such as *L. donovani, L. infantum* and/or *L. major*.

In particular embodiments, a fusion polypeptide of the present invention comprises at least 1, at least 2, at least 3, at least 4, at least 5, at least 6, at least 7, at least 8, at least 9, or at least 10 or more substitutions, deletions, additions and/or insertions within a *Leishmania* polypeptide, where the fusion polypeptide is capable of providing protection against, for example in an in vivo assay as described herein, *Leishmania* species such as *L. donovani, L. major* and/or *L. infantum*.

In related embodiments, a fusion polypeptide of the present invention comprises at least 1, at least 2, at least 3, at least 4, at least 5, at least 6, at least 7, at least 8, at least 9, or at least 10 or more substitutions, deletions, additions and/or insertions within a *Leishmania* polypeptide, where the fusion polypeptide is capable of serodiagnosis of *Leishmania* species such as *L. donovani, L. major* and/or *L. infantum*.

In many instances, a variant will contain conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. As described above, modifications may be made in the structure of the polynucleotides and polypeptides of the present invention and still obtain a functional molecule that encodes a variant or derivative polypeptide with desirable characteristics, e.g., with immunogenic characteristics. When it is desired to alter the amino acid sequence of a polypeptide to create an equivalent, or even an improved, immunogenic variant or portion of a polypeptide of the invention, one skilled in the art will typically change one or more of the codons of the encoding DNA sequence according to Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the peptide sequences of the disclosed compositions, or corresponding DNA sequences which encode said peptides without appreciable loss of their biological utility or activity.

TABLE 1

| Amino Acids | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAG | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |

TABLE 1-continued

| Amino Acids | | | Codons | | | | | |
|---|---|---|---|---|---|---|---|---|
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In making such changes, the hydropathic index of amino acids may be considered. The importance of the hydropathic amino acid index in conferring interactive biologic function on a protein is generally understood in the art (Kyte and Doolittle, 1982, incorporated herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Each amino acid has been assigned a hydropathic index on the basis of its hydrophobicity and charge characteristics (Kyte and Doolittle, 1982). These values are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e. still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine.

Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein, which co-translationally or post-translationally directs transfer of the protein. These sequences may be removed in the polypeptides are produced. The polypeptide may also be conjugated to a linker or other sequence for ease of synthesis, purification or identification of the polypeptide (e.g., poly-Histidine tag (6XHis), GST, MBP, TAP/TAG, FLAG epitope, MYC epitope, V5 epitope, VSV-G epitope, etc.), or to enhance binding of the polypeptide to a solid support. For example, a polypeptide may be conjugated to an immunoglobulin Fc region.

When comparing polynucleotide or polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Alignment of sequences for comparison may be conducted using, for example, the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogenes pp. 626]645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) MoL Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, alignment of sequences for comparison may be conducted by the local identity algorithm of Smith and Waterman (1981) Add. APL. Math 2:482, by the identity alignment algorithm of Needleman and Wunsch (1970) J.

MoL Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=-4 and a comparison of both strands.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Therefore, as noted above, the present invention encompasses polynucleotide and polypeptide sequences having substantial identity to the sequences disclosed herein, for example those comprising at least 70%, 75%, 80%, 85%, 90%, 95%, 96%, 97%, 98%, or 99% or higher, sequence identity compared to a polynucleotide or polypeptide sequence of this invention (e.g., as set out in SEQ ID NOs: 1-44) using the methods described herein, (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like. Furthermore, it would be understood by of ordinary skill in the art that fusion polypeptides of the present invention may comprise at least 2, at least 3, or at least 4 or more antigenic/immunogenic portions or fragments of a polypeptide comprising at least 70%, 75%, 80%, 85%, 90%, 95%, 96%, 97%, 98%, or 99% or higher, sequence identity to a Leishmania polypeptide that is capable of providing protection against, for example in an in vivo assay as described herein, or serodiagnosis of Leishmania species such as L. donovani, L. major and/or L. infantum.

In another aspect of the invention, fusion polypeptides are provided that comprise at least an immunogenic portion of a polypeptide and further comprise a heterologous fusion partner, as well as polynucleotides encoding such fusion polypeptides. For example, in one embodiment, a fusion polypeptide comprises one or more immunogenic portions or fragments of a Leishmania polypeptide and one or more additional immunogenic Leishmania sequences, which are joined via a peptide linkage into a single amino acid chain.

In another embodiment, a fusion polypeptide may comprise multiple Leishmania antigenic or immunogenic portions. In some embodiments, an immunogenic portion is a portion of an antigen that reacts with blood samples from Leishmania-infected individuals (i.e. an epitope is specifically bound by one or more antibodies and/or T-cells present in such blood samples). The immunogenic portions in a fusion polypeptide may be covalently linked, either directly or via an amino acid linker. The polypeptides forming the fusion protein are typically linked C-terminus to N-terminus, although they can also be linked C-terminus to C-terminus, N-terminus to N-terminus, or N-terminus to C-terminus. The immunogenic portions in the fusion polypeptide can be arranged in any order.

In certain embodiments, a fusion polypeptide may further comprise at least one heterologous fusion partner having a sequence that assists in providing T helper epitopes (an immunological fusion partner), preferably T helper epitopes recognized by humans, or that assists in expressing the protein (an expression enhancer) at higher yields than the native recombinant protein. Certain preferred fusion partners include both immunological and expression-enhancing fusion partners. Other fusion partners may be selected so as to increase the solubility of the protein or to enable the protein to be targeted to desired intracellular compartments. Still further fusion partners include affinity tags, such as V5, 6XHIS, MYC, FLAG, and GST, which facilitate purification of the protein. It would be understood by one having ordinary skill in the art that those unrelated sequences may, but need not, be present in a fusion polypeptide used in accordance with the present invention. Within a particular embodiment, an immunological fusion partner comprises sequence derived from protein D, a surface protein of the gram-negative bacterium *Haemophilus* influenza B (WO 91/18926). For example, one protein D derivative comprises approximately the first third of the protein (e.g., the first N-terminal 100 110 amino acids), and a protein D derivative may be lipidated. Within certain embodiments, the first 109 residues of a lipoprotein D fusion partner is included on the N-terminus to provide the polypeptide with additional exogenous T cell epitopes and to increase the expression level in *E. coli* (thus functioning as an expression enhancer). The lipid tail ensures optimal presentation of the antigen to antigen presenting cells. Other illustrative fusion partners include the non-structural protein from *influenzae* virus, NS 1 (hemaglutinin). Typically, the N-terminal 81 amino acids are used, although different fragments that include T-helper epitopes may also be used.

In another particular embodiment, an immunological fusion partner comprises an amino acid sequence derived from the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; Gene 43:265-292 (1986)). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795-798 (1992)). Within a particular embodiment, a repeat portion of LYTA may be incorporated into a fusion protein. A repeat portion is found in the C-terminal region starting at residue 178. A more particular repeat portion incorporates residues 188-305.

Fusion sequences may be joined directly (i.e., with no intervening amino acids) or may be joined by way of a linker sequence (e.g., Gly-Cys-Gly) that does not significantly diminish the immunogenic properties of the component polypeptides. The polypeptides forming the fusion protein are typically linked C-terminus to N-terminus, although they can also be linked C-terminus to C-terminus, N-terminus to N-terminus, or N-terminus to C-terminus. The polypeptides of the fusion protein can be in any order. Fusion polypeptides or fusion proteins can also include conservatively modified variants, polymorphic variants, alleles, mutants, subsequences, interspecies homologs, and immunogenic fragments of the antigens that make up the fusion protein.

Fusion polypeptides may generally be prepared using standard techniques, including recombinant technology, chemical conjugation and the like. For example, DNA sequences encoding the polypeptide components of a fusion may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in frame. This permits translation into a single fusion polypeptide that retains or in some cases exceeds the biological activity of the component polypeptides.

A peptide linker sequence may be employed to separate the fusion components by a distance sufficient to ensure that each polypeptide folds into its desired secondary and/or tertiary structures. Such a peptide linker sequence may be incorporated into the fusion polypeptide using standard techniques well known in the art. Suitable peptide linker sequences may be chosen, for example, based on one or more of the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Certain preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., Gene 40:39-46, 1985; Murphy et al., Proc. Natl. Acad. Sci. USA 83:8258-8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

In addition to recombinant fusion polypeptide expression, *Leishmania* polypeptides, immunogenic portions, variants and fusions thereof may be generated by synthetic or recombinant means. Synthetic polypeptides having fewer than about 100 amino acids, and generally fewer than about 50 amino acids, may be generated using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain (Merrifield, J. Am. Chem. Soc. 85:2149-2146, 1963). Equipment for automated synthesis of polypeptides is commercially available from suppliers such as Perkin Elmer/Applied BioSystems Division, Foster City, Calif., and may be operated according to the manufacturer's instructions. Thus, for example, *Leishmania* antigens, or portions thereof, may be synthesized by this method.

Recombinant polypeptides containing portions and/or variants of a native *Leishmainia* polypeptide may be readily prepared from a DNA sequence encoding the antigen, using well known and established techniques. In particular embodiments, a fusion polypeptide comprising *Leishmania* antigens may be readily prepared from a DNA sequence encoding the cloned fused antigens. For example, supernatants from suitable host/vector systems which secrete recombinant protein into culture media may be first concentrated using a commercially available filter. Following concentration, the concentrate may be applied to a suitable purification matrix such as an affinity matrix, a size exclusion chromatography matrix or an ion exchange resin.

Alternatively, any of a variety of expression vectors known to those of ordinary skill in the art may be employed to express recombinant polypeptides of this invention. Expression may be achieved in any appropriate host cell that has been transformed or transfected with an expression vector containing a polynucleotide that encodes a recombinant polypeptide. Preferably, the host cells are *E. coli*, yeast, an insect cell line (such as *Spodoptera* or *Trichoplusia*) or a mammalian cell line, including (but not limited to) CHO, COS, HEK-293T and NS-1. The DNA sequences expressed in this manner may encode naturally occurring proteins, and fusion proteins comprising *Leishmania* antigens, such as those described herein, portions thereof, and repeats or other variants of such proteins. Expressed fusion polypeptides of this invention are generally isolated in substantially pure form. Preferably, the fusion polypeptides are isolated to a purity of at least 80% by weight, more preferably, to a purity of at least 95% by weight, and most preferably to a purity of at least 99% by weight. In general, such purification may be achieved using, for example, the standard techniques of ammonium sulfate fractionation, SDS-PAGE electrophoresis, and affinity chromatography.

*Leishmania* polypeptides and polynucleotides of the invention may be prepared or isolated using any of a variety of procedures and using any of a variety of *Leishmania* species including, but not limited to, *L. donovani, L. chagasi, L. infantum, L. major, L. amazonensis, L. braziliensis, L. panamensis, L. mexicana,* L. tropics, and *L. guyanensis.* Such species are available, for example, from the American Type Culture Collection (ATCC), Rockville, Md.

Regardless of the method of preparation, the polypeptides or fusion polypeptides produced as described above are preferably immunogenic. In certain embodiments, for example, the polypeptides (or immunogenic portions thereof) are capable of eliciting an immune response in cultures of lymph node cells and/or peripheral blood mononuclear cells (PBMC) isolated from presently or previously *Leishmania*-infected individuals. More specifically, in certain embodiments, the antigens, and immunogenic portions thereof, have the ability to induce T-cell proliferation and/or to elicit a dominantly Th1-type cytokine response (e.g., IL-2, IFN-$\gamma$, and/or TNF-$\alpha$ production by T-cells and/or NK cells; and/or IL-12 production by monocytes, macrophages and/or B cells) in cells isolated from presently or previously *Leishmania*-infected individuals. A *Leishmania*-infected individual may be afflicted with a form of leishmaniasis (such as subclinical, cutaneous, mucosal or active visceral) or may be asymptomatic. Such individuals may be identified using methods known to those of ordinary skill in the art. Individuals with leishmaniasis may be identified based on clinical findings associated with, for example, at least one of the following: isolation of parasite from lesions, a positive skin test with *Leishmania* lysate or a positive serodiagnostic test. Asymptomatic individuals are infected individuals who have no signs or symptoms of the disease. Such individuals can be identified, for example, based on a positive serological test and/or skin test with *Leishmania* lysate.

The term "PBMC," which refers to a preparation of nucleated cells consisting primarily of lymphocytes and monocytes that are present in peripheral blood, encompasses both mixtures of cells and preparations of one or more purified cell types. PBMC may be isolated by methods known to those in the art. For example, PBMC may be isolated by density centrifugation through, for example, Ficoll™ (Winthrop Laboratories, New York). Lymph node cultures may generally be prepared by immunizing BALB/c mice (e.g., in the rear foot pad) with *Leishmania* promastigotes emulsified in complete Freund's adjuvant. The draining lymph nodes may be excised following immunization and T-cells may be purified in an anti-mouse Ig column to remove the B cells, followed by a passage through a Sephadex G10 column to remove the macrophages. Similarly, lymph node cells may be isolated from a human following biopsy or surgical removal of a lymph node.

The ability of a fusion polypeptide of the invention to induce a response in PBMC or lymph node cell cultures may be evaluated, for example, by contacting the cells with the polypeptide and measuring a suitable response. In general, the amount of polypeptide that is sufficient for the evaluation of about $2\times10^5$ cells ranges from about 10 ng to about 100 ng or 100 ng to about 50 µg, and preferably is about 1 µg, to 10 µg. The incubation of polypeptide (e.g., a fusion polypeptide) with cells is typically performed at 37° C. for about 1-3 days. Following incubation with polypeptide, the cells are assayed for an appropriate response. If the response is a proliferative response, any of a variety of techniques well known to those of ordinary skill in the art may be employed. For example, the cells may be exposed to a pulse of radioactive thymidine and the incorporation of label into cellular DNA measured. In general, a polypeptide that results in at least a three fold increase in proliferation above background (i.e., the proliferation observed for cells cultured without polypeptide) is considered to be able to induce proliferation.

Alternatively, the response to be measured may be the secretion of one or more cytokines (such as interferon-$\gamma$ (IFN-$\gamma$), interleukin-4 (IL-4), interleukin-12 (p70 and/or p40), interleukin-2 (IL-2) and/or tumor necrosis factor-a (TNF-$\alpha$)) or the change in the level of mRNA encoding one or more specific cytokines. For example, the secretion of interferon-$\gamma$, interleukin-2, tumor necrosis factor-$\alpha$ and/or interleukin-12 is indicative of a Th1 response, which contributes to the protective effect against *Leishmania*. Assays for any of the above cytokines may generally be performed using methods known to those of ordinary skill in the art, such as an enzyme-linked immunosorbent assay (ELISA). Suitable antibodies for use in such assays may be obtained from a variety of sources such as Chemicon, Temucula, Calif. and PharMingen, San Diego, Calif., and may generally be used according to the manufacturer's instructions. The level of mRNA encoding one or more specific cytokines may be evaluated by, for example, amplification by polymerase chain reaction (PCR). In general, a polypeptide that is able to induce, in a preparation of about $1-3\times10^5$ cells, the production of 30 pg/mL of IL-12, IL-4, IFN-$\gamma$, TNF-$\alpha$ or IL-12 p40, or 10 pg/mL of IL-12 p'70, is considered able to stimulate production of a cytokine.

Polynucleotide Compositions

The present invention also provides isolated polynucleotides, particularly those encoding the polypeptide combinations and/or fusion polypeptides of the invention, as well as compositions comprising such polynucleotides. As used herein, the terms "DNA" and "polynucleotide" and "nucleic acid" refer to a DNA molecule that has been isolated free of total genomic DNA of a particular species. Therefore, a DNA segment encoding a polypeptide refers to a DNA segment that contains one or more coding sequences yet is substantially isolated away from, or purified free from, total genomic DNA of the species from which the DNA segment is obtained. Included within the terms "DNA segment" and "polynucleotide" are DNA segments and smaller fragments of such segments, and also recombinant vectors, including, for example, plasmids, cosmids, phagemids, phage, viruses, and the like.

As will be understood by those skilled in the art, the polynucleotide sequences of this invention can include genomic sequences, extra-genomic and plasmid-encoded sequences and smaller engineered gene segments that express, or may be adapted to express, proteins, fusion polypeptides, peptides and the like. Such segments may be naturally isolated, recombinant, or modified synthetically by the hand of man.

As will be recognized by the skilled artisan, polynucleotides may be single-stranded (coding or antisense) or double-stranded, and may be DNA (genomic, cDNA or synthetic) or RNA molecules. Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-methyl-, thio- and other modified forms of adenine, cytidine, guanine, thymine and uridine. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a *Leishmania* antigen or a portion thereof) or may comprise a variant, or a biological or antigenic functional equivalent of such a sequence. In particular embodiments, polynucleotides may encode for two or more antigenic/immunogenic portions, fragments, or variants derived from the *Leishmania* antigens described herein. In some embodiments, polynucleotides of the present invention comprise a sequence encoding any of the immunogenic portions described herein. In some embodiments, the polynucleotide comprises the sequence of SEQ ID NO: 1, 3, 5, 7, 9, 11, 13, 15, 17, 19, 21, 23, 25, 38, or 40. Of course, portions of these sequences and variant sequences sharing identity to these sequences may also be employed (e.g., those having at least about any of 80%, 85%, 90%, 95% or 98% thereto).

Polynucleotide variants may contain one or more substitutions, additions, deletions and/or insertions, as further described below, preferably such that the immunogenicity of the encoded polypeptide is not diminished, relative to the native protein. The effect on the immunogenicity of the encoded polypeptide may generally be assessed as described herein.

For example, in certain embodiments, variants of the invention include cysteine-modified polynucleotides in which the cysteine-encoding codons are replaced with codons encoding other amino acids not capable of forming intrachain or interchain disulfide bonds. In more specific embodiments, some or all of the replacement codons encode serine because of the spatial similarity of the serine sidechain to the cysteine sidechain in the resulting polypeptide. In another specific embodiment, some or all of the replacement codons encode alanine. Illustrative methods of replacing cysteine and other codons within a polynucleotide are well known (e.g., U.S. Pat. No. 4,816,566, the contents of which are incorporated herein by reference, and Proc Natl Acad Sci 97 (15): 8530, 2000).

The term "variants" also encompasses homologous genes of xenogenic origin.

In additional embodiments, isolated polynucleotides of the present invention comprise various lengths of contiguous stretches of sequence identical to or complementary to the sequence encoding *Leishmania* polypeptides, such as those sequences disclosed herein. For example, polynucleotides are provided by this invention that comprise at least about 15, 20, 30, 40, 50, 75, 100, 150, 200, 300, 400, 500 or 1000 or more contiguous nucleotides of two or more of the sequences disclosed herein as well as all intermediate lengths there between. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a polynucleotide fragment of almost any length may be employed; with the total length preferably being limited by the ease of preparation and use in the intended recombinant DNA protocol.

Moreover, it will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention, for example polynucleotides that are optimized for human and/or primate codon selection. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

*Leishmania* polynucleotides and fusions thereof may be prepared, manipulated and/or expressed using any of a variety of well established techniques known and available in the art. In particular embodiments, fusions comprise two or more polynucleotide sequences encoding *Leishmania* polypeptides.

For example, polynucleotide sequences or fragments thereof which encode polypeptides of the invention, or fusion proteins or functional equivalents thereof, may be used in recombinant DNA molecules to direct expression of a polypeptide in appropriate host cells. Due to the inherent degeneracy of the genetic code, other DNA sequences that encode substantially the same or a functionally equivalent amino acid sequence may be produced and these sequences may be used to clone and express a given polypeptide of the present invention.

As will be understood by those of skill in the art, it may be advantageous in some instances to produce fusion polypeptide-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

Moreover, the polynucleotide sequences of the present invention can be engineered using methods generally known in the art in order to alter fusion polypeptide encoding sequences for a variety of reasons, including but not limited to, alterations which modify the cloning, processing, expression and/or immunogenicity of the gene product.

In order to express a desired fusion polypeptide comprising two or more antigenic/immunogenic fragments or portions of *Leishmania* polypeptides, a nucleotide sequence encoding the fusion polypeptide, or a functional equivalent, may be inserted into appropriate expression vector, i.e., a vector which contains the necessary elements for the transcription and translation of the inserted coding sequence. Methods which are well known to those skilled in the art may be used to construct expression vectors containing sequences encoding a polypeptide of interest and appropriate transcriptional and translational control elements. These methods include in vitro recombinant DNA techniques, synthetic techniques, and in vivo genetic recombination. Such techniques are described in Sambrook et al., Molecular Cloning, A Laboratory Manual (2001), and Ausubel et al., Current Protocols in Molecular Biology (January 2008, updated edition).

A variety of expression vector/host systems are known and may be utilized to contain and express polynucleotide sequences. These include, but are not limited to, microorganisms such as bacteria transformed with recombinant bacteriophage, plasmid, or cosmid DNA expression vectors; yeast (such as *Saccharomyces* or *Pichia*) transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" present in an expression vector are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the PBLUESCRIPT phagemid (Stratagene, La Jolla, Calif.) or PSPORTI plasmid (Gibco BRL, Gaithersburg, Md.) and the like may be used. In mammalian cell systems, promoters from mammalian genes or from mammalian viruses are generally preferred. If it is necessary to generate a cell line that contains multiple copies of the sequence encoding a polypeptide, vectors based on SV40 or EBV may be advantageously used with an appropriate selectable marker.

In bacterial systems, a number of expression vectors may be selected depending upon the use intended for the expressed polypeptide. For example, when large quantities are needed, vectors which direct high level expression of fusion proteins that are readily purified may be used. Such vectors include, but are not limited to, the multifunctional *E. coli* cloning and expression vectors such as PBLUESCRIPT (Stratagene), in which the sequence encoding the polypeptide of interest may be ligated into the vector in frame with sequences for the amino-terminal Met and the subsequent 7 residues of B-galactosidase so that a hybrid protein is produced; pIN vectors (Van Heeke & Schuster, J. Biol. Chem. 264:5503 5509 (1989)); and the like. pGEX Vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae*, a number of vectors containing constitutive or inducible promoters such as alpha factor, alcohol oxidase, and PGH may be used. For reviews, see Ausubel et al. (supra) and Grant et al., Methods Enzymol. 153:516-544 (1987).

In cases where plant expression vectors are used, the expression of sequences encoding polypeptides may be driven by any of a number of promoters. For example, viral promoters such as the 35S and 19S promoters of CaMV may be used alone or in combination with the omega leader sequence from TMV (Takamatsu, EMBO J. 6:307-311 (1987)). Alternatively, plant promoters such as the small subunit of RUBISCO or heat shock promoters may be used (Coruzzi et EMBO J. 3:1671-1680 (1984); Broglie et al., Science 224:838-843 (1984); and Winter et al., Results Probl. Cell Differ. 17:85-105 (1991)). These constructs can be introduced into plant cells by direct DNA transformation or pathogen-mediated transfection. Such techniques are described in a number of generally available reviews (see, e.g., Hobbs in McGraw Hill, Yearbook of Science and Technology, pp. 191-196 (1992)).

An insect system may also be used to express a polypeptide of interest. For example, in one such system, *Autographa californica* nuclear polyhedrosis virus (AcNPV) is used as a vector to express foreign genes in *Spodoptera frugiperda* cells or in *Trichoplusia* larvae. The sequences encoding the polypeptide may be cloned into a non-essential region of the virus, such as the polyhedrin gene, and placed under control of the polyhedrin promoter. Successful insertion of the polypeptide-encoding sequence will render the polyhedrin gene inactive and produce recombinant virus lacking coat protein. The recombinant viruses may then be used to infect, for example, *S. frugiperda* cells or *Trichoplusia* larvae in which the polypeptide of interest may be expressed (Engelhard et al., Proc. Natl. Acad. Sci. U.S.A. 91:3224-3227 (1994)).

In mammalian host cells, a number of viral-based expression systems are generally available. For example, in cases where an adenovirus is used as an expression vector, sequences encoding a polypeptide of the present invention may be ligated into an adenovirus transcription/translation complex consisting of the late promoter and tripartite leader sequence. Insertion in a non-essential E1 or E3 region of the viral genome may be used to obtain a viable virus which is capable of expressing the polypeptide in infected host cells (Logan & Shenk, Proc. Natl. Acad. Sci. U.S.A. 81:3655-3659 (1984)). In addition, transcription enhancers, such as the Rous sarcoma virus (RSV) enhancer, may be used to increase expression in mammalian host cells.

Specific initiation signals may also be used to achieve more efficient translation of sequences encoding a fusion polypeptide of interest. Such signals include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf. et al., Results ProbL Cell Differ. 20:125-162 (1994)).

In addition, a host cell strain may be chosen for its ability to modulate the expression of the inserted sequences or to process the expressed fusion protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and W138, which have specific cellular machinery and characteristic mechanisms for such post-translational activities, may be chosen to ensure the correct modification and processing of the foreign protein.

For long-term, high-yield production of recombinant proteins, stable expression is generally preferred. For example, cell lines which stably express a fusion polynucleotide of the present invention may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler et al., Cell 11:223-232 (1977)) and adenine phosphoribosyltransferase (Lowy et al., Cell 22:817-823 (1990)) genes which can be employed in tk- or aprt-cells, respectively. Also, antimetabolite, antibiotic or herbicide resistance can be used as the basis for selection; for example, dhfr which confers resistance to methotrexate (Wigler et al., Proc. Natl. Acad. Sci. U.S.A. 77:3567-70 (1980)); npt, which confers resistance to the aminoglycosides, neomycin and G-418 (Colbere-Garapin et al., J. Mol. Biol. 150:1-14 (1981)); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman & Mulligan, Proc. Natl. Acad. Sci. U.S.A. 85:8047-51 (1988)). The use of visible markers has gained popularity with such markers as anthocyanins, B-glucuronidase and its substrate GUS, and luciferase and its substrate luciferin, being widely used not only to identify transformants, but also to quantify the amount of transient or stable protein expression attributable to a specific vector system (Rhodes et al., Methods MoL Biol. 55:121-131 (1995)).

A variety of protocols for detecting and measuring the expression of polynucleotide-encoded products, using either polyclonal or monoclonal antibodies specific for the product are known in the art. Examples include enzyme-linked immunosorbent assay (ELISA), radioimmunoassay (RIA), and fluorescence activated cell sorting (FACS). These and other assays are described, among other places, in Hampton et al., Serological Methods, a Laboratory Manual (1990) and Maddox et al., J. Exp. Med. 158:1211-1216 (1983).

A wide variety of labels and conjugation techniques are known by those skilled in the art and may be used in various nucleic acid and amino acid assays. Means for producing labeled hybridization or PCR probes for detecting sequences related to polynucleotides include oligolabeling, nick translation, end-labeling or PCR amplification using a labeled nucleotide. Alternatively, the sequences, or any portions thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits. Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a polynucleotide sequence of interest may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides of the invention may be designed to contain signal sequences which direct secretion of the encoded polypeptide through a prokaryotic or eukaryotic cell membrane. Other recombinant constructions may be used to join sequences encoding a polypeptide of interest to nucleotide sequence encoding a polypeptide domain which will facilitate purification of soluble proteins. In addition to recombinant production methods, fusion polypeptides of the invention, and fragments thereof, may be produced by direct peptide synthesis using solid-phase techniques (Merrifield, J. Am. Chem. Soc. 85:2149-2154 (1963)). Protein synthesis may be performed using manual techniques or by automation. Automated synthesis may be achieved, for example, using Applied Biosystems 431A Peptide Synthesizer (Perkin Elmer). Alternatively, various fragments, for example, immunogenic fragments from *Leishmania* polypeptides, may be chemically synthesized separately and combined using chemical methods to produce the full length molecule.

Pharmaceutical and Vaccine Compositions

In certain aspects, the polypeptides, polynucleotides, portions, variants, fusion polypeptides, etc., as described herein, are incorporated into pharmaceutical compositions or vaccines. Pharmaceutical compositions generally comprise one or more polypeptides, polynucleotides, portions, variants, fusion polypeptides, etc., as described herein, in combination with a physiologically acceptable carrier. Vaccines, also referred to as immunogenic compositions, generally comprise one or more of the polypeptides, polynucleotides, portions, variants, fusion proteins, etc., as described herein, in combination with an immunostimulant, such as an adjuvant. In particular embodiments, the pharmaceutical compositions comprise fusion polypeptides containing *Leishmania* antigens (or portions or variants thereof) that are capable of providing protection against, for example in an in vivo assay as described herein, *Leishmania* species such as *L. donovani*, *L. major* and/or *L. infantum*.

An immunostimulant may be any substance that enhances or potentiates an immune response (antibody and/or cell-mediated) to an exogenous antigen. Examples of immunostimulants include adjuvants, biodegradable microspheres (e.g., polylactic galactide) and liposomes (into which the compound is incorporated; see, e.g., Fullerton, U.S. Pat. No. 4,235,877). Vaccine preparation is generally described in, for example, Powell & Newman, eds., Vaccine Design (the subunit and adjuvant approach) (1995).

Any of a variety of immunostimulants may be employed in the vaccines of this invention. For example, an adjuvant may be included. Many adjuvants contain a substance designed to protect the antigen from rapid catabolism, such as aluminum hydroxide or mineral oil, and a stimulator of immune responses, such as lipid A (natural or synthetic), *Bordatella pertussis* or *Mycobacterium* species or *Mycobacterium*-derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 and derivatives thereof (GlaxoSmith-Kline Beecham, Philadelphia, Pa.); CWS, TDM, LeIF, aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quit A. Cytokines, such as GM-CSF or interleukin-2, -7, or -12, may also be used as adjuvants.

Certain embodiments of the present invention contemplate vaccine and pharmaceutical compositions that include one or more toll-like receptor agonists (TLR agonist). In more specific embodiments, for example, the compositions of the invention include Toll-like receptor agonists, such as TLR7 agonists and TLR7/8 agonists. In certain embodiments the TLR agonist is capable of delivering a biological signal by interacting with at least one TLR that is selected from TLR-2, TLR-3, TLR-4, TLR-5, TLR-6, TLR-7, TLR-8 and TLR-9.

Toll-like receptors (TLR) include cell surface transmembrane receptors of the innate immune system that confer early-phase recognition capability to host cells for a variety of conserved microbial molecular structures such as may be present in or on a large number of infectious pathogens. (e.g., Armant et al., 2002 Genome Biol. 3(8):reviews3011.1-3011.6; Fearon et al., 1996 Science 272:50; Medzhitov et al., 1997 Curr. Opin. Immunol. 9:4; Luster 2002 Curr. Opin. Immunol. 14:129; Lien et al. 2003 Nat. Immunol. 4:1162; Medzhitov, 2001 Nat. Rev. Immunol. 1:135; Takeda et al., 2003 Ann Rev Immunol. 21:335; Takeda et al. 2005 Inf. Immunol. 17:1; Kaisho et al., 2004 Microbes Infect. 6:1388; Datta et al., 2003 J. Immunol. 170:4102).

Induction of TLR-mediated signal transduction to potentiate the initiation of immune responses via the innate immune system may be effected by TLR agonists, which engage cell surface TLR or cytoplasmic TLR. For example, lipopolysaccharide (LPS) may be a TLR agonist through TLR2 or TLR4 (Tsan et al., 2004 J. Leuk. Biol. 76:514; Tsan et al., 2004 Am. J. Physiol. Cell Phsiol. 286:C739; Lin et al., 2005 Shock 24:206); poly(inosine-cytidine) (polyI:C) may be a TLR agonist through TLR3 (Salem et al., 2006 Vaccine 24:5119); CpG sequences (oligodeoxynucleotides containing unmethylated cytosine-guanosine or "CpG" dinucleotide motifs, e.g., CpG 7909, Cooper et al., 2005 AIDS 19:1473; CpG 10101 Bayes et al. Methods Find Exp Clin Pharmacol 27:193; Vollmer et al. Expert Opinion on Biological Therapy 5:673; Vollmer et al., 2004 Antimicrob. Agents Chemother. 48:2314; Deng et al., 2004 J. Immunol. 173:5148) may be TLR agonists through TLR9 (Andaloussi et a., 2006 Glia 54:526; Chen et al., 2006 J. Immunol. 177:2373); peptidoglycans may be TLR2 and/or TLR6 agonists (Soboll et al., 2006 Biol. Reprod. 75:131; Nakao et al., 2005 J. Immunol. 174:1566); 3M003 (4-amino-2-(ethoxymethyl)-a,a-dimethyl-617,8,9-tetrahydro-1H-imidazo[4,5-c]quinoline-1-ethanol hydrate, Mol. Wt. 318 Da from 3M Pharmaceuticals, St. Paul, Minn., which is also a source of the related compounds 3M001 and 3M002; Gorden et al., 2005 J. Immunol. 174:1259) may be a TLR7 agonist (Johansen 2005 Clin. Exp. Allerg. 35:1591) and/or a TLR8 agonist (Johansen 2005); flagellin may be a TLRS agonist (Feuillet et al., 2006 Proc. Nat. Acad. Sci. USA 103:12487); and hepatitis C antigens may act as TLR agonists through TLR7 and/or TLR9 (Lee et al., 2006 Proc. Nat. Acad. Sci. USA 103:1828; Horsmans et al., 2005 Hepatol. 42:724). Other TLR agonists are known (e.g., Schirmbeck et al., 2003 J. Immunol. 171:5198) and may be used according to certain of the presently described embodiments.

For example, and by way of background (see, e.g., U.S. Pat. No. 6,544,518) immunostimulatory oligonucleotides containing ummethylated CpG dinucleotides ("CpG") are known as being adjuvants when administered by both systemic and mucosal routes (WO 96/02555, EP 468520, Davis et al., J. Immunol. 1998. 160(2):870-876; McCluskie and Davis, J. Immunol., 1998, 161(9):4463-6). CpG is an abbreviation for cytosine-guanosine dinucleotide motifs present in DNA. The central role of the CG motif in immunostimulation was elucidated by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the dinucleotide CG motif is not methylated, but other unmethylated CpG sequences are known to be immunostimulatory and may be used in certain embodiments of the present invention. CpG when formulated into vaccines, may be administered in free solution together with free antigen (WO 96/02555; McCluskie and Davis, supra) or covalently conjugated to an antigen (PCT Publication No. WO 98/16247), or formulated with a carrier such as aluminium hydroxide (e.g., Davis et al. supra, Brazolot-Millan et al., Proc. NatLAcad. Sci., USA, 1998, 95(26), 15553-8).

Other illustrative oligonucleotides for use in compositions of the present invention will often contain two or more dinucleotide CpG motifs separated by at least three, more preferably at least six or more nucleotides. The oligonucleotides of the present invention are typically deoxynucleotides. In one embodiment the internucleotide in the oligonucleotide is phosphorodithioate, or more preferably a phosphorothioate bond, although phosphodiester and other internucleotide bonds are within the scope of the invention including oligonucleotides with mixed internucleotide linkages. Methods for producing phosphorothioate oligonucleotides or phosphorodithioate are described in U.S. Pat. Nos. 5,666,153, 5,278,302 and WO95/26204.

Other examples of oligonucleotides have sequences that are disclosed in the following publications; for certain herein disclosed embodiments the sequences preferably contain phosphorothioate modified internucleotide linkages:

CPG 7909: Cooper et al., "CPG 7909 adjuvant improves hepatitis B virus vaccine seroprotection in antiretroviral-treated HIV-infected adults." AIDS, 2005 Sep. 23; 19(14): 1473-9.

CpG 10101: Bayes et al., "Gateways to clinical trials." Methods Find. Exp. Clin. Pharmacol. 2005 April; 27(3):193-219.

Vollmer J., "Progress in drug development of immunostimula-tory CpG oligodeoxynucleotide ligands for TLR9." Expert Opinion on Biological Therapy. 2005 May; 5(5): 673-682

Alternative CpG oligonucleotides may comprise variants of the preferred sequences described in the above-cited publications that differ in that they have inconsequential nucleotide sequence substitutions, insertions, deletions and/or additions thereto. The CpG oligonucleotides utilized in certain embodiments of the present invention may be synthesized by any method known in the art (e.g., EP 468520). Conveniently, such oligonucleotides may be synthesized utilising an automated synthesizer. The oligonucleotides are typically deoxynucleotides. In a preferred embodiment the internucleotide bond in the oligonucleotide is phosphorodithioate, or more preferably phosphorothioate bond, although phosphodiesters are also within the scope of the presently contemplated embodiments. Oligonucleotides comprising different internucleotide linkages are also contemplated, e.g., mixed phosphorothioate phophodiesters. Other internucleotide bonds which stabilize the oligonucleotide may also be used.

In certain more specific embodiments the TLR agonist is selected from lipopolysaccharide, peptidoglycan, polyI:C, CpG, 3M003, flagellin, *Leishmania* homolog of eukaryotic ribosomal elongation and initiation factor 4a (LeIF) and at least one hepatitis C antigen.

Still other illustrative adjuvants include imiquimod, gardiquimod and resiquimod (all available from Invivogen), and related compounds, which are known to act as TLR7/8 agonists. A compendium of adjuvants that may be useful in vaccines is provided by Vogel et al., Pharm Biotechnol 6:141 (1995), which is herein incorporated by reference.

Compositions of the invention may also employ adjuvant systems designed to induce an immune response predominantly of the Th1 type. High levels of Th1-type cytokines (e.g., IFN-γ, TNF-α., IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly of the Th1-type, the level of Th1-type cytokines will increase to a greater extent than the level of Th2-type cytokines. The levels of these cytokines may be readily assessed using standard assays. For a review of the families of cytokines, see Mossman & Coffman, Ann. Rev. Immunol. 7:145-173 (1989).

Certain adjuvants for use in eliciting a predominantly Th1-type response include, for example, a combination of monophosphoryl lipid A, preferably 3-de-O-acylated monophosphoryl lipid A (3D-MPLTM), together with an aluminum salt (U.S. Pat. Nos. 4,436,727; 4,877,611; 4,866,034; and 4,912,094). CpG-containing oligonucleotides (in which the CpG dinucleotide is unmethylated) also induce a predominantly Th1 response. Such oligonucleotides are well known and are described, for example, in WO 96/02555, WO 99/33488 and U.S. Pat. Nos. 6,008,200 and 5,856,462. Immunostimulatory DNA sequences are also described, for example, by Sato et al., Science 273:352 (1996). Another illustrative adjuvant comprises a saponin, such as Quil A, or derivatives thereof, including QS21 and QS7 (Aquila Biopharmaceuticals Inc., Framingham, Mass.); Escin; Digitonin; or *Gypsophila* or *Chenopodium quinoa* saponins. Other illustrative formulations include more than one saponin in the adjuvant combinations of the present invention, for example combinations of at least two of the following group comprising QS21, QS7, Quil A, 0-escin, or digitonin.

In a particular embodiment, the adjuvant system includes the combination of a monophosphoryl lipid A and a saponin derivative, such as the combination of QS21 and 3D-MPLTM adjuvant, as described in WO 94/00153, or a less reactogenic composition where the QS21 is quenched with cholesterol, as described in WO 96/33739. Other formulations comprise an oil-in-water emulsion and tocopherol. Another adjuvant formulation employing QS21, 3D-MPLTM adjuvant and tocopherol in an oil-in-water emulsion is described in WO 95/17210.

In certain preferred embodiments, the adjuvant used in the present invention is a glucopyranosyl lipid A (GLA) adjuvant, as described in U.S. Patent Application Publication No. 20080131466, the disclosure of which is incorporated herein by reference in its entirety. In one embodiment, the GLA adjuvant used in the context of the present invention has the following structure:

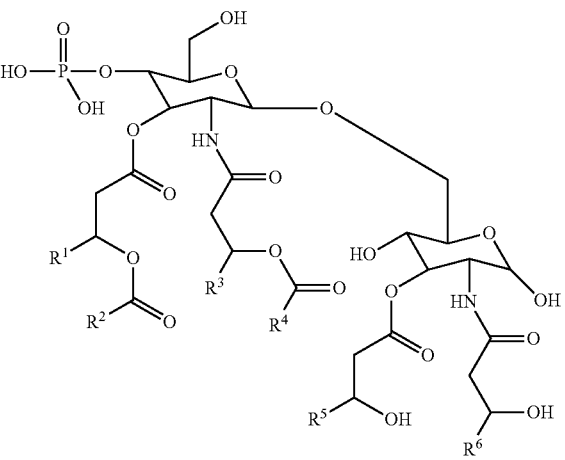

where: $R^1$, $R^3$, $R^5$ and $R^6$ are $C_{11}$-$C_{20}$ alkyl; and $R^2$ and $R^4$ are $C_9$-$C_{20}$ alkyl.

In a more specific embodiment, the GLA has the formula set forth above wherein $R^1$, $R^3$, $R^5$ and $R^6$ are $C_{11-14}$ alkyl; and $R^2$ and $R^4$ are $C_{12-15}$ alkyl.

In a more specific embodiment, the GLA has the formula set forth above wherein $R^1$, $R^3$, $R^5$ and $R^6$ are $C_{11}$ alkyl; and $R^2$ and $R^4$ are $C_{13}$ alkyl.

In a more specific embodiment, the GLA has the formula set forth above wherein $R^1$, $R^3$, $R^5$ and $R^6$ are $C_{11}$ alkyl; and $R^2$ and $R^4$ are $C_9$ alkyl.

In certain embodiments, the adjuvant is a GLA adjuvant (e.g., synthetic) having the following structure:

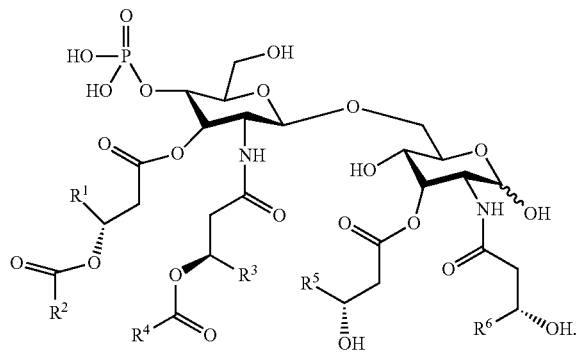

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a synthetic GLA adjuvant having the following structure:

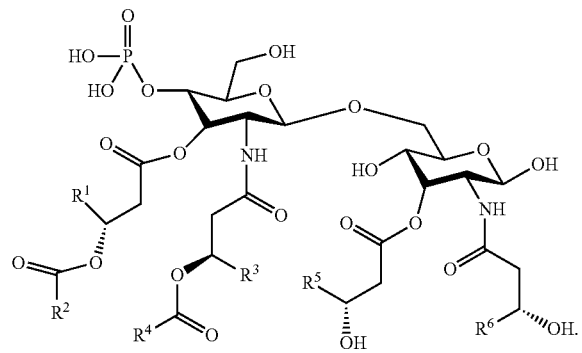

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a synthetic GLA adjuvant having the following structure:

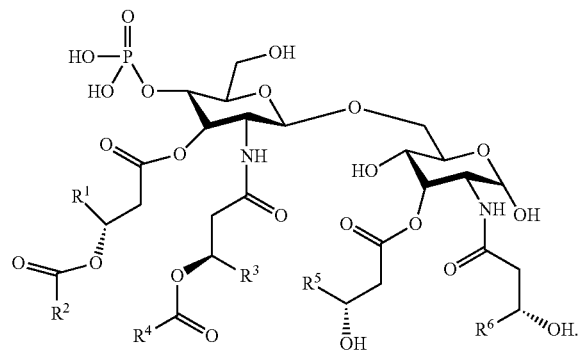

In certain embodiments of the above GLA structure, $R^1$, $R^3$, $R^5$ and $R^6$ are $C_{11}$-$C_{20}$ alkyl; and $R^2$ and $R^4$ are $C_9$-$C_{20}$ alkyl. In certain embodiments, $R^1$, $R^3$, $R^5$ and $R^6$ are $C_{11}$ alkyl; and $R^2$ and $R^4$ are $C_9$ alkyl.

In certain embodiments, the adjuvant is a synthetic GLA adjuvant having the following structure:

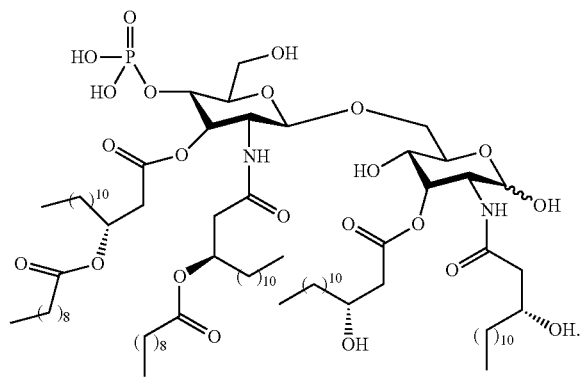

In certain embodiments, the adjuvant is a synthetic GLA adjuvant having the following structure:

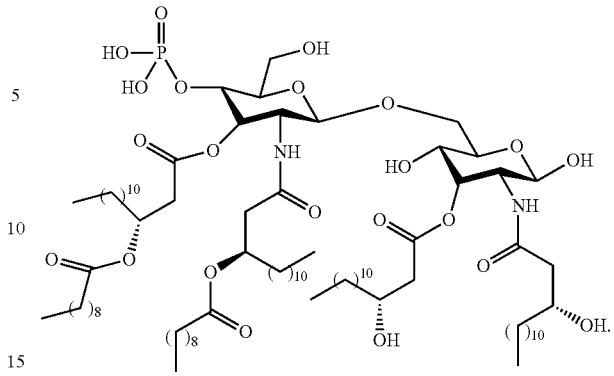

In certain embodiments, the adjuvant is a synthetic GLA adjuvant having the following structure:

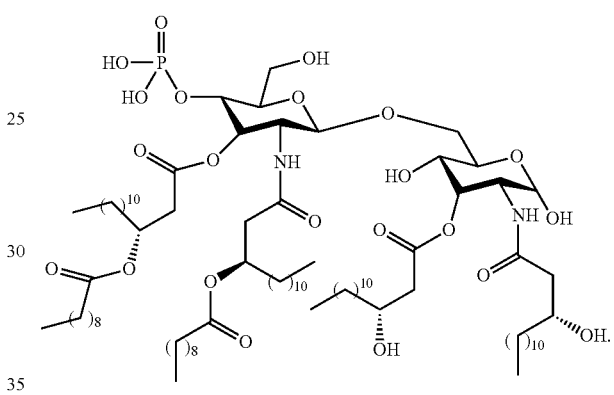

Another enhanced adjuvant system involves the combination of a CpG-containing oligonucleotide and a saponin derivative as disclosed in WO 00/09159.

Other illustrative adjuvants include Montanide ISA 720 (Seppic, France), SAF (Chiron, Calif., United States), ISCOMS (CSL), MF-59 (Chiron), the SBAS series of adjuvants (e.g., SBAS-2, AS2', AS2," SBAS-4, or SBAS6, available from SmithKline Beecham, Rixensart, Belgium), Detox, RC-529 (Corixa, Hamilton, Mont.) and other aminoalkyl glucosaminide 4-phosphates (AGPs), such as those described in pending U.S. patent application Ser. Nos. 08/853,826 and 09/074,720, the disclosures of which are incorporated herein by reference in their entireties, and polyoxyethylene ether adjuvants such as those described in WO 99/52549A1.

The vaccine and pharmaceutical compositions of the invention may be formulated using any of a variety of well known procedures. In certain embodiments, the vaccine or pharmaceutical compositions are prepared as stable emulsions (e.g., oil-in-water emulsions) or as aqueous solutions.

Compositions of the invention may also, or alternatively, comprise T cells specific for fusion polypeptide comprising immunogenic/antigenic portions or fragments of *Leishmania* antigens or variants thereof, described herein. Such cells may generally be prepared in vitro or ex vivo, using standard procedures. For example, T cells may be isolated from bone marrow, peripheral blood, or a fraction of bone marrow or peripheral blood of a patient. Alternatively, T cells may be derived from related or unrelated humans, non-human mammals, cell lines or cultures.

T cells may be stimulated with a fusion polypeptide comprising *Leishmania* polypeptides or immunogenic portions or variants thereof, polynucleotide encoding such a fusion polypeptide, and/or an antigen presenting cell (APC) that expresses such a fusion polypeptide. Such stimulation is performed under conditions and for a time sufficient to permit the generation of T cells that are specific for the polypeptide. In certain embodiments, the polypeptide or polynucleotide is present within a delivery vehicle, such as a microsphere, to facilitate the generation of specific T cells.

T cells are considered to be specific for a fusion polypeptide of the invention if the T cells specifically proliferate, secrete cytokines or kill target cells coated with the fusion polypeptide or expressing a gene encoding the fusion polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., Cancer Res. 54:1065-1070 (1994)). Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with a polypeptide of the invention (10 Ong/ml-1001.1 g/ml, preferably 20 Ong/ml-251.1 g/ml) for 3-7 days should result in at least a two fold increase in proliferation of the T cells. Contact as described above for 2-3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1 (1998)). T cells that have been activated in response to a polypeptide, polynucleotide or polypeptide-expressing APC may be CD4+ and/or CD8+. Protein-specific T cells may be expanded using standard techniques. Within preferred embodiments, the T cells are derived from a patient, a related donor or an unrelated donor, and are administered to the patient following stimulation and expansion.

In the compositions of the invention, formulation of pharmaceutically-acceptable excipients and carrier solutions is well-known to those of skill in the art, as is the development of suitable dosing and treatment regimens for using the particular compositions described herein in a variety of treatment regimens, including e.g., oral, parenteral, intravenous, intranasal, intradermal, subcutaneous and intramuscular administration and formulation.

In certain applications, the compositions disclosed herein may be delivered via oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

In certain circumstances it will be desirable to deliver the compositions disclosed herein parenterally, intravenously, intramuscularly, or even intraperitoneally as described, for example, in U.S. Pat. No. 5,543,158; U.S. Pat. No. 5,641,515 and U.S. Pat. No. 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions (U.S. Pat. No. 5,466,468, specifically incorporated herein by reference in its entirety). In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion (see, e.g., Remington's Pharmaceutical Sciences, 15th Edition, pp. 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity standards as required by FDA Office of Biologics standards.

Sterile injectable solutions are prepared by incorporating the active compounds in the required amount in the appropriate solvent with the various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxy groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective for treatment of leishmaniasis. The formulations are easily administered in a variety of dosage forms such as injectable solutions, drug-release capsules, and the like.

As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known to one of ordinary skill in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood to one of ordinary skill in the art. Typically, such compositions are prepared as injectables, either as liquid solutions or suspensions; solid forms suitable for solution in, or suspension in, liquid prior to injection can also be prepared. The preparation can also be emulsified.

In certain embodiments, the compositions of the present invention may be delivered by intranasal sprays, inhalation, and/or other aerosol delivery vehicles. Methods for delivering genes, polynucleotides, and peptide compositions directly to the lungs via nasal aerosol sprays has been described e.g., in U.S. Pat. No. 5,756,353 and U.S. Pat. No. 5,804,212 (each specifically incorporated herein by reference in its entirety). Likewise, the delivery of drugs using intranasal microparticle resins (Takenaga et al., 1998) and lysophosphatidyl-glycerol compounds (U.S. Pat. No. 5,725,871, specifically incorporated herein by reference in its entirety) are also well-known in the pharmaceutical arts. Likewise, transmucosal drug delivery in the form of a polytetrafluoroetheylene support matrix is described in U.S. Pat. No. 5,780,045 (specifically incorporated herein by reference in its entirety).

In certain embodiments, the delivery may occur by use of liposomes, nanocapsules, microparticles, microspheres, lipid particles, vesicles, and the like, for the introduction of compositions comprising a fusion polypeptide as describe herein into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

A pharmaceutical or immunogenic composition may, alternatively, contain an immunostimulant and a DNA molecule encoding one or more of the polypeptides or fusion polypeptides as described above, such that a desired polypeptide is generated in situ. In such compositions, the DNA encoding the fusion protein may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a particular embodiment, the DNA may be introduced using a viral expression system (e.g., vaccinia or other pox virus, retrovirus, or adenovirus), which may involve the use of a non-pathogenic (defective), replication competent virus. Techniques for incorporating DNA into such expression systems are well known to those of ordinary skill in the art. The DNA may also be "naked," as described, for example, in Ulmer et al., Science 259: 1745-1749 (1993) and reviewed by Cohen, Science 259: 1691-1692 (1993). The uptake of naked DNA may be increased by coating the DNA onto biodegradable beads, which are efficiently transported into the cells.

The pharmaceutical compositions and vaccines of the invention may be used, in certain embodiments, to induce protective immunity against *Leishmania* species such as *L. donovani*, *L. major* and/or *L. infantum* in a patient, such as a human or a dog, to prevent leishmaniasis or diminish its severity. The compositions and vaccines may also be used to stimulate an immune response, which may be cellular and/or humoral, in a patient, for treating an individual already infected. In one embodiment, for *Leishmania*-infected patients, the immune responses generated include a preferential Th1 immune response (i.e., a response characterized by the production of the cytokines interleukin-1, interleukin-2, interleukin-12 and/or interferon-y, as well as tumor necrosis factor-a). In another embodiment, for uninfected patients, the immune response involves production of interleukin-12 and/or interleukin-2, or the stimulation of gamma delta T-cells. In either category of patient, the response stimulated may include IL-12 production. Such responses may also be elicited in biological samples of PBMC or components thereof derived from *Leishmania*-infected or uninfected individuals. As noted above, assays for any of the above cytokines, as well as other known cytokines, may generally be performed using methods known to those of ordinary skill in the art, such as an enzyme-linked immunosorbent assay (ELISA).

Appropriate doses and methods of fusion polypeptide administration for these purposes can be readily determined by a skilled artisan using available knowledge in the art and/or routine techniques. Routes and frequency of administration, as well as dosage, for the above aspects of the present invention may vary from individual to individual and may parallel those currently being used in immunization against other infections, including protozoan, viral and bacterial infections. For example, in one embodiment, between 1 and 12 doses of composition having a fusion polypeptide, which comprises *Leishmania* polypeptides or immunogenic/antigenic portions, fragments or variants thereof, are administered over a 1 year period. Booster vaccinations may be given periodically thereafter as needed or desired. Of course, alternate protocols may be appropriate for individual patients. In a particular embodiment, a suitable dose is an amount of fusion polypeptide or DNA encoding such a peptide that, when administered as described above, is capable of eliciting an immune response in an immunized patient sufficient to protect the patient from leishmaniasis caused by *Leishmania* species such as *L. donovani*, *L. major* and/or *L. infantum* for at least 1]2 years. In general, the amount of fusion polypeptide present in a dose (or produced in situ by the DNA in a dose) ranges from about 100 ng to about 1 mg per kg of host, typically from about 101.1 g to about 100 ug. Suitable dose sizes will vary with the size of the patient, but will typically range from about 0.1 mL to about 5 mL.

Diagnostic Compositions, Methods and Kits

In another aspect, this invention provides compounds and methods for detecting leishmaniasis in individuals and in blood supplies. In particular embodiments, the individual is a mammal. In more particular embodiments, the mammal is a human or canine.

For example, the fusion polypeptides and polynucleotides of the present invention can be used as effective diagnostic reagents for detecting and/or monitoring Leishmania infection in a patient. For example, the compositions, fusion polypeptides, and polynucleotides of the invention may be used in in vitro and in vivo assays for detecting humoral antibodies or cell-mediated immunity against Leishmania for diagnosis of infection, monitoring of disease progression or test-of-cure evaluation. In particular embodiments, the fusion polypeptides and polynucleotides are useful diagnostic reagents for serodiagnosis and whole blood assay in patients having leishmaniasis caused by Leishmania species such as L. donovani, L. major and/or L. infantum.

In one aspect, the diagnostic methods and kits preferably employ a polypeptide or fusion polypeptide as described herein, repeats of polypeptide fragments, or multimeric polypeptide fragments, including antigenic/immunogenic fragments. In another more specific aspect, fusion polypeptides of the present invention may comprise two or more Leishmania antigen fragments. In a more particular embodiment, an illustrative fusion polypeptide comprises the amino acid sequence set forth in SEQ ID NO: 2, 4, 6, 8, 10, 12, 14, 16, 18, 20, 22, 24, 26, 27, 28, 29, 30, 31, 32, 33, 34, 35, 36, 37, 39, 41, 43 or 44. In another embodiment, the diagnostic methods and kits preferably employ a fusion polypeptide comprising at least 1, at least 2, at least 3, or at least 4 immunogenic/antigenic portions or fragments of Leishmania polypeptides, variants or the like, optionally in combination with one or more other Leishmania antigens or non-Leishmania sequences, as described herein or obtainable in the art.

The antigens or polypeptides may be used in essentially any assay format desired, e.g., as individual antigens assayed separately, as multiple antigens assays simultaneously (e.g., a fusion polypeptide), as antigens immobilized on a solid support such as an array, or the like.

In one embodiment, there are provided diagnostic kits for detecting Leishmania infection in a biological sample, comprising (a) a polypeptide or a fusion polypeptide described herein or variants thereof as described herein, and (b) a detection reagent.

In another embodiment, there are provided diagnostic kits for detecting Leishmania infection in a biological sample, comprising (a) antibodies or antigen binding fragments thereof that are specific for a polypeptide or a fusion polypeptides described herein or variants thereof as described herein, and (b) a detection reagent.

In another embodiment, methods are provided for detecting the presence of Leishmania infection in a biological sample, comprising (a) contacting a biological sample with a polypeptide or a fusion polypeptide described herein or variants thereof described herein; and (b) detecting in the biological sample the presence of antibodies that bind to the fusion polypeptide.

In another embodiment, methods are provided for detecting the presence of Leishmania infection in a biological sample, comprising (a) contacting a biological sample with at least 2 monoclonal antibodies that bind to a polypeptide or a polypeptide described herein or variants thereof described herein; and (b) detecting in the biological sample the presence of Leishmania proteins that bind to the monoclonal antibody.

One of ordinary skill in the art would recognize that the methods and kits described herein may be used to detect all types of leishmaniasis, depending on the particular combination of immunogenic portions of Leishmania antigens present in the fusion polypeptide.

There are a variety of assay formats known to those of ordinary skill in the art for using a fusion polypeptide to detect antibodies in a sample. See, e.g., Harlow and Lane, Antibodies. A Laboratory Manual, Cold Spring Harbor Laboratory Press, 1988, which is incorporated herein by reference. In one embodiment, the assay involves the use of fusion polypeptide immobilized on a solid support to bind to and remove the antibody from the sample. The bound antibody may then be detected using a detection reagent that binds to the antibody/peptide complex and contains a detectable reporter group. Suitable detection reagents are well known and include, for example, antibodies that bind to the antibody/polypeptide complex and free polypeptide labeled with a reporter group (e.g., in a semi-competitive assay). Suitable reporter groups are also well known and include, for example, fluorescent labels, enzyme labels, radioisotopes, chemiluminescent labels, electrochemiluminescent labels, bioluminescent labels, polymers, polymer particles, metal particles, haptens, and dyes. Alternatively, a competitive assay may be utilized, in which an antibody that binds to a fusion polypeptide of the present invention labeled with a reporter group and allowed to bind to the immobilized fusion polypeptide after incubation of the fusion polypeptide with the sample. The extent to which components of the sample inhibit the binding of the labeled antibody to the fusion polypeptide is indicative of the reactivity of the sample with the immobilized fusion polypeptide.

The solid support may be any material known to those of ordinary skill in the art to which the fusion polypeptide may be attached. For example, the support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The fusion polypeptide may be bound to the solid support using a variety of techniques known to those in the art, which are amply described in the patent and scientific literature. In the context of the present invention, the term "bound" refers to both non-covalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of fusion polypeptide ranging from about 10 ng to about 1 pg, and preferably about 100 ng, is sufficient to bind an adequate amount of antigen. Nitrocellulose will bind approximately 100 pg of protein per 3 cm.

Covalent attachment of fusion polypeptide to a solid support may generally be achieved by first reacting the support with a bifunctional reagent that will react with both the support and a functional group, such as a hydroxyl or amino group, on the fusion polypeptide. For example, the fusion polypeptide may be bound to a support having an appropriate polymer coating using benzoquinone or by condensation of an aldehyde group on the support with an amine and an active hydrogen on the polypeptide (see, e.g., Pierce Immunotechnology Catalog and Handbook (1991) at A12-A13).

In certain embodiments, the assay is an enzyme linked immunosorbent assay (ELISA). This assay may be performed by first contacting a fusion polypeptide of the present invention that has been immobilized on a solid support, commonly the well of a microtiter plate, with the sample, such that antibodies to the Leishmania antigens of the fusion polypeptide within the sample are allowed to bind to the immobilized fusion polypeptide. Unbound sample is then removed from the immobilized fusion polypeptide and a detection reagent capable of binding to the immobilized antibody-polypeptide complex is added. The amount of detection reagent that remains bound to the solid support is then determined using a method appropriate for the specific detection reagent.

Once the fusion polypeptide is immobilized on the support, the remaining protein binding sites on the support are typically blocked. Any suitable blocking agent known to those of ordinary skill in the art, such as bovine serum albumin (BSA) or Tween 2OTM (Sigma Chemical Co., St. Louis, Mo.) may be employed. The immobilized polypeptide is then incubated with the sample, and antibody (if present in the sample) is allowed to bind to the antigen. The sample may be diluted with a suitable diluent, such as phosphate-buffered saline (PBS) prior to incubation. In general, an appropriate contact time (i.e., incubation time) is that period of time that is sufficient to permit detection of the presence of antibody within a Leishmania-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 2OTM. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups, colloidal gold and biotin. The conjugation of binding agent to reporter group may be achieved using standard methods known to those of ordinary skill in the art. Common binding agents may also be purchased conjugated to a variety of reporter groups from many sources (e.g., Zymed Laboratories, San Francisco, Calif. and Pierce, Rockford, Ill.).

The detection reagent is then incubated with the immobilized antibody polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Leishmania antibodies in the sample, the signal detected from the reporter group that remains bound to the solid support is generally compared to a signal that corresponds to a predetermined cut-off value. In one embodiment, the cut-off value is preferably the average mean signal obtained when the immobilized polypeptide is incubated with samples from an uninfected patient. In general, a sample generating a signal that is three standard deviations above the predetermined cut-off value is considered positive (i.e., reactive with the polypeptide). In an alternate embodiment, the cut-off value is determined using a Receiver Operator Curve, according to the method of Sackett et al., Clinical Epidemiology: A Basic Science for Clinical Medicine, p. 106-7 (Little Brown and Co., 1985). Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper lefthand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate.

In other embodiments, an assay is performed in a flow-through assay format, wherein the antigen is immobilized on a membrane such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above.

In other embodiments, an assay if performed in a strip test format, also known as a lateral flow format. Here, one end of the membrane to which polypeptide is bound is immersed in a solution containing the sample. The sample migrates along the membrane through a region containing detection reagent and to the area of immobilized fusion polypeptide. Concentration of detection reagent at the fusion polypeptide indicates the presence of Leishmania antibodies in the sample. Typically, the concentration of detection reagent at that site generates a pattern, such as a line, that can be read visually. The absence of such a pattern indicates a negative result. In general, the amount of fusion polypeptide immobilized on the membrane is selected to generate a visually discernible pattern when the biological sample contains a level of antibodies that would be sufficient to generate a positive signal in an ELISA, as discussed above. Preferably, the amount of fusion polypeptide immobilized on the membrane ranges from about 25 ng to about 1 fag, and more preferably from about 50 ng to about 500 ng. Such tests can typically be performed with a very small amount (e.g., one drop) of patient serum or blood. Lateral flow tests can operate as either competitive or sandwich assays.

In still other embodiments, a fusion polypeptide of the invention is adapted for use in a dual path platform (DPP) assay. Such assays are described, for example, in U.S. Pat. No. 7,189,522, the contents of which are incorporated herein by reference.

Of course, numerous other assay protocols exist that are suitable for use with the fusion polypeptides of the present invention. It will be understood that the above descriptions are intended to be exemplary only.

The assays discussed above may be used, in certain aspects of the invention, to specifically detect visceral leishmaniasis. In this aspect, antibodies in the sample may be detected using a fusion polypeptide of the present invention, e.g., comprising an amino acid sequence of antigenic/immunogenic fragments or epitopes of *Leishmania* antigens. Preferably, the *Leishmania* antigens are immobilized by adsorption to a solid support such as a well of a microtiter plate or a membrane, as described above, in roughly similar amounts such that the total amount of fusion polypeptide in contact with the support ranges from about 10 ng to about 100 pg. The remainder of the steps in the assay may generally be performed as described above. It will be readily apparent to those of ordinary skill in the art that, by combining polypeptides described herein with other polypeptides that can detect cutaneous and mucosal leishmaniasis, the polypeptides disclosed herein may be used in methods that detect all types of leishmaniasis.

In another aspect of this invention, immobilized fusion polypeptides may be used to purify antibodies that bind thereto. Such antibodies may be prepared by any of a variety of techniques known to those of ordinary skill in the art. See, e.g., Harlow and Land, Antibodies. A Laboratory Manual, Cold Spring Harbor Laboratory Press, 1988. In one such technique, an immunogen comprising a fusion polypeptide of the present invention is initially injected into any of a wide variety of mammals (e.g., mice, rats, rabbits, sheep and goats). In this step, the polypeptide may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for the antigenic fusion polypeptide of interest may be prepared, for example, using the technique of Kohler and Milstein, Eur. J. Immunol. 6:511-519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and tested for binding activity against the polypeptide. Hybridomas having high reactivity and specificity are preferred.

Monoclonal antibodies may be isolated from the supernatants of growing hybridoma colonies. In this process, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. One or more polypeptides may be used in the purification process in, for example, an affinity chromatography step.

Monospecific antibodies that bind to a fusion polypeptide comprising two or more immunogenic portions of *Leishmania* antigens may be used, for example, to detect *Leishmania* infection in a biological sample using one of a variety of immunoassays, which may be direct or competitive. Briefly, in one direct assay format, a monospecific antibody may be immobilized on a solid support (as described above) and contacted with the sample to be tested. After removal of the unbound sample, a second monospecific antibody, which has been labeled with a reporter group, may be added and used to detect bound antigen. In an exemplary competitive assay, the sample may be combined with the monoclonal or polyclonal antibody, which has been labeled with a suitable reporter group. The mixture of sample and antibody may then be combined with polypeptide antigen immobilized on a suitable solid support. Antibody that has not bound to an antigen in the sample is allowed to bind to the immobilized antigen and the remainder of the sample and antibody is removed. The level of antibody bound to the solid support is inversely related to the level of antigen in the sample. Thus, a lower level of antibody bound to the solid support indicates the presence of *Leishmania* in the sample. Other formats for using monospecific antibodies to detect *Leishmania* in a sample will be apparent to those of ordinary skill in the art, and the above formats are provided solely for exemplary purposes.

As used in this specification and the appended claims, the singular forms "a", "an" and "the" include plural referents unless the content clearly dictates otherwise. Thus, for example, reference to "a polypeptide" optionally includes two or more polypeptides, and the like.

It is understood that aspect and embodiments of the invention described herein include "comprising," "consisting," and "consisting essentially of" aspects and embodiments.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments.

EXAMPLES

Example 1

Construction of Fusion Polypeptides of the Invention

NSC Fusion Polypeptide.

The fusion polypeptide referred to as NSC was generated by the tandem linkage of *Leishmania* open reading frames of polynucleotides encoding the polypeptides for the full length nonspecific nucleoside hydrolase (NH, Nh or N), the full length sterol 24-c-methyltransferase (SMT or S), and a carboxy-terminal fragment of the cysteine polypeptidease B polypeptide (CPB, CpB or C). NSC has a 2,868 nucleotide sequence as set forth in SEQ ID NO: 1 which comprises nucleotides 1 to 942 which encodes amino acids 1 to 314 of the NH polypeptide from *Leishmania infantum*/or *L donovani*, polynucleotides 943 to 1998 which encodes amino acids 2 to 353 of the *Leishmania infantum* SMT polypeptide, and nucleotides 1999 to 2868 which encode amino acids 154 to 443 of the carboxy-terminus of the CPB polypeptide from *Leishmania infantum*. NSC has a polypeptide sequence set forth in SEQ ID NO: 2 which comprises amino acids 1 to 314 of the full length NH, H polypeptide from *Leishmania infantum/donovani*, amino acids 2 to 353 of the full length *Leishmania infantum* SMT polypeptide, and amino acids 154 to 443 of the carboxy-terminus of the CPB polypeptide from *Leishmania infantum*. The 956 amino acid fusion polypeptide with a predicted mass of 105,106 Daltons was expressed in *E. coli* and purified by column chromatography.

NSA Fusion Polypeptide.

The fusion polypeptide referred to as NSA was generated by the tandem linkage of *Leishmania* open reading frames of polynucleotides encoding the polypeptides, full length nonspecific nucleoside hydrolase (NH, Nh or H), the full length sterol 24-c-methyltransferase (SMT or S), and the mature A2 polypeptide (A2 or A). NSA has a 2,640 nucleotide sequence as set forth in SEQ ID NO: 3 which comprises polynucleotides 1-942 which encodes amino acids 1 to 314 of the NH polypeptide from *Leishmania infantum* or *L donovani*, polynucleotides 943 to 1998 which encodes amino acids 2 to 353 of the *Leishmania infantum* SMT polypeptide, and nucleotides 1999 to 2640 which encodes amino acids 23 to 236 of the mature A2 polypeptide from *Leishmania donovani*. NSA has a polypeptide sequence set forth in SEQ ID NO: 2 which comprises amino acids 1 to 314 of the full length NH polypeptide from *Leishmania infantum* or *L donovani*, amino acids 2 to 353 of the full length *Leishmania infantum* SMT polypeptide, and amino acids 23-236 of the mature A2 polypeptide from *Leishmania donovani*. The 880 amino acid fusion polypeptide with a predicted mass of 93,729 Daltons was expressed in *E. coli* and purified by column chromatography.

NSAfl Fusion Polypeptide.

The fusion polypeptide referred to as NSAfl was generated by the tandem linkage of *Leishmania* open reading frames of polynucleotides encoding the polypeptides for the full length nonspecific nucleoside hydrolase (NH, Nh or H), full length sterol 24-c-methyltransferase (SMT or S), and the full length A2 polypeptide (A2fl or Afl). NSAfl has a 2,703 nucleotide sequence as set forth in SEQ ID NO: 5 which comprises polynucleotides 1-942 which encodes amino acids 1 to 314 of the NH polypeptide from *Leishmania infantum* or *L donovani*, polynucleotides 943 to 1998 which encodes amino acids 2 to 353 of the *Leishmania infantum* SMT polypeptide, and nucleotides 1999 to 2778 which encodes amino acids 1 to 236 of the full length A2 polypeptide from *Leishmania donovani*. NSAfl has a polypeptide sequence set forth in SEQ ID NO: 6 which comprises amino acids 1 to 314 of the full length NH, H polypeptide from *Leishmania infantum* or *L donovani*, amino acids 2 to 353 of the full length *Leishmania infantum* SMT polypeptide, and amino acids 1-236 of the full length A2 polypeptide from *Leishmania donovani*. The 926 amino acid fusion polypeptide with a predicted mass of 95,928 Daltons kDa was expressed in *E. coli* and purified by column chromatography.

HNSA Fusion Polypeptide.

The fusion polypeptide referred to as HNSA was generated by the tandem linkage of open reading frame of polynucleotides encoding the amino-terminal fragment of the histone H2BN polypeptide (H2BN, h2Bn, or H), the full length nonspecific nucleoside hydrolase (NH, N, or H), the full length sterol 24-c-methyltransferase (SMT), and the mature A2 polypeptide (A2 or A). HNSA has a 2,778 nucleotide sequence as set forth in SEQ ID NO: 7 which comprises polynucleotides 1 to 138 which encodes amino acids 1 to 46 of the amino terminus of the histone H2BN polypeptide from *L infantum*, polynucleotides 139 to 1080 which encodes amino acids 1 to 314 of the NH polypeptide from *Leishmania infantum* or *L donovani*, polynucleotides 1081 to 2136 which encodes amino acids 2 to 353 of the *Leishmania infantum* SMT polypeptide, and nucleotides 2137 to 2778 which encodes amino acids 23-236 of the mature A2 polypeptide (A2 is referred to as mature because the sequence lacks the signal sequence of the full length polypeptide) from *Leishmania donovani*. HNSA has a polypeptide sequence set forth in SEQ ID NO: 8 which comprises amino acids 1 to 46 of the amino terminus of the histone H2BN polypeptide, amino acids 1 to 314 of the full length NH polypeptide from *Leishmania infantum* or *L donovani*, amino acids 2 to 353 of the full length *Leishmania infantum* SMT polypeptide, and amino acids 23-236 of the mature A2 polypeptide from *Leishmania donovani*. The 926 amino acid fusion polypeptide with a predicted mass of 98,942 Daltons was expressed in *E. coli* and purified by column chromatography.

8NSA Fusion Polypeptide.

The fusion polypeptide referred to as 8NSA was generated by the tandem linkage of an open reading frame of polynucleotides encoding a methionine initiation codon (ATG) added to the 5' end of a fragment of the carboxy-terminus of the putative mitochondrial HSP70 (8E or 8) polypeptide, two *Leishmania* open reading frames encoding the polypeptides, nonspecific nucleoside hydrolase (NH, H) and sterol 24-c-methyltransferase (SMT), and the open reading frame for the mature A2, A polypeptide (A2, A). 8NSA has a 3,099 polynucleotide sequence as set forth in SEQ ID NO: 9 which comprises polynucleotides 1 to 459 which encodes amino acids 509 to 660 of the carboxy-terminus of the putative mitochondrial HSP70 (8E or 8) polypeptide from *L infantum*, polynucleotides 460 to 1401 which encodes amino acids 1 to 314 of the NH, H polypeptide from *Leishmania infantum/donovani*, polynucleotides 1402 to 2457 which encodes amino acids 2 to 353 of the *Leishmania infantum* SMT polypeptide, and nucleotides 2458 to 3099 which encodes amino acids 23 to 236 of the mature A2, A polypeptide (the A2, A is referred to as mature because the sequence lacks the signal sequence of the full length polypeptide) from *Leishmania donovani*. 8NSA has a polypeptide sequence set forth in SEQ ID NO: 10 which comprises amino acids 509 to 660 of the carboxy-terminus of the putative mitochondrial HSP70 (8E or 8) polypeptide from *L infantum*, amino acids1 to 314 of the full length NH, H polypeptide from *Leishmania infantum/donovani*, amino acids 2 to 353 of the full length *Leishmania infantum* SMT polypeptide, and amino acids 23-236 of the mature A2, A polypeptide from *Leishmania donovani*. The 1033 amino acid fusion polypeptide with a predicted mass of 110,948 Daltons was expressed in *E. coli* and purified by column chromatography.

21NSA Fusion Polypeptide.

The fusion polypeptide referred to as 21NSA was generated by the tandem linkage of three *Leishmania* open reading frames encoding the polypeptides p21 antigen, nonspecific nucleoside hydrolase (NH, H) and sterol 24-c-methyltransferase (SMT), and the open reading frame for the mature A2, A polypeptide (A2, A). 21NSA has a 3,213 nucleotide sequence as set forth in SEQ ID NO: 11 which comprises polynucleotides 1 to 573 which encodes amino acids 1 to 191 of the p21 antigen of *Leishmania infantum*, polynucleotides 574 to 1515 which encodes amino acids 1 to 314 of the NH polypeptide from *Leishmania infantum/donovani*, polynucleotides 1516 to 2571 which encodes amino acids 2 to 353 of the *Leishmania infantum* SMT polypeptide, and nucleotides 2572 to 3213 which encodes amino acids 23-236 of the mature A2, A polypeptide from *Leishmania donovani*. NSA has a polypeptide sequence set forth in SEQ ID NO: 12 which comprises amino acids 1 to 191 of the p21 antigen of *Leishmania infantum*, amino acids 1 to 314 of the full length NH, H polypeptide from *Leishmania infantum/donovani*, amino acids 2 to 353 of the full length *Leishmania infantum* SMT polypeptide, and amino acids 23-236 of the mature A2, A polypeptide from *Leishmania donovani*. The 1071 amino acid fusion polypeptide with a predicted mass of 115,082 Daltons was expressed in *E. coli* and purified by column chromatography.

821NS Fusion Polypeptide.

The fusion polypeptide referred to as 821NS was generated by the tandem linkage of an open reading frame of polynucleotides encoding a methionine initiation codon (ATG) added to the 5' end of a fragment of the carboxy-terminus of the putative mitochondrial HSP70 (8E or 8) polypeptide, the open reading frame encoding the p21 antigen, and two *Leishmania* open reading frames encoding the polypeptides, nonspecific nucleoside hydrolase (NH, H) and sterol 24-c-methyltransferase (SMT). 821NS has a 3,030 polynucleotide sequence as set forth in SEQ ID NO: 13 which comprises polynucleotides 1 to 459 which encodes amino acids 509 to 660 of the carboxy-terminus of the putative mitochondrial HSP70 (8E or 8) polypeptide from *L infantum*, polynucleotides 460 to 1032 which encodes amino acids 1 to 191 of the of the p21 antigen of *Leishmania infantum*, nucleotides 1033 to 1974 which encodes amino acids 1 to 314 of the NH polypeptide from *Leishmania infantum/donovani*, polynucleotides 1975 to 3030 which encodes amino acids 2 to 353 of the *Leishmania infantum* SMT polypeptide. 821NS has a polypeptide sequence set forth in SEQ ID NO: 14 which comprises amino acids 509 to 660 of the carboxy-terminus of the putative mitochondrial HSP70 (8E or 8) polypeptide from *L infantum*, amino acids1 to 191 of the p21 antigen polypeptide from *Leishmania donovani*, amino acids 1 to 314 of the full length NH, H polypeptide from *Leishmania infantum/donovani*, amino acids 2 to 353 of the full length *Leishmania infantum* SMT polypeptide. The 1,010 amino acid fusion polypeptide with a predicted mass of 112,565 Daltons was expressed in *E. coli* and purified by column chromatography.

HNS Fusion Polypeptide.

The fusion polypeptide referred to as HNS was generated by the tandem linkage of an open reading frame for the amino terminus of the histone H2BN (H) polypeptide (H2BN (H)) and two *Leishmania* open reading frames encoding the polypeptides, nonspecific nucleoside hydrolase (NH, H) and sterol 24-c-methyltransferase (SMT). HNS has a 2,136 nucleotide sequence as set forth in SEQ ID NO: 15 which comprises polynucleotides 1 to 138 which encodes amino acids 1 to 46 of the amino terminus of the histone H2BN (H) polypeptide from *L infantum*, polynucleotides 139-1080 which encodes amino acids 1 to 314 of the NH, H polypeptide from *Leishmania infantum/donovani*, and polynucleotides 1081 to 2136 which encodes amino acids 2 to 353 of the *Leishmania infantum* SMT polypeptide. HNS has a polypeptide sequence set forth in SEQ ID NO: 16 which comprises amino acids 1 to 46 of the amino terminus of the histone H2BN (H) polypeptide, amino acids 1 to 314 of the full length NH, H polypeptide from *Leishmania infantum/donovani*, and amino acids 2 to 353 of the full length *Leishmania infantum* SMT polypeptide. The 712 amino acid fusion polypeptide with a predicted mass of 79,205 Daltons was expressed in *E. coli* and purified by column chromatography.

8NS Fusion Polypeptide.

The fusion polypeptide referred to as 8NS was generated by the tandem linkage of an open reading frame of polynucleotides encoding a methionine initiation codon (ATG) added to the 5' end of a fragment of the of the carboxy-terminus of the putative mitochondrial HSP70 (8E or 8) polypeptide and two *Leishmania* open reading frames encoding the polypeptides, nonspecific nucleoside hydrolase (NH, H) and sterol 24-c-methyltransferase (SMT). 8NS has a 2457 polynucleotide sequence as set forth in SEQ ID NO: 17 which comprises polynucleotides 1 to 459 which encodes amino acids 509 to 660 of the carboxy-terminus of the putative mitochondrial HSP70 (8E or 8) polypeptide from *L infantum*, polynucleotides 460 to 1401 which encodes amino acids 1 to 314 of the NH, H polypeptide from *Leishmania infantum/donovani*, and polynucleotides 1042 to 2457 of the *Leishmania infantum* SMT polypeptide. 8NS has a polypeptide sequence set forth in SEQ ID NO: 18 which comprises amino acids 509 to 660 of the carboxy-terminus of the putative mitochondrial HSP70 (8E or 8) polypeptide from *L infantum*, amino acids1 to 314 of the full length NH, H polypeptide from *Leishmania infantum/donovani*, and amino acids 2 to 353 of the full length *Leishmania infantum* SMT polypeptide. The 819 amino acid fusion polypeptide with a predicted mass of 90,970 Daltons was expressed in *E. coli* and purified by column chromatography.

21NS Fusion Polypeptide.

The fusion polypeptide referred to as 21NS was generated by the tandem linkage of three *Leishmania* open reading frames encoding the polypeptides p21 antigen, nonspecific nucleoside hydrolase (NH, H) and sterol 24-c-methyltransferase (SMT). 21NS has a 2,571 nucleotide sequence as set forth in SEQ ID NO: 19 which comprises polynucleotides 1 to 573 which encodes amino acids 1 to 191 of the p21 antigen of *Leishmania infantum*, poly nucleotides 574 to 1515 which encodes amino acids 1 to 314 of the NH, H polypeptide from *Leishmania infantum/donovani*, and polynucleotides 1516 to 2571 which encodes amino acids 2 to 353 of the *Leishmania infantum* SMT polypeptide. 21NS has a polypeptide sequence set forth in SEQ ID NO: 20 which comprises amino acids 1 to 191 of the p21 antigen of

*Leishmania infantum*, amino acids 1 to 314 of the full length NH, H polypeptide from *Leishmania infantum/donovani*, and amino acids 2 to 353 of the full length *Leishmania infantum* SMT polypeptide. The 857 amino acid fusion polypeptide with a predicted mass of 94 KDa was expressed in *E. coli* and purified by column chromatography.

21SC Fusion Polypeptide.

The fusion polypeptide referred to as 21SC was generated by the tandem linkage of *Leishmania* open reading frames encoding the polypeptides p21 antigen, sterol 24-c-methyltransferase (SMT), and an open reading frame encoding a fragment of the cysteine polypeptidease B polypeptide (CPB). 21SC has a 2,499 nucleotide sequence as set forth in SEQ ID NO: 21 which comprises polynucleotides 1 to 573 which encodes amino acids 1 to 191 of the p21 antigen of *Leishmania infantum*, polynucleotides 574 to 1629 which encodes amino acids 2 to 353 of the *Leishmania infantum* SMT polypeptide and nucleotides 1630 to 2499 which encodes amino acids154 to 443 of the carboxy-terminus of the CPB polypeptide from *Leishmania infantum*. 21SC has a polypeptide sequence set forth in SEQ ID NO: 22 which comprises amino acids 1 to 191 of the p21 antigen of *Leishmania infantum*, amino acids 2 to 353 of the full length *Leishmania infantum* SMT polypeptide, amino acids 154 to 443 of the carboxy-terminus of the CPB polypeptide from *Leishmania infantum*. The 833amino acid fusion polypeptide with a predicted mass of 92,239 Daltons was expressed in *E. coli* and purified by column chromatography.

821S Fusion Polypeptide.

The fusion polypeptide referred to as 821S was polypeptiderated by the tandem linkage of an open reading frame of polynucleotides encoding a methionine initiation codon (ATG) added to the 5' end of a fragment of the carboxy-terminus of the putative mitochondrial HSP70 (8E or 8) polypeptide, the open reading frame encoding the p21 antigen, and the open reading frames encoding sterol 24-c-methyltransferase (SMT, S). 821S has a 2,091 polynucleotide sequence as set forth in SEQ ID NO: 23 which comprises polynucleotides 1 to 459 which encodes amino acids 509 to 660 of the carboxy-terminus of the putative mitochondrial HSP70 (8E or 8) polypeptide from *L infantum*, polynucleotides 460 to 1032 which encodes amino acids 1 to 191 of the of the p21 antigen of *Leishmania infantum*, and polynucleotides 1033 to 2091 which encodes amino acids 2 to 353 of the *Leishmania infantum* SMT polypeptide. 821S has a polypeptide sequence set forth in SEQ ID NO: 24 which comprises amino acids 509 to 660 of the carboxy-terminus of the putative mitochondrial HSP70 (8E or 8) polypeptide from *L infantum*, amino acids1 to 191 of the p21 antigen polypeptide from *Leishmania donovani*, and amino acids 2 to 353 of the full length *Leishmania infantum* SMT polypeptide. The 697 amino acid fusion polypeptide with a predicted mass of 78,510 Daltons was expressed in *E. coli* and purified by column chromatography.

8HS Fusion Polypeptide.

The fusion polypeptide referred to as 8HS was generated by the tandem linkage of an open reading frame of polynucleotides encoding a methionine initiation codon (ATG) added to the 5' end of a fragment of the carboxy-terminus of the putative mitochondrial HSP70 (8E or 8) polypeptide, an open reading frame for the amino terminus of the histone H2BN (H) polypeptide (H2BN (H)) and an open reading frame for sterol 24-c-methyltransferase (SMT). 8HS has a 1,653 polynucleotide sequence as set forth in SEQ ID NO: 25 which comprises polynucleotides 1 to 459 which encodes amino acids 509 to 660 of carboxy-terminus of the putative mitochondrial HSP70 (8E or 8) polypeptide from *Leishmania infantum*, polynucleotides 460 to 597 which encodes amino acids 1 to 46 of the amino terminus of the histone H2BN (H) polypeptide from *L infantum*, and polynucleotides 598 to 1653 which encodes amino acids2 to 353 of the *Leishmania infantum* SMT polypeptide. 8HS has a polypeptide sequence set forth in SEQ ID NO: 26 which comprises amino acids 509 to 660 of the carboxy-terminus of the putative mitochondrial HSP70 (8E or 8) polypeptide from *L infantum*, amino acids 1 to 46 of the amino terminus of the histone H2BN (H) polypeptide from *L infantum*, and amino acids 2 to 353 of the full length *Leishmania infantum* SMT polypeptide. The 550 amino acid fusion polypeptide with a predicted mass of 62,204 Daltons was expressed in *E. coli* and purified by column chromatography.

8HNS

The fusion polypeptide referred to as 8HNS was generated by the tandem linkage of an open reading frame of polynucleotides encoding a methionine initiation codon (ATG) added to the 5' end of a fragment of the carboxy-terminus of the putative mitochondrial HSP70 (8E or 8) polypeptide the amino terminus of the histone H2BN (H) polypeptide (H2BN (H)) and two *Leishmania* open reading frames encoding the polypeptides, nonspecific nucleoside hydrolase (NH, H) and sterol 24-c-methyltransferase (SMT). 8HNS has a 2,591 nucleotide sequence as set forth in SEQ ID NO: 38 which comprises polynucleotides which comprises polynucleotides 1 to 459 which encodes amino acids 509 to 660 of carboxy-terminus of the putative mitochondrial HSP70 (8E or 8) polypeptide from *Leishmania infantum* poly nucleotides 460 to 697 which encodes amino acids 1 to 46 of the amino terminus of the histone H2BN (H) polypeptide from *L infantum*, polynucleotides 698-1539 which encodes amino acids 1 to 314 of the NH, (H) polypeptide from *Leishmania infantum/donovani*, and polynucleotides 1540 to 2595 which encodes amino acids 2 to 353 of the *Leishmania infantum* SMT polypeptide. 8HNS has a polypeptide sequence comprising 863 amino acids set forth in SEQ ID NO: 39 which comprises amino acids 509 to 660 of the carboxy-terminus of the putative mitochondrial HSP70 (8E or 8) polypeptide from *L infantum*, amino acids 1 to 46 of the amino terminus of the histone H2BN (H) polypeptide, amino acids1 to 314 of the full length NH, H polypeptide from *Leishmania infantum/donovani*, and amino acids 2 to 353 of the full length *Leishmania infantum* SMT polypeptide. The amino acid fusion polypeptide was expressed in *E. coli* and purified by column chromatography.

H21NS.

The fusion polypeptide referred to as H21NS was generated by the tandem linkage of four *Leishmania* open reading frames encoding the polypeptides of the amino terminus of the histone H2BN (H) polypeptide (H2BN (H)), p21 antigen, nonspecific nucleoside hydrolase (NH, H) and sterol 24-c-methyltransferase (SMT). H21NS has a 2,617 nucleotide sequence as set forth in SEQ ID NO: 40 which comprises polynucleotides 1-46 which encodes amino acids 1 to 46 of the amino terminus of the histone H2BN (H) polypeptide from *L infantum* 47 to 622 which encodes amino acids 1 to 191 of the p21 antigen of *Leishmania infantum*, polynucleotides 623 to 1664 which encodes amino acids 1 to 314 of the NH, H polypeptide from *Leishmania infantum/donovani*, and polynucleotides 1665 to 2617 which encodes amino acids 2 to 353 of the *Leishmania infantum* SMT polypeptide. H21NS has a polypeptide sequence set forth in SEQ ID NO: 41 which comprises amino acids 1 to 46 of the amino terminus of the histone H2BN (H) polypeptide, amino acids 1 to 191 of the p21 antigen of *Leishmania infantum*, amino acids 1 to 314 of the full length NH, H polypeptide from *Leishmania infantum/donovani*, and amino acids 2 to 353 of the full length *Leishmania infantum* SMT polypeptide. The 902 amino acid fusion polypeptide was expressed in *E. coli* and purified by column chromatography.

Example 2

Immunogencity of Polypeptides and Fusion Polypeptides

The Polypeptides and Fusions Polypeptides of the invention were analyzed for their ability to generate an immune response or confer protection against a visceral *Leishmania donovani* infection according to the methods described herein. The individual polypeptides and fusion polypeptides of the invention were for the purposes of these examples formulated within stable emulsions with the TLR4 adjuvant, GLA. Mice received a total of three immunization three weeks apart in a prime, boost, boost strategy known in the art. Representative data for the 8NS, 821NS, 21SC and NSC fusion polypeptides are presented but are not intended to be limiting of the *Leishmania* fusion polypeptides of the invention.

Methods for Assessing Immunogenicity of Leish Fusions.
Humoral Responses:

Briefly, BALB/C mice (10 mice per group) were immunized with either 5 μg of recombinant fusion polypeptide, 5 μg of individual polypeptides of the fusions, or 5 μg of a mixture of individual polypeptides of the fusions formulated in 5 μg of an adjuvant formulation, in some examples aTLR4 stable emulsion (GLA-SE) in a total volume of 1004 Controls may include 5 μg of recombinant fusion polypeptide, 5 μg of individual polypeptides of the fusions, or 5 μg of a mixture of individual polypeptides of the fusions formulated within a stable emulsion without GLA (SE), saline, GLA-SE, or SE or in in a total volume of 100 μl. All immunizations were administered in 100 μl subcutaneously in the base of the tail (Week 0). The mice were immunized two more times (for a total of three immunizations, prime, boost, boost) at 3 week intervals with an additional 5 μg of test article in a total volume of 100 μl subcutaneously in the base of the tail (Week 3 and Week 6). Two weeks after the third immunization (Week 8) animals are bled by insertion of a tube into the capillary bed of the eye. Serum is prepared and tested for antigen-specific antibody responses to the fusion protein as well as the individual components of the protein by ELISA. Serum from immunized mice is titrated to find an endpoint titer (last optical density (OD) value greater than a threshold determined by sera from unimmunized mice). The antigen-specific antibody response is analyzed for total IgG against the specific antigen, and also IgG2 and IgG 1 isotypes to reveal any immune bias (for example, IFNγ stimulates IgG2a/c responses while IL-4/5 stimulate IgG1 responses).

Cellular Responses:

One month (Week 10) after the final immunization, one cohort of animals was sacrificed and their spleens harvested. Briefly, duplicate wells of $2 \times 10^5$ single cell spleen suspensions were incubated with 10 μg/ml of the appropriate polypeptide antigen to assess antigen-specific recall responses. In some experiments the animals were immunized with fusion polypeptides of the invention and replicate wells were stimulated with either or fusion polypeptide, individual polypeptides of the fusion, mixtures of individual polypeptides of the fusion, or irradiated whole or prepared lysates of *Leishmania* parasites, or saline as a control. In some experiments the *Leishmania* lysates were prepared from *L. donovani, L infantum*, or *L major*. The immune response is assessed by determining the particular cell type producing cytokines by intracellular cytokine staining after 1 day (as determined by flow cytometry) and measuring secretion of cytokines into the culture supernatant after 4 days (as determined by cytokine ELISA according to the manufacturer's instructions (eBioScience). The anticipated protective response for both cutaneous and visceral leishmaniasis (CL and VL respectively) is a $T_{helper}^1$ profile, characterized by the secretion of one more cytokines including but not limited to IFNγ, TNF and IL-2 production from CD4 T cells in response to specific antigen (either the fusion polypeptide, the individual polypeptides of the fusion, or whole irradiated *Leishmania* parasites or lysates of *Leishmania* parasites. Data is presented as percentage of cytokine positive CD4+ T cells secreting the indicated cytokine or cytokines (i.e. IFNγ, IL-2, TNFα, as examples). The frequency of multifunctional effector cells (T cells secreting more than one cytokine in response to recall antigen stimulation) has previously been correlated with protection against *Leishmania* infection.

Prophylactic Studies:

The fusion polypeptides were also evaluated for their ability to protect against visceral leishmaniasis (VL) using the Balb/c mouse model. Briefly, mice were immunized subcutaneously 3 times at 3 weeks apart (prime/boost/boost) with individual polypeptides of the fusions, mixtures of individual polypeptides of the fusion polypeptides, fusion polypeptides, irradiated *Leishmania* parasites, or GLA-SE or saline alone as controls. One month after the last immunization mice were challenged via intra-cardiac injection with up to $5 \times 10^6$ *L. donovani* promastigotes. Livers were harvested one month post-challenge and parasite burdens determined by limiting dilution assay or real time PCR quantitation by methods known in the art. Reductions in parasite burden following immunization with fusion polypeptides, individual polypeptides of the fusions, mixtures of individual polypeptides of the fusions or control saline or adjuvant formulations are presented.

Immunogenicity of the Fusion Polypeptide 8NS

Mice immunized with the fusion polypeptide 8NS according to the methods of the invention, generated a CD4 T cell population that produced both IFNγ and TNF in response to restimulation with 8NS, the immunizing fusion polypeptide, or a fusion polypeptide comprising only the S an N polypeptides, NS, of the 8NS fusion polypeptide. CD4 T cells producing only IFNγ or TNF in response to NS restimulation were also detected in these mice.

Immunogenicity of the Fusion Polypeptides 821NS and 821S

Mice immunized with 821NS generated a multifunctional CD4 T cell population that produced both IFNγ and TNF in response to restimulation with NS. Mice immunized with 821S similarly demonstrated a multifunctional CD4 T cell population (IFNγ, TNF, IL-2-secreting CD4 T cells, or combinations of at least 2 of these cytokines) in response to restimulation with 821S (FIG. 1).

Immunogenicity of the Fusion Polypeptide 21SC

Figure 2:
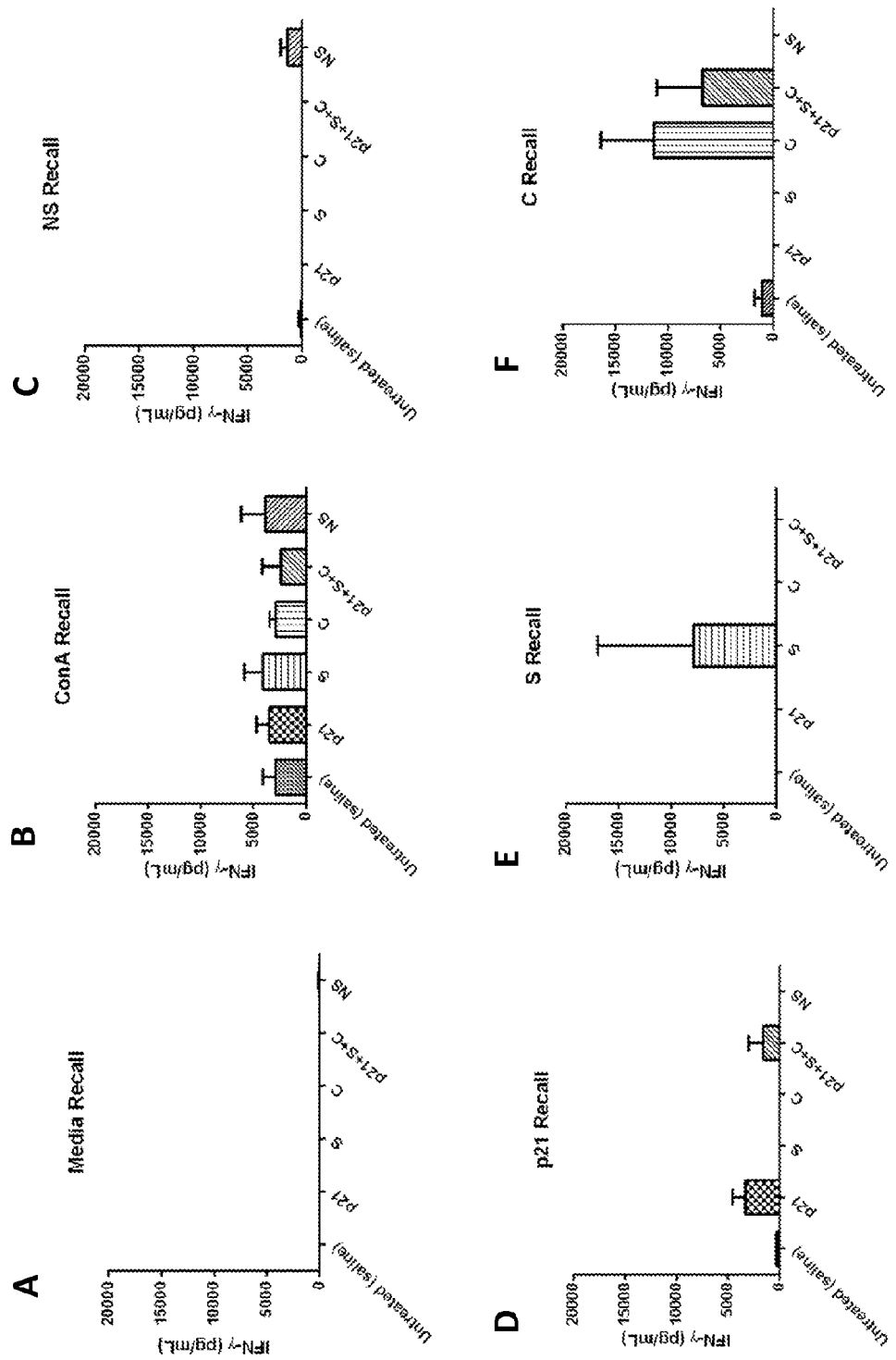
FIG. 2 shows immunogencity as measured by IFN-γ secretion of spleen cell cultures from mice immunized with a mixture of the individual polypeptides of the fusion 21SC (p21, SMT, and CpB). Data in panels A-F represent spleen cell cultures from mice immunized with the mixture (p21+ SMT+CpB), the individual polypeptides or saline as a negative control and the fusion polypeptide NS as a positive control as indicated on the horizontal axis then restimulated in vitro (a recall response) with the indicated antigen and the secretion of IFN-γ measured by ELISA: A) Media restimulation; B) ConA restimulation; C) NS fusion polypeptide (fusion of NH and SMT); D) p21 restimulation; E) SMT restimulation (S) and; F) CpB restimulation (C).

Mice immunized with a mixture of the individual polypeptides of the fusion 21SC fusion, p21, SMT, and CpB, had a lower parasite burden than control mice one month after experimental infection with *L donovani* with a mean of $2.98 \times 10^6$ versus a mean of $7.57 \times 10^6$ for unimmunized mice, as determined by limiting dilution. Mice immunized with a mixture of the individual polypeptides of the fusion 21SC, namely p21, SMT (S), and CpB (C), demonstrated IFNγ secretion in response to p21 (FIG. 2D), SMT (FIG. 2E) and CpB (FIG. 2F) as well as the positive control, Con A (FIG. 2B). Flow cytometry identified CD4 T cells producing IFNγ, of which a proportion were multifunctional and were also producing TNF. Indicative of cross-species immuno-reactivity, IFNγ was also secreted by spleen cell cultures of mice immunized with a mixture of the individual polypeptides of the fusion 21SC p21, SMT (S), and CpB (C), but not negative control mice, in response to incubation with lysates of L. major and L. brasiliensis.

Immunogenicity of the Fusion Polypeptide NSC

Figure 3:
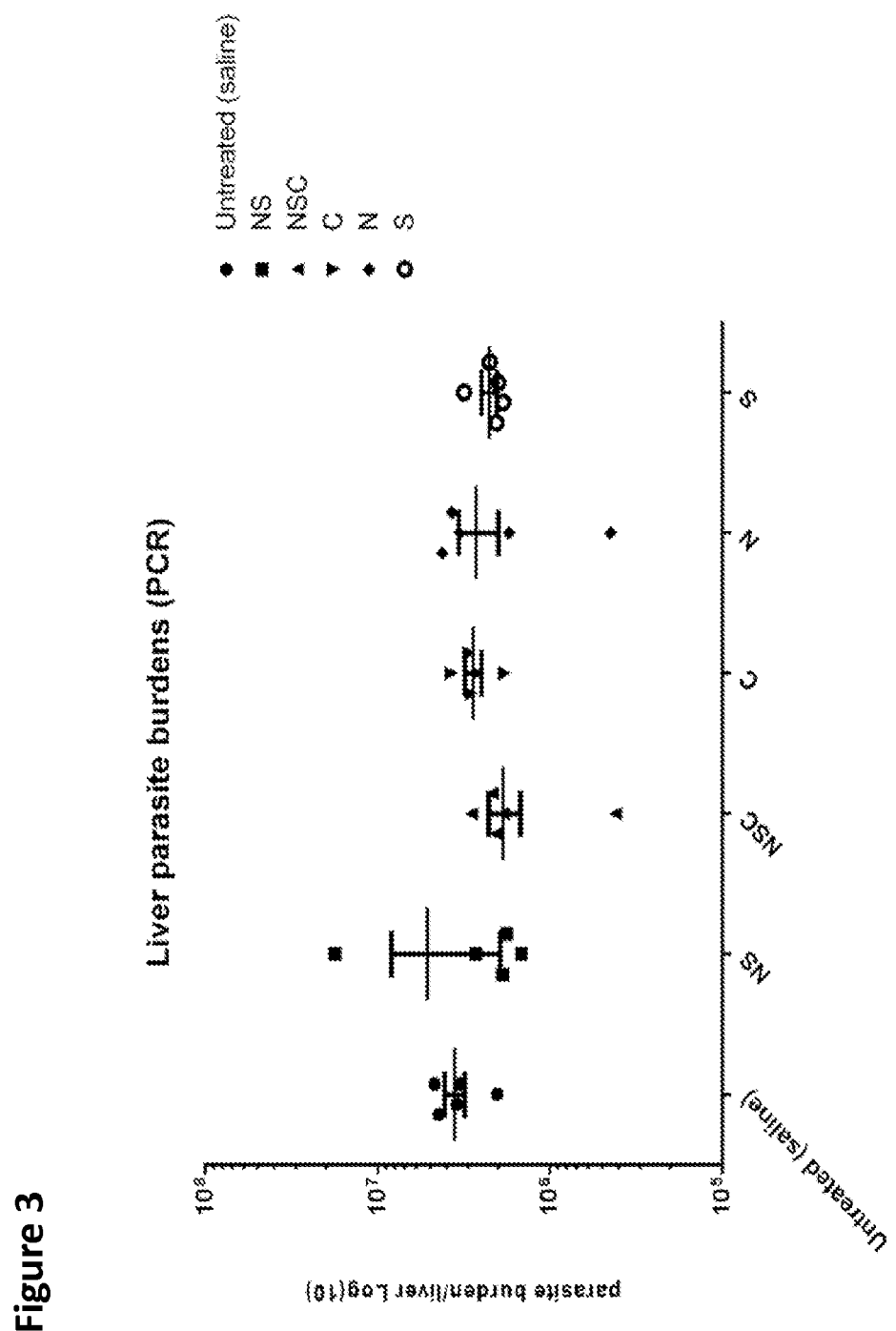
FIG. 3 shows PCR analysis of the parasite burden in the livers of BALB/c mice immunized with saline, NS fusion polypeptide, NSC fusion polypeptide, CpB (C), NH (N), and SMT (S) and challenged with *L. donovanni* promastigotes.
Figure 4:
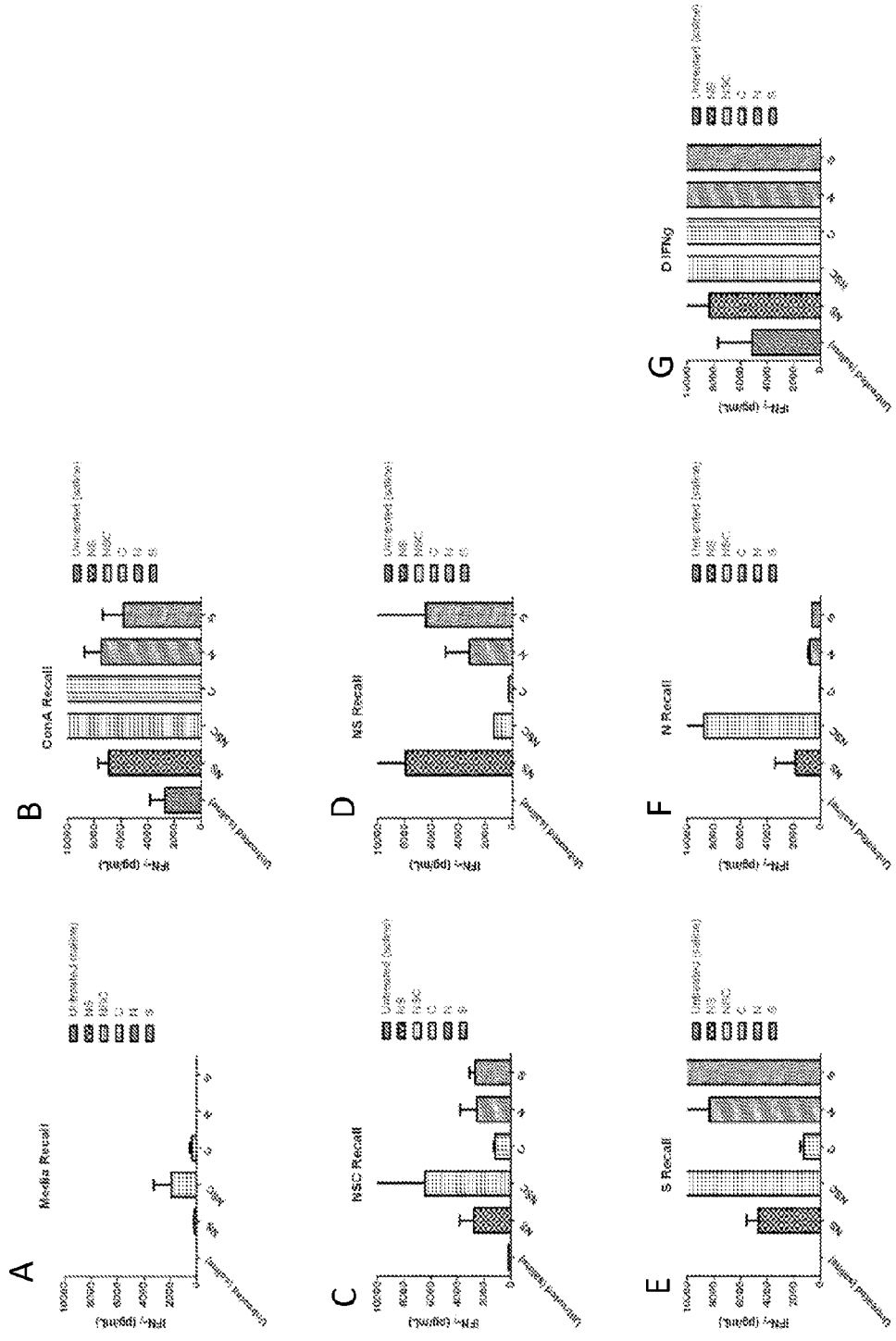
FIG. 4 shows immunogencity as measured by IFN-γ secretion of spleen cell cultures from mice immunized with NSC fusion polypeptide (NH, SMT, and CpB). Data in panels A-F represent spleen cell cultures from mice immunized with the NSC fusion polypeptide, the individual polypeptides or saline as a negative control and the fusion polypeptide NS as a positive control as indicated on the horizontal axis then restimulated in vitro (a recall response) with the indicated antigen and the secretion of IFN-γ measured by ELISA: A) Media restimulation; B) ConA restimulation; C) NSC fusion polypeptide (fusion of NH, SMT and CpB); D) NS restimulation; E) SMT restimulation (S); F) NH restimulation (N) and; G) Compilation data in A-F for restimulation spleen cell cultures with of the matched immunizing polypeptide.
Figure 5:
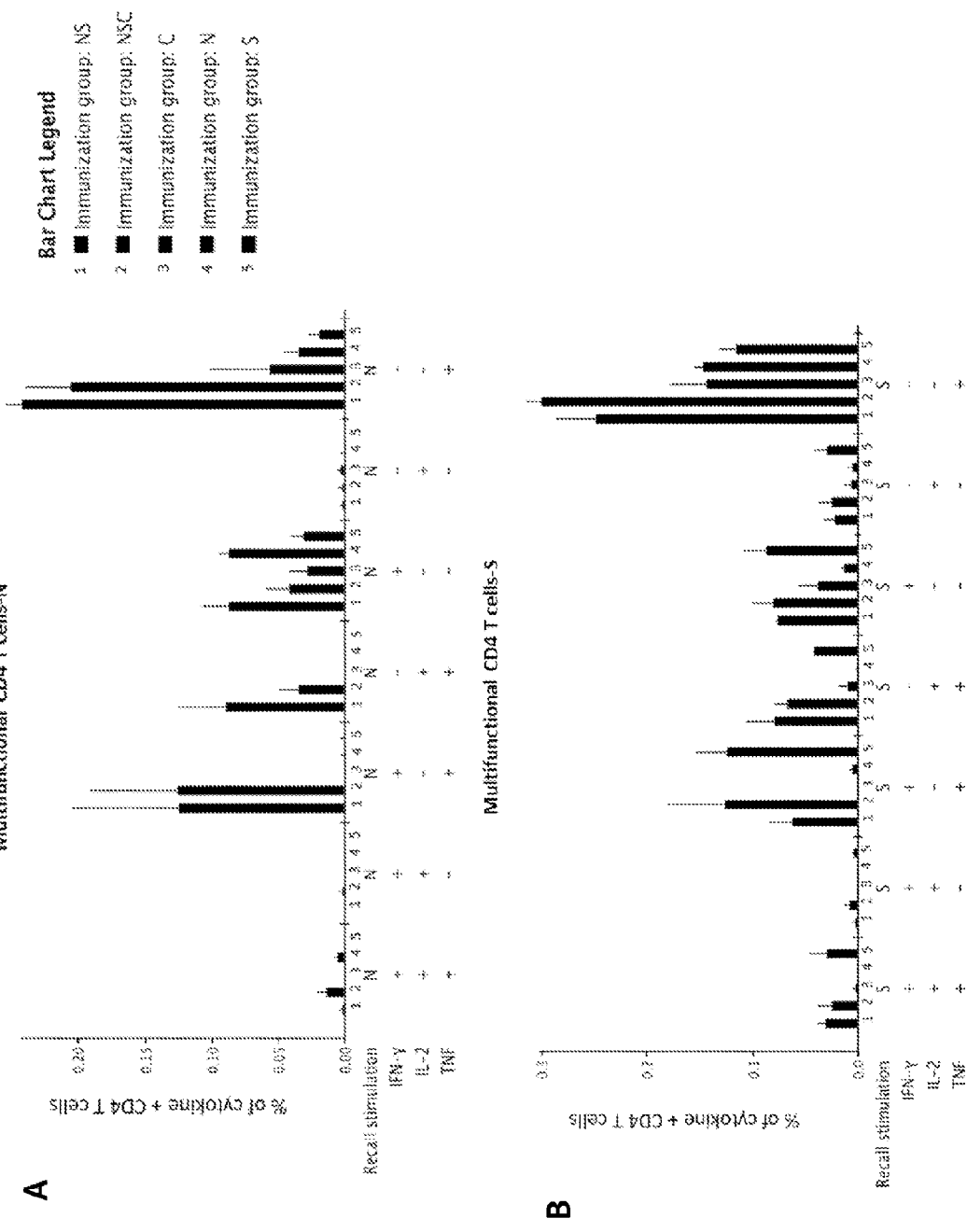
FIG. 5 shows flow cytometry analysis of spleen cell cultures from mice immunized with NS, NSC, CpB, NH or SMT and restimulated in vitro with A) NH, B) SMT, C) CpB or D) NSC for the percentage of cells secreting IFN-γ, IL-2, or TNF. CD4 T cells that produce multiple cytokines are termed multifunctional.
Figure 5:
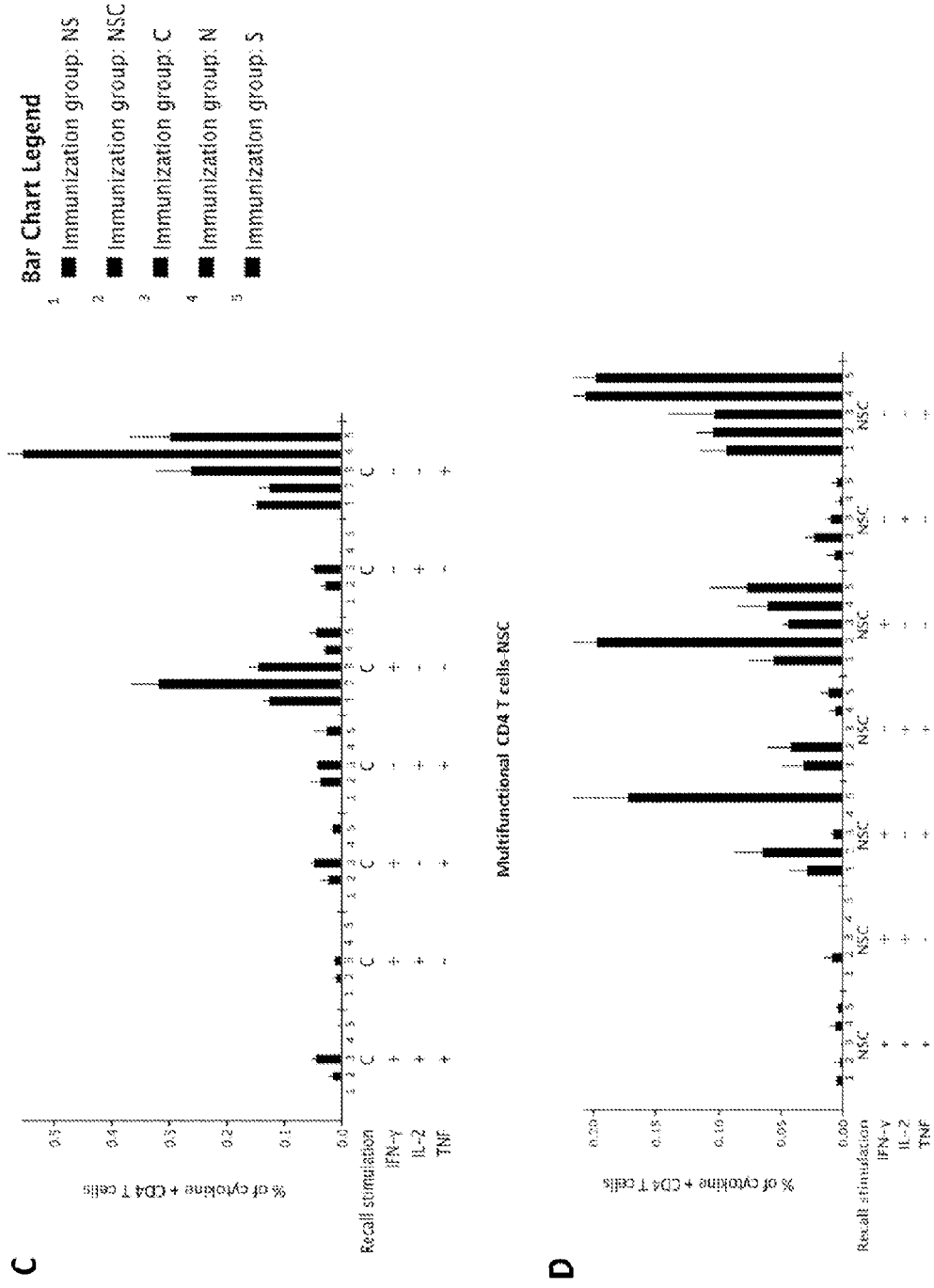

Mice immunized with the fusion polypeptide NSC had a lower parasite burden than control mice one month after experimental infection with mean $1.88 \times 10^6$ versus a mean of $3.60 \times 10^6$ for unimmunized mice as determined by real time PCR (FIG. 3). Antigen-specific IFNγ secretion was measured 1 month after completion of immunization by incubating spleen cells with antigen for 4 days, collection of the culture supernatant then ELISA. Mice immunized with NSC demonstrated IFNγ secretion in response to N, S, C and NSC (FIG. 4 A-G). Flow cytometry analysis of spleen cell culture stimulated with either the fusion polypeptide, NSC, or the individual polypeptides of the fusion (N, S, or C) demonstrates that the antigen specific secretion of IFNγ was predominantly by CD4 T cells including multifunctional CD4 T cells secreting IFNγ and TNF, and single positive IFNγ T cells (FIG. 5A-D). Indicative of wide spread cross-species reactivity, IFNγ was also secreted from cells obtained from NS immunized mice, but not negative control mice, in response to incubation with lysates of L. donovani, L. infantum, L. major, L. brasiliensis, L. mexicana and L. tropica (data not shown). Although IL-5 was also secreted in response to these stimulants, levels were minor in comparison to the IFNγ levels measured (data not shown).

Potentiation or Enhancement of the Immune Response to an Individual Polypeptide when Presented in the Context of a Fusion Polypeptide.

Figure 6:
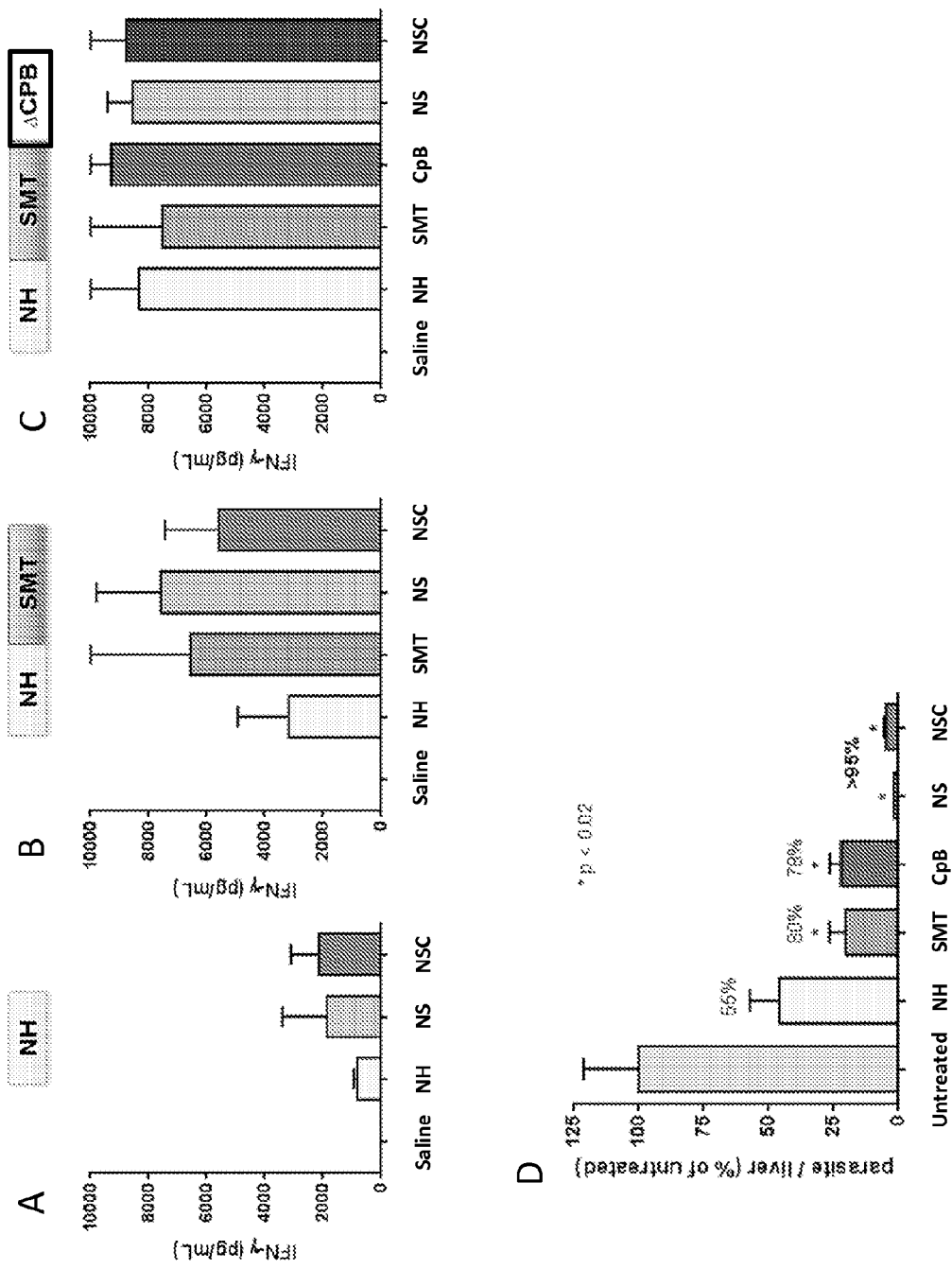
FIG. 6 shows immunogenicity as measured by IFN-γ secretion of spleen cell cultures from mice immunized with A) the peptide NH, B) the NS fusion polypeptide (fusion of NH and SMT) or C) the NSC fusion polypeptide (fusion of NH, SMT, and CpB) and restimulated in vitro (a recall response) with saline (negative control) or the indicated antigens including: the individual peptides of the fusions (NH, SMT CpB), the fusion polypeptide NS, or the NSC fusion polypeptide. The quantitation of the secretion of IFN-γ was measured by ELISA.

The individual polypeptides and fusion polypeptides of the invention were for the purposes of these examples formulated within stable emulsions with the TLR4 adjuvant, GLA. Balb/C mice were immunized subcutaneously 3 times at 3 weeks apart (prime/boost/boost) with 5 μg of either FIG. 6, Panel A) the individual polypeptide NH of the fusions, or 5 μg of FIG. 6, Panel B) the fusion polypeptides NS or 5 μg of FIG. 6, Panel C) the fusion polypeptide NSC formulated in 5 μg of GLA-SE in a total volume of 100 μl. One month (Week 10) after the final immunization, animals were sacrificed and their spleens harvested. Duplicate wells of $2 \times 10^5$ single cell spleen suspensions were incubated with 10 μg/ml of the individual polypeptides of the fusions (NH, SMT, CpB) or 10 μg/ml of the NS or NSC fusion polypeptides to assess antigen-specific recall responses by quantitation of γIFN secretion by ELISA. The data in FIG. 6, Panel A shows that spleen cells from animals immunized with the polypeptide NH secrete γIFN in response to in vitro restimulation with the NH polypeptide as well as NH presented in the context of the NS or NSC fusion polypeptides of the invention. FIG. 6, Panel B shows that spleen cells from animals immunized with the fusion polypeptide NS secrete γIFN in response to in vitro restimulation with the individual polypeptides NH or SMT as well as the fusions NS or NSC. FIG. 6, Panel C demonstrates spleen cells from animals immunized with the fusion polypeptide NSC secrete γIFN in response to in vitro restimulation with the individual polypeptides NH, SMT or CpB as well and the fusions NS or NSC. Comparing FIG. 6, Panels A-C demonstrates that the immune response to the NH polypeptide is improved or enhanced when it is presented in the context of a fusion polypeptide. This improvement or enhancement of the recognition of an individual polypeptide of a fusion is best demonstrated by comparing the secretion of γIFN produced from animals immunized with NS to those immunized with NSC. In animals immunized with NS the recall response to the NH polypeptide is approximately half the response to SMT (FIG. 6, Panel B), however, animals immunized with NSC (FIG. 6, Panel C) (in which CpB is added to the NS fusion) the recall response to the NH, SMT, or CpB individual polypeptides is not only enhanced but the recall responses are equivalent when stimulated by any of the individual polypeptides of the fusion or the fusion polypeptides NS and NSC.

In addition, a cohort of animal immunized as described above was assessed for reduction in parasite burden by challenge via intravenous injection with up to $5 \times 10^6$ L. donovani promastigotes. Livers were harvested one month post-challenge and parasite burdens determined by real time PCR quantitation by methods known in the art. Data in FIG. 6, Panel D shows that animals immunized with the fusion polypeptides demonstrated greater reductions in parasite burden when immunized with the fusion polypeptides (NS or NSC) compared to the individual polypeptides of the fusions (NH, SMT, or CpB).

Ability of Fusion Polypetides of the Invention to Provide Protection Against Visceral Leishmaniasis (VL) in a Balb/C Model by Assessing the Reduction in Parasite Burden in Mice Immunized with the Fusion Polypeptide and Challenged with L. Donovani Promastigotes.

Figure 7:
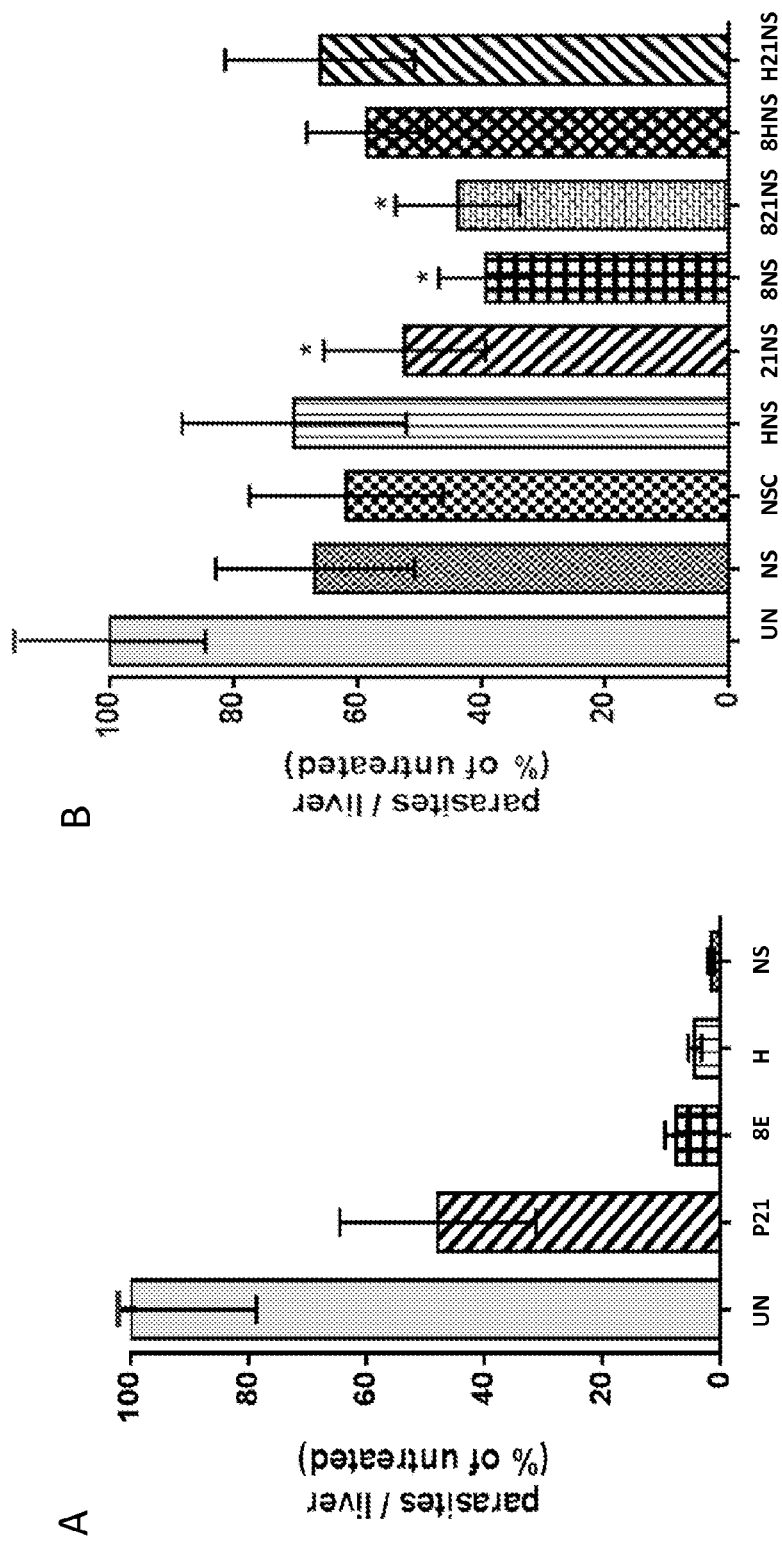
FIG. 7 shows PCR analysis of the parasite burden in the livers of BALB/c mice immunized with saline, individual polypeptides, or the fusion polypeptides of the invention. Panel A shows the parasite burden in the livers of mice immunized with saline, the P21polypeptide (21), the mtHSP70 polypeptide (8E), the H2b polypeptide (H) or the NS fusion polypeptide and challenged with *L. donovanni* promastigotes. Panel B shows the parasite burden in the livers of mice immunized with saline, the NS, NSC, HNS, 21NS, 8NS, 821NS, 8HNS, or H21NS fusion polypeptides challenged with *L. donovanni* promastigotes.

The fusion polypeptides were also evaluated for their ability to protect against visceral Leishmaniasis (VL) using the Balb/c mouse model. Briefly, mice were immunized subcutaneously 3 times at 3 weeks apart (prime/boost/boost) with 5 μg individual polypeptides of the fusions, or 5 μg fusion polypeptides formulated in 5 μg of GLA-SE in a total volume of 100 μl or 100 μl of saline alone as controls. One month after the last immunization, mice were challenged via intravenous injection with up to 5×106 L. donovani promastigotes. Livers were harvested one month post-challenge and parasite burdens determined by real time PCR quantitation by methods known in the art. Reductions in parasite burden following immunization with fusion polypeptides or the individual polypeptides of the fusions or control saline are presented. Data presented is normalized to 100% for unimmunized and infected animals. Data in FIG. 7A demonstrate that comparison of animals immunized with individual polypeptides of the inventions P21(designated P), 8E (designated E), H2b (designated H) and the fusion polypeptide NS all demonstrate reduction in parasite burden in the livers of infected animals with the greatest protection produced by the fusion polypeptide NS (a fusion of NH and SMT). Data in FIG. 7B demonstrates the improved protection afforded by fusion polypeptides of the invention by the addition of additional polypeptide antigens to the NS fusion.

As would be recognized by the skilled artisan, these and other changes can be made to the embodiments of the invention in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled

SEQUENCES

NSC: NH$_{1-314}$ + SMT$_{2-353}$ + CPB$_{154-443}$
Nh (1 . . . 942) + SMT (943 . . . 1998) + CPB (1999 . . . 2868)
MW = 105,106 Daltons

```
N ─┤ NH │ SMT │ CPB(154-443) ├─ C
```

SEQ ID NO: 1 Polynucleotide encoding NSC Fusion Polypeptide
ATGCCGCGCAAGATTATTCTCGATTGTGATCCCGGGATCGATGATGCCGTGGCCATCTTTCTCGCCCACGGCAACCCGGAGGTCGAGCTGCTGG
CCATTACGACGGTGGTGGGCAACCAGACCCTGGAGAAGGTGACCCGGAACGCGCGGCTGGTAGCTGACGTAGCCGGCATCGTTGGTGTGCCCGT
CGCGGCTGGTTGCACCAAGCCCCTCGTGCGCGGTGTGCGGAATGCCTCTCAGATTCATGGCGAAACCGGCATGGGTAACGTCTCCTACCCACCA
GAGTTCAAGACAAAGTTGGACGGCCGTCATGCAGTGCAGCTGATCATCGACCTTATCATGTCGCACGAGCCGAAGACGATCACGCTTGTGCCTA
CGGGTGGCCTGACGAACATTGCGATGGCTGTCCGTCTTGAGCCGCGCATCGTGGACCGTGTGAAGGAGGTGGTTCTGATGGGTGGCGGCTACCA
TACTGGTAATGCGTCCCCTGTAGCGGAGTTCAACGTCTTCGTCGACCCGGAGGCGGCGCACATTGTGTTCAACGAGAGCTGGAACGTAACGATG
GTGGGGCTGGACCTAACGCACCAGGCACTCGCCACGCCGGCGGTCCAGAAGCGAGTGAAGGAGGTGGGCACGAAGCCGGCTGCCTTCATGCTGC
AGATTTTGGACTTTTACACGAAGGTGTACGAAAAGGAGCGCAACACGTACGCGACGGTGCACGATCCCTGCGCTGTGGCGTACGTGATTGACCC
CACCGTGATGACGACGGAGCAAGTGCCAGTGGACATCGAGCTGAATGGGCACTGACGACTGGGATGACGGTCGCGGACTTCCGCTACCCACGG
CCAAAGCACTGCCACACGCAGGTGGCTGTGAAGCTGGACTTCGACAAGTTTTGGTGCCTCGTGATTGACGCACTCAAGCGCATCGGCGATCCTC
AATCCGCCGGTGGCCGTGAGACCGCGCCGACGAACCTGATTCGTCGCCGCAACAAGGACGAGACAAACGGGGATGTCAGCGCCGCCGCCGACCG
CTTCCGCGACCGCTTCGAGAAGGCAACCCTCGAGGAGCGCAAGGCCGCCACCACGACGATGGTCAACGAGTACTACGACCTGGTGACGGACTTC
TACGAGTACGGCTGGGGCCAGAACTTCCATTTCGCGCCGCGCTACCGCGGCGAGACCTTCTTCGAGTCCCTCGCGCGCCACGAGTACTTCCTGG
CCGCTCGCGGCGGCTTCATGGAGGGCGACCACATCGTCGACGTGGGCTGCGGCGTCGGCGGCCGCCAACATGGTTCGCCTCACGCGCTG
CAACGTCATCGGCGTCAACAACAACGATTACCAGATCAGCCGCGCTCGCCGTCATGACGCGCTCGCCGGTATGAGCTCCAAGATCGACTACGTC
AAGACCGACTTCTGCAACATGAGCTTAGCCGACAACACCTTCGACGGCGCCTACGCCATCGAGGCCACCTGCCACGCAAAGGACAAGGTCAAGT
GCTATAGCGAGGTCTTCCGTGTCATCAAGCCCGGCACCTGCTTTGTCCTGTACGAGTGGTGCATGACCGACAAGTACAACCCCAATGACGAGTA
CCACCGCACAATCAAGCACCGCATCGAGCTGGGCGACGGCTGCCGGAGATGGAGACGTGCAAACAGGTGATCGAGTACATGAAGCAGGCCGGC
TTCGTGGTGGAGGAGGCCATAGACGTCATCAGTCAGTTCGAGTCCAGCCCCATCAAGAGTATCCCGTGGTACCAGCCGCTCCTCGGCGACTATT
CGTCCCTGCAGGGCCTGCGCTCTACCCCGATTGGCCGCATCCTCACGAACGTCATGTGTCGCGTGCTGGAGTTCGTGCGCCTAGCTCCGAAGGG
CACGTACAAGGCGACGGAGATTTTGGAGGAGGCTGCGGAAAGCCTGGTGGTCGGTCAGCTCGGCATCTTCACGCCGTCCTTCTACATCCGC
GCTCGCAAGCCGTCCAAGCAGGCTTCGGCGGTCGGCAACATCGAGTCGCAGTGGGCCCGTGCCGGCCACGGCTTGGTGAGCCTGTCGGAGCAGC
AGCTGGTGAGCTGCGATGACAAAGACAATGGCTGCAACGGCGGGCTGATGCTGCAGGCGTTCGAGTGGCTGCTGCGACACATGTACGGGATCGT
GTTCACGGAGAAGAGCTACCCCTACACGTCCGGCAACGGTGATGTGGCCGAGTGCTTGAACAGCAGTAAACTCGTTCCCGGCGCGCAAATCGAC
GGCTACGTGATGATCCCGAGCAACGAAACGGTTATGGCTGCGTGGCTTGCGGAGAATGGCCCCATCGCATTGCGGTCGACGCCAGCTCCTTCA
TGTCTTACCAGAGCGGCGTGCTGACCAGCTGCGCTGGCGATGCACTGAACCACGGCGTGCTGCTCGTGGGTACAACAAGACCGGTGGGGTTCC
GTACTGGGTGATCAAGAACTCGTGGGGTGAGGACTGGGGCGAGAAGGGCTACGTGCGCGTGGTCATGGGGCTGAACGCGTGCCTGCTCAGTGAA
TACCCCGTGTCCGCGCATGTGCCGCGGAGTCTCACCCCTGGCCCGGGCACGGAGAGCGAGGAGCGCGCCCCTAAACGGGTGACGGTGGAGCAGA
TGATGTGCACCGATATGTACTGCAGGGAGGGGTGCAAGAAGAGTCTTCTCACCGCGAACGTGTGCTACAAGAACGGGGAGGCGGCTCCTCTAT
GACGAAGTGCGGTCCGCAGAAGGTGCTGATGTGCTCGTACTCGAACCCTCATTGCTTTGGTCCTGGGCTGTGCCTCGAGACTCCTGATGGCAAG
TGCGCGCCGTACTTCTTGGGCTCGATCATGAACACCTGCCAGTACACG SEQ ID NO: 2 Amino Acid Sequence of the NSC Fusion Polypeptide
MPRKIILDCDPGIDDAVAIFLAHGNPEVELLAITTVV SEQUENCES-continued

```
CGTCCCTGCAGGGCCTGCGCTCTACCCCGATTGGCCGCATCCTCACGAACGTCATGTGTCGCGTGCTGGAGTTCGTGCGCCCTAGCTCCGAAGGG
CACGTACAAGGCGACGGAGATTTTGGAGGAGGCTGCGGAAAGCCTGGTGGTGGGCGGTCAGCTCGGCATCTTCACGCCGTCCTTCTACATCCGC
GCTCGCAAGCCGTCCAAGCAGGCTAGCGCCTCCGCTGAGCCGCACAAGGCGGCCGTTGACGTCGGCCCGCTGAGCGTTGGCCCGCAGAGCGTCG
GCCCGCTGAGCGTTGGCCCGCAGGCGGTTGGCCCGCTGAGCGTTGGCCCGCAGAGCGTCGGCCCGCTGAGCGTTGGCCCGCAGGCGGTTGGCCC
GCTGAGCGTTGGCCCGCAGAGCGTTGGCCCGCTGAGCGTTGGCCCGCTGAGCGTTGGCCCGCAGAGCGTTGGCCCGCTGAGCGTTGGCAGCCAG
AGCGTCGGCCCGCTGAGCGTTGGTCCGCAGAGCGTCGGCCCGCTGAGCGTTGGCCCGCAGGCGGTTGGCCCGCTGAGCGTTGGCCCGCAGAGC
GTCGGCCCGCTGAGCGTTGGCCCGCAGGCGGTTGGCCCGCTGAGCGTTGGCCCGCAGAGCGTTGGCCCGCTGAGCGTTGGCCCGCAGAGCGTTGG
CCCGCTGAGCGTTGGCAGCCAGAGCGTCGGCCCGCTGAGCGTTGGTCCGCAGAGCGTCGGCCCGCTGAGCGTTGGCCCGCAGAGCGTCGGCCCG
CTGAGCGTTGGCCCGCAGAGCGTCGGCCCGCTGAGCGTTGGTCCGCAGAGCGTTGGCCCGCTGAGCGTTGGCCCGCAGAGCGTTGACGTTAGCC
CGGTGAGC

SEQ ID NO: 4 Amino Acid Sequence of the NSA Fusion Polypeptide
MPRKIILDCDPGIDDAVAIFLAHGNPEVELLAITTVVGNQTLEKVTRNARLVADVAGIVGVPVAAGCTKPLVRGVRNASQIHGETGMGNVSYPP
EFKTKLDGRHAVQLIIDLIMSHEPKTITLVPTGGLTNIAMAVRLEPRIVDRVKEVVLMGGGYHTGNASPVAEFNVFVDPEAAHIVFNESWNVTM
VGLDLTHQALATPAVQKRVKEVGTKPAAFMLQILDFYTKVYEKERNTYATVHDPCAVAYVIDPTVMTTEQVPVDIELNGALTTGMTVADFRYPR
PKHCHTQVAVKLDFDKFWCLVIDALKRIGDPQSAGGRETAPTNLIRRRNKDETNGDVSAAADRFRDRFEKATLEERKAATTTMVNEYYDLVTDF
YEYGWGQNFHFAPRYAGETFFESLARHEYFLAARGGFMEGDHIVDVGCGVGGPARNMVRLTRCNVIGVNNNDYQISRARRHDALAGMSSKIDYV
KTDFCNMSLADNTFDGAYAIEATCHAKDKVKCYSEVFRVIKPGTCFVLYEWCMTDKYNPNDEYHRTIKHRIELGDGLPEMETCKQVIEYMKQAG
FVVEEAIDVISQFESSPIKSIPWYQPLVGDYSSLQGLRSTPIGRILTNVMCRVLEFVRLAPKGTYKATEILEEAAESLVVGGQLGIFTPSFYIR
ARKPSKQASASAEPHKAAVDVGPLSVGPQSVGPLSVGPQAVGPLSVGPQSVGPLSVGPQAVGPLSVGPQSVGPLSVGPLSVGPQSVGPLSVGSQ
SVGPLSVGPQSVGPLSVGPQAVGPLSVGPQSVGPLSVGPQAVGPLSVGPQSVGPLSVGPQSVGPLSVGSQSVGPLSVGPQSVGPLSVGPQSVGP
LSVGPQSVGPLSVGPQSVGPLSBGPQSVDVSPVS NSAf1: NH$_{1-314}$ + SMT$_{2-353}$ + A2$_{1-236}$
Nh (1 . . . 942) + SMT (943 . . . 1998) + A2 (1999 . . . 2703)
MW = 95,928 Daltons
```

```
N | NH | SMT | A2F1 | C
```

```
SEQ ID NO: 5 Polynucleotide encoding NSAfl Fusion Polypeptide
ATGCCGCGCAAGATTATTCTCGATTGTGATCCCGGGATCGATGATGCCGTGGCCATCTTTCTCGCCCACGGCAACCCGGAGGTCGAGCTGCTGG
CCATTACGACGGTGGTGGGCAACCAGACCCTGGAGAAGGTGACCCGGAACGCGCGGCTGGTAGCTGACGTAGCCGGCATCGTTGGTGTGCCCGT
CGCGGCTGGTTGCACCAAGCCCCTCGTGCGCGGTGTGCGGAATGCCTCTCAGATTCATGGCGAAACCGGCATGGGTAACGTCTCCTACCCACCA
GAGTTCAAGACAAAGTTGGACGGCCGTCATGCAGTTGCAGCTGATCATCGACCTTATCATGTCGCACGAGCCGAAGACGATCACGTTGTGCCTA
CGGGTGGCCTGACGAACATTGCGATGGCTGTCCGTCTTGAGCCGCGCATCGTGGACCGTGTGAAGGAGGTGGTTCTGATGGGTGGCGGCTACCA
TACTGGTAATGCGTCCCCTGTAGCGGAGTTCAACGTCTTCGTCGACCCGGAGGCGGCGCACATTGTGTTCAACGAGAGCTGGAACGTAACGATG
GTGGGGCTGGACCTAACGCACCAGGCACTCGACCACGCCGGCGGTCCAGAAGCGAGTGAAGGAGGTGGGCACGAAGCCGGCTGCCTTCATGCTGC
AGATTTTGGACTTTTACACGAAGGTGTACGAAAAGGAGCGCAACACGTACGCGACGGTGCACGATCCCTGCGCTGTGGCGTACGTGATTGACCC
CACCGTGATGACGACGGAGCAAGTGCCAGTGGACATCGAGCTCAATGGGGCACTGACGACTGGGATGACGGTCGCGGACTTCCGCTACCCACGG
CCAAAGCACTGCCACACGCAGGTGGCTGTGAAGCTGGACTTCGACAAGTTTTGGTGCCTCGTGATTGACGCACTCAAGCGCATCGGCGATCCTC
AATCCGCCGGTGGCCGTGAGACCGCGCCGACGAACCTGATTCGTCGCCGCAACAAGGACGAGACCAACGGGGATGTCAGCGCCGCCGCGCCC
CTTCCGCGACCGCTTGAGAAGGCAACCCTGCAGGAGCGCAAGGCCGCCACCACGACGATGGTCAACGAGTACTACGACCTGGTGACGGACTTC
TACGAGTACGGCTGGGGCCAGAACTTCCATTTCGCGCCGCGCTACGCCGGCGAGACCTTCTTCGAGTCCCTGCGCGCCACGAGTACTTCCTGG
CCGCTCGCGGCGGCTTCATGGAGGGCGACCACATCGTCGACGTGGGCTGCGGCGTCGGCGGTCCGGCGCGCAACATGGTTCGCCTCACGCGCTG
CAACGTCATCGGCGTGCAACAACAACGATTACCAGATCAGCCGCGCTCGCCGTCATGACGCGCTCGCCGGATGAGCTCCAAGATCGACTACGTC
AAGACCGACTTCTGCAACATGAGCTTAGCCGACAACACCTTCGACGGCGCCTACGCCATCGAGGCCACCTGCCACGCAAAGGACAAGGTCAAGT
GCTATAGCGAGGTCTTCCGTGTCATCAAGCCCGGCACCTGCTTTGTCCTGTACGAGTGGTGCATGACCGACAAGTACAACCCCAATGACGAGTA
CCACCGCACAATCAAGCACCGCATCGAGCTGGGCGACGGCCTGCCGGAGATGGAGACGTGCAAACAGGTGATCGAGTACATGAAGCAGGCCGGC
TTCGTGGTGGAGGAGGCCATAGACGTCATCAGTCAGTTCGAGTCCAGCCCCATCAAGAGTATCCCGTGGTACCAGCCGCTGGTCGGCGACTATT
CGTCCCTGCAGGGCCTGCGCTCTACCCCGATTGGCCGCATCCTCACGAACGTCATGTGTCGCGTGCTGGAGTTCGTGCGCCCTAGCTCCGAAGGG
CACGTACAAGGCGACGGAGATTTTGGAGGAGGCTGCGGAAAGCCTGGTGGTGGGCGGTCAGCTCGGCATCTTCACGCCGTCCTTCTACATCCGC
GCTCGCAAGCCGTCCAAGCAGGCTATGAAGATCCGCAGCGTGCGTCCGCTTGTGGTGTTGCTGGTGTCCGTCGCGGCGGTGCTCGCACTCAGCG
CCTCCGCTGAGCCACAAGGCGGCCGTTGACGTCGGCCCGCTGAGCGTTGGCCCGCAGAGCGTCGGCCCGCTGAGCGTTGGCCCGCAGGCGGT
TGGCCCGCTGAGCGTTGGCCCGCAGAGCGTCGGCCCGCTGAGCGTTGGCCCGCAGGCGGTTGGCCCGCTGAGCGTTGGCCCGCAGAGCGTTGGC
CCGCTGAGCGTTGGCCCGCTGAGCGTTGGCCCGCAGAGCGTTGGCCCGCTGAGCGTTGGCAGCCAGAGCGTCGGCCCGCTGAGCGTTGGTCCGC
AGAGCGTCGGCCCGCTGAGCGTTGGCCCGCAGGCGGTTGGCCCGCTGAGCGTTGGCCCGCAGAGCGTCGGCCCGCTGAGCGTTGGCCCGCAGGC
GGTTGGCCCGCTGAGCGTTGGCCCGCAGAGCGTTGGCCCGCTGAGCGTTGGCCCGCAGAGCGTTGGCCCGCTGAGCGTTGGCAGCCAGAGCGTC
GGCCCGCTGAGCGTTGGTCCGCAGAGCGTCGGCCCGCTGAGCGTTGGCCCGCAGAGCGTTGGCCCGCTGAGCGTTGGCCCGCAGAGCGTCGGCC
CGCTGAGCGTTGGTCCGCAGAGCGTTGGCCCGCTGAGCGTTGGCCCGCAGAGCGTTGACGTTAGCCCGGTGAGC SEQ ID NO: 6 Amino Acid Sequence of the NSAfl Fusion Polypeptide
MPRKIILDCDPGIDDAVAIFLAHGNPEVELLAITTVVGNQTLEKVTRNARLVADVAGIVGVPVAAGCTKPLVRGVRNASQIHGETGMGNVSYPP
EFKTKLDGRHAVQLIIDLIMSHEPKTITLVPTGGLTNIAMAVRLEPRIVDRVKEVVLMGGGYHTGNASPVAEFNVFVDPEAAHIVFNESWNVTM
VGLDLTHQALATPAVQKRVKEVGTKPAAFMLQILDFYTKVYEKERNTYATVHDPCAVAYVIDPTVMTTEQVPVDIELNGALTTGMTVADFRYPR
PKHCHTQVAVKLDFDKFWCLVIDALKRIGDPQSAGGRETAPTNLIRRRNKDETNGDVSAAADRFRDRFEKATLEERKAATTTMVNEYYDLVTDF
YEYGWGQNFHFAPRYAGETFFESLARHEYFLAARGGFMEGDHIVDVGCGVGGPARNMVRLTRCNBIGVNNNDYQISRARRHDALAGMSSKIDYV
KTDFCNMSLADNTFDGAYAIEATCHAKDKVKCYSEVFRVIKPGTCFVLYEWCMTDKYNPNDEYHRTIKHRIELGDGLPEMETCKQVIEYMKQAG
FVVEEAIDVISQFESSPIKSIPWYQPLVGDYSSLQGLRSTPIGRILTNVMCRVLEFVRLAPKGTYKATEILEEAAESLVVGGQLGIFTPSFYIR
ARKPSKQAMKIRSVRPLVVLLVSVAAVLALSASAEPHKAAVDVGPLSVGPQSVGPLSVGPQAVGPLSVGPQSVGPLSVGPQAVGPLSVGPQSVG
PLSVGPQSVGPLSVGSQSVGPLSVGPQSVGPLSVGPQAVGPLSVGPQSVGPLSVGPQAVGPLSVGPQSVGPLSVGPQSVGPLSVGSQSV
GPLSVGPQSVGPLSVGPQSVGPLSVGPQSVGPLSVGPQSVGPLSVGPQSVDVSPVS HNSA: H2B$_{1-46}$ + NH$_{1-314}$ + SMT$_{2-353}$ + A2$_{23-236}$
H2BN (1 . . . 138) + NH (139 . . . 1080) + SMT (1081 . . . 2136) + A2 (2137 . . . 2778)
MW = 98,942 Daltons
```

```
N | H2BN | NH | SMT | A2 | C
```

SEQUENCES-continued

SEQ ID NO: 7 Polynucleotide encoding HNSA Fusion Polypeptide
```
ATGGCCTCTTCTCGCTCTGCTCCCCGCAAGGCTTCCCACGCGCACAAGTCGCACCGCAAGCCGAAGCGCTCGTGGAACGTGTACGTGGGCCGCT
CGCTGAAGGCGATCAACGCCCAGATGTCGATGTCGCACCGCACGATGCCGCGCAAGATTATTCTCGATTGTGATCCCGGGATCGATGATGCCGT
GGCCATCTTTCTCGCCCACGGCAACCCGGAGGTCGAGCTGCTTGCCATTACGACGGTGGTGGGCAACCAGACCCTGGAGAAGGTGACCCGGAAC
GCGCGGCTGGTAGCTGACGTAGCCGGCATCGTTGGTGTGCCCGTCGCGGCTGGTTGCACCAAGCCCCTCGTGCGCGGTGTGCGGAATGCCTCTC
AGATTCATGGCGAAACCGGCATGGGTAACGTCTCCTACCCACCAGAGTTCAAGACAAAGTTGGACGGCCGTCATGCAGTGCAGCTGATCATCGA
CCTTATCATGTCGCACGAGCCGAAGACGATCACGCTTGTGCCTACGGGTGGCCTGACGAACATTGCGATGGCTGTCCGTCTTGAGCCGCGCATC
GTGGACCGTGTGAAGGAGGTGGTTCTGATGGGTGGCGGCTACCATACTGGTAATGCGTCCCCTGTAGCGGAGTTCAACGTCTTCGTCGACCCGG
AGGCGGCGCACATTGTGTTCAACGAGAGCTGGAACGTAACGATGGTGGGCTGGACCTAACGCACCAGGCACTCGCCACGCCGGCGGTCCAGAA
GCGAGTGAAGGAGGTGGGCACGAAGCCGGCTGCCTTCATGCTGCAGATTTTGGACTTTTACACGAAGGTGTACGAAAAGGAGCGCAACACGTAC
GCGACGGTGCACGATCCCTGCGCTGTGGCGTACGTGATTGACCCCACCGTGATGACGACGGAGCAAGTGCCAGTGGACATCGAGCTCAATGGGG
CACTGACGACTGGGGATGACGGTCGCGGACTTCCGCTACCCACGGCCAAAGCACTGCCACACGCAGGTGGCTGTGAAGCTGGACTTCGACAAGTT
TTGGTGCCTCGTGATTGACGCACTCAAGCGCATCGGCGATCCTCAATCCGCCGGTGGCCGCAACGCGCCGACGAACCTGATTCGTCGCCGC
AACAAGGACGAGACAAACGGGGATGTCAGCGCCGCCGCCGACCGCTTCCGCGACCGCTTCGAGAAGGCAACCCTCGAGGAGCGCAAGGCCGCCA
CCACGACGATGGTCAACGAGTACTACGACCTGGTGACGGACTTCTACGAGTACGGCTGGGGCCAGAACTTCCATTTCGCCGCCGCGCTACGCCGG
CGAGACCTTCTTCGAGTCCCTCGCGCGCCACGAGTACTTCCTGGCCGCTCGCGGCGGCTTCATGGAGGGCGACCACATCGTCGACGTGGGCTGC
GGCTTCGGCGGTCCGGCGCGCAACATGGTTCGCCTCACGCGCTGCAACGTCATCGGCGTCAACAACAACGATTACCAGATCAGCCGCGCTGCC
GTCATGACGCGCTCGCCGGTATGAGCTCCAAGATCGACTACGTCAAGACCGACTTCTGCAACATGAGCTTAGCCGACAACACCTTCGACGGCGCA
CTACGCCATCGAGGCCACCTGCCACGCAAAGGACAAGGTCAAGTGCTATAGCGAGGTCTTCCGTGTCATCAAGCCCGGCACCTGCTTTGTCCTG
TACGAGTGGTGCATGACCGACAAGTACAACCCCAATGACGAGTACCACCGCACAATCAAGCACCGCATCGAGCTGGGCGACGGCCTGCCGGAGA
TGGAGACGTGCAAACAGGTGATCGAGTACATGAAGCAGGCCGGCTTCGTGGTGGAGGAGCCATAGACGTCATCAGTCAGTTCGAGTCCAGCCC
CATCAAGAGTATCCCGTGGTACCAGCCGCTGGTCGGCGACTATTCGTCCCTGCAGGGCCTGCGCTCTACCCCGATTGGCCGCATCCTCACGAAC
GTCATGTGTCGCGTGCTGGAGTTCGTGCGCCTAGCTCCGAAGGGCACGTACAAGGCGACGGAGATTTTGGAGGAGGCTGCGGAAAGCCTGGTGG
TGGGCGGTCAGCTCGGCATCTTCACGCCGTCCTTCTACATCCGCGCTCGCAAGCCGTCCAAGCAGGCTAGCGCCTCCGCTGAGCCGCACAAGGC
GGCCGTTGACGTCGGCCCGCTGAGCGTTGGCCCGCAGAGCGTCGGCCCGCTGAGCGTTGGCCCGCAGGCGGTTGGCCCGCTGAGCGTTGGCCCG
CAGAGCGTCGGCCCGCTGAGCGTTGGCCCGCAGGCGGTTGGCCCGCTGAGCGTTGGCCCAGAGCGTTGGCCCGCTGAGCGTTGGCCGCTGA
GCGTTGGCCCGCAGAGCGTTGGCCCGCTGAGCGTTGGCAGCCAGAGCGTCGGCCCGCTGAGCGTTGGTCCGCAGAGCGTCGGCCCGCTGAGCGT
TGGCCCGCAGGCGGTTGGCCCGCTGAGCGTTGGCCCGCAGAGCGTCGGCCCGCTGAGCGTTGGCCCGCAGGCGGTTGGCCCGCTGAGCGTTGGC
CCGCAGAGCGTTGGCCCGCTGAGCGTTGGCCCGCAGAGCGTTGGCCCGCTGAGCGTTGGCAGCCAGAGCGTCGGCCCGCTGAGCGTTGGTCCGC
AGAGCGTCGGCCCGCTGAGCGTTGGCCCGCAGAGCGTCGGCCCGCTGAGCGTTGGCCCGCAGAGCGTCGGCCCGCTGAGCGTTGGTCCGCAGAG
CGTTGGCCCGCTGAGCGTTGGCCCGCAGAGCGTTGACGTTAGCCCGGTGAGC
```

SEQ ID NO: 8 Amino Acid Sequence of the HNSA Fusion Polypeptide
<u>MASSRSAPRKASHAHKSHRKPKRSWVNYVGRSLKAINAQMSMSHRTMPRKIILDCDPGIDDAVAIFLAHGNPEVELLAITTVVGNQTLEKVTRN
ARLVADVAGIVGVPVAAGCTKPLVRGVRNASQIHGETGMGNVSYPPEFKTKLDGRHAVQLIIDLIMSHEPKTITLVPTGGLTNIAMAVRLEPRI
VDRVKEVVLMGGGYHTGNASPVAEFNVFVDPEAAHIVFNESWNVTMVGLDLTHQALATPAVQKRVKEVGTKPAAFMLQILDFYTKVYEKERNTY
ATVHDPCAVAYVIDPTVMTTEQVPVDIELNGALTTGMTVADFRYPRPKHCHTQVAVDLDFDKFWCLVIDALKRIGDPQ<u>SAGGRETAPTNLIRRR
NKDETNGDVSAAADRFRDRFEKATLEERKAATTMVNEYYDLVTDFYEYGWGQNFHFAPRYAGETFFESLARHEYFLAARGGFMEGDHIVDVGC
GVGGPARNMVRLTRCNVIGVNNNDYQISRARRHDALAGMSSKIDYVKTDFCNMSLADNTFDGAYAIEATCHAKDKVKCYSEVFRVIKPGTCFVL
YEWCMTDKYNPNDEYHRTIKHRIELGDGLPEMETCKQVIEYMKQAGFVVEEAIDVISQFESSPIKSIPWYQPLVGDYSSLQGLRSTPIGRILTN
VMCRVLEFVRLAPKGTYKATEILEEAAESLVVGGQLGIFTPSFYIRARKPSKQ</u>ASASAEPHKAAVDVGPLSVGPQSVGPLSVGPQAVGPLSVGP
QSVGPLSVGPQAVGPLSVGPQSVGPLSVGPLSVGPQSVGPLSVGSQSVGPLSVGPQSVGPLSVGPQAVGPLSVGPQSVGPLSVGPQAVGPLSVG
PQSVGPLSVGPQSVGPLSVGSQSVGPLSVGPQSVGPLSVGPQSVGPLSVGPQSVGPLSVGPQSVDVSPVS</u>

8NSA: (8E)mtHSP70₅₀₉₋₆₆₀ + NH₁₋₃₁₄ + SMT₂₋₃₅₃ + A2₂₃₋₂₃₆
8E (1 . . . 459) + NH (460 . . . 1401) + SMT (1402 . . . 2457) + A2 (2458 . . . 3099)
MW = 110,948 Daltons

| N | 8E | NH | SMT | A2 | C |

SEQ ID NO: 9 Polynucleotide encoding 8NSA Fusion Polypeptide
```
ATGAAGGACAAGGCGACGGGCAAGACGCAGAACATCACGATCACGGCGAACGGCGGGCTGTCGAAGGAGCAGATCGAGCAGATGATCCGCGACT
CGGAGCAGCACGCGGAGGCCGACCGCGTGAAGCGCGAGCTTGTCGAGGTGCGCAACAACGCGGAGACGCAGCTGACAACGGCGGAGAGGCAGCT
CGGCGAGTGGAAGTACGTGAGCGATGCGGAGAAGGAGAACGTGAAGACGCTGGTGGCGGAGCTGCGCAAGGCGATGGAGAACCCGAACGTCGCG
AAGGATGACCTTGCGGCTGCGACGGACAAGCTGCAGAAGGCTGTGATGGAGTGCGGCCGCACAGAGTACCAGCAGGCTGCCGCGGCCAACTCCG
GCAGCACCAGCAACTCCGGTGAGCAGCAGCAGCAGCAGGGCCAAGGTGAGCAGCAGCAGCAGCAGAACAGCGAAGAGAAGAAGATGCCGCGCAA
GATTATTCTCGATTGTGATCCCGGGATCGATGATGCCGTGGCCATCTTTCTCGCCCACGGCAACCCGGAGGTCGAGCTGCTGGCCATTACGACG
GTGGTGGGCAACCAGACCCTGGAGAAGGTGACCCGGAACGCGCGGCTGGTAGCTGACGTAGCCGGCATCGTTGGTGTGCCCGTCGCGGCTGGTT
GCACCAAGCCCCTCGTGCGCGGTGTGCGGAATGCCTCTCAGATTCATGGCGAAACCGGCATGGGTAACGTCTCCTACCCACCAGAGTTCAAGAC
AAAGTTGGACGGCCGTCATGCAGTGCAGCTGATCATCGACCTTATCATGTCGCACGAGCCGAAGACGATCACGCTTGTGCCTACGGGTGGCCTG
ACGAACATTGCGATGGCTGTCCGTCTTGAGCCGCGCATCGTGGACCGTGTGAAGGAGGTGGTTCTGATGGGTGGCGGCTACCATACTGGTAATG
CGTCCCCTGTAGCGGAGTTCAACGTCTTCGTCGACCCGGAGGCGGCGCACATTGTGTTCAACGAGAGCTGGAACGTAACGATGGTGGGCTGGA
CCTAACGCACCAGGCACTCGCCACGCCGGCGGTCCAGAAGCGAGTGAAGGAGGTGGGCACGAAGCCGGCTGCCTTCATGCTGCAGATTTTGGAC
TTTTACACGAAGGTGTACGAAAAGGAGCGCAACACGTACGCGACGGTGCACGATCCCTGCGCTGTGGCGTACGTGATTGACCCCACCGTGATGA
CGACGGAGCAAGTGCCAGTGGACATCGAGCTCAATGGGGCACTGACGACTGGGATGACGGTCGCGGACTTCCGCTACCCACGGCCAAAGCACTG
CCACACGCAGGTGGCTGTGAAGCTGGACTTCGACAAGTTTTGGTGCCTCGTGATTGACGCACTCAAGCGCATCGGCGATCCTCAATCCGCCGGT
GGCCGTGAGACCGCCGCCGACGAACCTGATTCGTCGCCGCAACAAGGACGAGACAAACGGGGATGTCAGCGCCGCCGCCGACCGCTTCCGCGACC
GCTTCGAGAAGGCAACCCTCGAGGAGCGCAAGGCCGCCACCACGACGATGGTCAACGAGTACTACGACCTGGTGACGGACTTCTACGAGTACG
GCTGGGGCCAGAACTTCCATTTCGCCGCCGCGCTACGCCGGCGAGACCTTCTTCGAGTCCCTCGCGCGCCACGAGTACTTCCTGGCCGCTCGCG
GCGGCTTCATGGAGGGCGACCACATCGTCGACGTGGGCTGCGGCGTCGGCGGTCCGGCGCGCAACATGGTTCGCCTCACGCGCTGCAACGTCATCG
GCGTCAACAACAACGATTACCAGATCAGCCGCGCTCGCCGTCATGACGCGCTCGCCGGTATGAGCTCCAAGATCGACTACGTCAAGACCGACTT
CTGCAACATGAGCTTAGCCGACAACACCTTCGACGGCGCCTACGCCATCGAGGCCACCTGCCACGCAAAGGACAAGGTCAAGTGCTATAGCGAG
GTCTTCCGTGTCATCAAGCCCGGCACCTGCTTTGTCCTGTACGAGTGGTGCATGACCGACAAGTACAACCCCAATGACGAGTACCACCGCACAA
TCAAGCACCGCATCGAGCTGGGCGACGGCCTGCCGGAGATGGAGACGTGCAAACAGGTGATCGAGTACATGAAGCAGGCCGGCTTCGTGGTGGA
GGAGGCCATAGACGTCATCAGTCAGTTCGAGTCCAGCCCCATCAAGAGTATCCCGTGGTACCAGCCGCTGGTCGGCGACTATTCGTCCCTGCAG
GGCCTGCGCTCTACCCCGATTGGCCGCATCCTCACGAACGTCATGTGTCGCGTGCTGGAGTTCGTGCGCCTAGCTCCGAAGGGCACGTACAAGG
CGACGGAGATTTTGGAGGAGGCTGCGGAAAGCCTGGTGGTGGGCGGTCAGCTCGGCATCTTCACGCCGTCCTTCTACATCCGCGCTCGCAAGCC
GTCCAAGCAGGCTAGCGCCTCCGCTGAGCCGCACAAGGCGGCCGTTGACGTCGGCCCGCTGAGCGTTGGCCCGCAGAGCGTCGGCCCGCTGAGC
GTTGGCCCGCAGGCGGTTGGCCCGCTGAGCGTTGGCCCGCAGAGCGTCGGCCCGCTGAGCGTTG
```

SEQUENCES-continued

GCCCGCAGAGCGTTGGCCCGCTGAGCGTTGGCCCGCTGAGCGTTGGCCCGCAGAGCGTTGGCCCGCTGAGCGTTGGCAGCCAGAGCGTCGGCCC
GCTGAGCGTTGGTCCGCAGAGCGTCGGCCCGCTGAGCGTTGGCCCGCAGGCGGTTGGCCCGCTGAGCGTTGGCCCGCAGAGCGTCGGCCCGCTG
AGCGTTGGCCCGCAGGCGGTTGGCCCGCTGAGCGTTGGCCCGCAGAGCGTTGGCCCGCTGAGCGTTGGCCCGCAGAGCGTTGGCCCGCTGAGCG
TTGGCAGCCAGAGCGTCGGCCCGCTGAGCGTTGGTCCGCAGAGCGTCGGCCCGCTGAGCGTTGGCCCGCAGAGCGTCGGCCCGCTGAGCGTTGG
CCCGCAGAGCGTCGGCCCGCTGAGCGTTGGTCCGCAGAGCGTTGGCCCGCTGAGCGTTGGCCCGCAGAGCGTTGACGTTAGCCCGGTGAGC

SEQ ID NO: 10 Amino Acid Sequence of the 8NSA Fusion Polypeptide
MKDKATGKTQNITITANGGLSKEQIEQMIRDSEQHAEADRVKRELVEVRNNAETQLTTAERQLGEWKYVSDAEKENVKTLVAELRKAMENPNVA
KDDLAAATDKLQKAVMECGRTEYQQAAAANSGSTSNSGEQQQQQGQGEQQQQQNSEEKKMPRKIILDCDPGIDDAVAIFLAHGNPEVELLAITT
VVGNQTLEKVTRNARLVADVAGIVGVPVAAGCTKPLVRGVRNASQIHGETGMGNVSYPPEFKTKLDGRHAVQLIIDLIMSHEPKTITLVPTGGL
TNIAMAVRLEPRIVDRVKEVVLMGGGYHTGNASPVAEFNVFVDPEAAHIVFNESWNVTMVGLDLTHQALATPAVQKRVKEVGTKPAAFMLQILD
FYTKVYEKERNTYATVHDPCAVAYVIDPTVMTTEQVPVDIELNGALTTGMTVADFRYPRPKHCHTQVAVKLDFDKFWCLVIDALKRIGDPQSAG
GRETAPTNLIRRRNKDETNGDVSAAADRFRDRFEKATLEERKAATTTMVNEYYDLVTDFYEYGWGQNFHFAPRYAGETFFESLARHEYFLAARG
GFMEGDHIVDVGCGVGGPARNMVRLTRCNVIGVNNNDYQISRARRHDALAGMSSKIDYVKTDFCNMSLADNTFDGAYAIEATCHAKDKVKCYSE
VFRVIKPGTCFVLYEWCMTDKYNPNDEYHRTIKHRIELGDGLPEMETCKQVIEYMKQAGFVVEEAIDVISQFESSPIKSIPWYQPLVGDYSSLQ
GLRSTPIGRILTNVMCRVLEFVRLAPKGTYKATEILEEAAESLVVGGQLGIFYPSFYIRARKPSKQASASAEPHKAAVDVGPLSVGPQSVGPLS
VGPQAVGPLSVGPQSVGPLSVGPQAVGPLSVGPQSVGPLSVGPLSVGPQSVGPLSVGSQSVGPLSVGPQSVGPLSVGPQAVGPLSVGPQSVGPL
SVGPQAVGPLSVGPQSVGPLSVGPQSVGPLSVGSQSVGPLSVGPQSVGPLSVGPQSVGPLSVGPQSVGPLSVGPQSVGPLSVGPQSVDVDSPVS 21NSA: p21₁₋₁₉₁ + NH₁₋₃₁₄ + SMT₂₋₃₅₃ + A2₂₃₋₂₃₆
P21 (1 . . . 573) + NH (574 . . . 1515) + SMT (1516 . . . 2571) + A2 (2572 . . . 3213)
MW = 115,082 Daltons N | p21 | NH | SMT | A2 | C SEQ ID NO: 11 Polynucleotide encoding 21NSA Fusion Polypeptide
ATGAGCATTATCAAGGAGGACGACGCCGTGGGCTGCTACATGACGGTGACCCTCGTGGACGACACCAAGGTGGAGGGTACCATCTTCACCTACA
ATCCCAAGGAAGGCATCATAGTACTTCTGTCCCTCCGCGACGATCAGACGAACATGAAGCTGATCCGCACTCCATACATCAAAGAGTTCAGTAT
TTCACACGCTGAGGAGGGAACGCACCTGCCTCCGGCACTGGACTCCGTCATCGTGCCGGCCGCGACAAGTCCATCTTC
AAGCACGCCAGCACGCAGCTCAAGAACGCCGAGGCGAACCGCGAAAAGCACTTCAACTCTGTCACGACCGACACACCGATTGCCACACTCGATG
CGTACCTCAAGCTCCTGCGGCTATACCCCTTCATTGAGTGGAACAGCGACGAGGGTGTCATCCAGGTCTCGGATACCGTCATTGTCGTAGGGGA
CCCCGACTGGCGGACGCCCAAGGCGATGCTGGTAGACGGCGCCCCTGAGAAGGACAGACCGCTCGTAGACCGCCTGCAGGTTGCGCTCGGAAAC
GGCAAGAAGATGCCGCGCAAGATTATTCTCGATTGTGATCCCGGGATCGATGATGCCGTGGCCATCTTTCTCGCCCACGGCAACCCGGAGGTCG
AGCTGCTGGCCATTACGACGGTGGTGGGCAACCAGACCCTGGAGAAGGTGACCCGGAACGCCCGGCTGGTAGCTGACGTAGCCGGCATCGTTGG
TGTGCCCGTCGCGGCTGGTTGCACCAAGCCCCTCGTGCGCGGTGTGCGGAATGCCTCTCAGATTCATGGCGAAACCGGCATGGGTAACGTCTCC
TACCCACCAGAGTTCAAGACAAAGTTGGACGGCCGTCATGCAGTGCAGCTGATCATCGACCTTATCATGTCGCACGAGCCGAAGACGATCACGC
TTGTGCCTACGGGTGGCCTGACGAACATTGCGATGGCTGTCCGTCTTGAGCCGCGCATCGTGGACCGTGTGAAGGAGGTGGTTCTGATGGGTGG
CGGCTACCATACTGGTAATGCGTCCCCTGTAGCGGAGTTCAACGTCTTCGTCGACCCGGAGGCGGCGCACATTGTGTTCAACGAGAGCTGGAAC
GTAACGATGGTGGGCGTGGACCTAACGCACCAGGCACTCGCCACGCCGGCGGTCCAGAAGCGAGTGAAGGAGGTGGGCACGAAGCCGGCTGCCT
TCATGCTGCAGATTTTGGACTTTTACACGAAGGTGTACGAAAAGGAGCGCAACACGTACGCAGGTGCACGATCCCTGCGCTGTGACTACGT
GATTGACCCCACCGTGATGACGACGGAGCAAGTGCCAGTGGACATCGAGCTCAATGGGGCACTGACGACTGGGATGACGGTCGCGGACTTCCGC
TACCCACGGCCAAAGCACTGCCACACGCAGGTGGCTGTGAAGCTGGACTTCGACAAGTTTTGGTGCCTCGTGATTGACGCACTCAAGCGCATCG
GCGATCCTCAATCCGCCGGTGGCCGTGAGACCGCGCCGACGAACCTGATTCGTCGCCGCAACAAGGACGAGACAAACGGGGATGTCAGCGCCGC
CGCCGACCGCTTCCGCGACCGCTTCGAGAAGGCAACCCTCGAGGAGCGCAAGGCCGCCACCACGACGATGGTCAACGAGTACTACGACCTGGTG
ACGGACTTCTACGAGTACGGCTGGGGCCAGAACTTCCATTTCGCGCCGCGCTACGCCGGCGAGACCTTCTTCGAGTCCCTCGCGCACGAGT
ACTTCCTGGCCGCTCGCGGCGGCTTCATGGAGGGCGACCACATCGTCGACGTGGGCTGCGGCGTCGGCGGTCCGGCGCGCAACATGGTTCGCCT
CACGCGCTGCAACGTCATCGGCGTCAACAACAACGATTACCAGATCAGCCGCGCTCGCCGTCATGACGCGCTCGCCGGTATGAGCTCCAAGATC
GACTACGTCAAGACCGACTTCTGCAACATGAGCTTAGCCGACAACACCTTCGACGGCGCCTACGCCATCGAGGCCACCTGCCACGCAAAGGACA
AGGTCAAGTGCTATAGCGAGGTCTTCCGTGTCATCAAGCCCGGCACCTGCTTTGTCCTGTACGAGTGGTGCATGACCGACAAGTACAACCCCAA
TGACGAGTACCACCGCACAATCAAGCACCGCATCGAGCTGGGCGACGGCCTGCCGGAGATGGAGACGTGCAAACAGGTGATCGAGTACATGAAG
CAGGCCGGCTTCGTGGTGGAGGAGGCCATAGACGTCATCAGTCAGTTCGAGTCCAGCCCCATCAAGAGTATCCCGTGGTACCAGCCGCTGGTCG
GCGACTATTCGTCCCTGCAGGGCCTGCGCTCTACCCCGATTGGCCGCATCCTCACGAACGTCATGTGTCGCGTGCTGGAGTTCGTGCGCCTAGC
TCCGAAGGGCACGTACAAGGCGACGGAGATTTTGGAGGAGGCTGCGGAAAGCCTGGTGGTGGGCGGTCAGCTCGGCATCTTCACGCCGTCCTTC
TACATCCGCGCTCGCAAGCCGTCCAAGCAGGCTAGCGCCTCCGCTGAGCCGCACAAGGCGGCCGTTGACGTCGGCCCGCTGAGCGTTGGCCCGC
AGAGCGTCGGCCCGCTGAGCGTTGGCCCGCAGAGCGTTGGCCCGCTGAGCGTTGGCCCGCAGAGCGTCGGCCCGCTGAGCGTTGGCCCGCAGGC
GGTTGGCCCGCTGAGCGTTGGCCCGCAGAGCGTTGGCCCGCTGAGCGTTGGCCCGCTGAGCGTTGGCCCGCAGAGCGTTGGCCCGCTGAGCGTT
GGCAGCCAGAGCGTCGGCCCGCTGAGCGTTGGTCCGCAGAGCGTCGGCCCGCTGAGCGTTGGCCCGCAGGCGGTTGGCCCGCTGAGCGTTGGCC
CGCAGAGCGTCGGCCCGCTGAGCGTTGGCCCGCAGGCGGTTGGCCCGCTGAGCGTTGGCCCGCAGAGCGTTGGCCCGCTGAGCGTTGGCCCGCA
GAGCGTTGGCCCGCTGAGCGTTGGCAGCCAGAGCGTCGGCCCGCTGAGCGTTGGTCCGCAGAGCGTCGGCCCGCTGAGCGTTGGCCCGCAGAGC
GTCGGCCCGCTGAGCGTTGGCCCGCAGAGCGTCGGCCCGCTGAGCGTTGGTCCGCAGAGCGTTGGCCCGCTGAGCGTTGGCCCGCAGAGCGTTG
ACGTTAGCCCGGTGAGC SEQ ID NO: 12 Amino Acid Sequence of the 21NSA Fusion Polypeptide
MSIIKEDDAVGCYMTVTLVDDTKVEGTIFTYNPKEGIIVLLSLRDDQTNMKLIRTPYIKEFSISHAEEGTHLPPALDSFNELPSMHAGRDKSIF
KHASTQLKNAEANREKHFNSVTTDTPIATLDAYLKLLRLYPPIEWNSDEGVIQVSDTVIVVGDPDWRTPKAMLVDGAPEKDRPLVDRLQVALGN
GKKMPRKIILDCDPGIDDAVAIFLAHGNPEVELLAITTVVGNQTLEKVTRNARLVADVAGIVGVPVAAGCTKPLVRGVRNASQIHGETGMGNVS
YPPEFKTKLDGRHAVQLIIDLIMSHEPKTITLVPTGGLTNIAMAVRLEPRIVDRVKEVVLMGGGYNTGNASPVAEFNVFVDPEAAHIVFNESWN
VTMVGLDLTHQALATPAVQKRVKEVGTKPAAFMLQILDFYTKVYEKERNTYATVHDPCAVAYVIDPTVMTTEQVPVDIELNGALTTGMTVADFR
YPRPKHCHTQVAVKLDFDKFWCLVIDALKRIGDPQSAGGRETAPTNLIRRRNKDETNGDVSAAADRFRDRFEKATLEERKAATTTMVNEYYDLV
TDFYEYGWGQNFHFAPRYAGETFFESLARHEYFLAARGGFMEGDHIVDVGCGVGGPARNMVRLTRCNVIGVNNNDYQISRARRHDALAGMSSKI
DYVKTDFCNMSLADNTFDGAYAIEATCHAKDKVKCYSEVFRVIKPGTCFVLYEWCMTDKYNPNDEYHRTIKHRIELGDGLPEMETCKQVIEYMK
QAGFVVEEAIDVISQFESSPIKSIPWYQPLVGDYSSLQGLRSTPIGRILTNVMCRVLEFVRLAPKGTYKATEILEEAAESLVVGGQLGIFTPSF
YIRARKPSKQASASAEPHKAAVDVGPLSVGPQSVGPLSVGPQAVGPLSVGPQSVGPLSVGPQAVGPLSVGPQSVGPLSVGPQSVGPLSV
GSQSVGPLSVGPQSVGPLSVGPQAVGPLSVGPQSVGPLSVGPQAVGPLSVGPQSVGPLSVGPQSVGPLSVGSQSVGPLSVGPQSVGPLSVGPQS
VGPLSVGPQSVGPLSVGPQSVGPLSVGPQSVDVSPVS SEQUENCES-continued 821NS: mtHSP70$_{509-660}$ + p21$_{1-191}$ + NH$_{1-314}$ + SMT$_{2-353}$
8E (1 . . . 459) + p21 (460 . . . 1032) + NH (1033 . . . 1974) + SMT (1975 . . . 3030)
MW = 112,565 Daltons

```
N ─┤ 8E │ p21 │ NH │ SMT ├─ C
```

SEQ ID NO: 13 Polynucleotide encoding 821NS Fusion Polypeptide
ATGAAGGACAAGGCGACGGGCAAGACGCAGAACATCACGATCACGGCGAACGGCGGGCTGTCGAAGGAGCAGATCGAGCAGATGATCCGCGACT
CGGAGCAGCACGCGGAGGCCGACCGCGTGAAGCGCGAGCTTGTGGAGGTGCGCAACAACGCGGAGACGCAGCTGACAACGGCGGAGAGGCAGCT
CGGCGAGTGGAAGTACGTGAGCGATGCGGAGAAGGAGAACGTGAAGACGCTGGTGGCGGAGCTGCGCAAGGCGATGGAGAACCCGAACGTCGCG
AAGGATGACCTTGCGGCTGCGACGGACAAGCTGCAGAAGGCTGTGATGGAGTGCGGCCGCACAGAGTACCAGCAGGCTGCCGCGGCCAACTCCG
GCAGCACCAGCAACTCCGGTGAGCAGCAGCAGCAGGGCCAAGGTGAGCAGCAGCAGCAGAACAGCGAAGGAGAAGAGATGAGCATTAT
CAAGGAGGACGACGCCGTGGGCTGCTACATGACGGTGACCCTCGTGGACGACACCAAGGTGGAGGGTACCATCTTCACCTACAATCCCAAGGAA
GGCATCATAGTACTTCTGTCCCTCCGCGACGATCAGACGAACATGAAGCTGATCCGCACTCCATACATCAAAGAGTTCAGTATTTCACACGCTG
AGGAGGGAACGCACCTGCCTCCGGCACTGGACTCCTTCAACGAGCTTCCGTCCATGCATGCCGGCCGCGACAAGTCCATCTTCAAGCACGCCAG
CACGCAGCTCAAGAACGCCGAGGCGAACCGCGAAAAGCACTTCAACTCTGTCACGACAGACACTCCGATCCATCTCCACACTCGATGCGTACCTCAAG
CTCCTGCGGCTATACCCCTTCATTGAGTGGAACAGCGACGAGGGTGTCATCCAGGTCTCGGATACCGTCATTGTCGTAGGGGACCCCGACTGGC
GGACGCCCAAGGCGATGCTGGTAGACGGCGCCCCTGAGAAGGACAGACCGCTCGTAGACCGCCTGCAGGTTGCGCTCGGAAACGGCAAGAAGAT
GCCGCGCAAGATTATTCTCGATTGTGATCCCGGGATCGATGATGCCGTGGCCATCTTTCTCGCCCACGGCAACCCGGAGGTCGAGCTGCTGGCC
ATTACGACGGTGGTGGGCAACCAGACCCTGGAGAAGGTGACCCGGACGGCTGGTAGCTGACGTAGCCGGCATCGTTGGTGTGCCCGTCG
CGGCTGGTTGCACCAAGCCCCTCGTGCGCGGTGTGCGGAATGCCTCTCAGATTCATGGCGAAACCGGCATGGGTAACGTCTCCTACCCACCAGA
GTTCAAGACAAAGTTGGACGGCCGTCATGCAGTCAGCTGATCATCGACTTATCATGTCGCACGAGCCGAAGACGATCACGCTTGTGCCTACG
GGTGGCCTGACGAACATTGCGATGGCTGTCCGTCTTGAGCCGCGCATCGTGGACCGTGTGAAGGAGGTGGTTCTGATGGGTGGCGGCTACCATA
CTGGTAATGCGTCCCCTGTAGCGGAGTTCAACGTCTTCGTCGACCCGGAGGCGCACATTGTGTTCAACGAGAGCTGGAACGTAACGATGGT
GGGGCTGGACCTAACGCACCAGGCACTCGCCACGCCGGCGGTCCAGAAGCGAGTGAAGGAGGTGGGCACGAAGCCGGCTGCCTTCATGCTGCAG
ATTTTGGACTTTTACACGAAGGTGTACGAAAAGGAGCGCAACACGTACGCGACGGTGCACGATCCCTGCGCTGTGGCGTACGTGATTGACCCCA
CCGTGATGACGACGGAGCAAGTGCCAGTGGACATCGAGCTCAATGGGCACTGACGACTGGGATGACGGTCGCGGACTTCCGCTACCCACGGCC
AAAGCACTGCCACACGCAGGTGGCTGTGAAGCTGGACTTCGACAAGTTTTGGTGCCTCGTGATTGACGCACTCAAGCGCATCGGCGATCCTCAA
TCCGCCGGTGGCCGTGAGACCGCGCCGACGAACCTGATTCGTCGCCGCAACAAGGACGAGACAAACGGGGATGTCAGCGCCGCCGCCGACCGCT
TCCGCGACCGCTTCGAGAAGGCAACCCTCGAGGAGCGCAAGGCCGCCACCACGACGATGGTCAACGAGTACTACGACCTGGTGACGGACTTCTA
CGAGTACGGCTGGGGCCAGAACTTCCATTTCGCGCCGCGCTACGCCGGCGAGACCTTCTTCGAGTCCCTCGCGCGCCACGAGTACTTCCTGGCC
GCTCGCGGCGGCTTCATGGAGGGCGACCACATCGTCGACGTGGGCTGCGGCGTCGGCGGTCCGGCGCGCAACATGGTTCGCTCACGCGTGCA
ACGTCATCGGCGTCAACAACAACGATTACCAGATCAGCCGCGCTCGCGTCATGACGCGCTCGCCGGTATGAGCTCCAAGATCGACTACGTCAA
GACCGACTTCTGCAACATGAGCTTAGCCGACAACACCTTCGACGGCGCCTACGCCATCGAGGCCACCTGCCACGCAAAGGACAAGGTCAAGTGC
TATAGCGAGGTCTTCCGTGTCATCAAGCCCGGCACCTGCTTTGTCCTGTACGAGTGGTGCATGACCGACAAGTACAACCCCAATGACGAGTACC
ACCGCACAATCAAGCACCGCATCGAGCTGGGCGACGGCCTGCCGGAGATGGAGACGTGCAAACAGGTGATCGAGTACATGAAGCAGGCCGGCTT
CGTGGTGGAGGAGGCCATAGACGTCATCAGTCAGTTCGAGTCCAGCCCCATCAAGAGTATCCCGTGGTACCAGCCGCTGGTCGGCGACTATTCG
TCCCTGCAGGGCCTGCGCTCTACCCCGATTGGCCGCATCCTCACGAACGTCATGTGTCGCGTGCTGGAGTTCGTGCGCCTAGCTCCGAAGGGCA
CGTACAAGGCGACGGAGATTTTGGAGGAGGCTGCGGAAAGCCTGGTGGTGGGCGGTCAGCTCGGCATCTTCACGCCGTCCTTCTACATCCGCGC
TCGCAAGCCGTCCAAGCAGGCT SEQ ID NO: 14 Amino Acid Sequence of the 821NS Fusion Polypeptide
MKDKATGKTQNITITANGGLSKEQIEQMIRDSEQHAEADRVKRELVEVRNNAETQLTTAERQLGEWKYVSDAEKENVKTLVAELRKAMENPNVA
KDDLAATDKLQKAVMECGRTEYQQAAAANSGSTSNSGEQQQQQGQGEQQQQQNSEEKK<u>MSIIKEDDAVGCYMTVTLVDDTKVEGTIFTYNPKE</u>
<u>GIIVLLSLRDDQTNMKLIRTPYIKEFSISHAEEGTHLPPALDSFNELPSMHAGRDKSIFKHASTQLKNAEANREKHFNSVTTDTPIATLDAYLK</u>
<u>LLRLYPFIEWNSDEGVIQVSDTVIVVGDPDWRTPKAMLVDGAPEKDRPLVDRLQVALGNGKKMPRKIILDCDPGIDDAVAIFLAHGNPEVELLA</u>
<u>ITTVVGNQTLEKVTRNARLVADVAGIVGVPVAAGCTKPLVRGVRNASQIHGETGMGNVSYPPEFKTKLDGRHAVQLIIDLIMSHEPKTITLVPT</u>
<u>GGLTNIAMAVRLEPRIVDRVKEVVLMGGGYHTGNASPVAEFNVFVDPEAAHIVFNESWNVTMVGLDLTHQALATPAVQKRVKEVGTKPAAFMLQ</u>
<u>ILDFYTKVYEKERNTYATVHDPCAVAYVIDPTVMTTEQVPVDIELNGALTTGMTVADFRYPRPKHCHTQVAVKLDFDKFWCLVIDALKRIGDPQ</u>
<u>SAGGRETAPTNLIRRRNKDETNGDVSAAADRFRDRFEKATLEERKAATTTMVNEYYDLVTDFYEYGWGQNFHFAPRYAGETFFESLARHEYFLA</u>
<u>ARGGFMEGDHIVDVGCGVGGPARNMVRLTRCNVIGVNNNDYQISRARRHDALAGMSSKIDYVKTDFCNMSLADNTFDGAYAIEATCHAKDKVKC</u>
<u>YSEVFRVIKPGTCFVLYEWCMTDKYNPNDEYHRTIKHRIELGDGLPEMETCKQVIEYMKQAGFVVEEAIDVISQFESSPIKSIPWYQPLVGDYS</u>
<u>SLQGLRSTPIGRILTNVMCRVLEFVRLAPKGTYKATEILEEAAESLVVGGQLGIFTPSFYIRARKPSKQA</u>

HNS: H2B$_{1-46}$ + NH$_{1-314}$ + SMT$_{2-353}$
H2BN (1 . . . 138) + NH (139 . . . 1080) + SMT (1081 . . . 2136)
MW = 79,205 Daltons

```
N ─┤ H2BN │ NH │ SMT ├─ C
```

SEQ ID NO: 15 Polynucleotide encoding HNS Fusion Polypeptide
ATGGCCTCTTCTCGCTCTGCTCCCCGCAAGGCTTCCCACGCGCACAAGTCGCACCGCAAGCCGAAGCGCTCGTGGAACGTGTACGTGGGCCGCT
CGCTGAAGGCGATCAACGCCCAGATGTCGATGTCGCACCGCACG<u>ATGCCGCGCAAGATTATTCTCGATTGTGATCCCGGGATCGATGATGCCGT</u>
<u>GGCCATCTTTCTCGCCCACGGCAACCCGGAGGTCGAGCTGCTGGCCATTACGACGGTGGTGGGCAACCAGACCCTGGAGAAGGTGACCCGGAAC</u>
<u>GCGCGGCTGGTAGCTGACGTAGCCGGCATCGTTGGTGTGCCCGTCGCCGGCTGGTTGCACCAAGCCCCTCGTGCGCGGTGTGCGGAATGCCTCTC</u>
<u>AGATTCATGGCGAAACCGGCATGGGTAACGTCTCCTACCCACCAGAGTTCAAGACAAAGTTGGACGGCCGTCATGCAGTCAGCTGATCATCGA</u>
<u>CCTTATCATGTCGCACGAGCCGAAGACGATCACGCTTGTGCCTACGGGTGGCCTGACGAACATTGCGATGGCTGTCCGTCTTGAGCCGCGCATC</u>
<u>GTGGACCGTGTGAAGGAGGTGGTTCTGATGGGTGGCGGCTACCATACTGGTAATGCGTCCCCTGTAGCGGAGTTCAACGTCTTCGTCGACCCGG</u>
<u>AGGCCGCACATTGTGTTCAACGAGAGCTGGAACGTAACGATGGTGGGGCTGGACCTAACGCACCAGGCACTCGCCACGCCGGCGGTCCAGAA</u>
<u>GCGAGTGAAGGAGGTGGGCACGAAGCCGGCTGCCTTCATGCTGCAGATTTTGGACTTTTACACGAAGGTGTACGAAAAGGAGCGCAACACGTAC</u>
<u>GCGACGGTGCACGATCCCTGCGCTGTGGCGTACGTGATTGACCCCACCGTGATGACGACGGAGCAAGTGCCAGTGGACATCGAGCTCAATGGGC</u>
<u>ACTGACGACTGGGATGACGGTCGCGGACTTCCGCTACCCACGGCCAAAGCACTGCCACACGCAGGTGGCTGTGAAGCTGGACTTCGACAAGTT</u>
<u>TTGGTGCCTCGTGATTGACGCACTCAAGCGCATCGGCGATCCTCAATCCGCCGGTGGCCGTGAGACCGCGCCGACGAACCTGATTCGTCGCCGC</u>
<u>AACAAGGACGAGACAAACGGGGATGTCAGCGCCGCCGCCGACCGCTTCCGCGACCGCTTCGAGAAGGCAACCCTCGAGGAGCGCAAGGCCGCCA</u>
<u>CCACGACGATGGTCAACGAGTACTACGACCTGGTGACGGACTTCTACGAGTACGGCTGGGGCCAGAACTTCCATTTCGCGCCGCGCTACGCCGG</u>
<u>CGAGACCTTCTTCGAGTCCCTCGCGCGCCACGAGTACTTCCTGGCCGCTCGCGGCGGCTTCATGGAGGGCGACCACATCGTCGACGTGGGCTGC</u>
<u>GGCGTCGGCGGTCCGGCGCGCAACATGGTTCGCCTCACGCGCTGCAACGTCATCGGCGTCAACAACAACGATTACCAGATCAGCCGCGCTCGCC</u>
<u>GTCATGACGCGCTCGCCGGTATGAGCTCCAAGATCGACTACGTCAAGACCGACTTCTGCAACATGAGCTTAGCCGACAACACCTTCGACGGCGC</u>

SEQUENCES-continued

```
CTACGCCATCGAGGCCACCTGCCACGCAAAGGACAAGGTCAAGTGCTATAGCGAGGTCTTCCGTGTCATCAAGCCCGGCACCTGCTTTGTCCTG
TACGAGTGGTGCATGACCGACAAGTACAACCCCAATGACGAGTACCACCGCACAATCAAGCACCGCATCGAGCTGGGCGACGGCCTGCCGGAGA
TGGAGACGTGCAAACAGGTGATCGAGTACATGAAGCAGGCCGGCTTCGTGGTGGAGGAGGCCATAGACGTCATCAGTCAGTTCGAGTCCAGCCC
CATCAAGAGTATCCCGTGGTACCAGCCGCTGGTCGGCGACTATTCGTCCCTGCAGGGCCTGCGCTCTACCCCGATTGGCCGCATCCTCACGAAC
GTCATGTGTCGCGTGCTGGAGTTCGTGCGCCTAGCTCCGAAGGGCACGTACAAGGCGACGGAGATTTTGGAGGAGGCTGCGGAAAGCCTGGTGG
TGGGCGGTCAGCTCGGCATCTTCACGCCGTCCTTCTACATCCGCGCTCGCAAGCCGTCCAAGCAGGCT
```

SEQ ID NO: 16 Amino Acid Sequence of the HNS Fusion Polypeptide
MASSRSAPRKASHAHKSHRKPKRSWNVYVGRSLKAINAQMSMSHRT<u>MPRKIILDCDPGIDDAVAIFLAHGNPEVELLAITTVVGNQTLEKVTRN</u>
<u>ARLVADVAGIVGVPVAAGCTKPLVRGVRNASQIHGETGMGNVSYPPEFKTKLDGRHAVQLIIDLIMSHEPKTITLVPTGGLTNIAMAVRLEPRI</u>
<u>VDRVKEVVLMGGGYHTGNASPVAEFNVGVDPEAAHIVFNESWNVTMVGLDLTHQALATPAVQKRVKEVGTKPAAFMLQILDFYTKVYEKERNTY</u>
<u>ATVHDPCAVAYVIDPTVMTTEQVPVDIELNGALTTGMTVADFRYPRPKHCHTQVAVKLDFDKFWCLVIDALKRIGDPQSAGGRETAPTNLIRRR</u>
<u>NKDETNGDVSAAADRFRDRFEKATLEERKAATTTMVNEYYDLVTDFYEYGWGQNFHFAPRYAGETFFESLARHEYFLAARGGFMEGDHIVDVGC</u>
<u>GVGGPARNMVRLTRCNVIGVNNNDYQISRARRHDALAGMSSKIDYVKTDFCNMSLADNTFDGAYAIEATCHAKDKVKCYSEVFRVIKPGTCFVL</u>
<u>YEWCMTDKYNPNDEYHRTIKHRIELGDGLPEMETCKQVIEYMQAGFVVEEAIDVISQFESSPIKSIPWYQPLVGDYSSLQGLRSTPIGRILTNV</u>
<u>MCRVLEFVRLAPKGTYKATEILEEAAESLVVGGQLGIFTPSFYIRARKPSKQA</u>

8NS: mtHSP70$_{509-660}$ + NH$_{1-314}$ + SMT$_{2-353}$
8E (1 . . . 459) + NH (460 . . . 1401) + SMT (1402 . . . 2457)
MW = 90,970 daltons

```
N | 8E | NH | SMT | C
```

SEQ ID NO: 17 Polynucleotide encoding 8NS Fusion Polypeptide
ATGAAGGACAAGGCGACGGGCAAGACGCAGAACATCACGATCACGGCGAACGGCGGGCTGTCGAAGGAGCAGATCGAGCAGATGATCCGCGACT
CGGAGCAGCACGCGGAGGCCGACCGCGTGAAGCGCGAGCTTGTGGAGGTGCGCAACAACGCGGAGACGCAGCTGACAACGGCGGAGAGGCAGCT
CGGCGAGTGGAAGTACGTGAGCGATGCGGAGAAGGAGAACGTGAAGACGCTGGTGGCGGAGCTGCGCAAGGCGATGGAGAACCCGAACGTCGCG
AAGGATGACCTTGCGGCTGCGACGGACAAGCTGCAGAAGGCTGTGATGGAGTGCGGGCGTCGCACAGAGTACCAGCAGGCTGCCGCGGCCAACTCCG
GCAGCACCAGCAACTCCGGTGAGCAGCAGCAGCAGCAGGGCCAAGGTGAGCAGCAGCAGCAGCAGAACAGCAAGGAAGAAGAA<u>ATGCCGCGCAA</u>
<u>GATTATTCTCGATTGTGATCCCGGGATCGATGATGCCGTGGCCATCTTTCTCGCCCACGGCAACCCGGAGGTCGAGCTGCTGGCCATTACGACG</u>
<u>GTGGTGGGCAACCAGACCCTGGAGAAGGTGACCCGGAACGCGCGGCTGGTAGCTGACGTAGCCGGCATCGTTGGTGTGCCCGTCGCGGCTGGTT</u>
<u>GCACCAAGCCCCTCGTGCGCGGTGTGCGGAATGCCTCTCAGATTCATGGCGAAACCGGCATGGGTAACGTCTCCTACCCACCAGAGTTCAAGAC</u>
<u>AAAGTTGGACGGCCGTCATGCAGTGCAGCTGATCATCGACCTTATCATGTCGCACGAGCCGAAGACGATCACGCTTGTGCCTACGGGTGGCCTG</u>
<u>ACGAACATTGCGATGGCTGTCCGTCTTGAGCCGCGCATCGTGGACCGTGTGAAGGAGGTGGTTCTGATGGGTGGCGGCTACCATACTGGTAATG</u>
<u>CGTCCCCTGTAGCGGAGTTCAACGTCTTCGTCGACCCGGAGGCGGCGCACATTGTGTTCAACGAGAGCTGGAACGTAACGATGGTGGGGCTGGA</u>
<u>CCTAACGCACCAGGCACTCGCCACGCCGGCGGTCCAGAAGCGAGTGAAGGAGGTGGGCACGAAGCCGGCTGCCTTCATGCTGCAGATTTTGGAC</u>
<u>TTTTACACGAAGGTGTACGAAAAGGAGCGCAACACGTACGCGAGGTGCATGATCCTGCGCTGTGGCGTACGTGATTGACCCCACCGTGATGA</u>
<u>CGACGGAGCAAGTGCCAGTGGACATCGAGCTCAATGGGGCACTGACGACTGGGATGACGGTCGCGGACTTCCGCTACCCACGGCCAAAGCACTG</u>
<u>CCACACGCAGGTGGCTGTGAAGCTGGACTTCGACAAGTTTTGGTGCCTCGTGATTGACGCACTCAAGCGCATCGGCGATCCTCAATCCGCCGGT</u>
<u>GGCCGTGAGACCGCGCCGACGAACCTGATTCGTCGCCGCAACAAGGACGAGACAAACGGGGATGTCAGCGCCGCCGCCGACCGCTTCCGCGACC</u>
<u>GCTTCGAGAAGGCAACCCTCGAGGAGCGCAAGGCCGCCACCACGACGATGGTCAACGAGTACTACGACCTGGTGACGGACTTCTACGAGTACGG</u>
<u>CTGGGGCCAGAACTTCCATTTCGCGCCGCGCTACGCCGGCGAGACCTTCTTCGAGTCCCTCGCGCGCCACGAGTACTTCCTGGCCGCTCGCGGC</u>
<u>GGCTTCATGGAGGGCGACCACATCGTCGACGTGGGCTGCGGCGTCGGCGGTCCGGCGCGCAACATGGTTCGCCTCACGCGCTGCAACGTCATCG</u>
<u>GCGTCAACAACAACGATTACCAGATCAGCCGCGCTCGCCGTCATGACGCGCTCGCCGGTATGAGCTCCAAGATCGACTACGTCAAGACCGACTT</u>
<u>CTGCAACATGAGCTTAGCCGACAACACCTTCGACGGCGCCTACGCCATCGAGGCCACCTGCCACGCAAAGGACAAGGTCAAGTGCTATAGCGAG</u>
<u>GTCTTCCGTGTCATCAAGCCCGGCACCTGCTTTGTCCTGTACGAGTGGTGCATGACCGACAAGTACAACCCCAATGACGAGTACCACCGCACAA</u>
<u>TCAAGCACCGCATCGAGCTGGGCGACGGCCTGCCGGAGATGGAGACGTGCAAACAGGTGATCGAGTACATGAAGCAGGCCGGCTTCGTGGTGGA</u>
<u>GGAGGCCATAGACGTCATCAGTCAGTTCGAGTCCAGCCCCATCAAGAGTATCCCGTGGTACCAGCCGCTGGTCGGCGACTATTCGTCCCTGCAG</u>
<u>GGCCTGCGCTCTACCCCGATTGGCCGCATCCTCACGAACGTCATGTGTCGCGTGCTGGAGTTCGTGCGCCTAGCTCCGAAGGGCACGTACAAGG</u>
<u>CGACGGAGATTTTGGAGGAGGCTGCGGAAAGCCTGGTGGTGGGCGGTCAGCTCGGCATCTTCACGCCGTCCTTCTACATCCGCGCTCGCAAGCC</u>
<u>GTCCAAGCAGGCT</u>

SEQ ID NO: 18 Amino Acid Sequence of the 8NS Fusion Polypeptide
MKDKATGKTQNITITANGGLSKEQIEQMRDSEQHAEADRVKRELVEVRNNAETQLTTAERQLGEWKYVSDAEKENVKTLVAELRKAMENPNVA
KDDLAAATDKLQKAVMECGRTEYQQAAAANSGSTSNSGEQQQQQGQGEQQQQQNSEEKK<u>MPRKIILDCDPGIDDAVAIFLAHGNPEVELLAITT</u>
<u>VVGNQTLEKVTRNARLVADVAGIVGVPVAAGCTKPLVRGVRNASQIHGETGMGNVSYPPEFKTKLDGRHAVQLIIDLIMSHEPKTITLVPTGGL</u>
<u>TNIAMAVRLEPRIVDRVKEVVLMGGGYHTGNASPVAEFNVGVDPEAAHIVFNESWNVTMVGLDLTHQALATPAVQKRVKEVGTKPAAFMLQILD</u>
<u>FYTKVYEKERNTYATVHDPCAVAYVIDPTVMTTEQVPVDIELNGALTTGMTVADFRYPRPKHCHTQVAVKLDFDKFWCLVIDALKRIGDPQSAG</u>
<u>GRETAPTNLIRRRNKDETNGDVSAAADRFRDRFEKATLEERKAATTTMVNEYYDLVTDFYEYGWGQNFHFAPRYAGETFFESLARHEYFLAARG</u>
<u>GFMEGDHIVDVGCGVGGPARNMVRLTRCNVIGVNNNDYQISRARRHDALAGMSSKIDYVKTDFCNMSLADNTFDGAYAIEATCHAKDKVKCYSE</u>
<u>VFRVIKPGTCFVLYEWCMTDKYNPNDEYHRTIKHRIELGDGLPEMETCKQVIEYMKQAGFVVEEAIDVISQFESSPIKSIPWYQPLVGDYSSLQ</u>
<u>GLRSTPIGRILTNVMCRVLEFVRLAPKGTYKATEILEEAAESLVVGGQLGIFTPSFYIRARKPSKQA</u>

21NS: p21$_{1-191}$ + NH$_{1-314}$ + SMT$_{2-353}$
P21 (1 . . . 573) + NH (574 . . . 1515) + SMT (1516 . . . 2571)
MW = 95,346 daltons

```
N ─| p21 |╌╌| NH |╌|╌ SMT ╌|─ C
```

SEQ ID NO: 19 Polynucleotide encoding 21NS Fusion Polypeptide
ATGAGCATTATCAAGGAGGACGACGCCGTGGGCTGCTACATGACGGTGACCCTCGTGGACGACACCAAGGTGGAGGGTACCATCTTCACCTACA
ATCCCAAGGAAGGCATCATAGTACTTCTGTCCCTCCGCGACGATCAGACGAACATGAAGCTGATCCGCACTCCATACATCAAAGAGTTCAGTAT
TTCACACGCTGAGGAGGGAACGCACCTGCCTCCGGCACTGGACTCCTGTCAACGAGCTTGCGTCCATGCATGCCGGCCGCGACAAGTCCATCTTC
AAGCACGCCAGCACGCAGCTCAAGAACGCCGAGGCGAACCGCGAAAAGCACTTCAACTCTGTCACGACCGACACGCAGGATTGCCACACTCGATG
CGTACCTCCAAGCTCCTGCGGCTATACCCCTTCATTGAGTGGAACAGCGACGAGGGTGTCATCCAGGTCTCGGATACCGTCATTGTCGTAGGGGA
CCCCGACTGGCGGACGCCCAAGGCGATGCTGGTAGACGGCGCCCCTGAGAAGGACAGACCGCTCGTAGACCGCCTGCAGGTTGCGCTCGGAAAC
GGCAAGAAG<u>ATGCCGCGCAAGATTATTCTCGATTGTGATCCCGGGATCGATGATGCCGTGGCCATCTTTCTCGCCCACGGCAACCCGGAGGTCG</u>
<u>AGCTGCTGGCCATTACGACGGTGGTGGGCAACCAGACCCTGGAGAAGGTGACCCGGAACGCGCGGCTGGTAGCTGACGTAGCCGGCATCGTTGG</u>
```

SEQUENCES-continued

```
TGTGCCCGTCGCGGCTGGTTGCACCAAGCCCCTCGTGCGCGGTGTGCGGAATGCCTCTCAGATTCATGGCGAAACCGGCATGGGTAACGTCTCC
TACCCACCAGAGTTCAAGACAAAGTTGGACGGCCGTCATGCAGTGCAGCTGATCATCGACCTTATCATGTCGCACGAGCCGAAGACGATCACGC
TTGTGCCTACGGGTGGCCTGACGAACATTGCGATGGCTGTCCGTCTTGAGCCGCGCATCGTGGACCGTGTGAAGGAGGTGGTTCTGATGGGTGG
CGGCTACCATACTGGTAATGCGTCCCCGTAGCGGAGTTCAACGTCTTCGTCGACCCGGAGGCGGCGCACATTGTGTTCAACGAGACGTGGAAC
GTAACGATGGTGGGGCTGGACCTAACGCACCAGGCACTCGCCACGCCGGCGGTCCAGAAGCGAGTGAAGGAGGTGGGCACGAAGCCGGCTGCCT
TCATGCTGCAGATTTTGGACTTTTACACGAAGGTGTACGAAAAGGAGCGCAACACGTACGCGACGGTGCACGATCCCTGCGCGTGGCGTACGT
GATTGACCCCACCGTGATGACGACGGAGCAAGTGCCAGTGGACATCGAGCTCAATGGGGCACTGACGACTGGGATGACGGTCGCGGACTTCCGC
TACCCACGGCCAAAGCACTGCCACACGCAGGTGGCTGTGAAGCTGGACTTCGACAAGTTTTGGTGCCTCGTGATTGACGCACTCAAGCGCATCG
GCGATCCTCAATCCGCCGGTGGCCGTGAGACCGCGCCGACGAACCTGATTCGTCGCCGCAACAAGGACGAGACAAACGGGGATGTCAGCGCCGC
CGCCGACCGCTTCCGCGACCGCTTCGAGAAGGCAACCCTCGAGGAGCGCAAGGCCGCCACCACGACGATGGTCAACGAGTACTACGACCTGGTG
ACGGACTTCTACGAGTACGGCTGGGGCCAGAACTTCCATTTCGCCGCCGCGCTACGCCGGCGAGACCTTCTTCGAGTCCCTCGCGCGCCACGAGT
ACTTCCTGGCCGCTCGCGGCGGCTTCATGGAGGGCGACCACATCGTCGACGTGGGCTGCGGCGTCGGCGGTCCGGCGCGCAACATGGTTCGCCT
CACGCGCTGCAACGTCATCGGCGTCAACAACAACGATTACCAGATCAGCCGCCGTCGCCGTCATGACGCGCTCGCCGGTATGAGCTCCAAGATC
GACTACGTCAAGACCGACTTCTGCAACATGAGCTTAGCCGACAACACCTTCGACGGCGCCTACGCCATCGAGGCCACCTGCCACGCAAAGGACA
AGGTCAAGTGCTATAGCGAGGTCTTCCGTGTCATCAAGCCCGGCACCTGCTTTGTCCTGTACGAGTGGTGCATGACCGACAAGTACAACCCCAA
TGACGAGTACCACCGCACAATCAAGCACCGCATCGAGCTGGGCGACGGCCTGCCGGAGATGGAGACGTGCAAACAGGTGATCGAGTACATGAAG
CAGGCCGGCTTCGTGGTGGAGGAGGCCATAGACGTCATCAGTCAGTTCGAGTCCAGCCCCATCAAGAGTATCCCGTGGTACCAGCCGCTGGTCG
GCGACTATTCGTCCCTGCAGGGCCTGCGCTCTACCCCGATTGGCCGCATCCTCACGAACGTCATGTGTCGCGTGCTGGAGTTCGTGCGCCTAGC
TCCGAAGGGCACGTACAAGGCGACGGAGATTTTGGAGGAGGCTGCGGAAAGCCTGGTGGTGGGCGGTCAGCTCGGCATCTTCACGCCGTCCTTC
TACATCCGCGCTCGCAAGCCGTCCAAGCAGGCT
```

SEQ ID NO: 20 Amino Acid Sequence of the 21NS Fusion Polypeptide
MSIIKEDDAVGCYMTVTLVDDTKVEGTIFTYNPKEGIIVLLSLRDDQTNMKLIRTPYIKEFSISHAEEGTHLPPALDSFNELPSMHAGRDKSIF
KHASTQLKNAEANREKHFNSVTTDTPIATLDAYLKLLRLYPFIEWNSDEGVIQVSDTVIVVGDPDWRTPKAMLVDGAPEKDRPLVDRLQVALGN
GKKMPRKIILDCDPGIDDAVAIFLAHGNPEVELLAITTVVGNQTLEKVTRNARLVADVAGIVGVPVAAGCTKPLVRGVRNASQIHGETGMGNVS
YPPEFKTKLDGRHAVQLIIDLIMSHEPKTITLVPTGGLTNIAMAVRLEPRIVDRVKEVVLMGGGYHTGNASPVAEFNVFVDPEAAHIVFNESWN
VTMVGLDLTHQALATPAVQKRVKEVGTKPAAFMLQILDFYTKVYEKERNTYATVHDPCAVAYVIDPTVMTTEQVPVDIELNGALTTGMTVADFR
YPRPKHCHTQVAVKLDFDKFWCLVIDALKRIGDPQSAGGRETAPTNLIRRRNKDETNGDVSAAADRFRDRFEKATLEERKAATTTMVNEYYDLV
TDFYEYGWGQNFHFAPRYAGETFFESLARHEYFLAARGGFMEGDHIVDVGCGVGGPARNMVRLTRCNVIGVNNNDYQISRARRHDALAGMSSKI
DYVKTDFCNMSLADNTFDGAYAIEATCHAKDKVKCYSEVFRVIKPGTCFVLYEWCMTDKYNPNDEYHRTIKHRIELGDGLPEMETCKQVIEYMK
QAGFVVEEAIDVISQFESSPIKSIPWYQPLVGDYSSLQGLRSTPIGRILTNVMCRVLEFVRLAPKGTYKATEILEEAAESLVVGGQLGIFTPSF
YIRARKPSKQA 21SC: p21$_{1-191}$ + SMT$_{2-353}$ + CPB$_{154-443}$
P21 (1 . . . 573) + SMT (574 . . . 1629) + CPB (1630 . . . 2499)
MW = 92,239 daltons

```
N─┤ p21 │ SMT ┊ CPB(154-443) ├─C
```

SEQ ID NO: 21 Polypeptide encoding 21SC Fusion Polypeptide
ATGAGCATTATCAAGGAGGACGACGCCGTGGGCTGCTACATGACAGTGACCCTCGTGGACGACACCAAGGTGGAGGGTACCATCTTCACCTACA
ATCCCAAGGAAGGCATCATAGTACTTCTGTCCCTCCGCGACGATCAGACGAACATGAAGCTGATCCGCACTCCATACATCAAAGAGTTCAGTAT
TTCACACGCTGAGGAGGGAACGCACCTGCCTCCGGCACTGGACTCCTTCAACGAGCTTCCGTCCATGCATGCCGGCCGCGACAAGTCCATCTTC
AAGCACGCCAGCACGCAGCTCAAGAACGCCGAGGCGAACCGCGAAAAGCACTTCAACTCTGTCACGACCGACACACCGATTGCCACACTCGATG
CGTACCTCAAGCTCCTGCGGCTATACCCCTTCATTGAGTGGAACAGCGACGAGGGTGTCATCCAGGTCTCGGATACCGTCATTGTCGTAGGGGA
CCCCGACTGGCGGACGCCCAAGGCGATGCTGGTAGACGGCGCCCCTGAGAAGGACAGACCGCTCGTAGACCGCCTGCAGGTTGCGCTCGGAAAC
GGCAAGAAGTCCGCCGGTGGCCGTGAGACCGCGCCGACGAACCTGATTCGTCGCCGCAACAAGGACGAGACAAACGGGGATGTCAGCGCCGCC
CCGACCGCTTCCGCGACCGCTTCGAGAAGGCAACCCTCGAGGAGCGCAAGGCCGCCACCACGACGATGGTCAACGAGTACTACGACCTGGTGAC
GGACTTCTACGAGTACGGCTGGGGCCAGAACTTCCATTTCGCCGCCGCTACGCCGGCGAGACCTTCTTCGAGTCCCTCGCGCGCCACGAGTAC
TTCCTGGCCGCTCGCGGCGGCTTCATGGAGGGCGACCACATCGTCGACGTGGGCTGCGGCGTCGGCGGTCCGGCGCGCAACATGGTTCGCCTCA
CGCGCTGCAACGTCATCGGCGTCAACAACAACGATTACCAGATCAGCCGCCGTCGCCGTCATGACGCGCTCGCCGGTATGAGCTCCAAGATCGA
CTACGTCAAGACCGACTTCTGCAACATGAGCTTAGCCGACAACACCTTCGACGGCGCCTACGCCATCGAGGCCACCTGCCACGCAAAGGACAAG
GTCAAGTGCTATAGCGAGGTCTTCCGTGTCATCAAGCCCGGCACCTGCTTTGTCCTGTACGAGTGGTGCATGACCGACAAGTACAACCCCAATG
ACGAGTACCACCGCACAATCAAGCACCGCATCGAGCTGGGCGACGGCCTGCCGGAGATGGAGACGTGCAAACAGGTGATCGAGTACATGAAGCA
GGCCGGCTTCGTGGTGGAGGAGGCCATAGACGTCATCAGTCAGTTCGAGTCCAGCCCCATCAAGAGTATCCCGTGGTACCAGCCGCTGGTCGGC
GACTATTCGTCCCTGCAGGGCCTGCGCTCTACCCCGATTGGCCGCATCCTCACGAACGTCATGTGTCGCGTGCTGGAGTTCGTGCGCCTAGCTC
CATCCGCGCTCGCAAGCCGTCCAAGCAGGCTTCGGCGGTCGCAACATCGAGTCGCAGTGGGCCCGTGCCGGCCACGGCTTGGTGAGCCTGTCG
GAGCAGCAGCTGGTGAGCTGCGATGACAAAGACAATGGCTGCAACGGCGGGCTGATGCTGCAGGCGTTCGAGTGGCTGCTGCGACACATGTACG
GGATCGTGTTCACGGAGAAGAGCTACCCCTACACGTCCGGCAACGGTGATGGCCGAGTGCTTGAACAGCAGTAAATCGTTCCCGGCGCGCA
AATCGACGGCTACGTGATGATCCCGAGCAACGAAACGGTTATGGCTGCGTGGCTTGCGGAGAATGGCCCCATCGCGATTGCGGTCGACGCCAGC
TCCTTCATGTCTTACCAGAGCGGCGTGCTGACCAGCTGCGCTGGCGATGCACTGAACCACGGCGTGCTGCTCGGGTACAACAAGACCGGTG
GGGTTCCGTACTGGGTGATCAAGAACTCGTGGGGTGAGGACTGGGGCGAGAAGGGCTACGTGCGCGTGGTCATGGGGCTGAACGCGTGCCTGCT
CAGTGAATACCCCGTGTCCGCGCATGTGCCGGGAGTCTCACCCCTGGCCCGGGCACGGAGAGCGAGGAGCGCGCCCCTAAACGGGTGACGGTG
GAGCAGATGATGTGCACCGATATGTACTGCAGGGAGGGGTGCAAGAAGAGTCTTCTCACCGCGAACGTGTGCTACAAGAACGGGGAGGCGGCT
CCTCTATGACGAAGTGCGGTCCGCAGAAGGTGCTGATGTGCTCGTACTCGAACCCTCATTGCTTTGGTCCTGGGCTGCCTCGAGACTCCTGA
TGGCAAGTGCGCGCCGTACTTCTTGGGCTCGATCATGAACACCTGCCAGTACACG SEQ ID NO: 22 Amino Acid Sequence of the 21SC Fusion Polypeptide
MSIIKEDDAVGCYMTVTLVDDTKVEGTIFTYNPKEGIIVLLSLRDDQTNMKLIRTPYIKEFSISHAEEGTHLPPALDSFNELPSMHAGRDKSIF
KHASTQLKNAEANREKHFNSVTTDTPIATLDAYLKLLRLYPFIEWNSDEGVIQVSDTVIVVGDPDWRTPKAMLVDGAPEKDRPLVDRLQVALGN
GKKSAGGRETAPTNLIRRRNKDETNGDVSAAADRFRDRFEKATLEERKAATTTMVNEYYDLVTDFYEYGWGQNFHFAPRYAGETFFESLARHEY
FLAARGGFMEGDHIVDVGCGVGGPARNMVRLTRCNVIGVNNNDYQISRARRHDALAGMSSKIDYVKTDFCNMSLADNTFDGAYAIEATCHAKDK
VKCYSEVFRVIKPGTCFVLYEWCMTDKYNPNDEYHRTIKHRIELGDGLPEMETCKQVIEYMKQAGFVVEEAIDVISQFESSPIKSIPWYQPLVG
DYSSLQGLRSTPIGRILTNVMCRVLEFVRLAPKGTYKATEILEEAAESLVVGGQLGIFTPSFYIRARKPSKQASAVGNIESQWARAGHGLVSLS
EQQLVSCDDKDNGCNGGLMLQAFEWLLRHMYGIVFTEKSYPYTSGNGDVAECLNSSKLVPGAQIDGYVMIPSNETVMAAWLAENGPIAIAVDAS
SFMSYQSGVLTSCAGDALNHGVLLVGYNKTGGVPYWVIKNSWGEDWGEKGYVRVVMGLNACLLSEYPVSAHVPRSLTPGPGTESEERAPKRVTV
EQMMCTDMYCREGCKKSLLTANVCYKNGGGGSSMTKCGPQKVLMCSYSNPHCFGPGLCLETPDGKCAPYFLGSIMNTCQYT SEQUENCES-continued 821S: mtHSP70$_{509-660}$ + p21$_{1-191}$ + SMT$_{2-353}$
8E (1 . . . 459) + p21 (460 . . . 1032) + SMT (10333 . . . 2091)
MW = 78,510 daltons

```
N [ 8E | p21 | SMT ] C
```

SEQ ID NO: 23 Polynucleotide encoding 821S Fusion Polypeptide
ATGAAGGACAAGGCGACGGGCAAGACGCAGAACATCACGATCACGGCGAACGGCGGGCTGTCGAAGGAGCAGATCGAGCAGATGATCCGCGACT
CGGAGCAGCACGCGGAGGCCGACCGCGTGAAGCGCGAGCTTGTGGAGGTGCGCAACAACGCGGAGACGCAGCTGACAACGGCGGAGAGGCAGCT
CGGCGAGTGGAAGTACGTGAGCGATGCGGAGAAGGAGAACGTGAAGACGCTGGTGGCGGAGCTGCGCAAGGCGATGGAGAACCCGAACGTCGCG
AAGGATGACCTTGCGGCTGCGACGGACAAGCTGCAGAAGGCTGTGATGGAGTGCGGCCGCACAGAGTACCAGCAGGCTGCCGCGGCCAACTCCG
GCAGCACCAGCAACTCCGGTGAGCAGCAGCAGCAGCAGGGCCAAGGTGAGCAGCAGCAGCAGAACAGCGAAGAGAAGAAGATGAGCATTAT
CAAGGAGGACGACGCCGTGGGCTGCTACATGACGGTGACCCTCGTGGACGACACCAAGGTGGAGGGTACCATCTTCACCTACAATCCCAAGGAA
GGCATCATAGTACTTCTGTCCCTCCGCGACGATCAGACGAACATGAAGCTGATCCGCACTCCATACATCAAAGAGTTCAGTATTTCACACGCTG
AGGAGGGAACGCACCTGCCTCCGGCACTGGACTCCTTCAACGAGCTTCCGTCCATGCATGCCGGCCGCGACAAGTCCATCTTCAAGCACGCCAG
CACGCAGCTCAAGAACGCCGAGGCGAACCGCGAAAAGCACTTCAACTCTGTCACGACACACTGATTGCCACACTCGATGCGTACCTCAAG
CTCCTGCGGCTATACCCCTTCATTGAGTGGAACAGCGACGAGGGTGTCATCCAGGTCTCGGATACCGTCATTGTCGTAGGGGACCCCGACTGGC
GGACGCCCAAGGCGATGCTGGTAGACGGCGCCCCTGAGAAGGACAGACCGCTCGTAGACCGCCTGCAGGTTGCGCTCGGAAACGGCAAGAAGAT
GTCCGCCGGTGGCCGTGAGACCGCGCCGACGAACCTGATTCGTCGCCGCAACAAGGACGAGACAAACGGGGATGTCAGCGCCGCCGCCGACCGC
TTCCGCGACCGCTTCGAGAAGGCAACCCTCGAGGAGCGCAAGGCCGCCACCACAGCAGCAGCGATTACTACGACCTGGTGACGGACTTCT
ACGAGTACGGCTGGGGCCAGAACTTCCATTTCGCCGCCGCTACGCCGGCGAGACCTTCTTCGAGTCCCTCGCGCGCCACGAGTACTTCCTGGC
CGCTCGCGGCGGCTTCATGGAGGGCGACCACATCGTCGACGTGGGCTGCGGCGTCGGCGTCCGGCGCGAACATGGTTCGCCTCACGCGCTGC
AACGTCATCGGCGTCAACAACAACGATTACCAGATCAGCCGCGCTCGCCGTCATGACGCGCTCGCCGGTATGAGCTCCAAGATCGACTACGTCA
AGACCGACTTCTGCAACATGAGCTTAGCCGACAACACCTTCGACGGAGCCTACGCAATTCGAGGCCACCTGCCACGCAAAGGACAAGGTCAAGTG
CTATAGCGAGGTCTTCCGTGTCATCAAGCCCGGCACCTGCTTTGTCCTGTACGAGTGGTGCATGACCGACAAGTACAACCCCAATGACGAGTAC
CACCGCACAATCAAGCACCGCATCGAGCTGGGCGACGGCCTGCCGGAGATGGAGACGTGCAAACAGGTGATCGAGTACATGAAGCAGGCCGGCT
TCGTGGTGGAGGAGGCCATAGACGTCATCAGTCAGTTCGAGTCCAGCCCCATCAAGAGTATCCCGTGGTACCAGCCGCTGGTCGGCGACTATTC
GTCCCTGCAGGGCCTGCGCTCTACCCCGATTGGCCGCATCCTCACGAACGTCATGTGTCGCGTGCTGGAGTTCGTGCGCCTAGCTCCGAAGGGC
ACGTACAAGGCGACGGAGATTTTGGAGGAGGCTGCGGAAAGCCTGGTGGTGGGCGGTCAGCTCGGCATCTTCACGCCGTCCTTCTACATCCGCG
CTCGCAAGCCGTCCAAGCAGGCT SEQ ID NO: 24 Amino Acid Sequence of the 821S Fusion Polypeptide
MKDKATGKTQNITITANGGLSKEQIEQMIRDSEQHAEADRVKRELVEVRNNAETQLTTAERQLGEWKYVSDAEKENVKTLVAELRKAMENPNVA
KDDLAAATDKLQKAVMECGRTEYQQAAAANSGSTSNSGEQQQQQGQGEQQQQQNSEEKK<u>MSIIKEDDAVGCYMTVTLVDDTKVEGTIFTYNPKE</u>
<u>GIIVLLSLRDDQTNMKLIRTPYIKEFSISHAEEGTHLPPALDSFNELPSMHAGRDKSIFKHASTQLKNAEANREKHFNSVTTDTPIATLDAYLK</u>
<u>LLRLYPFIEWNSDEGVIQVSDTVIVVGDPDWRTPKAMLVDGAPEKDRPLVKRLQVALGNGKKMSAGGRETAPTNLIRRRNKDETNGDVSAAADR</u>
FRDRFEKATLEERKAATTTMVNEYYDLVTDFYEYGWGQNFHFAPRYAGETFFESLARHEYFLAARGGFMEGDHIVDVGCGVGGPARNMVRLTRC
NVIGVNNNDYQISRARRHDALAGMSSKIDYVKTDFCNMSLADNTFDGAYAIEATCHAKDVKCYSEVFRVIKPGTCFVLYEWCMTDKYNPNDEY
HRTIKHRIELGDGLPEMETCKQVIEYMKQAGFVVEEAIDVISQFESSPIKSIPWYQPLVGDYSSLQGLRSTPIGRILTNVMCRVLEFVRLAPKG
TYKATEILEEAAESLVVGGQLFIGTPSFYIRARKPSKQA 8HS: mtHSP70$_{509-660}$ + H2B$_{1-46}$ + SMT$_{2-353}$
8E (1 . . . 459) + H2Bn (460 . . . 597) + SMT (598 . . . 1653)
MW = 62,201 daltons

```
N [ 8E | H2Bn | SMT ] C
```

SEQ ID NO: 25 Polynucleotide encoding 8HS Fusion Polypeptide
ATGAAGGACAAGGCGACGGGCAAGACGCAGAACATCACGATCACGGCGAACGGCGGGCTGTCGAAGGAGCAGATCGAGCAGATGATCCGCGACT
CGGAGCAGCACGCGGAGGCCGACCGCGTGAAGCGCGAGCTTGTGGAGGTGCGCAACAACGCGGAGACGCAGCTGACAACGGCGGAGAGGCAGCT
CGGCGAGTGGAAGTACGTGAGCGATGCGGAGAAGGAGAACGTGAAGACGCTGGTGGCGGAGCTGCGCAAGGCGATGGAGAACCCGAACGTCGCG
AAGGATGACCTTGCGGCTGCGACGGACAAGCTGCAGAAGGCTGTGATGGAGTGCGGCCGCACAGAGTACCAGCAGGCTGCCGCGGCCAACTCCG
GCAGCACCAGCAACTCCGGTGAGCAGCAGCAGCAGCAGGGCCAAGGTGAGCAGCAGCAGCAGAACAGCGAAGAAGAAGATGGCCTCTTC
TCGCTCTGCTCCCCGCAAGGCTTCCCACGCGCACAAGTCGCACCGCAAGCCGAAGCGCTCGTGGAACGTGTACGTGGGCCGCTCGCTGAAGGCG
ATCAACGCCCAGATGTCGATGTCGCACCGCACGTCCGCCGGTGGCCGTGAGACCGCGCCGACGAACCTGATTCGTCGCCGCAACAAGGACGAGA
CAAACGGGGATGTCAGCGCCGCCGCCGACCGCTTCCGCGACCGCTTCGAGAAGGCAACCCTCGAGGAGCGCAAGGCCGCCACCACGACGATGGT
CAACGAGTACTACGACCTGGTGACGGACTTCTACGAGTACGGCTGGGGCCAGAACTTCCATTTCGCCGCCGCTACGCCGGCGAGACCTTCTTC
GAGTCCCTCGCGCGCCACGAGTACTTCCTGGCCGCTCGCGGCGGCTTCATGGAGGGCGACCACATCGTCGACGTGGGCTGCGGCGTCGGCGGTC
CGGCGCGCAACATGGTTCGCCTCACGCGCTGCAACGTCATCGGCGTCAACAACAACGATTACCAGATCAGCCGCGCTCGCCGTCATGACGCGCT
CGCCGGTATGAGCTCCAAGATCGACTACGTCAAGACCGACTTCTGCAACATGAGCTTAGCCGACAACACCTTCGACGGCGCCTACGCCATCGAG
GCCACCTGCCACGCAAAGGACAAGGTCAAGTGCTATAGCGAGGTCTTCCGTGTCATCAAGCCCGGCACCTGCTTTGTCCTGTACGAGTGGTGCA
TGACCGACAAGTACAACCCCAATGACGAGTACCACCGCACAATCAAGCACCGCATCGAGCTGGGCGACGGCCTGCCGGAGATGGAGACGTGCAA
ACAGGTGATCGAGTACATGAAGCAGGCCGGCTTCGTGGTGGAGGAGGCCATAGACGTCATCAGTCAGTTCGAGTCCAGCCCCATCAAGAGTATC
CCGTGGTACCAGCCGCTGGTCGGCGACTATTCGTCCCTGCAGGGCCTGCGCTCTACCCCGATTGGCCGCATCCTCACGAACGTCATGTGTCGCG
TGCTGGAGTTCGTGCGCCTAGCTCCGAAGGGCACGTACAAGGCGACGGAGATTTTGGAGGAGGCTGCGGAAAGCCTGGTGGTGGGCGGTCAGCT
CGGCATCTTCACGCCGTCCTTCTACATCCGCGCTCGCAAGCCGTCCAAGCAGGCT SEQ ID NO: 26 Amino Acid Sequence encoding the 8HS Fusion Polypeptide
MKDKATGKTQNITITANGGLSKEQIEQMIRDSEQHAEADRVKRELVEVRNNAETQLTTAERQLGEWKYVSDAEKENVKTLVAELRKAMENPNVA
KDDLAAATDKLQKAVMECGRTEYQQAAAANSGSTSNSGEQQQQQGQGEQQQQQNSEEKK<u>MASSRSAPRKASHAHKSHRKPKRSWNVYVGRSLKA</u>
<u>INAQMSMSHRTS</u>AGGRETAPTNLIRRRNKDETNGDVSAAADRFRDRFEKATLEERKAATTTMVNEYYDLVTDFYEYGWGQNFHFAPRYAGETFFF
ESLARHEYFLAARGGFMEGDHIVDVGCGVGGPARNMVRLTRCNVIGVNNNDYQISRARRHDALAGMSSKIDYVKTDFCNMSLADNTFDGAYAIE
ATCHAKDVKCYSEVFRVIKPGTCFVLYEWCMTDKYNPNDEYHRTIPHRIELGDGLPEMETCKQVIEYMKQAGFVVEEAIDVISQFESSPIKSI
PWYQPLVGDYSSLQGLRSTPIGRILTNVMCRVLEFVRLAPKGTYKATEILEEAAESLVVGGQLGIFTPSFYIRARKPSKQ SEQ ID NO: 27 Amino Acid Sequence of the 8E Polypeptide from *Leishmania infantum* or
*donovani*
KDKATGKTQNITITANGGLSKEQIEQMIRDSEQHAEADRVKRELVEVRNNAETQLTTAERQLGEWKYVSDAEKENVKTLVAELRKAMENPNVAK SEQUENCES-continued

DDLAAATDKLQKAVMECGRTEYQQAAAANSGSTSNSGEQQQQQGQGEQQQQQNSEEKK

SEQ ID NO: 28 Amino Acid Sequence of the 8E Polypeptide from *Leishmania major*
KDKATGKTQNITITANGGLSKEQIEQMIRDSEQHAEADRVKRELVEVRNNAETQLTTAERQLGEWKYVSDAEKENVKTLVAELRKAMENPNVAK
DDLAAATDKLQKAVMECGRTEYQQAAAANSGSTSNSGEQQQQSQGEQQQQQNSEEKK SEQ ID NO: 29 Amino Acid Sequence of the 8E Polypeptide from *Leishmania mexicana*
KDKATGKTQNITITANGGLSKEQIEQMIRDSEQHAEADRVKRELVEVRNNAETQLTTAIEQLSEWKYVSDAEKENVRTLVAELRKAMENPNVAK
DDLSAATDKLQKAVMECGRTEYQQAAAANSGSTSNSGEQQQQQQQSQGEQQQQQQQQQAEER SEQ ID NO: 30 Amino Acid Sequence of the 8E Polypeptide from *Leishmania braziliensis*
KDKATGKTQNITITAHGGLSKEQIEQMVRDSEQHAEADRVKRELVEARNNAETQLTTAERQLGEWKYVSDAEKENVKTHVAELRKAMENPNVAK
DDLAAATDKLQKAVMECGRTEYQQAAAANSGSSSNSGEQQQQQQQGDQQQQQSSEKN SEQ ID NO: 31 Amino Acid Sequence of a carboxy terminus fragment of cysteine
polypeptidease B polypeptide (CPB) from *Leishmania infantum*
SAVGNIESQWARAGHGLVSLSEQQLVSCDDKDNGCNGGLMLQAFEWLLRHMYGIVFTEKSYPYTSGNGDVAECLNSSKLVPGAQIDGYVMIPSN
ETVMAAWLAENGPIAIAVDASSFMSYQSGVLTSCAGDALNHGVLLVGYNKTGGVPYWVIKNSWGEDWGEKGYVRVVMGLNACLLSEYPVSAHVP
RSLTPGPGTESEERAPKRVTVEQMMCTDMYCREGCKKSLLTANVCYKNGGGGSSMTKCGPQKVLMCSYSNPHCFGPGLCLETPDGKCAPYFLGS
IMNTCQYT SEQ ID NO: 32 Amino Acid Sequence of an amino terminus fragment of histone H2BN
polypeptide (H2BN) from *Leishmania infantum*
MASSRSAPRKASHAHKSHRKPKRSWNVYVGRSLKAINAQMSMSHRT SEQ ID NO: 33 Amino Acid Sequence of a mature A2 polypeptide (A) from *Leishmania
donovani*
SASAEPHKAAVDVGPLSVGPQSVGPLSVGPQAVGPLSVGPQSVGPLSVGPQAVGPLSVGPQSVGPLSVGPLSVGPQSVGPLSVGSQSVGPLSVG
PQSVGPLSVGPQAVGPLSVGPQSVGPLSVGPQAVGPLSVGPQSVGPLSVGPQSVGPLSVGSQSVGPLSVGPQSVGPLSVGPQSVGPLSVGPQSV
GPLSVGPQSVGPLSVGPQSVDVDPVS SEQ ID NO: 34 Amino Acid Sequence of a full length p21 antigen polypeptide (p21) from
*Leishmania infantum*
SIIKEDDAVGCYMTVTLVDDTKVEGTIFTYNPKEGIIVLLSLRDDQTNMKLIRTPYIKEFSISHAEEGTHLPPALDSFNELPSMHAGRDKSIFK
HASTQLKNAEANREKHFNSVTTDTPIATLDAYLKLLRLYPFIEWNSDEGVIQVSDTVIVVGDPDWRTPKAMLVDGAPEKDRPLVDRLQVALGNG
KK SEQ ID NO: 35 Amino Acid Sequence of a full length nonspecific nucleoside hydrolase
polypeptide (NH) from *Leishmania infantum* or *donovani*
MPRKIILDCDPGIDDAVAIFLAHGNPEVELLAITTVVGNQTLEKVTRNARLVADVAGIVGVPVAAGCTKPLVRGVRNASQIHGETGMGNVSYPP
EFKTKLDGRHAVQLIIDLIMSHEPKTITLVPTGGLTNIAMAVRLEPRIVDRVKEVVLMGGGYHTGNASPVAEFNVFVDPEAAHIVFNESWNVTM
VGLDLTHQALATPAVQKRVKEVGTKPAAFMLQILDFYTKVYEKERNTYATVHDPCAVAYVIDPTVMTTEQVPVDIELNGALTTGMTVADFRYPR
PKHCHTQVAVKLDFDKFWCLVIDALKRIGPQ SEQ ID NO: 36 Amino Acid Sequence of a full length sterol 24-c-methyltransferase
polypeptide (SMT) from *Leishmania infantum*
SAGGRETAPTNLIRRRNKDETNGDVSAAADRFRDRFEKATLEERKAATTTMVNEYYDLVTDFYEYGWGQNFHFAPRYAGETFFESLARHEYFLA
ARGGFMEGDHIVDVGCGVGGPARNMVRLTRCNVIGVNNNDYQISRARRHDALAGMSSKIDYVKTDFCNMSLADNTFDGAYAIEATCHAKDKVKC
YSEVFRVIKPGTCFVLYEWCMTDKYNPNDEYHRTIKHRIELGDGLPEMETCKQVIEYMKQAGFVVEEAIDVISQFESSPIKSIPWYQPLVGDYS
SLQGLRSTPIGRILTNVMCRVLEFVRLAPKGTYKATEILEEAAESLVVGGQLGIFTPSFYIRARKPSKQA SEQ ID NO: 37 Amino Acid Sequence of a full length A2 polypeptide (Afl) from *Leishmania
donovani*
MKIRSVRPLVVLLVSVAAVLALSASAEPHKAAVDVGPLSVGPQSVGPLSVGPQAVGPLSVGPQSVGPLSVGPQAVGPLSVGPQSVGPLSVGPLS
VGPQSVGPLSVGSQSVGPLSVGPQSVGPLSVGPQAVGPLSVGPQSVGPLSVGPQAVGPLSVGPQSVGPLSVGPQSVGPLSVGSQSVGPLSVGPQ
SVGPLSVGPQSVGPLSVGPQSVGPLSVGPQSVGPLSVGPQSVDVSPVS
SEQ ID NO: 38 Polynucleotide encoding 8HNS Fusion Polypeptide
ATGAAGGACAAGGCGACGGGCAAGACGCAGAACATCACGATCACGGCAAACGGCGGCTGTCGAAGGAGCAGATCGAGCAGATGATCCGCGACT
CGGAGCAGCACGCGGAGGCCGACCGCGTGAAGCGCGAGCTTGTGGAGGTGCGCAACAACGCGGAGACGCAGCTGACAACGGCGGAGAGGCAGCT
CGGCGAGTGGAAGTACGTGAGCGATGCGGAGAAGGAGAACGTGAAGACGCTGGTGGCGGAGCTGCGCAAGGCGATGGAGAACCCGAACGTCGCG
AAGGATGACCTTGCGGCTGCGACGGACAAGCTGCAGAAGGCTGTGATGGAGTGCGGCCGCACAGAGTACCAGCAGGCTGCCGCGGCCAACTCCG
GCAGCACCAGCAACTCCGGTGAGCAGCAGCAGCAGCAGGGCCAAGGTGAGCAGCAGCAGCAGCAGAACAGCGAAGAGAAGAAGCCTCTTCTCGC
TCTGCTCCCCGCAAGGCTTCCCACGCACGACAAGTCGCACCGCAAGCCGAAGCGCTCGTGGAACGTGTACGTGGGCCGCTCGCTGAAGGCGATCA
ACGCCCAGATGTCGATGTCGCACCGCACGATGCCGCGCAAGATTATTCTCGATTGTGATCCCGGGATCGATGATGCCGTGGCCATCTTTCTCGC
CCACGGCAACCCGGAGGTCGAGCTGCTGGCCATTACGACGGTGGTGGGCAACCAGACCCTGGAGAAGGTGACCCGGAACGCGCGGCTGGTAGCT
GACGTAGCCGGCATCGTTGGTGTGCCCGTCGCGGCTGGTTGCACCAAGCCCCTCGTGCGCGGTGTGCGGAATGCCTCTCAGATTCATGGCGAAA
CCGGCATGGGTAACGTCTCCTACCCACCAGAGTTCAAGACAAAGTTGACGGCCGTCATGCAGTCGCGAGTTGATCATCGACCTTATCATGTCGCA
CGAGCCGAAGACGATCACGCTTGTGCCTACGGGTGGCCTGACGAACATTGCGATGGCTGTCCGTCTTGAGCCGCGCATCGTGGACGGTGTGAAG
GAGGTGGTTCTGATGGGTGGCGGCTACCATACTGGTAATGCGTCCCCTGTAGCGGAGTTCAACGTCTTCGTCGACCCGGAGGCGGCCACATTG
TGTTCAACGAGAGCTGGAACGTAACGATGGTGGGGCTGGACCTAACGCACCAGGCACTCGCCACGCCGGCGGTCCAGAAGCGAGTGAAGGAGGT
GGGCACGAAGCCGGCTGCCTTCATGCTGCAGATTTTGGACTTTTACACGAAGGTGTACGAAAAGGAGCGCAACACGTACGCGACGGTGCACGAT
CCCTGCGCTGTGGCGTACGTGATTGACCCCACCGTGATGACGACGGAGCAAGTGCCAGTGGACATCGAGCTCAATGGGGCGCTGACGACTGGGA
TGACGGTCGCGGACTTCCGCTACCCACGGCCAAAGCACTGCCACACGCAGGTGGCTGTGAAGCTGGACTTCGACAAGTTTTGGTGCCTCGTGAT
TGACGCACTCAAGCGCATCGGCGATCCTCAATCCGCCGGTGGCCGTGAGACCGCGCCGACGAACCTGATTCGTCGCCGCAACAAGGACGAGACA
AACGGGGATGTCAGCGCCGCGCCGACCGCTTCCGCGACCGCTTCGAGAAGGCAACCCTCGAGGAGCGCAAGGCCGCCACCACGACGATGGTCA
ACGAGTACTACGACCTGGTGACGGACTTCTACGAGTACGGCTGGGGCCAGAACTTCCATTTCGCCGCGCGCTACGCCGGCGAGACCTTCTTCGA
GTCCCTCGCGCGCCACGAGTACTTCCTGGCCGCTCGCGGCGGCTTCATGGAGGGCGACCACATCGTCGACGTGGGCTGCGGCGTCGGCGGTCCG
GCGCGCAACATGGTTCGCCTCACGCGCTGCAACGTCATCGGCGTCAACAACAACGATTACCAGATCAGCCGCGCTCGCCGTCATGACGCGCTCG
CCGGTATGAGCTCCAAGATCGACTACGTCAAGACCGACTTCTGCAACATGAGCTTAGCCGACAACACCTTCGACGGCGCCTACGCCATCGAGGC
CACCTGCCACGCAAAGGACAAGGTCAAGTGCTATAGCGAGGTCTTCCGTGTCATCAAGCCCGGCACCTGCTTTGTCCTGTACGAGTGGTGCATG SEQUENCES-continued

```
ACCGACAAGTACAACCCCAATGACGAGTACCACCGCACAATCAAGCACCGCATCGAGCTGGGCGACGGCCTGCCGGAGATGGAGACGTGCAAAC
AGGTGATCGAGTACATGAAGCAGGCCGGCTTCGTGGTGGAGGAGGCCATAGACGTCATCAGTCAGTTCGAGTCCAGCCCCATCAAGAGTATCCC
GTGGTACCAGCCGCTGGTCGGCGACTATTCGTCCCTGCAGGGCCTGCGCTCTACCCCGATTGGCCGCATCCTCACGAACGTCATGTGTCGCGTG
CTGGAGTTCGTGCGCCTAGCTCCGAAGGGCACGTACAAGGCGACGGAGATTTTGGAGGAGGCTGCGGAAAGCCTGGTGGTGGGCGGTCAGCTCG
GCATCTTCACGCCGTCCTTCTACATCCGCGCTCGCAAGCCGTCCAAGCAGGCT
```

SEQ ID NO: 39 Amino Acid Sequence of the 8HNS Fusion Polypeptide
<u>MKDKATGKTQNITITANGGLSKEQIEQMIRDSEQHAEADRVKRELVEVRNNAETQLTTAERQLGEWKYVSDAEKENVKTLVAELRKAMENPNVA
KDDLAAATDKLQKAVMECGRTEYQQAAAANSGSTSNSGEQQQQQGQGEQQQQQNSEEKKASSRSAPRKASHAHKSHRKPKRSWNVYVGRSLKAI
NAQMSMSHRT</u><u>MPRKIILDCDPGIDDAVAIFLAHGNPEVELLAITTVVGNQTLEKVTRNARLVADVAGIVGVPVAAGCTKPLVRGVRNASQIHGE
TGMGNVSYPPEFKTKLDGRHAVQLIIDLIMSHEPKTITLVPTGGLTNIAMAVRLEPRIVDRVKEVVLMGGGYHTGNASPVAEFNVFVDPEAAHI
VFNESWNVTMVGLDLTHQALATPAVQKRVKEVGTKPAAFMLQILDFYTKVYEKERNTYATVHDPCAVAYVIDPTVMTTEQVPVDIELNGALTTG
M</u><u>TVADFRYPRPKHCHTQVAVKLDFDKFWCLVIDALKRIGDPQSAGGRETAPTNLIRRRNKDETNGDVSAAADRFRDRFEKATLEERKAATTTMV
NEYYDLVTDFYEYGWGQNFHFAPRYAGETFFESLARHEYFLAARGGFMEGDHIVDVGCGVGGPARNMVRLTRCNVIGVNNNDYQISRARRHDAL
AGMSSKIDYVKTDFCNMSLADNTFDGAYAIEATCHAKDKVKCYSEVFRVIKPGTCFVLYEWCMTDKYNPNDEYHRTIKHRIELGDGLPEMETCK
QVIEYMQAGFVVEEAIDVISQFESSPIKSIPWQYPLVGDYSSLQGLRSTPIGRILTNVMCRVLEFVRLAPKGTYKATEILEEAAESLVVGGQLG
IFTPSFYIRARKPSKQA</u>

SEQ ID NO: 40 Polynucleotide encoding H21NS Fusion Polypeptide
```
ATGGCCTCTTCTCGCTCTGCTCCCCGCAAGGCTTCCCACGCGCACAAGTCGCACCGCAAGCCGAAGCGCTCGTGGAACGTGTACGTGGGCCGCT
CGCTGAAGGCGATCAACGCCCAGATGTCGATGTCGCACCGCACGAGCATTATCAAGGAGGACGACCCTGGGCTGCTACATGACGGTGACCCT
CGTGGACGACACCAAGGTGGAGGGTACCATCTTCACCTACAATCCCAAGGAAGGCATCATAGTACTTCTGTCCCTCCGCGACGATCAGACGAAC
ATGAAGCTGATCCGCACTCCATACATCAAAGAGTTCAGTATTTCACACGCTGAGGAGGGAACGCACCTGCCTCCGGCACTGGACTCCTTCAACG
AGCTTCCGTCCATGCATGCCGGCCGCGACAAGTCCATCTTCAAGCACGCCAGCACGCAGCTCAAGAACGCCGAGGCGAACCGCGAAAAGCACTT
CAACTCTGTCACGACCGACACACCGATTGCCACACTCGATGCGTACCTCAAGCTCCTGCGGCTATACCCCTTCATTGAGTGGAACAGCGACGAG
GGTGTCATCCAGGTCTCGGATACCGTCATTGTCGTAGGGGACCCCGACTGGCGGACGCCCAAGGCGATGCTGGTAGACGGCGCCCTGAGAAGG
ACAGACCGCTCGTAGACCGCCTGCAGGTTGCGCTCGGAAACGGCAAGAAGATGCCGCGCAAGATTATTCTCGATTGTGATCCCGGGATCGATGA
TGCCGTGGCCATCTTTCTCGCCCACGGCAACCCGGAGGTCGAGCTGCTGGCCATTACGACGGTGGTGGGCAACCAGACCCTGGAGAAGGTGACC
CGGAACGCGCGGCTGGTAGCTGACGTAGCCGGCATCGTTGGTGTGCCCGTCGGTTGCACCAAGCCCCCTCGTGCGCGGTGTGCGGAATG
CCTCTCAGATTCATGGCGAAACCGGCATGGGTAACGTCTCCTACCACCAGAGTTCAAGACAAAGTTGGACGGCCGTCATGCAGTGCAGCTGAT
CATCGACCTTATCATGTCGCACGAGCCGAAGACGATCACGCTTGTGCCTACGGGTGGCCTGACGAACATTGCGATGGCTGTCCGTCTTGAGCCG
CGCATCGTGGACCGTGTGAAGGAGGTGGTTCTGATGGGTGGCGGCTACCATACTGGTAATGCGTCCCCTGTAGCGGAGTTCAACGTCTTCGTCG
ACCCGGAGGCGGCGCACATTGTGTTCAACGAGAGCTGGAACGTAACGATGGTGGGGCTGGACCTAACGCACCAGGCACTCGCCACGCCGGCGGT
CCAGAAGCGAGTGAAGGAGGTGGGCACGAAGCCGGCTGCCTTCATGCTGCAGATTTTGGACTTTTACACGAAGGTGTACGAAAAGGAGCGCAAT
ACGTACGCGACGGTGCACGATGGGTGCGCTGTGGCGTACGTGATTGACCCCACCGTGATGACGACGGAGCAAGTGCCAGTGGACATCGAGCTCA
ATGGGGCACTGACGACTGGGATGACGGTCGCGGACTTCCGCTACCCACGGCCAAAGCACTGCCACACGCAGGTGGCTGTGAAGCTGGACTTCGA
CAAGTTTTGGTGCCTCGTGATTGACGCACTCAAGCGCATCGGCGATCCTCAATCCGCCGGTGGCCGTGAGACCGCGCCGACGAACCTGATTCGT
CGCCGCAACAAGGACGAGACAAACGGGGATGTCAGCGCCGCCGCCGACAGCCTTCCGCGACCGCTTCGAGAAGGCAACCCTCGAGGAGCGCAAGG
CCGCCACCACGACGATGGTCAACGAGTACTACGACCTGGTGACGGACTTCTACGAGTACGGCTGGGGCCAGAACTTCCATTCGCGCCGCGCTA
CGCCGGCGAGACCTTCTTCGAGTCCCTCGCGCGCCACGAGTACTTCCTGGCCGCTCGCGGCGGCTTCATGGAGGGCGACCACATCGTCGACGTG
GGCTGCGGCGTCGGCGGTCCGGCGCGCAACATGGTTCGCCTCACGCGCTGCAACGTCATCGGCGTCAACAACAACGATTACCAGATCAGCCGCG
CTCGCCGTCATGACGCGCTCGCCGGTATGAGCTCCAAGATCGACTACGTCAAGACCGACTTCTGCAACATGAGCTTAGCCGACAACACCTTCGA
CGGCGCCTACGCCATCGAGGCCACCTGCCACGCAAAGGACAAGGTCAAGTGCTATAGCGAGGTCTTCCGTGTCATCAAGCCCGGCACCTGCTTT
GTCCTGTACGAGTGGTGCATGACCGACAAGTACAACCCCAATGACGAGTACCACCGCACAATCAAGCACCGCATCGAGCTGGGCGACGGCCTGC
CGGAGATGGAGACGTGCAAACAGGTGATCGAGTACATGAAGCAGGCCGGCTTCGTGGTGGAGGAGGCCATAGACGTCATCAGTCAGTTCGAGTC
CAGCCCCATCAAGAGTATCCCGTGGTACCAGCCGCTGGTCGGCGACTATTCGTCCCTGCAGGGCCTGCGCTCTACCCCGATTGGCCGCATCCTC
ACGAACGTCATGTGTCGCGTGCTGGAGTTCGTGCGCCTAGCTCCGAAGGGCACGTACAAGGCGACGGAGATTTTGGAGGAGGCTGCGGAAAGCC
TGGTGGTGGGCGGTCAGCTCGGCATCTTCACGCCGTCCTTCTACATCCGCGCTCGCAAGCCGTCCAAGCAGGCT
```

SEQ ID NO: 41 Amino Acid Sequence of the H21NS Fusion Polypeptide
<u>MASSRSAPRKASHAHKSHRKPKRSWNVYVGRSLKAINAQMSMSHRTS</u>IIKEDDAVGCYMTVTLVDDTKVEGTIFTYNPKEGIIVLLSLRDDQTN
MKLIRTPYIKEFSISHAEEGTHLPPALDSFNELPSMHAGRDKSIFKHASTQLKNAEANREKHFNSVTTDTPIATLDAYLKLLRLYPFIEWNSDE
GVIQVSDTVIVVGDPDWRTPKAMLVDGAPEKDRPLVDRLQVALGNGKK<u>MPRKIILDCDPGIDDAVAIFLAHGNPEVELLAITTVVGNQTLEKVT
RNARLVADVAGIVGVPVAAGCTKPLVRGVRNASQIHGETGMGNVSYPPEFKTKLDGRHAVQLIIDLIMSHEPKTITLVPTGGLTNIAMAVRLEP
RIVDRVKEVVLMGGGYHTGNASPVAEFNVFVDPEAAHIVFNESWNVTMVGLDLTHQALATPAVQKRVKEVGTKPAAFMLQILDFYTKVYEKERN
TYATVHDPCAVAYVIDPTVMTTEQVPVDIELNGALTTGMTVADFRYPRPKHCHTQVAVKLDFDKFWCLVIDALKRIGDPQSAGGRETAPTNLIR
RRNKDETNGDVSAAADRFRDRFEKATLEERKAATTTMVNEYYDLVTDFYEYGWGQNFHFAPRYAGETFFESLARHEYFLAARGGFMEGDHIVDV
GCGVGGPARNMVRLTRCNVIGVNNNDYQISRARRHDALAGMSSKIDYVKTDFCNMSLADNTFDGAYAIEATCHAKDKVKCYSEVFRVIKPGTCF
VLYEWCMTDKYNPNDEYHRTIKHRIELGDGLPEMETCKQVIEYMKQAGFVVEEAIDVISQFESSPIKSIPWYQPLVGDYSSLQGLRSTPIGRIL
TNVMCRVLEFVRLAPKGTYKATEILEEAAESLVVGGQLGIFTPSFYIRARKPSKQA</u>

SEQ ID NO: 42 Amino Acid Sequence of a putative eukaryotic initiation factor 4a polypeptide
(Leif) from *Leishmania major*
MAQNDKIAPQDQDSFLDDQPGVRPIPSFDDMPLHQNLLRGIYSYGFEKPSSIQQRAIAPFTRGGDIIAQAQSGTGKTGAFSIGLLQRLDFRHNL
IQGLVLSPTRELALQTAEVISRIGEFLSNSSKFCETFVGGTRVQDDLRKLQAGVIVAVGTPGRVSDVIKRGALRTESLRVLVLDEADEMLSQGF
ADQIYEIFRFLPKDIQVALFSATMPEEVLELTKKFMRD SEQ ID NO: 43 is amino acid sequence of the NSL fusion polypeptide
NH$_{1-314}$ + SMT$_{2-353}$ + Leif$_{1-226}$
Nh(1 . . . 942) + SMT(943 . . . 1998) + Leif(1999 . . . 2224) nucleotide numbers
MPRKIILDCDPGIDDAVAIFLAHGNPEVELLAITTVVGNQTLEKVTRNARLVADVAGIVGVPVAAGCTKPLVRGVRNASQIHGETGMGNVSYPP
EFKTKLDGRHAVQLIIDLIMSHEPKTITLVPTGGLTNIAMAVRLEPRIVDRVKEVVLMGGGYHTGNASPVAEFNVFVDPEAAHIVFNESWNVTM
VGLDLTHQALATPAVQKRVKEVGTKPAAFMLQILDFYTKVYEKERNTYATVHDPCAVAYVIDPTVMTTEQVPVDIELNGALTTGMTVADFRYPR
PKHCHTQVAVKLDFDKFWCLVIDALKRIGDPQ<u>SAGGRETAPTNLIRRRNKDETNGDVSAAADRFRDRFEKATLEERKAATTTMVNEYYDLVTDF
YEYGWGQNFHFAPRYAGETFFESLARHEYFLAARGGFMEGDHIVDVGCGVGGPARNMVRLTRCNVIGVNNNDYQISRARRHDALAGMSSKIDYV
KTDFCNMSLADNTFDGAYAIEATCHAKDKVKCYSEVFRVIKPGTCFVLYEWCMTDKYNPNDEYHRTIKHRIELGDGLPEMETCKQVIEYMKQAG
FVVEEAIDVISQFESSPIKSIPWYQPLVGDYSSLQGLRSTPIGRILTNVMCRVLEFVRLAPKGTYKATEILEEAAESLVVGGQLGIFTPSFYIR
ARKPSKQA</u>MAQNDKIAPQDQDSFLDDQPGVRPIPSFDDMPLHQNLLRGIYSYGFEKPSSIQQRAIAPFTRGGDIIAQAQSGTGKTGAFSIGLLQ
RLDFRHNLIQGLVLSPTRELALQTAEVISRIGEFLSNSSKFCETFVGGTRVQDDLRKLQAVVIVAVGTPGRVSDVIKRGALRTESLRVLVLDEA
DEMLQGFADQIYEIFRFLPKDIQVALFSATMPEEVLELTKKFMRD SEQUENCES-continued SEQ ID NO: 44 is an amino acid sequence for an HNSC fusion polypeptide.
HNSC: H2BN$_{1-46}$ + NH$_{1-314}$ + SMT$_{2-353}$ + CPB$_{154-443}$
H2BN$_{1-138}$(1 . . . 138) + Nh(139 . . . 1080) + SMT(1081 . . . 2136) + CPB(2137 . . . 3006)
(nuceotide Sequence number)
MASSRSAPRKASHAHKSHRKPKRSWNVYVGRSLKAINAQMSMSHRTPRKIILDCDPGIDDAVAIFLAHGNPEVELLAITTVVGNQTLEKVTRNA
RLVADVAGIVGVPVAAGCTKPLVRGVRNASQIHGETGMGVNSYPPEFKTKLDGRHAVQLIIDLMSHEPKTITLVPTGGLTNIAMAVRLEPRIV
DRVKEVVLMGGGYHTGNASPVAEFNVFVDPEAAHIVGNESWNVTMVGLDLTHQALATPAVQKRVKEVGTKPAAFMLQILDFYTKVYEKERNTYA
TVHDPCAVAYVIDPTVMTTEQVPVDIELNGALTTGMTVADFRYPRPKHCHTQVAVKLDFDKFWCLVIDALKRIGDPQSAGGRETAPTNLIRRRN
KDETNGDVSAAADRFRDRFEKATLEERKAATTTMVNEYYDLVTDFYEYGWGQNFHFAPRYAGETFFESLARHEYFLAARGGFMEGDHIVDVGCG
VGGPARNMVRLTRCNVIGVNNNDYQISRARRHDALAGMSSKIDYVKTDFCNMSLADNTFDGAYAIEATCHAKDKVKCYSEVFRVIKPGTCFVLY
EWCMTDKYNPNDEYHRTIKHRIELGDGLPEMETCKQVIEYMKQAGFVVEEAIDVISQFESSPIKSIPWYQPLVGDYSSLQGLRSTPIGRILTNV
MCRVLEFVRLAPKGTYKATEILEEAAESLVVGGQLGIFTPSFYIRARKPSKQASAVGNIESQWARAGHGLVSLSEQQLVSCDDKDNGCNGGLML
QAFEWLLRHMYGIVFTEKSYPYTSGNGDVAECLNSSKLVPGAQIDGYVMIPSNETVMAAWLAENGPIAIAVDASSFMSYQSGVLTSCAGDALNH
GVLLVGYNKTGGVPYWVIKNSWGEDWGEKGYVRVVMGLNACLLSEYPVSAHVPRSLTPGPGTESEERAPKRVTVEQMMCTDMYCREGCKKSLLT
ANVCYKNGGGGSSMTKCGPQKVLMCSYSNPHCFGPGLCLETPDGKCAPYFLGSIMNTCQYT

SEQUENCE LISTING

<160> NUMBER OF SEQ ID NOS: 45

<210> SEQ ID NO 1
<211> LENGTH: 2868
<212> TYPE: DNA
<213> ORGANISM: Artificial Sequence
<220> FEATURE:
<223> OTHER INFORMATION: Synthetic Construct

<400> SEQUENCE: 1

```
atgccgcgca agattattct cgattgtgat cccgggatcg atgatgccgt ggccatcttt      60
ctcgcccacg gcaacccgga ggtcgagctg ctggccatta cgacggtggt gggcaaccag     120
accctggaga aggtgacccg gaacgcgcgg ctggtagctg acgtagccgg catcgttggt     180
gtgcccgtcg cggctggttg caccaagccc ctcgtgcgcg gtgtgcggaa tgcctctcag     240
attcatggcg aaaccggcat gggtaacgtc tcctacccac cagagttcaa gacaaagttg     300
gacggccgtc atgcagtgca gctgatcatc gaccttatca tgtcgcacga gccgaagacg     360
atcacgcttg tgcctacggg tggcctgacg aacattgcga tggctgtccg tcttgagccg     420
cgcatcgtgg accgtgtgaa ggaggtggtt ctgatgggtg cggctacca tactggtaat     480 gcgtcccctg tagcggagtt caacgtcttc gtcgacccgg aggcggcgca cattgtgttc     540
aacgagagct ggaacgtaac gatggtgggg ctggacctaa cgcaccaggc actcgccacg     600
ccggcggtcc agaagcgagt gaaggaggtg ggcacgaagc cggctgcctt catgctgcag     660
attttggact tttacacgaa ggtgtacgaa aaggagcgca cacgtacgc gacggtgcac     720 gatccctgcg ctgtggcgta cgtgattgac cccaccgtga tgacgacgga gcaagtgcca     780
gtggacatcg agctcaatgg ggcactgacg actgggatga cggtcgcgga cttccgctac     840
ccacggccaa agcactgcca cacgcaggtg gctgtgaagc tggacttcga caagttttgg     900
tgcctcgtga ttgacgcact caagcgcatc ggcgatcctc aatccgccgg tggccgtgag     960
accgcgccga cgaacctgat tcgtcgccgc aacaaggacg agacaaacgg ggatgtcagc    1020
gccgccgccg accgcttccg cgaccgcttc gagaaggcaa ccctcgagga cgcaaggcc    1080 gccaccacga cgatggtcaa cgagtactac gacctggtga cggacttcta cgagtacggc    1140
tggggccaga acttccattt cgcgccgcgc tacgccggcg agaccttctt cgagtccctc    1200
gcgccgcacg agtacttcct ggccgctcgc ggcggcttca tggagggcga ccacatcgtc    1260
gacgtgggct gcggcgtcgg cggtccggcg cgcaacatgg ttcgcctcac cgctgcaac    1320 gtcatcggcg tcaacaacaa cgattaccag atcagccgcg ctcgccgtca cgacgcgctc    1380
```

```
gccggtatga gctccaagat cgactacgtc aagaccgact tctgcaacat gagcttagcc    1440
gacaacacct tcgacggcgc ctacgccatc gaggccacct gccacgcaaa ggacaaggtc    1500
aagtgctata gcgaggtctt ccgtgtcatc aagcccggca cctgctttgt cctgtacgag    1560
tggtgcatga ccgacaagta caaccccaat gacgagtacc accgcacaat caagcaccgc    1620
atcgagctgg cgacggcct gccggagatg gagacgtgca acaggtgat cgagtacatg    1680 aagcaggccg gcttcgtggt ggaggaggcc atagacgtca tcagtcagtt cgagtccagc    1740
cccatcaaga gtatcccgtg gtaccagccg ctggtcggcg actattcgtc cctgcagggc    1800
ctgcgctcta ccccgattgg ccgcatcctc acgaacgtca tgtgtcgcgt gctggagttc    1860
gtgcgcctag ctccgaaggg cacgtacaag gcgacggaga ttttggagga ggctgcggaa    1920
agcctggtgg tgggcggtca gctcggcatc ttcacgccgt ccttctacat ccgcgctcgc    1980
aagccgtcca gcaggcttc ggcggtcggc aacatcgagt cgcagtgggc ccgtgccggc    2040
cacggcttgg tgagcctgtc ggagcagcag ctggtgagct cgatgacaa agacaatggc    2100 tgcaacggcg ggctgatgct gcaggcgttc gagtggctgc tgcgacacat gtacgggatc    2160
gtgttcacgg agaagagcta ccctacacg tccggcaacg tgatgtggc cgagtgcttg    2220 aacagcagta aactcgttcc cggcgcgcaa atcgacggct acgtgatgat cccgagcaac    2280
gaaacggtta tggctgcgtg gcttgcggag aatggcccca tcgcgattgc ggtcgacgcc    2340
agctccttca tgtcttacca gagcggcgtg ctgaccagct gcgctggcga tgcactgaac    2400
cacggcgtgc tgctcgtcgg gtacaacaag accggtgggg ttccgtactg ggtgatcaag    2460
aactcgtggg gtgaggactg gggcgagaag ggctacgtgc gcgtggtcat ggggctgaac    2520
gcgtgcctgc tcagtgaata ccccgtgtcc gcgcatgtgc cgcggagtct caccctggc    2580 ccgggcacgg agagcgagga gcgcgcccct aaacgggtga cggtggagca gatgatgtgc    2640
accgatatgt actgcaggga ggggtgcaag aagagtcttc tcaccgcgaa cgtgtgctac    2700
aagaacgggg gaggcggctc ctctatgacg aagtgcggtc cgcagaaggt gctgatgtgc    2760
tcgtactcga accctcattg ctttggtcct gggctgtgcc tcgagactcc tgatggcaag    2820
tgcgcgccgt acttcttggg ctcgatcatg aacacctgcc agtacacg    2868
```

<210> SEQ ID NO 2
<211> LENGTH: 956
<212> TYPE: PRT
<213> ORGANISM: Artificial Sequence
<220> FEATURE:
<223> OTHER INFORMATION: Synthetic Construct

<400> SEQUENCE: 2

```
Met Pro Arg Lys Ile Ile Leu Asp Cys Asp Pro Gly Ile Asp Asp Ala
1               5                   10                  15

Val Ala Ile Phe Leu Ala His Gly Asn Pro Glu Val Glu Leu Leu Ala
            20                  25                  30

Ile Thr Thr Val Val Gly Asn Gln Thr Leu Glu Lys Val Thr Arg Asn
        35                  40                  45

Ala Arg Leu Val Ala Asp Val Ala Gly Ile Val Gly Val Pro Val Ala
    50                  55                  60

Ala Gly Cys Thr Lys Pro Leu Val Arg Gly Val Arg Asn Ala Ser Gln
65                  70                  75                  80

Ile His Gly Glu Thr Gly Met Gly Asn Val Ser Tyr Pro Pro Glu Phe
                85                  90                  95
```

```
Lys Thr Lys Leu Asp Gly Arg His Ala Val Gln Leu Ile Ile Asp Leu
            100                 105                 110

Ile Met Ser His Glu Pro Lys Thr Ile Thr Leu Val Pro Thr Gly Gly
        115                 120                 125

Leu Thr Asn Ile Ala Met Ala Val Arg Leu Glu Pro Arg Ile Val Asp
    130                 135                 140

Arg Val Lys Glu Val Val Leu Met Gly Gly Tyr His Thr Gly Asn
145                 150                 155                 160

Ala Ser Pro Val Ala Glu Phe Asn Val Phe Val Asp Pro Glu Ala Ala
                165                 170                 175

His Ile Val Phe Asn Glu Ser Trp Asn Val Thr Met Val Gly Leu Asp
            180                 185                 190

Leu Thr His Gln Ala Leu Ala Thr Pro Ala Val Gln Lys Arg Val Lys
        195                 200                 205

Glu Val Gly Thr Lys Pro Ala Ala Phe Met Leu Gln Ile Leu Asp Phe
    210                 215                 220

Tyr Thr Lys Val Tyr Glu Lys Glu Arg Asn Thr Tyr Ala Thr Val His
225                 230                 235                 240

Asp Pro Cys Ala Val Ala Tyr Val Ile Asp Pro Thr Val Met Thr Thr
                245                 250                 255

Glu Gln Val Pro Val Asp Ile Glu Leu Asn Gly Ala Leu Thr Thr Gly
            260                 265                 270

Met Thr Val Ala Asp Phe Arg Tyr Pro Arg Pro Lys His Cys His Thr
        275                 280                 285

Gln Val Ala Val Lys Leu Asp Phe Asp Lys Phe Trp Cys Leu Val Ile
    290                 295                 300

Asp Ala Leu Lys Arg Ile Gly Asp Pro Gln Ser Ala Gly Gly Arg Glu
305                 310                 315                 320

Thr Ala Pro Thr Asn Leu Ile Arg Arg Arg Asn Lys Asp Glu Thr Asn
                325                 330                 335

Gly Asp Val Ser Ala Ala Ala Asp Arg Phe Arg Asp Arg Phe Glu Lys
            340                 345                 350

Ala Thr Leu Glu Glu Arg Lys Ala Ala Thr Thr Thr Met Val Asn Glu
        355                 360                 365

Tyr Tyr Asp Leu Val Thr Asp Phe Tyr Glu Tyr Gly Trp Gly Gln Asn
    370                 375                 380

Phe His Phe Ala Pro Arg Tyr Ala Gly Glu Thr Phe Phe Glu Ser Leu
385                 390                 395                 400

Ala Arg His Glu Tyr Phe Leu Ala Ala Arg Gly Gly Phe Met Glu Gly
                405                 410                 415

Asp His Ile Val Asp Val Gly Cys Gly Val Gly Gly Pro Ala Arg Asn
            420                 425                 430

Met Val Arg Leu Thr Arg Cys Asn Val Ile Gly Val Asn Asn Asn Asp
        435                 440                 445

Tyr Gln Ile Ser Arg Ala Arg Arg His Asp Ala Leu Ala Gly Met Ser
    450                 455                 460

Ser Lys Ile Asp Tyr Val Lys Thr Asp Phe Cys Asn Met Ser Leu Ala
465                 470                 475                 480

Asp Asn Thr Phe Asp Gly Ala Tyr Ala Ile Glu Ala Thr Cys His Ala
                485                 490                 495

Lys Asp Lys Val Lys Cys Tyr Ser Glu Val Phe Arg Val Ile Lys Pro
            500                 505                 510

Gly Thr Cys Phe Val Leu Tyr Glu Trp Cys Met Thr Asp Lys Tyr Asn
```

```
            515                 520                 525
Pro Asn Asp Glu Tyr His Arg Thr Ile Lys His Arg Ile Glu Leu Gly
            530                 535                 540

Asp Gly Leu Pro Glu Met Glu Thr Cys Lys Gln Val Ile Glu Tyr Met
545                 550                 555                 560

Lys Gln Ala Gly Phe Val Glu Glu Ala Ile Asp Val Ile Ser Gln
                565                 570                 575

Phe Glu Ser Ser Pro Ile Lys Ser Ile Pro Trp Tyr Gln Pro Leu Val
            580                 585                 590

Gly Asp Tyr Ser Ser Leu Gln Gly Leu Arg Ser Thr Pro Ile Gly Arg
            595                 600                 605

Ile Leu Thr Asn Val Met Cys Arg Val Leu Glu Phe Val Arg Leu Ala
            610                 615                 620

Pro Lys Gly Thr Tyr Lys Ala Thr Glu Ile Leu Glu Glu Ala Ala Glu
625                 630                 635                 640

Ser Leu Val Val Gly Gly Gln Leu Gly Ile Phe Thr Pro Ser Phe Tyr
                645                 650                 655

Ile Arg Ala Arg Lys Pro Ser Lys Gln Ala Ser Ala Val Gly Asn Ile
            660                 665                 670

Glu Ser Gln Trp Ala Arg Ala Gly His Gly Leu Val Ser Leu Ser Glu
            675                 680                 685

Gln Gln Leu Val Ser Cys Asp Asp Lys Asp Asn Gly Cys Asn Gly Gly
            690                 695                 700

Leu Met Leu Gln Ala Phe Glu Trp Leu Leu Arg His Met Tyr Gly Ile
705                 710                 715                 720

Val Phe Thr Glu Lys Ser Tyr Pro Tyr Thr Ser Gly Asn Gly Asp Val
                725                 730                 735

Ala Glu Cys Leu Asn Ser Ser Lys Leu Val Pro Gly Ala Gln Ile Asp
            740                 745                 750

Gly Tyr Val Met Ile Pro Ser Asn Glu Thr Val Met Ala Ala Trp Leu
            755                 760                 765

Ala Glu Asn Gly Pro Ile Ala Ile Ala Val Asp Ala Ser Ser Phe Met
770                 775                 780

Ser Tyr Gln Ser Gly Val Leu Thr Ser Cys Ala Gly Asp Ala Leu Asn
785                 790                 795                 800

His Gly Val Leu Leu Val Gly Tyr Asn Lys Thr Gly Gly Val Pro Tyr
                805                 810                 815

Trp Val Ile Lys Asn Ser Trp Gly Glu Asp Trp Gly Glu Lys Gly Tyr
            820                 825                 830

Val Arg Val Val Met Gly Leu Asn Ala Cys Leu Leu Ser Glu Tyr Pro
            835                 840                 845

Val Ser Ala His Val Pro Arg Ser Leu Thr Pro Gly Pro Gly Thr Glu
            850                 855                 860

Ser Glu Glu Arg Ala Pro Lys Arg Val Thr Val Glu Gln Met Met Cys
865                 870                 875                 880

Thr Asp Met Tyr Cys Arg Glu Gly Cys Lys Lys Ser Leu Leu Thr Ala
                885                 890                 895

Asn Val Cys Tyr Lys Asn Gly Gly Gly Ser Ser Met Thr Lys Cys
                900                 905                 910

Gly Pro Gln Lys Val Leu Met Cys Ser Tyr Ser Asn Pro His Cys Phe
            915                 920                 925

Gly Pro Gly Leu Cys Leu Glu Thr Pro Asp Gly Lys Cys Ala Pro Tyr
            930                 935                 940
```

Phe Leu Gly Ser Ile Met Asn Thr Cys Gln Tyr Thr
945                 950                 955

<210> SEQ ID NO 3
<211> LENGTH: 2640
<212> TYPE: DNA
<213> ORGANISM: Artificial Sequence
<220> FEATURE:
<223> OTHER INFORMATION: Synthetic Construct

<400> SEQUENCE: 3

| | | | | |
|---|---|---|---|---|
| atgccgcgca | agattattct | cgattgtgat | cccgggatcg | atgatgccgt ggccatcttt | 60 |
| ctcgcccacg | gcaacccgga | ggtcgagctg | ctggccatta | cgacggtggt gggcaaccag | 120 |
| accctggaga | aggtgacccg | gaacgcgcgg | ctggtagctg | acgtagccgg catcgttggt | 180 |
| gtgcccgtcg | cggctggttg | caccaagccc | ctcgtgcgcg | gtgtgcggaa tgcctctcag | 240 |
| attcatggcg | aaaccggcat | gggtaacgtc | tcctacccac | cagagttcaa gacaaagttg | 300 |
| gacggccgtc | atgcagtgca | gctgatcatc | gaccttatca | tgtcgcacga gccgaagacg | 360 |
| atcacgcttg | tgcctacggg | tggcctgacg | aacattgcga | tggctgtccg tcttgagccg | 420 |
| cgcatcgtgg | accgtgtgaa | ggaggtggtt | ctgatgggtg | cggctacca tactggtaat | 480 |
| gcgtcccctg | tagcggagtt | caacgtcttc | gtcgacccgg | aggcggcgca cattgtgttc | 540 |
| aacgagagct | ggaacgtaac | gatggtgggg | ctggacctaa | cgcaccaggc actcgccacg | 600 |
| ccggcggtcc | agaagcgagt | gaaggaggtg | ggcacgaagc | cggctgcctt catgctgcag | 660 |
| attttggact | tttacacgaa | ggtgtacgaa | aaggagcgca | cacgtacgc gacggtgcac | 720 |
| gatccctgcg | ctgtggcgta | cgtgattgac | cccaccgtga | tgacgacgga gcaagtgcca | 780 |
| gtggacatcg | agctcaatgg | ggcactgacg | actgggatga | cggtcgcgga cttccgctac | 840 |
| ccacggccaa | agcactgcca | cacgcaggtg | gctgtgaagc | tggacttcga caagttttgg | 900 |
| tgcctcgtga | ttgacgcact | caagcgcatc | ggcgatcctc | aatccgccgg tggccgtgag | 960 |
| accgcgccga | cgaacctgat | tcgtcgccgc | aacaaggacg | agacaaacgg ggatgtcagc | 1020 |
| gccgccgccg | accgcttccg | cgaccgcttc | gagaaggcaa | ccctcgagga gcgcaaggcc | 1080 |
| gccaccacga | cgatggtcaa | cgagtactac | gacctggtga | cggacttcta cgagtacggc | 1140 |
| tggggccaga | acttccattt | cgccgccgcg | tacgccggcg | agaccttctt cgagtccctc | 1200 |
| gcgcgccacg | agtacttcct | ggccgctcgc | ggcggcttca | tggagggcga ccacatcgtc | 1260 |
| gacgtgggct | gcggcgtcgg | cggtccggcg | cgcaacatgg | ttcgcctcac gcgctgcaac | 1320 |
| gtcatcggcg | tcaacaacaa | cgattaccag | atcagccgcg | ctcgccgtca tgacgcgctc | 1380 |
| gccggtatga | gctccaagat | cgactacgtc | aagaccgact | tctgcaacat gagcttagcc | 1440 |
| gacaacacct | tcgacggcgc | ctacgccatc | gaggccacct | gccacgcaaa ggacaaggtc | 1500 |
| aagtgctata | gcgaggtctt | ccgtgtcatc | aagcccggca | cctgctttgt cctgtacgag | 1560 |
| tggtgcatga | ccgacaagta | caccccaat | gacgagtacc | accgcacaat caagcaccgc | 1620 |
| atcgagctgg | gcgacggcct | gccggagatg | gagacgtgca | acaggtgat cgagtacatg | 1680 |
| aagcaggccg | gcttcgtggt | ggaggaggcc | atagacgtca | tcagtcagtt cgagtccagc | 1740 |
| cccatcaaga | gtatcccgtg | gtaccagccg | ctggtcggcg | actattcgtc cctgcagggc | 1800 |
| ctgcgctcta | ccccgattgg | ccgcatcctc | acgaacgtca | tgtgtcgcgt gctggagttc | 1860 |
| gtgcgcctag | ctccgaaggg | cacgtacaag | gcgacggaga | ttttggagga ggctgcggaa | 1920 |
| agcctggtgg | tgggcggtca | gctcggcatc | ttcacgccgt | ccttctacat ccgcgctcgc | 1980 |

```
aagccgtcca agcaggctag cgcctccgct gagccgcaca aggcggccgt tgacgtcggc   2040
ccgctgagcg ttggcccgca gagcgtcggc ccgctgagcg ttggcccgca ggcggttggc   2100
ccgctgagcg ttggcccgca gagcgtcggc ccgctgagcg ttggcccgca ggcggttggc   2160
ccgctgagcg ttggcccgca gagcgttggc ccgctgagcg ttggcccgct gagcgttggc   2220
ccgcagagcg ttggcccgct gagcgttggc agccagagcg tcggcccgct gagcgttggt   2280
ccgcagagcg tcggcccgct gagcgttggc ccgcaggcgg ttggcccgct gagcgttggc   2340
ccgcagagcg tcggcccgct gagcgttggc ccgcaggcgg ttggcccgct gagcgttggc   2400
ccgcagagcg ttggcccgct gagcgttggc ccgcagagcg ttggcccgct gagcgttggc   2460
agccagagcg tcggcccgct gagcgttggt ccgcagagcg tcggcccgct gagcgttggc   2520
ccgcagagcg tcggcccgct gagcgttggc ccgcagagcg tcggcccgct gagcgttggt   2580
ccgcagagcg ttggcccgct gagcgttggc ccgcagagcg ttgacgttag cccggtgagc   2640
```

<210> SEQ ID NO 4
<211> LENGTH: 880
<212> TYPE: PRT
<213> ORGANISM: Artificial Sequence
<220> FEATURE:
<223> OTHER INFORMATION: Synthetic Construct

<400> SEQUENCE: 4

```
Met Pro Arg Lys Ile Ile Leu Asp Cys Asp Pro Gly Ile Asp Asp Ala
 1               5                   10                  15

Val Ala Ile Phe Leu Ala His Gly Asn Pro Glu Val Glu Leu Leu Ala
                20                  25                  30

Ile Thr Thr Val Val Gly Asn Gln Thr Leu Glu Lys Val Thr Arg Asn
            35                  40                  45

Ala Arg Leu Val Ala Asp Val Ala Gly Ile Val Gly Val Pro Val Ala
        50                  55                  60

Ala Gly Cys Thr Lys Pro Leu Val Arg Gly Val Arg Asn Ala Ser Gln
 65                 70                  75                  80

Ile His Gly Glu Thr Gly Met Gly Asn Val Ser Tyr Pro Pro Glu Phe
                85                  90                  95

Lys Thr Lys Leu Asp Gly Arg His Ala Val Gln Leu Ile Ile Asp Leu
            100                 105                 110

Ile Met Ser His Glu Pro Lys Thr Ile Thr Leu Val Pro Thr Gly Gly
        115                 120                 125

Leu Thr Asn Ile Ala Met Ala Val Arg Leu Glu Pro Arg Ile Val Asp
    130                 135                 140

Arg Val Lys Glu Val Val Leu Met Gly Gly Gly Tyr His Thr Gly Asn
145                 150                 155                 160

Ala Ser Pro Val Ala Glu Phe Asn Val Phe Val Asp Pro Glu Ala Ala
                165                 170                 175

His Ile Val Phe Asn Glu Ser Trp Asn Val Thr Met Val Gly Leu Asp
            180                 185                 190

Leu Thr His Gln Ala Leu Ala Thr Pro Ala Val Gln Lys Arg Val Lys
        195                 200                 205

Glu Val Gly Thr Lys Pro Ala Ala Phe Met Leu Gln Ile Leu Asp Phe
    210                 215                 220

Tyr Thr Lys Val Tyr Glu Lys Glu Arg Asn Thr Tyr Ala Thr Val His
225                 230                 235                 240

Asp Pro Cys Ala Val Ala Tyr Val Ile Asp Pro Thr Val Met Thr Thr
```

```
                245                 250                 255
Glu Gln Val Pro Val Asp Ile Glu Leu Asn Gly Ala Leu Thr Thr Gly
            260                 265                 270

Met Thr Val Ala Asp Phe Arg Tyr Pro Arg Pro Lys His Cys His Thr
        275                 280                 285

Gln Val Ala Val Lys Leu Asp Phe Asp Lys Phe Trp Cys Leu Val Ile
    290                 295                 300

Asp Ala Leu Lys Arg Ile Gly Asp Pro Gln Ser Ala Gly Gly Arg Glu
305                 310                 315                 320

Thr Ala Pro Thr Asn Leu Ile Arg Arg Asn Lys Asp Glu Thr Asn
            325                 330                 335

Gly Asp Val Ser Ala Ala Asp Arg Phe Arg Asp Arg Phe Glu Lys
        340                 345                 350

Ala Thr Leu Glu Glu Arg Lys Ala Ala Thr Thr Thr Met Val Asn Glu
            355                 360                 365

Tyr Tyr Asp Leu Val Thr Asp Phe Tyr Glu Tyr Gly Trp Gly Gln Asn
    370                 375                 380

Phe His Phe Ala Pro Arg Tyr Ala Gly Glu Thr Phe Phe Glu Ser Leu
385                 390                 395                 400

Ala Arg His Glu Tyr Phe Leu Ala Ala Arg Gly Gly Phe Met Glu Gly
            405                 410                 415

Asp His Ile Val Asp Val Gly Cys Gly Val Gly Gly Pro Ala Arg Asn
        420                 425                 430

Met Val Arg Leu Thr Arg Cys Asn Val Ile Gly Val Asn Asn Asn Asp
            435                 440                 445

Tyr Gln Ile Ser Arg Ala Arg Arg His Asp Ala Leu Ala Gly Met Ser
    450                 455                 460

Ser Lys Ile Asp Tyr Val Lys Thr Asp Phe Cys Asn Met Ser Leu Ala
465                 470                 475                 480

Asp Asn Thr Phe Asp Gly Ala Tyr Ala Ile Glu Ala Thr Cys His Ala
            485                 490                 495

Lys Asp Lys Val Lys Cys Tyr Ser Glu Val Phe Arg Val Ile Lys Pro
        500                 505                 510

Gly Thr Cys Phe Val Leu Tyr Glu Trp Cys Met Thr Asp Lys Tyr Asn
            515                 520                 525

Pro Asn Asp Glu Tyr His Arg Thr Ile Lys His Arg Ile Glu Leu Gly
    530                 535                 540

Asp Gly Leu Pro Glu Met Glu Thr Cys Lys Gln Val Ile Glu Tyr Met
545                 550                 555                 560

Lys Gln Ala Gly Phe Val Val Glu Glu Ala Ile Asp Val Ile Ser Gln
            565                 570                 575

Phe Glu Ser Ser Pro Ile Lys Ser Ile Pro Trp Tyr Gln Pro Leu Val
        580                 585                 590

Gly Asp Tyr Ser Ser Leu Gln Gly Leu Arg Ser Thr Pro Ile Gly Arg
    595                 600                 605

Ile Leu Thr Asn Val Met Cys Arg Val Leu Glu Phe Val Arg Leu Ala
            610                 615                 620

Pro Lys Gly Thr Tyr Lys Ala Thr Glu Ile Leu Glu Glu Ala Ala Glu
625                 630                 635                 640

Ser Leu Val Val Gly Gly Gln Leu Gly Ile Phe Thr Pro Ser Phe Tyr
            645                 650                 655

Ile Arg Ala Arg Lys Pro Ser Lys Gln Ala Ser Ala Ser Ala Glu Pro
        660                 665                 670
```

```
His Lys Ala Ala Val Asp Val Gly Pro Leu Ser Val Gly Pro Gln Ser
        675                 680                 685
Val Gly Pro Leu Ser Val Gly Pro Gln Ala Val Gly Pro Leu Ser Val
    690                 695                 700
Gly Pro Gln Ser Val Gly Pro Leu Ser Val Gly Pro Gln Ala Val Gly
705                 710                 715                 720
Pro Leu Ser Val Gly Pro Gln Ser Val Gly Pro Leu Ser Val Gly Pro
                725                 730                 735
Leu Ser Val Gly Pro Gln Ser Val Gly Pro Leu Ser Val Gly Ser Gln
            740                 745                 750
Ser Val Gly Pro Leu Ser Val Gly Pro Gln Ser Val Gly Pro Leu Ser
        755                 760                 765
Val Gly Pro Gln Ala Val Gly Pro Leu Ser Val Gly Pro Gln Ser Val
    770                 775                 780
Gly Pro Leu Ser Val Gly Pro Gln Ala Val Gly Pro Leu Ser Val Gly
785                 790                 795                 800
Pro Gln Ser Val Gly Pro Leu Ser Val Gly Pro Gln Ser Val Gly Pro
                805                 810                 815
Leu Ser Val Gly Ser Gln Ser Val Gly Pro Leu Ser Val Gly Pro Gln
            820                 825                 830
Ser Val Gly Pro Leu Ser Val Gly Pro Gln Ser Val Gly Pro Leu Ser
        835                 840                 845
Val Gly Pro Gln Ser Val Gly Pro Leu Ser Val Gly Pro Gln Ser Val
    850                 855                 860
Gly Pro Leu Ser Val Gly Pro Gln Ser Val Asp Val Ser Pro Val Ser
865                 870                 875                 880

<210> SEQ ID NO 5
<211> LENGTH: 2706
<212> TYPE: DNA
<213> ORGANISM: Artificial Sequence
<220> FEATURE:
<223> OTHER INFORMATION: Synthetic Construct

<400> SEQUENCE: 5
atgccgcgca agattattct cgattgtgat cccgggatcg atgatgccgt ggccatcttt      60
ctcgcccacg gcaacccgga ggtcgagctg ctggccatta cgacggtggt gggcaaccag     120
accctggaga aggtgacccg gaacgcgcgg ctggtagctg acgtagccgg catcgttggt     180
gtgcccgtcg cggctggttg caccaagccc ctcgtgcgcg gtgtgcggaa tgcctctcag     240
attcatggcg aaaccggcat gggtaacgtc tcctacccac cagagttcaa gacaaagttg     300
gacggccgtc atgcagtgca gctgatcatc gaccttatca tgtcgcacga gccgaagacg     360
atcacgcttg tgcctacggg tggcctgacg aacattgcga tggctgtccg tcttgagccg     420
cgcatcgtgg accgtgtgaa ggaggtggtt ctgatgggtg gcggctacca tactggtaat     480
gcgtcccctg tagcggagtt caacgtcttc gtcgacccgg aggcggcgca cattgtgttc     540
aacgagagct ggaacgtaac gatggtgggg ctggacctaa cgcaccaggc actcgccacg     600
ccggcggtcc agaagcgagt gaaggaggtg gcacgaagc cggctgcctt catgctgcag     660
attttggact tttacacgaa ggtgtacgaa aaggagcgca acacgtacgc gacggtgcac     720
gatccctgcg ctgtggcgta cgtgattgac cccaccgtga tgacgacgga gcaagtgcca     780
gtggacatcg agctcaatgg ggcactgacg actgggatga cggtcgcgga cttccgctac     840
ccacggccaa agcactgcca cacgcaggtg gctgtgaagc tggacttcga caagttttgg     900
```

```
tgcctcgtga ttgacgcact caagcgcatc ggcgatcctc aatccgccgg tggccgtgag   960
accgcgccga cgaacctgat tcgtcgccgc aacaaggacg agacaaacgg ggatgtcagc  1020
gccgccgccg accgcttccg cgaccgcttc gagaaggcaa ccctcgagga gcgcaaggcc  1080
gccaccacga cgatggtcaa cgagtactac gacctggtga cggacttcta cgagtacggc  1140
tggggccaga acttccattt cgcgccgcgc tacgccggcg agaccttctt cgagtccctc  1200
gcgcgccacg agtacttcct ggccgctcgc ggcggcttca tggagggcga ccacatcgtc  1260
gacgtgggct gcggcgtcgg cggtccggcg cgcaacatgg ttcgcctcac gcgctgcaac  1320
gtcatcggc tcaacaacaa cgattaccag atcagccgcg ctcgccgtca tgacgcgctc  1380
gccggtatga gctccaagat cgactacgtc aagaccgact tctgcaacat gagcttagcc  1440
gacaacacct tcgacggcgc ctacgccatc gaggccacct gccacgcaaa ggacaaggtc  1500
aagtgctata gcgaggtctt ccgtgtcatc aagcccggca cctgctttgt cctgtacgag  1560
tggtgcatga ccgacaagta caaccccaat gacgagtacc accgcacaat caagcaccgc  1620
atcgagctgg gcgacggcct gccggagatg gagacgtgca acaggtgat cgagtacatg  1680
aagcaggccg gcttcgtggt ggaggaggcc atagacgtca tcagtcagtt cgagtccagc  1740
cccatcaaga gtatcccgtg gtaccagccg ctggtcggcg actattcgtc cctgcagggc  1800
ctgcgctcta ccccgattgg ccgcatcctc acgaacgtca tgtgtcgcgt gctggagttc  1860
gtgcgcctag ctccgaaggg cacgtacaag gcgacggaga ttttggagga ggctgcggaa  1920
agcctggtgg tgggcggtca gctcggcatc ttcacgccgt ccttctacat ccgcgctcgc  1980
aagccgtcca gcaggctat gaagatccgc agcgtgcgtc cgcttgtggt gttgctggtg  2040
tccgtcgcgg cggtgctcgc actcagcgcc tccgctgagc cgcacaaggc ggccgttgac  2100
gtcggcccgc tgagcgttgg cccgcagagc gtcggcccgc tgagcgttgg cccgcaggcg  2160
gttggccccgc tgagcgttgg cccgcagagc gtcggcccgc tgagcgttgg cccgcaggcg  2220
gttggccccgc tgagcgttgg cccgcagagc gttggcccgc tgagcgttgg cccgctgagc  2280
gttggcccgc agagcgttgg cccgctgagc gttggcagcc agagcgtcgg cccgctgagc  2340
gttggtccgc agagcgtcgg cccgctgagc gttggcccgc aggcggttgg cccgctgagc  2400
gttggccccgc agagcgtcgg cccgctgagc gttggcccgc aggcggttgg cccgctgagc  2460
gttggccccgc agagcgttgg cccgctgagc gttggcccgc agagcgttgg cccgctgagc  2520
gttggcagcc agagcgtcgg cccgctgagc gttggtccgc agagcgtcgg cccgctgagc  2580
gttggccccgc agagcgtcgg cccgctgagc gttggcccgc agagcgtcgg cccgctgagc  2640
gttggtccgc agagcgttgg cccgctgagc gttggcccgc agagcgttga cgttagcccg  2700
gtgagc                                                             2706
```

<210> SEQ ID NO 6
<211> LENGTH: 902
<212> TYPE: PRT
<213> ORGANISM: Artificial Sequence
<220> FEATURE:
<223> OTHER INFORMATION: Synthetic Construct

<400> SEQUENCE: 6

Met Pro Arg Lys Ile Ile Leu Asp Cys Asp Pro Gly Ile Asp Asp Ala
 1               5                  10                  15

Val Ala Ile Phe Leu Ala His Gly Asn Pro Glu Val Glu Leu Leu Ala
            20                  25                  30

-continued

```
Ile Thr Thr Val Val Gly Asn Gln Thr Leu Glu Lys Val Thr Arg Asn
        35                  40                  45

Ala Arg Leu Val Ala Asp Val Ala Gly Ile Val Gly Val Pro Val Ala
 50                  55                  60

Ala Gly Cys Thr Lys Pro Leu Val Arg Gly Val Arg Asn Ala Ser Gln
 65                  70                  75                  80

Ile His Gly Glu Thr Gly Met Gly Asn Val Ser Tyr Pro Pro Glu Phe
                 85                  90                  95

Lys Thr Lys Leu Asp Gly Arg His Ala Val Gln Leu Ile Ile Asp Leu
                100                 105                 110

Ile Met Ser His Glu Pro Lys Thr Ile Thr Leu Val Pro Thr Gly Gly
            115                 120                 125

Leu Thr Asn Ile Ala Met Ala Val Arg Leu Glu Pro Arg Ile Val Asp
        130                 135                 140

Arg Val Lys Glu Val Val Leu Met Gly Gly Tyr His Thr Gly Asn
145                 150                 155                 160

Ala Ser Pro Val Ala Glu Phe Asn Val Phe Val Asp Pro Glu Ala Ala
                165                 170                 175

His Ile Val Phe Asn Glu Ser Trp Asn Val Thr Met Val Gly Leu Asp
            180                 185                 190

Leu Thr His Gln Ala Leu Ala Thr Pro Ala Val Gln Lys Arg Val Lys
        195                 200                 205

Glu Val Gly Thr Lys Pro Ala Ala Phe Met Leu Gln Ile Leu Asp Phe
    210                 215                 220

Tyr Thr Lys Val Tyr Glu Lys Glu Arg Asn Thr Tyr Ala Thr Val His
225                 230                 235                 240

Asp Pro Cys Ala Val Ala Tyr Val Ile Asp Pro Thr Val Met Thr Thr
                245                 250                 255

Glu Gln Val Pro Val Asp Ile Glu Leu Asn Gly Ala Leu Thr Thr Gly
            260                 265                 270

Met Thr Val Ala Asp Phe Arg Tyr Pro Arg Pro Lys His Cys His Thr
        275                 280                 285

Gln Val Ala Val Lys Leu Asp Phe Asp Lys Phe Trp Cys Leu Val Ile
    290                 295                 300

Asp Ala Leu Lys Arg Ile Gly Asp Pro Gln Ser Ala Gly Gly Arg Glu
305                 310                 315                 320

Thr Ala Pro Thr Asn Leu Ile Arg Arg Arg Asn Lys Asp Glu Thr Asn
                325                 330                 335

Gly Asp Val Ser Ala Ala Ala Arg Phe Arg Asp Arg Phe Glu Lys
            340                 345                 350

Ala Thr Leu Glu Glu Arg Lys Ala Ala Thr Thr Thr Met Val Asn Glu
        355                 360                 365

Tyr Tyr Asp Leu Val Thr Asp Phe Tyr Glu Tyr Gly Trp Gly Gln Asn
    370                 375                 380

Phe His Phe Ala Pro Arg Tyr Ala Gly Glu Thr Phe Phe Glu Ser Leu
385                 390                 395                 400

Ala Arg His Glu Tyr Phe Leu Ala Ala Arg Gly Gly Phe Met Glu Gly
                405                 410                 415

Asp His Ile Val Asp Val Gly Cys Gly Val Gly Gly Pro Ala Arg Asn
            420                 425                 430

Met Val Arg Leu Thr Arg Cys Asn Val Ile Gly Val Asn Asn Asn Asp
        435                 440                 445

Tyr Gln Ile Ser Arg Ala Arg Arg His Asp Ala Leu Ala Gly Met Ser
```

```
                450             455             460
Ser Lys Ile Asp Tyr Val Lys Thr Asp Phe Cys Asn Met Ser Leu Ala
465                 470                 475                 480

Asp Asn Thr Phe Asp Gly Ala Tyr Ala Ile Glu Ala Thr Cys His Ala
                485                 490                 495

Lys Asp Lys Val Lys Cys Tyr Ser Glu Val Phe Arg Val Ile Lys Pro
                500                 505                 510

Gly Thr Cys Phe Val Leu Tyr Glu Trp Cys Met Thr Asp Lys Tyr Asn
                515                 520                 525

Pro Asn Asp Glu Tyr His Arg Thr Ile Lys His Arg Ile Glu Leu Gly
                530                 535                 540

Asp Gly Leu Pro Glu Met Glu Thr Cys Lys Gln Val Ile Glu Tyr Met
545                 550                 555                 560

Lys Gln Ala Gly Phe Val Val Glu Glu Ala Ile Asp Val Ile Ser Gln
                565                 570                 575

Phe Glu Ser Ser Pro Ile Lys Ser Ile Pro Trp Tyr Gln Pro Leu Val
                580                 585                 590

Gly Asp Tyr Ser Ser Leu Gln Gly Leu Arg Ser Thr Pro Ile Gly Arg
                595                 600                 605

Ile Leu Thr Asn Val Met Cys Arg Val Leu Glu Phe Val Arg Leu Ala
                610                 615                 620

Pro Lys Gly Thr Tyr Lys Ala Thr Glu Ile Leu Glu Glu Ala Ala Glu
625                 630                 635                 640

Ser Leu Val Val Gly Gly Gln Leu Gly Ile Phe Thr Pro Ser Phe Tyr
                645                 650                 655

Ile Arg Ala Arg Lys Pro Ser Lys Gln Ala Met Lys Ile Arg Ser Val
                660                 665                 670

Arg Pro Leu Val Val Leu Leu Val Ser Val Ala Ala Val Leu Ala Leu
                675                 680                 685

Ser Ala Ser Ala Glu Pro His Lys Ala Ala Val Asp Val Gly Pro Leu
690                 695                 700

Ser Val Gly Pro Gln Ser Val Gly Pro Leu Ser Val Gly Pro Gln Ala
705                 710                 715                 720

Val Gly Pro Leu Ser Val Gly Pro Gln Ser Val Gly Pro Leu Ser Val
                725                 730                 735

Gly Pro Gln Ala Val Gly Pro Leu Ser Val Gly Pro Gln Ser Val Gly
                740                 745                 750

Pro Leu Ser Val Gly Pro Leu Ser Val Gly Pro Gln Ser Val Gly Pro
                755                 760                 765

Leu Ser Val Gly Ser Gln Ser Val Gly Pro Leu Ser Val Gly Pro Gln
                770                 775                 780

Ser Val Gly Pro Leu Ser Val Gly Pro Gln Ala Val Gly Pro Leu Ser
785                 790                 795                 800

Val Gly Pro Gln Ser Val Gly Pro Leu Ser Val Gly Pro Gln Ala Val
                805                 810                 815

Gly Pro Leu Ser Val Gly Pro Gln Ser Val Gly Pro Leu Ser Val Gly
                820                 825                 830

Pro Gln Ser Val Gly Pro Leu Ser Val Gly Ser Gln Ser Val Gly Pro
                835                 840                 845

Leu Ser Val Gly Pro Gln Ser Val Gly Pro Leu Ser Val Gly Pro Gln
                850                 855                 860

Ser Val Gly Pro Leu Ser Val Gly Pro Gln Ser Val Gly Pro Leu Ser
865                 870                 875                 880
```

Val Gly Pro Gln Ser Val Gly Pro Leu Ser Val Gly Pro Gln Ser Val
            885                 890                 895

Asp Val Ser Pro Val Ser
            900

<210> SEQ ID NO 7
<211> LENGTH: 2778
<212> TYPE: DNA
<213> ORGANISM: Artificial Sequence
<220> FEATURE:
<223> OTHER INFORMATION: Synthetic Construct

<400> SEQUENCE: 7

| | | | | | |
|---|---|---|---|---|---|
| atggcctctt | ctcgctctgc | tccccgcaag | gcttcccacg | cgcacaagtc | gcaccgcaag | 60 |
| ccgaagcgct | cgtggaacgt | gtacgtgggc | cgctcgctga | aggcgatcaa | cgcccagatg | 120 |
| tcgatgtcgc | accgcacgat | gccgcgcaag | attattctcg | attgtgatcc | cgggatcgat | 180 |
| gatgccgtgg | ccatctttct | cgcccacggc | aacccggagg | tcgagctgct | ggccattacg | 240 |
| acggtggtgg | gcaaccagac | cctggagaag | gtgacccgga | acgcgcggct | ggtagctgac | 300 |
| gtagccggca | tcgttggtgt | gcccgtcgcg | gctggttgca | ccaagcccct | cgtgcgcggt | 360 |
| gtgcggaatg | cctctcagat | tcatggcgaa | accggcatgg | gtaacgtctc | ctacccacca | 420 |
| gagttcaaga | caaagttgga | cggccgtcat | gcagtcagc | tgatcatcga | ccttatcatg | 480 |
| tcgcacgagc | cgaagacgat | cacgcttgtg | cctacgggtg | gcctgacgaa | cattgcgatg | 540 |
| gctgtccgtc | ttgagccgcg | catcgtggac | cgtgtgaagg | aggtggttct | gatgggtggc | 600 |
| ggctaccata | ctggtaatgc | gtcccctgta | gcggagttca | acgtcttcgt | cgacccggag | 660 |
| gcggcgcaca | ttgtgttcaa | cgagagctgg | aacgtaacga | tggtggggct | ggacctaacg | 720 |
| caccaggcac | tcgccacgcc | ggcggtccag | aagcgagtga | aggaggtggg | cacgaagccg | 780 |
| gctgccttca | tgctgcagat | tttggacttt | tacacgaagg | tgtacgaaaa | ggagcgcaac | 840 |
| acgtacgcga | cggtgcacga | tccctgcgct | gtggcgtacg | tgattgaccc | caccgtgatg | 900 |
| acgacggagc | aagtgccagt | ggacatcgag | ctcaatgggg | cactgacgac | tgggatgacg | 960 |
| gtcgcggact | tccgctaccc | acggccaaag | cactgccaca | cgcaggtggc | tgtgaagctg | 1020 |
| gacttcgaca | gttttggtg | cctcgtgatt | gacgcactca | agcgcatcgg | cgatcctcaa | 1080 |
| tccgccggtg | gccgtgagac | cgcgccgacg | aacctgattc | gtcgccgcaa | caaggacgag | 1140 |
| acaaacgggg | atgtcagcgc | cgccgccgac | cgcttccgcg | accgcttcga | gaaggcaacc | 1200 |
| ctcgaggagc | gcaaggccgc | caccacgacg | atggtcaacg | agtactacga | cctggtgacg | 1260 |
| gacttctacg | agtacggctg | gggccagaac | ttccatttcg | cgccgcgcta | cgccggcgag | 1320 |
| accttcttcg | agtccctcgc | gcgccacgag | tacttcctgg | ccgctcgcgg | cggcttcatg | 1380 |
| gagggcgacc | acatcgtcga | cgtgggctgc | ggcgtcggcg | gtccggcgcg | caacatggtt | 1440 |
| cgcctcacgc | gctgcaacgt | catcggcgtc | aacaacaacg | attaccagat | cagccgcgct | 1500 |
| cgccgtcatg | acgcgctcgc | cggtatgagc | tccaagatcg | actacgtcaa | gaccgacttc | 1560 |
| tgcaacatga | gcttagccga | caacaccttc | gacggcgcct | acgccatcga | ggccacctgc | 1620 |
| cacgcaaagg | acaaggtcaa | gtgctatagc | gaggtcttcc | gtgtcatcaa | gcccggcacc | 1680 |
| tgctttgtcc | tgtacgagtg | gtgcatgacc | gacaagtaca | ccccaatga | cgagtaccac | 1740 |
| cgcacaatca | agcaccgcat | cgagctgggc | gacggcctgc | cggagatgga | gacgtgcaaa | 1800 |
| caggtgatcg | agtacatgaa | gcaggccggc | ttcgtggtgg | aggaggccat | agacgtcatc | 1860 |

```
agtcagttcg agtccagccc catcaagagt atcccgtggt accagccgct ggtcggcgac   1920
tattcgtccc tgcagggcct gcgctctacc ccgattggcc gcatcctcac gaacgtcatg   1980
tgtcgcgtgc tggagttcgt gcgcctagct ccgaagggca cgtacaaggc gacggagatt   2040
ttggaggagg ctgcggaaag cctggtggtg ggcggtcagc tcggcatctt cacgccgtcc   2100
ttctacatcc gcgctcgcaa gccgtccaag caggctagcg cctccgctga gccgcacaag   2160
gcggccgttg acgtcggccc gctgagcgtt ggcccgcaga gcgtcggccc gctgagcgtt   2220
ggcccgcagg cggttggccc gctgagcgtt ggcccgcaga gcgtcggccc gctgagcgtt   2280
ggcccgcagg cggttggccc gctgagcgtt ggcccgcaga gcgttggccc gctgagcgtt   2340
ggcccgctga gcgttggccc gcagagcgtt ggcccgctga gcgttggcag ccagagcgtc   2400
ggcccgctga gcgttggtcc gcagagcgtc ggcccgctga gcgttggccc gcaggcggtt   2460
ggcccgctga gcgttggccc gcagagcgtc ggcccgctga gcgttggccc gcaggcggtt   2520
ggcccgctga gcgttggccc gcagagcgtt ggcccgctga gcgttggccc gcagagcgtt   2580
ggcccgctga gcgttggcag ccagagcgtc ggcccgctga gcgttggtcc gcagagcgtc   2640
ggcccgctga gcgttggccc gcagagcgtc ggcccgctga gcgttggccc gcagagcgtc   2700
ggcccgctga gcgttggtcc gcagagcgtt ggcccgctga gcgttggccc gcagagcgtt   2760
gacgttagcc cggtgagc                                                 2778
```

<210> SEQ ID NO 8
<211> LENGTH: 926
<212> TYPE: PRT
<213> ORGANISM: Artificial Sequence
<220> FEATURE:
<223> OTHER INFORMATION: Synthetic Construct

<400> SEQUENCE: 8

```
Met Ala Ser Ser Arg Ser Ala Pro Arg Lys Ala Ser His Ala His Lys
 1               5                  10                  15

Ser His Arg Lys Pro Lys Arg Ser Trp Asn Val Tyr Val Gly Arg Ser
            20                  25                  30

Leu Lys Ala Ile Asn Ala Gln Met Ser Met Ser His Arg Thr Met Pro
        35                  40                  45

Arg Lys Ile Ile Leu Asp Cys Asp Pro Gly Ile Asp Asp Ala Val Ala
    50                  55                  60

Ile Phe Leu Ala His Gly Asn Pro Glu Val Glu Leu Leu Ala Ile Thr
65                  70                  75                  80

Thr Val Val Gly Asn Gln Thr Leu Glu Lys Val Thr Arg Asn Ala Arg
                85                  90                  95

Leu Val Ala Asp Val Ala Gly Ile Val Gly Val Pro Val Ala Ala Gly
            100                 105                 110

Cys Thr Lys Pro Leu Val Arg Gly Val Arg Asn Ala Ser Gln Ile His
        115                 120                 125

Gly Glu Thr Gly Met Gly Asn Val Ser Tyr Pro Pro Glu Phe Lys Thr
    130                 135                 140

Lys Leu Asp Gly Arg His Ala Val Gln Leu Ile Ile Asp Leu Ile Met
145                 150                 155                 160

Ser His Glu Pro Lys Thr Ile Thr Leu Val Pro Thr Gly Gly Leu Thr
                165                 170                 175

Asn Ile Ala Met Ala Val Arg Leu Glu Pro Arg Ile Val Asp Arg Val
            180                 185                 190

Lys Glu Val Val Leu Met Gly Gly Gly Tyr His Thr Gly Asn Ala Ser
```

```
            195                 200                 205
Pro Val Ala Glu Phe Asn Val Phe Val Asp Pro Glu Ala Ala His Ile
210                 215                 220

Val Phe Asn Glu Ser Trp Asn Val Thr Met Val Gly Leu Asp Leu Thr
225                 230                 235                 240

His Gln Ala Leu Ala Thr Pro Ala Val Gln Lys Arg Val Lys Glu Val
                245                 250                 255

Gly Thr Lys Pro Ala Ala Phe Met Leu Gln Ile Leu Asp Phe Tyr Thr
            260                 265                 270

Lys Val Tyr Glu Lys Glu Arg Asn Thr Tyr Ala Thr Val His Asp Pro
        275                 280                 285

Cys Ala Val Ala Tyr Val Ile Asp Pro Thr Val Met Thr Thr Glu Gln
290                 295                 300

Val Pro Val Asp Ile Glu Leu Asn Gly Ala Leu Thr Thr Gly Met Thr
305                 310                 315                 320

Val Ala Asp Phe Arg Tyr Pro Arg Pro Lys His Cys His Thr Gln Val
                325                 330                 335

Ala Val Lys Leu Asp Phe Asp Lys Phe Trp Cys Leu Val Ile Asp Ala
            340                 345                 350

Leu Lys Arg Ile Gly Asp Pro Gln Ser Ala Gly Gly Arg Glu Thr Ala
        355                 360                 365

Pro Thr Asn Leu Ile Arg Arg Asn Lys Asp Glu Thr Asn Gly Asp
370                 375                 380

Val Ser Ala Ala Ala Asp Arg Phe Arg Asp Arg Phe Glu Lys Ala Thr
385                 390                 395                 400

Leu Glu Glu Arg Lys Ala Ala Thr Thr Thr Met Val Asn Glu Tyr Tyr
                405                 410                 415

Asp Leu Val Thr Asp Phe Tyr Glu Tyr Gly Trp Gly Gln Asn Phe His
            420                 425                 430

Phe Ala Pro Arg Tyr Ala Gly Glu Thr Phe Phe Glu Ser Leu Ala Arg
        435                 440                 445

His Glu Tyr Phe Leu Ala Ala Arg Gly Gly Phe Met Glu Gly Asp His
    450                 455                 460

Ile Val Asp Val Gly Cys Gly Val Gly Gly Pro Ala Arg Asn Met Val
465                 470                 475                 480

Arg Leu Thr Arg Cys Asn Val Ile Gly Val Asn Asn Asn Asp Tyr Gln
                485                 490                 495

Ile Ser Arg Ala Arg Arg His Asp Ala Leu Ala Gly Met Ser Ser Lys
            500                 505                 510

Ile Asp Tyr Val Lys Thr Asp Phe Cys Asn Met Ser Leu Ala Asp Asn
        515                 520                 525

Thr Phe Asp Gly Ala Tyr Ala Ile Glu Ala Thr Cys His Ala Lys Asp
    530                 535                 540

Lys Val Lys Cys Tyr Ser Glu Val Phe Arg Val Ile Lys Pro Gly Thr
545                 550                 555                 560

Cys Phe Val Leu Tyr Glu Trp Cys Met Thr Asp Lys Tyr Asn Pro Asn
                565                 570                 575

Asp Glu Tyr His Arg Thr Ile His Arg Ile Glu Leu Gly Asp Gly
            580                 585                 590

Leu Pro Glu Met Glu Thr Cys Lys Gln Val Ile Glu Tyr Met Lys Gln
        595                 600                 605

Ala Gly Phe Val Val Glu Glu Ala Ile Asp Val Ile Ser Gln Phe Glu
    610                 615                 620
```

```
Ser Ser Pro Ile Lys Ser Ile Pro Trp Tyr Gln Pro Leu Val Gly Asp
625                 630                 635                 640

Tyr Ser Ser Leu Gln Gly Leu Arg Ser Thr Pro Ile Gly Arg Ile Leu
            645                 650                 655

Thr Asn Val Met Cys Arg Val Leu Glu Phe Val Arg Leu Ala Pro Lys
        660                 665                 670

Gly Thr Tyr Lys Ala Thr Glu Ile Leu Glu Glu Ala Glu Ser Leu
    675                 680                 685

Val Val Gly Gly Gln Leu Gly Ile Phe Thr Pro Ser Phe Tyr Ile Arg
690                 695                 700

Ala Arg Lys Pro Ser Lys Gln Ala Ser Ala Ser Ala Glu Pro His Lys
705                 710                 715                 720

Ala Ala Val Asp Val Gly Pro Leu Ser Val Gly Pro Gln Ser Val Gly
            725                 730                 735

Pro Leu Ser Val Gly Pro Gln Ala Val Gly Pro Leu Ser Val Gly Pro
            740                 745                 750

Gln Ser Val Gly Pro Leu Ser Val Gly Pro Gln Ala Val Gly Pro Leu
            755                 760                 765

Ser Val Gly Pro Gln Ser Val Gly Pro Leu Ser Val Gly Pro Leu Ser
    770                 775                 780

Val Gly Pro Gln Ser Val Gly Pro Leu Ser Val Gly Ser Gln Ser Val
785                 790                 795                 800

Gly Pro Leu Ser Val Gly Pro Gln Ser Val Gly Pro Leu Ser Val Gly
            805                 810                 815

Pro Gln Ala Val Gly Pro Leu Ser Val Gly Pro Gln Ser Val Gly Pro
        820                 825                 830

Leu Ser Val Gly Pro Gln Ala Val Gly Pro Leu Ser Val Gly Pro Gln
    835                 840                 845

Ser Val Gly Pro Leu Ser Val Gly Pro Gln Ser Val Gly Pro Leu Ser
    850                 855                 860

Val Gly Ser Gln Ser Val Gly Pro Leu Ser Val Gly Pro Gln Ser Val
865                 870                 875                 880

Gly Pro Leu Ser Val Gly Pro Gln Ser Val Gly Pro Leu Ser Val Gly
            885                 890                 895

Pro Gln Ser Val Gly Pro Leu Ser Val Gly Pro Gln Ser Val Gly Pro
        900                 905                 910

Leu Ser Val Gly Pro Gln Ser Val Asp Val Ser Pro Val Ser
    915                 920                 925

<210> SEQ ID NO 9
<211> LENGTH: 3099
<212> TYPE: DNA
<213> ORGANISM: Artificial Sequence
<220> FEATURE:
<223> OTHER INFORMATION: Synthetic Construct

<400> SEQUENCE: 9
atgaaggaca aggcgacggg caagacgcag aacatcacga tcacggcgaa cggcgggctg      60
tcgaaggagc agatcgagca gatgatccgc gactcggagc agcacgcgga ggccgaccgc    120
gtgaagcgcg agcttgtgga ggtgcgcaac aacgcggaga cgcagctgac aacggcggag    180
aggcagctcg gcgagtggaa gtacgtgagc gatgcggaga aggagaacgt gaagacgctg    240
gtggcggagc tgcgcaaggc gatggagaac ccgaacgtcg cgaaggatga ccttgcgggt    300
gcgacggaca agctgcagaa ggctgtgatg gagtgcggcc gcacagagta ccagcaggct    360
```

-continued

```
gccgcggcca actccggcag caccagcaac tccggtgagc agcagcagca gcagggccaa      420
ggtgagcagc agcagcagca gaacagcgaa gagaagaaga tgccgcgcaa gattattctc      480
gattgtgatc ccgggatcga tgatgccgtg gccatctttc tcgcccacgg caacccggag      540
gtcgagctgc tggccattac gacggtggtg ggcaaccaga ccctggagaa ggtgacccgg      600
aacgcgcggc tggtagctga cgtagccggc atcgttggtg tgcccgtcgc ggctggttgc      660
accaagcccc tcgtgcgcgg tgtgcggaat gcctctcaga ttcatggcga aaccggcatg      720
ggtaacgtct cctacccacc agagttcaag acaaagttgg acggccgtca tgcagtgcag      780
ctgatcatcg accttatcat gtcgcacgag ccgaagacga tcacgcttgt gcctacgggt      840
ggcctgacga acattgcgat ggctgtccgt cttgagccgc gcatcgtgga ccgtgtgaag      900
gaggtggttc tgatgggtgg cggctaccat actggtaatg cgtcccctgt agcggagttc      960
aacgtcttcg tcgacccgga ggcggcgcac attgtgttca acgagagctg gaacgtaacg     1020
atggtggggc tggacctaac gcaccaggca ctcgccacgc cggcggtcca gaagcgagtg     1080
aaggaggtgg gcacgaagcc ggctgccttc atgctgcaga ttttggactt ttacacgaag     1140
gtgtacgaaa aggagcgcaa cacgtacgcg acggtgcacg atccctgcgc tgtggcgtac     1200
gtgattgacc ccaccgtgat gacgacggag caagtgccag tggacatcga gctcaatggg     1260
gcactgacga ctgggatgac ggtcgcggac ttccgctacc cacggccaaa gcactgccac     1320
acgcaggtgg ctgtgaagct ggacttcgac aagttttggt gcctcgtgat tgacgcactc     1380
aagcgcatcg gcgatcctca atccgccggt ggcgtgagga ccgcgccgac gaacctgatt     1440
cgtcgccgca acaaggacga gacaaacggg gatgtcagcg ccgccgccga ccgcttccgc     1500
gaccgcttcg agaaggcaac cctcgaggag cgcaaggccg ccaccacgac gatggtcaac     1560
gagtactacg acctggtgac ggacttctac gagtacggct ggggccagaa cttccatttc     1620
gcgccgcgct acgccggcga gaccttcttc gagtccctcg cgcgccacga gtacttcctg     1680
gccgctcgcg gcggcttcat ggagggcgac cacatcgtcg acgtgggctg cggcgtcggc     1740
ggtccggcgc gcaacatggt tcgcctcacg cgctgcaacg tcatcggcgt caacaacaac     1800
gattaccaga tcagccgcgc tcgccgtcat gacgcgctcg ccggtatgag ctccaagatc     1860
gactacgtca agaccgactt ctgcaacatg agcttagccg acaacaccct cgacggcgcc     1920
tacgccatcg aggccacctg ccacgcaaag gacaaggtca agtgctatag cgaggtcttc     1980
cgtgtcatca gcccggcac ctgctttgtc ctgtacgagt ggtgcatgac cgacaagtac     2040
aaccccaatg acgagtacca ccgcacaatc aagcaccgca tcgagctggg cgacggcctg     2100
ccggagatgg agacgtgcaa acaggtgatc gagtacatga agcaggccgg cttcgtggtg     2160
gaggaggcca tagacgtcat cagtcagttc gagtccagcc ccatcaagag tatcccgtgg     2220
taccagccgc tggtcggcga ctattcgtcc ctgcagggcc tgcgctctac cccgattggc     2280
cgcatcctca cgaacgtcat gtgtcgcgtg ctggagttcg tgcgcctagc tccgaagggc     2340
acgtacaagg cgacggagat tttggaggag gctgcggaaa gcctggtggt gggcggtcag     2400
ctcggcatct tcacgccgtc cttctacatc cgcgctcgca agccgtccaa gcaggctagc     2460
gcctccgctg agccgcacaa gcggccgtt gacgtcggcc cgctgagcgt tggcccgcag     2520
agcgtcggcc cgctgagcgt tggcccgcag gcggttggcc cgctgagcgt tggcccgcag     2580
agcgtcggcc cgctgagcgt tggcccgcag gcggttggcc cgctgagcgt tggcccgcag     2640
agcgttggcc cgctgagcgt tggcccgctg agcgttggcc cgcagagcgt tggcccgctg     2700
```

```
agcgttggca gccagagcgt cggcccgctg agcgttggtc cgcagagcgt cggcccgctg    2760
agcgttggcc cgcaggcggt tggcccgctg agcgttggcc cgcagagcgt cggcccgctg    2820
agcgttggcc cgcaggcggt tggcccgctg agcgttggcc cgcagagcgt tggcccgctg    2880
agcgttggcc cgcagagcgt tggcccgctg agcgttggca gccagagcgt cggcccgctg    2940
agcgttggtc cgcagagcgt cggcccgctg agcgttggcc cgcagagcgt cggcccgctg    3000
agcgttggcc cgcagagcgt cggcccgctg agcgttggtc cgcagagcgt tggcccgctg    3060
agcgttggcc cgcagagcgt tgacgttagc ccggtgagc                            3099

<210> SEQ ID NO 10
<211> LENGTH: 1033
<212> TYPE: PRT
<213> ORGANISM: Artificial Sequence
<220> FEATURE:
<223> OTHER INFORMATION: Synthetic Construct

<400> SEQUENCE: 10
```

Met Lys Asp Lys Ala Thr Gly Lys Thr Gln Asn Ile Thr Ile Thr Ala
 1               5                  10                  15

Asn Gly Gly Leu Ser Lys Glu Gln Ile Glu Gln Met Ile Arg Asp Ser
            20                  25                  30

Glu Gln His Ala Glu Ala Asp Arg Val Lys Arg Glu Leu Val Glu Val
        35                  40                  45

Arg Asn Asn Ala Glu Thr Gln Leu Thr Thr Ala Glu Arg Gln Leu Gly
    50                  55                  60

Glu Trp Lys Tyr Val Ser Asp Ala Glu Lys Glu Asn Val Lys Thr Leu
65                  70                  75                  80

Val Ala Glu Leu Arg Lys Ala Met Glu Asn Pro Asn Val Ala Lys Asp
                85                  90                  95

Asp Leu Ala Ala Ala Thr Asp Lys Leu Gln Lys Ala Val Met Glu Cys
            100                 105                 110

Gly Arg Thr Glu Tyr Gln Gln Ala Ala Ala Asn Ser Gly Ser Thr
        115                 120                 125

Ser Asn Ser Gly Glu Gln Gln Gln Gln Gly Gln Gly Glu Gln Gln
    130                 135                 140

Gln Gln Gln Asn Ser Glu Glu Lys Lys Met Pro Arg Lys Ile Ile Leu
145                 150                 155                 160

Asp Cys Asp Pro Gly Ile Asp Asp Ala Val Ala Ile Phe Leu Ala His
                165                 170                 175

Gly Asn Pro Glu Val Glu Leu Leu Ala Ile Thr Thr Val Val Gly Asn
            180                 185                 190

Gln Thr Leu Glu Lys Val Thr Arg Asn Ala Arg Leu Val Ala Asp Val
        195                 200                 205

Ala Gly Ile Val Gly Val Pro Val Ala Ala Gly Cys Thr Lys Pro Leu
    210                 215                 220

Val Arg Gly Val Arg Asn Ala Ser Gln Ile His Gly Glu Thr Gly Met
225                 230                 235                 240

Gly Asn Val Ser Tyr Pro Pro Glu Phe Lys Thr Lys Leu Asp Gly Arg
                245                 250                 255

His Ala Val Gln Leu Ile Ile Asp Leu Ile Met Ser His Glu Pro Lys
            260                 265                 270

Thr Ile Thr Leu Val Pro Thr Gly Gly Leu Thr Asn Ile Ala Met Ala
        275                 280                 285

Val Arg Leu Glu Pro Arg Ile Val Asp Arg Val Lys Glu Val Val Leu

-continued

```
                290                 295                 300
Met Gly Gly Tyr His Thr Gly Asn Ala Ser Pro Val Ala Glu Phe
305                 310                 315                 320

Asn Val Phe Val Asp Pro Glu Ala Ala His Ile Val Phe Asn Glu Ser
                325                 330                 335

Trp Asn Val Thr Met Val Gly Leu Asp Leu Thr His Gln Ala Leu Ala
                340                 345                 350

Thr Pro Ala Val Gln Lys Arg Val Lys Glu Val Gly Thr Lys Pro Ala
                355                 360                 365

Ala Phe Met Leu Gln Ile Leu Asp Phe Tyr Thr Lys Val Tyr Glu Lys
        370                 375                 380

Glu Arg Asn Thr Tyr Ala Thr Val His Asp Pro Cys Ala Val Ala Tyr
385                 390                 395                 400

Val Ile Asp Pro Thr Val Met Thr Thr Glu Gln Val Pro Val Asp Ile
                405                 410                 415

Glu Leu Asn Gly Ala Leu Thr Thr Gly Met Thr Val Ala Asp Phe Arg
                420                 425                 430

Tyr Pro Arg Pro Lys His Cys His Thr Gln Val Ala Val Lys Leu Asp
                435                 440                 445

Phe Asp Lys Phe Trp Cys Leu Val Ile Asp Ala Leu Lys Arg Ile Gly
        450                 455                 460

Asp Pro Gln Ser Ala Gly Gly Arg Glu Thr Ala Pro Thr Asn Leu Ile
465                 470                 475                 480

Arg Arg Arg Asn Lys Asp Glu Thr Asn Gly Asp Val Ser Ala Ala Ala
                485                 490                 495

Asp Arg Phe Arg Asp Arg Phe Glu Lys Ala Thr Leu Glu Glu Arg Lys
                500                 505                 510

Ala Ala Thr Thr Thr Met Val Asn Glu Tyr Tyr Asp Leu Val Thr Asp
                515                 520                 525

Phe Tyr Glu Tyr Gly Trp Gly Gln Asn Phe His Phe Ala Pro Arg Tyr
        530                 535                 540

Ala Gly Glu Thr Phe Phe Glu Ser Leu Ala Arg His Glu Tyr Phe Leu
545                 550                 555                 560

Ala Ala Arg Gly Gly Phe Met Glu Gly Asp His Ile Val Asp Val Gly
                565                 570                 575

Cys Gly Val Gly Gly Pro Ala Arg Asn Met Val Arg Leu Thr Arg Cys
                580                 585                 590

Asn Val Ile Gly Val Asn Asn Asn Asp Tyr Gln Ile Ser Arg Ala Arg
                595                 600                 605

Arg His Asp Ala Leu Ala Gly Met Ser Ser Lys Ile Asp Tyr Val Lys
        610                 615                 620

Thr Asp Phe Cys Asn Met Ser Leu Ala Asp Asn Thr Phe Asp Gly Ala
625                 630                 635                 640

Tyr Ala Ile Glu Ala Thr Cys His Ala Lys Asp Lys Val Lys Cys Tyr
                645                 650                 655

Ser Glu Val Phe Arg Val Ile Lys Pro Gly Thr Cys Phe Val Leu Tyr
                660                 665                 670

Glu Trp Cys Met Thr Asp Lys Tyr Asn Pro Asn Asp Glu Tyr His Arg
        675                 680                 685

Thr Ile Lys His Arg Ile Glu Leu Gly Asp Gly Leu Pro Glu Met Glu
        690                 695                 700

Thr Cys Lys Gln Val Ile Glu Tyr Met Lys Gln Ala Gly Phe Val Val
705                 710                 715                 720
```

Glu Glu Ala Ile Asp Val Ile Ser Gln Phe Glu Ser Ser Pro Ile Lys
            725                 730                 735
Ser Ile Pro Trp Tyr Gln Pro Leu Val Gly Asp Tyr Ser Ser Leu Gln
        740                 745                 750
Gly Leu Arg Ser Thr Pro Ile Gly Arg Ile Leu Thr Asn Val Met Cys
    755                 760                 765
Arg Val Leu Glu Phe Val Arg Leu Ala Pro Lys Gly Thr Tyr Lys Ala
770                 775                 780
Thr Glu Ile Leu Glu Glu Ala Ala Glu Ser Leu Val Val Gly Gly Gln
785                 790                 795                 800
Leu Gly Ile Phe Thr Pro Ser Phe Tyr Ile Arg Ala Arg Lys Pro Ser
                805                 810                 815
Lys Gln Ala Ser Ala Ser Ala Glu Pro His Lys Ala Ala Val Asp Val
            820                 825                 830
Gly Pro Leu Ser Val Gly Pro Gln Ser Val Gly Pro Leu Ser Val Gly
        835                 840                 845
Pro Gln Ala Val Gly Pro Leu Ser Val Gly Pro Gln Ser Val Gly Pro
    850                 855                 860
Leu Ser Val Gly Pro Gln Ala Val Gly Pro Leu Ser Val Gly Pro Gln
865                 870                 875                 880
Ser Val Gly Pro Leu Ser Val Gly Pro Leu Ser Val Gly Pro Gln Ser
                885                 890                 895
Val Gly Pro Leu Ser Val Gly Ser Gln Ser Val Gly Pro Leu Ser Val
            900                 905                 910
Gly Pro Gln Ser Val Gly Pro Leu Ser Val Gly Pro Gln Ala Val Gly
        915                 920                 925
Pro Leu Ser Val Gly Pro Gln Ser Val Gly Pro Leu Ser Val Gly Pro
    930                 935                 940
Gln Ala Val Gly Pro Leu Ser Val Gly Pro Gln Ser Val Gly Pro Leu
945                 950                 955                 960
Ser Val Gly Pro Gln Ser Val Gly Pro Leu Ser Val Gly Ser Gln Ser
                965                 970                 975
Val Gly Pro Leu Ser Val Gly Pro Gln Ser Val Gly Pro Leu Ser Val
            980                 985                 990
Gly Pro Gln Ser Val Gly Pro Leu Ser Val Gly Pro Gln Ser Val Gly
        995                 1000                1005
Pro Leu Ser Val Gly Pro Gln Ser Val Gly Pro Leu Ser Val Gly Pro
    1010                1015                1020
Gln Ser Val Asp Val Ser Pro Val Ser
1025                1030

<210> SEQ ID NO 11
<211> LENGTH: 3213
<212> TYPE: DNA
<213> ORGANISM: Artificial Sequence
<220> FEATURE:
<223> OTHER INFORMATION: Synthetic Construct

<400> SEQUENCE: 11
atgagcatta tcaaggagga cgacgccgtg ggctgctaca tgacggtgac cctcgtggac    60
gacaccaagg tggagggtac catcttcacc tacaatccca aggaaggcat catagtactt   120
ctgtccctcc gcgacgatca gacgaacatg aagctgatcc gcactccata catcaaagag   180
ttcagtattt cacacgctga ggagggaacg cacctgcctc cggcactgga ctccttcaac   240

| | |
|---|---|
| gagcttccgt ccatgcatgc cggccgcgac aagtccatct tcaagcacgc cagcacgcag | 300 |
| ctcaagaacg ccgaggcgaa ccgcgaaaag cacttcaact ctgtcacgac cgacacaccg | 360 |
| attgccacac tcgatgcgta cctcaagctc ctgcggctat acccccttcat tgagtggaac | 420 |
| agcgacgagg tgtcatcca ggtctcggat accgtcattg tcgtagggga ccccgactgg | 480 |
| cggacgccca aggcgatgct ggtagacggc gcccctgaga aggacagacc gctcgtagac | 540 |
| cgcctgcagg ttgcgctcgg aaacggcaag aagatgccgc gcaagattat tctcgattgt | 600 |
| gatcccggga tcgatgatgc cgtggccatc tttctcgccc acggcaaccc ggaggtcgag | 660 |
| ctgctggcca ttacgacggt ggtgggcaac cagaccctgg agaaggtgac ccggaacgcg | 720 |
| cggctggtag ctgacgtagc cggcatcgtt ggtgtgcccg tcgcggctgg ttgcaccaag | 780 |
| ccctcgtgc gcggtgtgcg gaatgcctct cagattcatg cgaaaccgg catgggtaac | 840 |
| gtctcctacc caccagagtt caagacaaag ttggacggcc gtcatgcagt gcagctgatc | 900 |
| atcgacctta tcatgtcgca cgagccgaag acgatcacgc ttgtgcctac gggtggcctg | 960 |
| acgaacattg cgatggctgt ccgtcttgag ccgcgcatcg tggaccgtgt gaaggaggtg | 1020 |
| gttctgatgg gtggcggcta ccatactggt aatgcgtccc ctgtagcgga gttcaacgtc | 1080 |
| ttcgtcgacc cggaggcggc gcacattgtg ttcaacgaga gctggaacgt aacgatggtg | 1140 |
| gggctggacc taacgcacca ggcactcgcc acgccggcgg tccagaagcg agtgaaggag | 1200 |
| gtgggcacga agccggctgc cttcatgctg cagatttttgg acttttacac gaaggtgtac | 1260 |
| gaaaaggagc gcaacacgta cgcgacggtg cacgatccct gcgctgtggc gtacgtgatt | 1320 |
| gacccccaccg tgatgacgac ggagcaagtg ccagtggaca tcgagctcaa tggggcactg | 1380 |
| acgactggga tgacggtcgc ggacttccgc tacccacggc caaagcactg ccacacgcag | 1440 |
| gtggctgtga agctggactt cgacaagttt tggtgcctcg tgattgacgc actcaagcgc | 1500 |
| atcggcgatc ctcaatccgc cggtggccgt gagaccgcgc cgacgaacct gattcgtcgc | 1560 |
| cgcaacaagg acgagacaaa cggggatgtc agccgccgcg ccgaccgctt ccgcgaccgc | 1620 |
| ttcgagaagg caaccctcga ggagcgcaag gccgccacca cgacgatggt caacgagtac | 1680 |
| tacgacctgg tgacggactt ctacgagtac ggctggggcc agaacttcca tttcgcgccg | 1740 |
| cgctacgccg gcgagacctt cttcgagtcc ctcgcgcgcc acgagtactt cctggccgct | 1800 |
| cgcggcggct tcatggaggg cgaccacatc gtcgacgtgg gctgcggcgt cggcggtccg | 1860 |
| gcgcgcaaca tggttcgcct cacgcgctgc aacgtcatcg gcgtcaacaa caacgattac | 1920 |
| cagatcagcc gcgctcgccg tcatgacgcg ctcgccggta tgagctccaa gatcgactac | 1980 |
| gtcaagaccg acttctgcaa catgagctta gccgacaaca ccttcgacgg cgcctacgcc | 2040 |
| atcgaggcca cctgccacgc aaaggacaag gtcaagtgct atagcgaggt cttccgtgtc | 2100 |
| atcaagcccg gcacctgctt tgtcctgtac gagtggtgca tgaccgacaa gtacaacccc | 2160 |
| aatgacgagt accaccgcac aatcaagcac cgcatcgagc tgggcgacgg cctgccggag | 2220 |
| atggagacgt gcaaacaggt gatcgagtac atgaagcagg ccggcttcgt ggtggaggag | 2280 |
| gccatagacg tcatcagtca gttcgagtcc agccccatca agagtatccc gtggtaccag | 2340 |
| ccgctggtcg cgactattc gtccctgcag ggcctgcgct ctaccccgat ggccgcatc | 2400 |
| ctcacgaacg tcatgtgtcg cgtgctggag ttcgtgcgcc tagctccgaa gggcacgtac | 2460 |
| aaggcgacgg agattttgga ggaggctgcg gaaagcctgg tggtgggcgg tcagctcggc | 2520 |
| atcttcacgc cgtccttcta catccgcgct cgcaagccgt ccaagcaggc tagcgcctcc | 2580 |
| gctgagccgc acaaggcggc cgttgacgtc ggcccgctga gcgttggccc gcagagcgtc | 2640 |

-continued

```
ggcccgctga gcgttggccc gcaggcggtt ggcccgctga gcgttggccc gcagagcgtc    2700
ggcccgctga gcgttggccc gcaggcggtt ggcccgctga gcgttggccc gcagagcgtt    2760
ggcccgctga gcgttggccc gctgagcgtt ggcccgcaga gcgttggccc gctgagcgtt    2820
ggcagccaga gcgtcggccc gctgagcgtt ggtccgcaga gcgtcggccc gctgagcgtt    2880
ggcccgcagg cggttggccc gctgagcgtt ggcccgcaga gcgtcggccc gctgagcgtt    2940
ggcccgcagg cggttggccc gctgagcgtt ggcccgcaga gcgttggccc gctgagcgtt    3000
ggcccgcaga gcgttggccc gctgagcgtt ggcagccaga gcgtcggccc gctgagcgtt    3060
ggtccgcaga gcgtcggccc gctgagcgtt ggcccgcaga gcgtcggccc gctgagcgtt    3120
ggcccgcaga gcgtcggccc gctgagcgtt ggtccgcaga gcgttggccc gctgagcgtt    3180
ggcccgcaga gcgttgacgt tagcccggtg agc                                 3213
```

<210> SEQ ID NO 12
<211> LENGTH: 1071
<212> TYPE: PRT
<213> ORGANISM: Artificial Sequence
<220> FEATURE:
<223> OTHER INFORMATION: Synthetic Construct

<400> SEQUENCE: 12

```
Met Ser Ile Ile Lys Glu Asp Asp Ala Val Gly Cys Tyr Met Thr Val
 1               5                  10                  15

Thr Leu Val Asp Asp Thr Lys Val Glu Gly Thr Ile Phe Thr Tyr Asn
             20                  25                  30

Pro Lys Glu Gly Ile Ile Val Leu Leu Ser Leu Arg Asp Asp Gln Thr
         35                  40                  45

Asn Met Lys Leu Ile Arg Thr Pro Tyr Ile Lys Glu Phe Ser Ile Ser
     50                  55                  60

His Ala Glu Glu Gly Thr His Leu Pro Pro Ala Leu Asp Ser Phe Asn
 65                  70                  75                  80

Glu Leu Pro Ser Met His Ala Gly Arg Asp Lys Ser Ile Phe Lys His
                 85                  90                  95

Ala Ser Thr Gln Leu Lys Asn Ala Glu Ala Asn Arg Glu Lys His Phe
            100                 105                 110

Asn Ser Val Thr Thr Asp Thr Pro Ile Ala Thr Leu Asp Ala Tyr Leu
        115                 120                 125

Lys Leu Leu Arg Leu Tyr Pro Phe Ile Glu Trp Asn Ser Asp Glu Gly
    130                 135                 140

Val Ile Gln Val Ser Asp Thr Val Ile Val Val Gly Asp Pro Asp Trp
145                 150                 155                 160

Arg Thr Pro Lys Ala Met Leu Val Asp Gly Ala Pro Glu Lys Asp Arg
                165                 170                 175

Pro Leu Val Asp Arg Leu Gln Val Ala Leu Gly Asn Gly Lys Lys Met
            180                 185                 190

Pro Arg Lys Ile Ile Leu Asp Cys Asp Pro Gly Ile Asp Asp Ala Val
        195                 200                 205

Ala Ile Phe Leu Ala His Gly Asn Pro Glu Val Glu Leu Leu Ala Ile
    210                 215                 220

Thr Thr Val Val Gly Asn Gln Thr Leu Glu Lys Val Thr Arg Asn Ala
225                 230                 235                 240

Arg Leu Val Ala Asp Val Ala Gly Ile Val Gly Val Pro Val Ala Ala
                245                 250                 255
```

-continued

```
Gly Cys Thr Lys Pro Leu Val Arg Gly Val Arg Asn Ala Ser Gln Ile
            260                 265                 270
His Gly Glu Thr Gly Met Gly Asn Val Ser Tyr Pro Pro Glu Phe Lys
            275                 280                 285
Thr Lys Leu Asp Gly Arg His Ala Val Gln Leu Ile Ile Asp Leu Ile
    290                 295                 300
Met Ser His Glu Pro Lys Thr Ile Thr Leu Val Pro Thr Gly Gly Leu
305                 310                 315                 320
Thr Asn Ile Ala Met Ala Val Arg Leu Glu Pro Arg Ile Val Asp Arg
                325                 330                 335
Val Lys Glu Val Val Leu Met Gly Gly Gly Tyr His Thr Gly Asn Ala
            340                 345                 350
Ser Pro Val Ala Glu Phe Asn Val Phe Val Asp Pro Glu Ala Ala His
            355                 360                 365
Ile Val Phe Asn Glu Ser Trp Asn Val Thr Met Val Gly Leu Asp Leu
    370                 375                 380
Thr His Gln Ala Leu Ala Thr Pro Ala Val Gln Lys Arg Val Lys Glu
385                 390                 395                 400
Val Gly Thr Lys Pro Ala Ala Phe Met Leu Gln Ile Leu Asp Phe Tyr
                405                 410                 415
Thr Lys Val Tyr Glu Lys Glu Arg Asn Thr Tyr Ala Thr Val His Asp
            420                 425                 430
Pro Cys Ala Val Ala Tyr Val Ile Asp Pro Thr Val Met Thr Thr Glu
            435                 440                 445
Gln Val Pro Val Asp Ile Glu Leu Asn Gly Ala Leu Thr Thr Gly Met
    450                 455                 460
Thr Val Ala Asp Phe Arg Tyr Pro Arg Pro Lys His Cys His Thr Gln
465                 470                 475                 480
Val Ala Val Lys Leu Asp Phe Asp Lys Phe Trp Cys Leu Val Ile Asp
                485                 490                 495
Ala Leu Lys Arg Ile Gly Asp Pro Gln Ser Ala Gly Gly Arg Glu Thr
            500                 505                 510
Ala Pro Thr Asn Leu Ile Arg Arg Asn Lys Asp Glu Thr Asn Gly
            515                 520                 525
Asp Val Ser Ala Ala Ala Asp Arg Phe Arg Asp Arg Phe Glu Lys Ala
    530                 535                 540
Thr Leu Glu Glu Arg Lys Ala Ala Thr Thr Met Val Asn Glu Tyr
545                 550                 555                 560
Tyr Asp Leu Val Thr Asp Phe Tyr Glu Tyr Gly Trp Gly Gln Asn Phe
                565                 570                 575
His Phe Ala Pro Arg Tyr Ala Gly Glu Thr Phe Phe Glu Ser Leu Ala
            580                 585                 590
Arg His Glu Tyr Phe Leu Ala Ala Arg Gly Gly Phe Met Glu Gly Asp
            595                 600                 605
His Ile Val Asp Val Gly Cys Gly Val Gly Gly Pro Ala Arg Asn Met
    610                 615                 620
Val Arg Leu Thr Arg Cys Asn Val Ile Gly Val Asn Asn Asn Asp Tyr
625                 630                 635                 640
Gln Ile Ser Arg Ala Arg Arg His Asp Ala Leu Ala Gly Met Ser Ser
                645                 650                 655
Lys Ile Asp Tyr Val Lys Thr Asp Phe Cys Asn Met Ser Leu Ala Asp
            660                 665                 670
Asn Thr Phe Asp Gly Ala Tyr Ala Ile Glu Ala Thr Cys His Ala Lys
```

```
                675                 680                 685
Asp Lys Val Lys Cys Tyr Ser Glu Val Phe Arg Val Ile Lys Pro Gly
    690                 695                 700

Thr Cys Phe Val Leu Tyr Glu Trp Cys Met Thr Asp Lys Tyr Asn Pro
705                 710                 715                 720

Asn Asp Glu Tyr His Arg Thr Ile Lys His Arg Ile Glu Leu Gly Asp
                725                 730                 735

Gly Leu Pro Glu Met Glu Thr Cys Lys Gln Val Ile Gly Tyr Met Lys
            740                 745                 750

Gln Ala Gly Phe Val Glu Glu Ala Ile Asp Val Ile Ser Gln Phe
        755                 760                 765

Glu Ser Ser Pro Ile Lys Ser Ile Pro Trp Tyr Gln Pro Leu Val Gly
    770                 775                 780

Asp Tyr Ser Ser Leu Gln Gly Leu Arg Ser Thr Pro Ile Gly Arg Ile
785                 790                 795                 800

Leu Thr Asn Val Met Cys Arg Val Leu Glu Phe Val Arg Leu Ala Pro
                805                 810                 815

Lys Gly Thr Tyr Lys Ala Thr Glu Ile Leu Glu Glu Ala Ala Glu Ser
            820                 825                 830

Leu Val Val Gly Gly Gln Leu Gly Ile Phe Thr Pro Ser Phe Tyr Ile
        835                 840                 845

Arg Ala Arg Lys Pro Ser Lys Gln Ala Ser Ala Ser Ala Glu Pro His
    850                 855                 860

Lys Ala Ala Val Asp Val Gly Pro Leu Ser Val Gly Pro Gln Ser Val
865                 870                 875                 880

Gly Pro Leu Ser Val Gly Pro Gln Ala Val Gly Pro Leu Ser Val Gly
                885                 890                 895

Pro Gln Ser Val Gly Pro Leu Ser Val Gly Pro Gln Ala Val Gly Pro
            900                 905                 910

Leu Ser Val Gly Pro Gln Ser Val Gly Pro Leu Ser Val Gly Pro Leu
        915                 920                 925

Ser Val Gly Pro Gln Ser Val Gly Pro Leu Ser Val Gly Ser Gln Ser
    930                 935                 940

Val Gly Pro Leu Ser Val Gly Pro Gln Ser Val Gly Pro Leu Ser Val
945                 950                 955                 960

Gly Pro Gln Ala Val Gly Pro Leu Ser Val Gly Pro Gln Ser Val Gly
                965                 970                 975

Pro Leu Ser Val Gly Pro Gln Ala Val Gly Pro Leu Ser Val Gly Pro
            980                 985                 990

Gln Ser Val Gly Pro Leu Ser Val Gly Pro Gln Ser Val Gly Pro Leu
        995                 1000                1005

Ser Val Gly Ser Gln Ser Val Gly Pro Leu Ser Val Gly Pro Gln Ser
    1010                1015                1020

Val Gly Pro Leu Ser Val Gly Pro Gln Ser Val Gly Pro Leu Ser Val
1025                1030                1035                1040

Gly Pro Gln Ser Val Gly Pro Leu Ser Val Gly Pro Gln Ser Val Gly
                1045                1050                1055

Pro Leu Ser Val Gly Pro Gln Ser Val Asp Val Ser Pro Val Ser
            1060                1065                1070

<210> SEQ ID NO 13
<211> LENGTH: 3030
<212> TYPE: DNA
<213> ORGANISM: Artificial Sequence
```

<220> FEATURE:
<223> OTHER INFORMATION: Synthetic Construct

<400> SEQUENCE: 13

| | |
|---|---|
| atgaaggaca aggcgacggg caagacgcag aacatcacga tcacggcgaa cggcgggctg | 60 |
| tcgaaggagc agatcgagca gatgatccgc gactcggagc agcacgcgga ggccgaccgc | 120 |
| gtgaagcgcg agcttgtgga ggtgcgcaac aacgcggaga cgcagctgac aacggcggag | 180 |
| aggcagctcg gcgagtggaa gtacgtgagc gatgcggaga aggagaacgt gaagacgctg | 240 |
| gtggcggagc tgcgcaaggc gatggagaac ccgaacgtcg cgaaggatga ccttgcggct | 300 |
| gcgacggaca agctgcagaa ggctgtgatg gagtgcggcc gcacagagta ccagcaggct | 360 |
| gccgcggcca actccggcag caccagcaac tccggtgagc agcagcagca gagggccaa | 420 |
| ggtgagcagc agcagcagca gaacagcgaa gagaagaaga tgagcattat caaggaggac | 480 |
| gacgccgtgg gctgctacat gacggtgacc ctcgtggacg acaccaaggt ggagggtacc | 540 |
| atcttcacct acaatcccaa ggaaggcatc atagtacttc tgtccctccg cgacgatcag | 600 |
| acgaacatga agctgatccg cactccatac atcaaagagt tcagtatttc acacgctgag | 660 |
| gagggaacgc acctgcctcc ggcactggac tccttcaacg agcttccgtc catgcatgcc | 720 |
| ggccgcgaca agtccatctt caagcacgcc agcacgcagc tcaagaacgc cgaggcgaac | 780 |
| cgcgaaaagc acttcaactc tgtcacgacc gacacaccga ttgccacact cgatgcgtac | 840 |
| ctcaagctcc tgcggctata ccccttcatt gagtggaaca gcgacgaggg tgtcatccag | 900 |
| gtctcggata ccgtcattgt cgtagggac cccgactggc ggacgcccaa ggcgatgctg | 960 |
| gtagacggcg cccctgagaa ggacagaccg ctcgtagacc gcctgcaggt tgcgctcgga | 1020 |
| aacggcaaga gatgccgcg caagattatt ctcgattgtg atcccgggat cgatgatgcc | 1080 |
| gtggccatct ttctcgccca cggcaacccg gaggtcgagc tgctggccat tacgacggtg | 1140 |
| gtgggcaacc agaccctgga gaaggtgacc cggaacgcgc ggctggtagc tgacgtagcc | 1200 |
| ggcatcgttg gtgtgcccgt cgcggctggt tgcaccaagc ccctcgtgcg cggtgtgcgg | 1260 |
| aatgcctctc agattcatgg cgaaaccggc atgggtaacg tctcctaccc accagagttc | 1320 |
| aagacaaagt tggacggccg tcatgcagtg cagctgatca tcgaccttat catgtcgcac | 1380 |
| gagccgaaga cgatcacgct tgtgcctacg ggtggcctga cgaacattgc gatggctgtc | 1440 |
| cgtcttgagc cgcgcatcgt ggaccgtgtg aaggaggtgg ttctgatggg tggcggctac | 1500 |
| catactggta atgcgtcccc tgtagcggag ttcaacgtct cgtcgaccc ggaggcggcg | 1560 |
| cacattgtgt tcaacgagag ctggaacgta acgatggtgg ggctggacct aacgcaccag | 1620 |
| gcactcgcca cgccggcggt ccagaagcga gtgaaggagg tgggcacgaa gccggctgcc | 1680 |
| ttcatgctgc agattttgga cttttacacg aaggtgtacg aaaaggagcg caacacgtac | 1740 |
| gcgacggtgc acgatccctg cgctgtggcg tacgtgattg accccaccgt gatgacgacg | 1800 |
| gagcaagtgc cagtggacat cgagctcaat ggggcactga cgactgggat gacggtcgcg | 1860 |
| gacttccgct acccacggcc aaagcactgc cacacgcagg tggctgtgaa gctggacttc | 1920 |
| gacaagtttt ggtgcctcgt gattgacgca ctcaagcgca tcggcgatcc tcaatccgcc | 1980 |
| ggtggccgtg agaccgcgcc gacgaacctg attcgtcgcc gcaacaagga cgagacaaac | 2040 |
| ggggatgtca gcgccgccgc cgaccgcttc cgcgaccgct tcgagaaggc aaccctcgag | 2100 |
| gagcgcaagg ccgccaccac gacgatggtc aacgagtact acgacctggt gacggacttc | 2160 |
| tacgagtacg gctggggcca gaacttccat ttcgcgccgc gctacgccgg cgagaccttc | 2220 |

```
ttcgagtccc tcgcgcgcca cgagtacttc ctggccgctc gcggcggctt catggagggc    2280
gaccacatcg tcgacgtggg ctgcggcgtc ggcggtccgg cgcgcaacat ggttcgcctc    2340
acgcgctgca acgtcatcgg cgtcaacaac aacgattacc agatcagccg cgctcgccgt    2400
catgacgcgc tcgccggtat gagctccaag atcgactacg tcaagaccga cttctgcaac    2460
atgagcttag ccgacaacac cttcgacggc gcctacgcca tcgaggccac ctgccacgca    2520
aaggacaagg tcaagtgcta tagcgaggtc ttccgtgtca tcaagcccgg cacctgcttt    2580
gtcctgtacg agtggtgcat gaccgacaag tacaaccccca atgacgagta ccaccgcaca    2640
atcaagcacc gcatcgagct gggcgacggc ctgccggaga tggagacgtg caaacaggtg    2700
atcgagtaca tgaagcaggc cggcttcgtg gtggaggagg ccatagacgt catcagtcag    2760
ttcgagtcca gccccatcaa gagtatcccg tggtaccagc cgctggtcgg cgactattcg    2820
tccctgcagg gcctgcgctc taccccgatt ggccgcatcc tcacgaacgt catgtgtcgc    2880
gtgctggagt tcgtgcgcct agctccgaag ggcacgtaca aggcgacgga gattttggag    2940
gaggctgcgg aaagcctggt ggtgggcggt cagctcggca tcttcacgcc gtccttctac    3000
atccgcgctc gcaagccgtc caagcaggct                                     3030
```

<210> SEQ ID NO 14
<211> LENGTH: 1010
<212> TYPE: PRT
<213> ORGANISM: Artificial Sequence
<220> FEATURE:
<223> OTHER INFORMATION: Synthetic Construct

<400> SEQUENCE: 14

```
Met Lys Asp Lys Ala Thr Gly Lys Thr Gln Asn Ile Thr Ile Thr Ala
 1               5                  10                  15

Asn Gly Gly Leu Ser Lys Glu Gln Ile Glu Gln Met Ile Arg Asp Ser
            20                  25                  30

Glu Gln His Ala Glu Ala Asp Arg Val Lys Arg Glu Leu Val Glu Val
        35                  40                  45

Arg Asn Asn Ala Glu Thr Gln Leu Thr Thr Ala Glu Arg Gln Leu Gly
    50                  55                  60

Glu Trp Lys Tyr Val Ser Asp Ala Glu Lys Glu Asn Val Lys Thr Leu
65                  70                  75                  80

Val Ala Glu Leu Arg Lys Ala Met Glu Asn Pro Asn Val Ala Lys Asp
                85                  90                  95

Asp Leu Ala Ala Ala Thr Asp Lys Leu Gln Lys Ala Val Met Glu Cys
            100                 105                 110

Gly Arg Thr Glu Tyr Gln Gln Ala Ala Ala Asn Ser Gly Ser Thr
        115                 120                 125

Ser Asn Ser Gly Glu Gln Gln Gln Gln Gly Gly Glu Gln Gln
    130                 135                 140

Gln Gln Gln Asn Ser Glu Glu Lys Lys Met Ser Ile Ile Lys Glu Asp
145                 150                 155                 160

Asp Ala Val Gly Cys Tyr Met Thr Val Thr Leu Val Asp Asp Thr Lys
                165                 170                 175

Val Glu Gly Thr Ile Phe Thr Tyr Asn Pro Lys Glu Gly Ile Ile Val
            180                 185                 190

Leu Leu Ser Leu Arg Asp Asp Gln Thr Asn Met Lys Leu Ile Arg Thr
        195                 200                 205

Pro Tyr Ile Lys Glu Phe Ser Ile Ser His Ala Glu Glu Gly Thr His
    210                 215                 220
```

```
Leu Pro Pro Ala Leu Asp Ser Phe Asn Glu Leu Pro Ser Met His Ala
225                 230                 235                 240

Gly Arg Asp Lys Ser Ile Phe Lys His Ala Ser Thr Gln Leu Lys Asn
            245                 250                 255

Ala Glu Ala Asn Arg Glu Lys His Phe Asn Ser Val Thr Thr Asp Thr
        260                 265                 270

Pro Ile Ala Thr Leu Asp Ala Tyr Leu Lys Leu Leu Arg Leu Tyr Pro
    275                 280                 285

Phe Ile Glu Trp Asn Ser Asp Glu Gly Val Ile Gln Val Ser Asp Thr
290                 295                 300

Val Ile Val Val Gly Asp Pro Asp Trp Arg Thr Pro Lys Ala Met Leu
305                 310                 315                 320

Val Asp Gly Ala Pro Glu Lys Asp Arg Pro Leu Val Asp Arg Leu Gln
                325                 330                 335

Val Ala Leu Gly Asn Gly Lys Lys Met Pro Arg Lys Ile Ile Leu Asp
            340                 345                 350

Cys Asp Pro Gly Ile Asp Asp Ala Val Ala Ile Phe Leu Ala His Gly
        355                 360                 365

Asn Pro Glu Val Glu Leu Leu Ala Ile Thr Thr Val Val Gly Asn Gln
    370                 375                 380

Thr Leu Glu Lys Val Thr Arg Asn Ala Arg Leu Val Ala Asp Val Ala
385                 390                 395                 400

Gly Ile Val Gly Val Pro Val Ala Ala Gly Cys Thr Lys Pro Leu Val
                405                 410                 415

Arg Gly Val Arg Asn Ala Ser Gln Ile His Gly Glu Thr Gly Met Gly
            420                 425                 430

Asn Val Ser Tyr Pro Pro Glu Phe Lys Thr Lys Leu Asp Gly Arg His
        435                 440                 445

Ala Val Gln Leu Ile Ile Asp Leu Ile Met Ser His Glu Pro Lys Thr
    450                 455                 460

Ile Thr Leu Val Pro Thr Gly Gly Leu Thr Asn Ile Ala Met Ala Val
465                 470                 475                 480

Arg Leu Glu Pro Arg Ile Val Asp Arg Val Lys Glu Val Val Leu Met
                485                 490                 495

Gly Gly Gly Tyr His Thr Gly Asn Ala Ser Pro Val Ala Glu Phe Asn
            500                 505                 510

Val Phe Val Asp Pro Glu Ala Ala His Ile Val Phe Asn Glu Ser Trp
        515                 520                 525

Asn Val Thr Met Val Gly Leu Asp Leu Thr His Gln Ala Leu Ala Thr
    530                 535                 540

Pro Ala Val Gln Lys Arg Val Lys Glu Val Gly Thr Lys Pro Ala Ala
545                 550                 555                 560

Phe Met Leu Gln Ile Leu Asp Phe Tyr Thr Lys Val Tyr Glu Lys Glu
                565                 570                 575

Arg Asn Thr Tyr Ala Thr Val His Asp Pro Cys Ala Val Ala Tyr Val
            580                 585                 590

Ile Asp Pro Thr Val Met Thr Thr Glu Gln Val Pro Val Asp Ile Glu
        595                 600                 605

Leu Asn Gly Ala Leu Thr Thr Gly Met Thr Val Ala Asp Phe Arg Tyr
    610                 615                 620

Pro Arg Pro Lys His Cys His Thr Gln Val Ala Val Lys Leu Asp Phe
625                 630                 635                 640
```

Asp Lys Phe Trp Cys Leu Val Ile Asp Ala Leu Lys Arg Ile Gly Asp
            645                 650                 655

Pro Gln Ser Ala Gly Gly Arg Glu Thr Ala Pro Thr Asn Leu Ile Arg
        660                 665                 670

Arg Arg Asn Lys Asp Glu Thr Asn Gly Asp Val Ser Ala Ala Ala Asp
    675                 680                 685

Arg Phe Arg Asp Arg Phe Glu Lys Ala Thr Leu Glu Glu Arg Lys Ala
690                 695                 700

Ala Thr Thr Thr Met Val Asn Glu Tyr Tyr Asp Leu Val Thr Asp Phe
705                 710                 715                 720

Tyr Glu Tyr Gly Trp Gly Gln Asn Phe His Phe Ala Pro Arg Tyr Ala
                725                 730                 735

Gly Glu Thr Phe Phe Glu Ser Leu Ala Arg His Glu Tyr Phe Leu Ala
            740                 745                 750

Ala Arg Gly Gly Phe Met Glu Gly Asp His Ile Val Asp Val Gly Cys
        755                 760                 765

Gly Val Gly Gly Pro Ala Arg Asn Met Val Arg Leu Thr Arg Cys Asn
    770                 775                 780

Val Ile Gly Val Asn Asn Asn Asp Tyr Gln Ile Ser Arg Ala Arg Arg
785                 790                 795                 800

His Asp Ala Leu Ala Gly Met Ser Ser Lys Ile Asp Tyr Val Lys Thr
                805                 810                 815

Asp Phe Cys Asn Met Ser Leu Ala Asp Asn Thr Phe Asp Gly Ala Tyr
            820                 825                 830

Ala Ile Glu Ala Thr Cys His Ala Lys Asp Lys Val Lys Cys Tyr Ser
        835                 840                 845

Glu Val Phe Arg Val Ile Lys Pro Gly Thr Cys Phe Val Leu Tyr Glu
    850                 855                 860

Trp Cys Met Thr Asp Lys Tyr Asn Pro Asn Asp Glu Tyr His Arg Thr
865                 870                 875                 880

Ile Lys His Arg Ile Glu Leu Gly Asp Gly Leu Pro Glu Met Glu Thr
                885                 890                 895

Cys Lys Gln Val Ile Glu Tyr Met Lys Gln Ala Gly Phe Val Val Glu
            900                 905                 910

Glu Ala Ile Asp Val Ile Ser Gln Phe Glu Ser Ser Pro Ile Lys Ser
        915                 920                 925

Ile Pro Trp Tyr Gln Pro Leu Val Gly Asp Tyr Ser Ser Leu Gln Gly
    930                 935                 940

Leu Arg Ser Thr Pro Ile Gly Arg Ile Leu Thr Asn Val Met Cys Arg
945                 950                 955                 960

Val Leu Glu Phe Val Arg Leu Ala Pro Lys Gly Thr Tyr Lys Ala Thr
                965                 970                 975

Glu Ile Leu Glu Glu Ala Ala Glu Ser Leu Val Val Gly Gly Gln Leu
            980                 985                 990

Gly Ile Phe Thr Pro Ser Phe Tyr Ile Arg Ala Arg Lys Pro Ser Lys
        995                 1000                1005

Gln Ala
    1010

<210> SEQ ID NO 15
<211> LENGTH: 2136
<212> TYPE: DNA
<213> ORGANISM: Artificial Sequence
<220> FEATURE:
<223> OTHER INFORMATION: Synthetic Construct

<400> SEQUENCE: 15

```
atggcctctt ctcgctctgc tccccgcaag gcttcccacg cgcacaagtc gcaccgcaag      60
ccgaagcgct cgtggaacgt gtacgtgggc cgctcgctga aggcgatcaa cgcccagatg     120
tcgatgtcgc accgcacgat gccgcgcaag attattctcg attgtgatcc cgggatcgat     180
gatgccgtgg ccatctttct cgcccacggc aacccggagg tcgagctgct ggccattacg     240
acggtggtgg gcaaccagac cctggagaag gtgacccgga acgcgcggct ggtagctgac     300
gtagccggca tcgttggtgt gcccgtcgcg gctggttgca ccaagcccct cgtgcgcggt     360
gtgcggaatg cctctcagat tcatggcgaa accggcatgg gtaacgtctc ctacccacca     420
gagttcaaga caaagttgga cggccgtcat gcagtgcagc tgatcatcga ccttatcatg     480
tcgcacgagc cgaagacgat cacgcttgtg cctacgggtg gcctgacgaa cattgcgatg     540
gctgtccgtc ttgagccgcg catcgtggac cgtgtgaagg aggtggttct gatgggtggc     600
ggctaccata ctggtaatgc gtccctgta gcggagttca acgtcttcgt cgacccggag     660
gcggcgcaca ttgtgttcaa cgagagctgg aacgtaacga tggtggggct ggacctaacg     720
caccaggcac tcgccacgcc ggcggtccag aagcgagtga aggaggtggg cacgaagccg     780
gctgccttca tgctgcagat tttggacttt tacacgaagg tgtacgaaaa ggagcgcaac     840
acgtacgcga cggtgcacga tccctgcgct gtggcgtacg tgattgaccc caccgtgatg     900
acgacggagc aagtgccagt ggacatcgag ctcaatgggg cactgacgac tgggatgacg     960
gtcgcggact ccgctaccc acggccaaag cactgccaca cgcaggtggc tgtgaagctg    1020
gacttcgaca gtttttggtg cctcgtgatt gacgcactca agcgcatcgg cgatcctcaa    1080
tccgccggtg gccgtgagac cgcgccgacg aacctgattc gtcgccgcaa caaggacgag    1140
acaaacgggg atgtcagcgc cgccgccgac cgcttccgcg accgcttcga gaaggcaacc    1200
ctcgaggagc gcaaggccgc caccacgacg atggtcaacg agtactacga cctggtgacg    1260
gacttctacg agtacggctg gggccagaac ttccatttcg cgccgcgcta cgccggcgag    1320
accttcttcg agtccctcgc gcgccacgag tacttcctgg ccgctcgcgg cggcttcatg    1380
gagggcgacc acatcgtcga cgtgggctgc ggcgtcggcg gtccggcgcg caacatggtt    1440
cgcctcacgc gctgcaacgt catcggcgtc aacaacaacg attaccagat cagccgcgct    1500
cgccgtcatg acgcgctcgc cggtatgagc tccaagatcg actacgtcaa gaccgacttc    1560
tgcaacatga gcttagccga caacaccttc gacggcgcct acgccatcga ggccacctgc    1620
cacgcaaagg acaaggtcaa gtgctatagc gaggtcttcc gtgtcatcaa gcccggcacc    1680
tgctttgtcc tgtacgagtg gtgcatgacc gacaagtaca accccaatga cgagtaccac    1740
cgcacaatca agcaccgcat cgagctgggc gacggcctgc cggagatgga gacgtgcaaa    1800
caggtgatcg agtacatgaa gcaggccggc ttcgtggtgg aggaggccat agacgtcatc    1860
agtcagttcg agtccagccc catcaagagt atcccgtggt accagccgct ggtcggcgac    1920
tattcgtccc tgcagggcct cgcgctctac ccgattggcc gcatcctcac gaacgtcatg    1980
tgtcgcgtgc tggagttcgt gcgcctagct ccgaagggca cgtacaaggc gacggagatt    2040
ttggaggagg ctgcggaaag cctggtggtg ggcggtcagc tcggcatctt cacgccgtcc    2100
ttctacatcc gcgctcgcaa gccgtccaag caggct                             2136
```

<210> SEQ ID NO 16
<211> LENGTH: 711
<212> TYPE: PRT

<213> ORGANISM: Artificial Sequence
<220> FEATURE:
<223> OTHER INFORMATION: Synthetic Construct

<400> SEQUENCE: 16

```
Met Ala Ser Ser Arg Ser Ala Pro Arg Lys Ala Ser His Ala His Lys
  1               5                  10                  15

Ser His Arg Lys Pro Lys Arg Ser Trp Asn Val Tyr Val Gly Arg Ser
             20                  25                  30

Leu Lys Ala Ile Asn Ala Gln Met Ser Met Ser His Arg Thr Met Pro
         35                  40                  45

Arg Lys Ile Ile Leu Asp Cys Asp Pro Gly Ile Asp Asp Ala Val Ala
     50                  55                  60

Ile Phe Leu Ala His Gly Asn Pro Glu Val Glu Leu Leu Ala Ile Thr
 65                  70                  75                  80

Thr Val Val Gly Asn Gln Thr Leu Glu Lys Val Thr Arg Asn Ala Arg
                 85                  90                  95

Leu Val Ala Asp Val Ala Gly Ile Val Gly Val Pro Ala Ala Gly
            100                 105                 110

Cys Thr Lys Pro Leu Val Arg Gly Val Arg Asn Ala Ser Gln Ile His
            115                 120                 125

Gly Glu Thr Gly Met Gly Asn Val Ser Tyr Pro Pro Glu Phe Lys Thr
        130                 135                 140

Lys Leu Asp Gly Arg His Ala Val Gln Leu Ile Ile Asp Leu Ile Met
145                 150                 155                 160

Ser His Glu Pro Lys Thr Ile Thr Leu Val Pro Thr Gly Gly Leu Thr
                165                 170                 175

Asn Ile Ala Met Ala Val Arg Leu Glu Pro Arg Ile Val Asp Arg Val
            180                 185                 190

Lys Glu Val Val Leu Met Gly Gly Gly Tyr His Thr Gly Asn Ala Ser
            195                 200                 205

Pro Val Ala Glu Phe Asn Val Phe Val Asp Pro Glu Ala Ala His Ile
        210                 215                 220

Val Phe Asn Glu Ser Trp Asn Val Thr Met Val Gly Leu Asp Leu Thr
225                 230                 235                 240

His Gln Ala Leu Ala Thr Pro Ala Val Gln Lys Arg Val Lys Glu Val
                245                 250                 255

Gly Thr Lys Pro Ala Ala Phe Met Leu Gln Ile Leu Asp Phe Tyr Thr
            260                 265                 270

Lys Val Tyr Glu Lys Glu Arg Asn Thr Tyr Ala Thr Val His Asp Pro
            275                 280                 285

Cys Ala Val Ala Tyr Val Ile Asp Pro Thr Val Met Thr Thr Glu Gln
        290                 295                 300

Val Pro Val Asp Ile Glu Leu Asn Gly Ala Leu Thr Thr Gly Met Thr
305                 310                 315                 320

Val Ala Asp Phe Arg Tyr Pro Arg Pro Lys His Cys His Thr Gln Val
                325                 330                 335

Ala Val Lys Leu Asp Phe Asp Lys Phe Trp Cys Leu Val Ile Asp Ala
            340                 345                 350

Leu Lys Arg Ile Gly Asp Pro Gln Ser Ala Gly Gly Arg Glu Thr Ala
            355                 360                 365

Pro Thr Asn Leu Ile Arg Arg Arg Asn Lys Asp Glu Thr Asn Gly Asp
        370                 375                 380

Val Ser Ala Ala Ala Asp Arg Phe Arg Asp Arg Phe Glu Lys Ala Thr
```

```
                385                 390                 395                 400
Leu Glu Glu Arg Lys Ala Thr Thr Thr Met Val Asn Glu Tyr Tyr
                    405                 410                 415

Asp Leu Val Thr Asp Phe Tyr Glu Tyr Gly Trp Gly Gln Asn Phe His
                420                 425                 430

Phe Ala Pro Arg Tyr Ala Gly Glu Thr Phe Phe Glu Ser Leu Ala Arg
            435                 440                 445

His Glu Tyr Phe Leu Ala Ala Arg Gly Gly Phe Met Glu Gly Asp His
        450                 455                 460

Ile Val Asp Val Gly Cys Gly Val Gly Pro Ala Arg Asn Met Val
465                 470                 475                 480

Arg Leu Thr Arg Cys Asn Val Ile Gly Val Asn Asn Asn Asp Tyr Gln
                485                 490                 495

Ile Ser Arg Ala Arg Arg His Asp Ala Leu Ala Gly Met Ser Ser Lys
                500                 505                 510

Ile Asp Tyr Val Lys Thr Asp Phe Cys Asn Met Ser Leu Ala Asp Asn
            515                 520                 525

Thr Phe Asp Gly Ala Tyr Ala Ile Glu Ala Thr Cys His Ala Lys Asp
        530                 535                 540

Lys Val Lys Cys Tyr Ser Glu Val Phe Arg Val Ile Lys Pro Gly Thr
545                 550                 555                 560

Cys Phe Val Leu Tyr Glu Trp Cys Met Thr Asp Lys Tyr Asn Pro Asn
                565                 570                 575

Asp Glu Tyr His Arg Thr Ile Lys His Arg Ile Glu Leu Gly Asp Gly
                580                 585                 590

Leu Pro Glu Met Glu Thr Cys Lys Gln Val Ile Glu Tyr Met Gln Ala
            595                 600                 605

Gly Phe Val Val Glu Glu Ala Ile Asp Val Ile Ser Gln Phe Glu Ser
        610                 615                 620

Ser Pro Ile Lys Ser Ile Pro Trp Tyr Gln Pro Leu Val Gly Asp Tyr
625                 630                 635                 640

Ser Ser Leu Gln Gly Leu Arg Ser Thr Pro Ile Gly Arg Ile Leu Thr
                645                 650                 655

Asn Val Met Cys Arg Val Leu Glu Phe Val Arg Leu Ala Pro Lys Gly
                660                 665                 670

Thr Tyr Lys Ala Thr Glu Ile Leu Glu Glu Ala Ala Glu Ser Leu Val
            675                 680                 685

Val Gly Gly Gln Leu Gly Ile Phe Thr Pro Ser Phe Tyr Ile Arg Ala
        690                 695                 700

Arg Lys Pro Ser Lys Gln Ala
705                 710

<210> SEQ ID NO 17
<211> LENGTH: 2457
<212> TYPE: DNA
<213> ORGANISM: Artificial Sequence
<220> FEATURE:
<223> OTHER INFORMATION: Synthetic Construct

<400> SEQUENCE: 17
atgaaggaca aggcgacggg caagacgcag aacatcacga tcacggcgaa cggcgggctg      60
tcgaaggagc agatcgagca gatgatccgc gactcggagc agcacgcgga ggccgaccgc    120
gtgaagcgcg agcttgtgga ggtgcgcaac aacgcggaga cgcagctgac aacggcggag    180
aggcagctcg gcgagtggaa gtacgtgagc gatgcggaga aggagaacgt gaagacgctg    240
```

```
gtggcggagc tgcgcaaggc gatggagaac ccgaacgtcg cgaaggatga ccttgcggct    300
gcgacggaca agctgcagaa ggctgtgatg gagtgcggcc gcacagagta ccagcaggct    360
gccgcggcca actccggcag caccagcaac tccggtgagc agcagcagca gcagggccaa    420
ggtgagcagc agcagcagca gaacagcgaa gagaagaaga tgccgcgcaa gattattctc    480
gattgtgatc ccgggatcga tgatgccgtg gccatctttc tcgcccacgg caacccggag    540
gtcgagctgc tggccattac gacggtggtg gcaaccaga ccctggagaa ggtgacccgg     600
aacgcgcggc tggtagctga cgtagccggc atcgttggtg tgcccgtcgc ggctggttgc    660
accaagcccc tcgtgcgcgg tgtgcggaat gcctctcaga ttcatggcga aaccggcatg    720
ggtaacgtct cctacccacc agagttcaag acaaagttgg acggccgtca tgcagtgcag    780
ctgatcatcg accttatcat gtcgcacgag ccgaagacga tcacgcttgt gcctacgggt    840
ggcctgacga acattgcgat ggctgtccgt cttgagccgc gcatcgtgga ccgtgtgaag    900
gaggtggttc tgatgggtgg cggctaccat actggtaatg cgtcccctgt agcggagttc    960
aacgtcttcg tcgacccgga ggcggcgcac attgtgttca acgagagctg gaacgtaacg   1020
atggtggggc tggacctaac gcaccaggca ctcgccacgc cggcggtcca gaagcgagtg   1080
aaggaggtgg gcacgaagcc ggctgccttc atgctgcaga ttttggactt ttacacgaag   1140
gtgtacgaaa aggagcgcaa cacgtacgcg acggtgcacg atccctgcgc tgtggcgtac   1200
gtgattgacc ccaccgtgat gacgacggag caagtgccag tggacatcga gctcaatggg   1260
gcactgacga ctgggatgac ggtcgcggac ttccgctacc cacggccaaa gcactgccac   1320
acgcaggtgg ctgtgaagct ggacttcgac aagttttggt gcctcgtgat tgacgcactc   1380
aagcgcatcg gcgatcctca atccgccggt ggccgtgaga ccgcgccgac gaacctgatt   1440
cgtcgccgca acaaggacga gacaaacggg gatgtcagcg ccgccgccga ccgcttccgc   1500
gaccgcttcg agaaggcaac cctcgaggag cgcaaggccg ccaccacgac gatggtcaac   1560
gagtactacg acctggtgac ggacttctac gagtacggct ggggccagaa cttccatttc   1620
gcgccgcgct acgccggcga gaccttcttc gagtccctcg cgcgcacga gtacttcctg    1680
gccgctcgcg gcggcttcat ggagggcgac cacatcgtcg acgtgggctg cggcgtcggc   1740
ggtccggcgc gcaacatggt tcgcctcacg cgctgcaacg tcatcggcgt caacaacaac   1800
gattaccaga tcagccgcgc tcgccgtcat gacgcgctcg ccggtatgag ctccaagatc   1860
gactacgtca agaccgactt ctgcaacatg agcttagccg acaacacctt cgacggcgcc   1920
tacgccatcg aggccacctg ccacgcaaag gacaaggtca agtgctatag cgaggtcttc   1980
cgtgtcatca gcccggcac ctgctttgtc ctgtacgagt ggtgcatgac cgacaagtac    2040
aaccccaatg acgagtacca ccgcacaatc aagcaccgca tcgagctggg cgacggcctg   2100
ccggagatgg agacgtgcaa acaggtgatc gagtacatga agcaggccgg cttcgtggtg   2160
gaggaggcca tagacgtcat cagtcagttc gagtccagcc ccatcaagag tatcccgtgg   2220
taccagccgc tggtcggcga ctattcgtcc ctgcagggcc tgcgctctac cccgattggc   2280
cgcatcctca cgaacgtcat gtgtcgcgtg ctggagttcg tgcgcctagc tccgaagggc   2340
acgtacaagg cgacggagat tttggaggag gctgcggaaa gctggtggt gggcggtcag    2400
ctcggcatct tcacgccgtc cttctacatc cgcgctcgca agccgtccaa gcaggct      2457
```

<210> SEQ ID NO 18
<211> LENGTH: 819
<212> TYPE: PRT

<213> ORGANISM: Artificial Sequence
<220> FEATURE:
<223> OTHER INFORMATION: Synthetic Construct

<400> SEQUENCE: 18

```
Met Lys Asp Lys Ala Thr Gly Lys Thr Gln Asn Ile Thr Ile Thr Ala
 1               5                  10                  15

Asn Gly Gly Leu Ser Lys Glu Gln Ile Glu Gln Met Ile Arg Asp Ser
            20                  25                  30

Glu Gln His Ala Glu Ala Asp Arg Val Lys Arg Glu Leu Val Glu Val
        35                  40                  45

Arg Asn Asn Ala Glu Thr Gln Leu Thr Thr Ala Glu Arg Gln Leu Gly
 50                  55                  60

Glu Trp Lys Tyr Val Ser Asp Ala Glu Lys Glu Asn Val Lys Thr Leu
 65                  70                  75                  80

Val Ala Glu Leu Arg Lys Ala Met Glu Asn Pro Asn Val Ala Lys Asp
                85                  90                  95

Asp Leu Ala Ala Ala Thr Asp Lys Leu Gln Lys Ala Val Met Glu Cys
            100                 105                 110

Gly Arg Thr Glu Tyr Gln Gln Ala Ala Ala Asn Ser Gly Ser Thr
        115                 120                 125

Ser Asn Ser Gly Glu Gln Gln Gln Gln Gly Gln Gly Glu Gln Gln
130                 135                 140

Gln Gln Gln Asn Ser Glu Lys Lys Met Pro Arg Lys Ile Ile Leu
145                 150                 155                 160

Asp Cys Asp Pro Gly Ile Asp Asp Ala Val Ala Ile Phe Leu Ala His
            165                 170                 175

Gly Asn Pro Glu Val Glu Leu Leu Ala Ile Thr Thr Val Val Gly Asn
        180                 185                 190

Gln Thr Leu Glu Lys Val Thr Arg Asn Ala Arg Leu Val Ala Asp Val
        195                 200                 205

Ala Gly Ile Val Gly Val Pro Val Ala Ala Gly Cys Thr Lys Pro Leu
210                 215                 220

Val Arg Gly Val Arg Asn Ala Ser Gln Ile His Gly Glu Thr Gly Met
225                 230                 235                 240

Gly Asn Val Ser Tyr Pro Pro Glu Phe Lys Thr Lys Leu Asp Gly Arg
            245                 250                 255

His Ala Val Gln Leu Ile Ile Asp Leu Ile Met Ser His Glu Pro Lys
        260                 265                 270

Thr Ile Thr Leu Val Pro Thr Gly Gly Leu Thr Asn Ile Ala Met Ala
        275                 280                 285

Val Arg Leu Glu Pro Arg Ile Val Asp Arg Val Lys Glu Val Val Leu
290                 295                 300

Met Gly Gly Gly Tyr His Thr Gly Asn Ala Ser Pro Val Ala Glu Phe
305                 310                 315                 320

Asn Val Phe Val Asp Pro Glu Ala Ala His Ile Val Phe Asn Glu Ser
            325                 330                 335

Trp Asn Val Thr Met Val Gly Leu Asp Leu Thr His Gln Ala Leu Ala
        340                 345                 350

Thr Pro Ala Val Gln Lys Arg Val Lys Glu Val Gly Thr Lys Pro Ala
        355                 360                 365

Ala Phe Met Leu Gln Ile Leu Asp Phe Tyr Thr Lys Val Tyr Glu Lys
370                 375                 380

Glu Arg Asn Thr Tyr Ala Thr Val His Asp Pro Cys Ala Val Ala Tyr
```

```
              385                 390                 395                 400
Val Ile Asp Pro Thr Val Met Thr Thr Glu Gln Val Pro Val Asp Ile
                    405                 410                 415

Glu Leu Asn Gly Ala Leu Thr Thr Gly Met Thr Val Ala Asp Phe Arg
                420                 425                 430

Tyr Pro Arg Pro Lys His Cys His Thr Gln Val Ala Val Lys Leu Asp
                435                 440                 445

Phe Asp Lys Phe Trp Cys Leu Val Ile Asp Ala Leu Lys Arg Ile Gly
            450                 455                 460

Asp Pro Gln Ser Ala Gly Gly Arg Glu Thr Ala Pro Thr Asn Leu Ile
465                 470                 475                 480

Arg Arg Arg Asn Lys Asp Glu Thr Asn Gly Asp Val Ser Ala Ala Ala
                485                 490                 495

Asp Arg Phe Arg Asp Arg Phe Glu Lys Ala Thr Leu Glu Glu Arg Lys
                500                 505                 510

Ala Ala Thr Thr Thr Met Val Asn Glu Tyr Tyr Asp Leu Val Thr Asp
            515                 520                 525

Phe Tyr Glu Tyr Gly Trp Gly Gln Asn Phe His Phe Ala Pro Arg Tyr
            530                 535                 540

Ala Gly Glu Thr Phe Phe Glu Ser Leu Ala Arg His Glu Tyr Phe Leu
545                 550                 555                 560

Ala Ala Arg Gly Gly Phe Met Glu Gly Asp His Ile Val Asp Val Gly
                565                 570                 575

Cys Gly Val Gly Gly Pro Ala Arg Asn Met Val Arg Leu Thr Arg Cys
            580                 585                 590

Asn Val Ile Gly Val Asn Asn Asn Asp Tyr Gln Ile Ser Arg Ala Arg
            595                 600                 605

Arg His Asp Ala Leu Ala Gly Met Ser Ser Lys Ile Asp Tyr Val Lys
        610                 615                 620

Thr Asp Phe Cys Asn Met Ser Leu Ala Asp Asn Thr Phe Asp Gly Ala
625                 630                 635                 640

Tyr Ala Ile Glu Ala Thr Cys His Ala Lys Asp Lys Val Lys Cys Tyr
                645                 650                 655

Ser Glu Val Phe Arg Val Ile Lys Pro Gly Thr Cys Phe Val Leu Tyr
                660                 665                 670

Glu Trp Cys Met Thr Asp Lys Tyr Asn Pro Asn Asp Glu Tyr His Arg
            675                 680                 685

Thr Ile Lys His Arg Ile Glu Leu Gly Asp Gly Leu Pro Glu Met Glu
        690                 695                 700

Thr Cys Lys Gln Val Ile Glu Tyr Met Lys Gln Ala Gly Phe Val Val
705                 710                 715                 720

Glu Glu Ala Ile Asp Val Ile Ser Gln Phe Glu Ser Ser Pro Ile Lys
                725                 730                 735

Ser Ile Pro Trp Tyr Gln Pro Leu Val Gly Asp Tyr Ser Ser Leu Gln
            740                 745                 750

Gly Leu Arg Ser Thr Pro Ile Gly Arg Ile Leu Thr Asn Val Met Cys
            755                 760                 765

Arg Val Leu Glu Phe Val Arg Leu Ala Pro Lys Gly Thr Tyr Lys Ala
        770                 775                 780

Thr Glu Ile Leu Glu Glu Ala Ala Glu Ser Leu Val Val Gly Gly Gln
785                 790                 795                 800

Leu Gly Ile Phe Thr Pro Ser Phe Tyr Ile Arg Ala Arg Lys Pro Ser
                805                 810                 815
```

Lys Gln Ala

<210> SEQ ID NO 19
<211> LENGTH: 2571
<212> TYPE: DNA
<213> ORGANISM: Artificial Sequence
<220> FEATURE:
<223> OTHER INFORMATION: Synthetic Construct

<400> SEQUENCE: 19

| | | | | | |
|---|---|---|---|---|---|
| atgagcatta | tcaaggagga | cgacgccgtg | ggctgctaca | tgacggtgac | cctcgtggac | 60 |
| gacaccaagg | tggagggtac | catcttcacc | tacaatccca | aggaaggcat | catagtactt | 120 |
| ctgtccctcc | gcgacgatca | gacgaacatg | aagctgatcc | gcactccata | catcaaagag | 180 |
| ttcagtattt | cacacgctga | ggagggaacg | cacctgcctc | cggcactgga | ctccttcaac | 240 |
| gagcttccgt | ccatgcatgc | cggccgcgac | aagtccatct | tcaagcacgc | cagcacgcag | 300 |
| ctcaagaacg | ccgaggcgaa | ccgcgaaaag | cacttcaact | ctgtcacgac | cgacacaccg | 360 |
| attgccacac | tcgatgcgta | cctcaagctc | ctgcggctat | acccctcat | tgagtggaac | 420 |
| agcgacgagg | tgtcatcca | ggtctcggat | accgtcattg | tcgtagggga | ccccgactgg | 480 |
| cggacgccca | aggcgatgct | ggtagacggc | gcccctgaga | aggacagacc | gctcgtagac | 540 |
| cgcctgcagg | ttgcgctcgg | aaacggcaag | aagatgccgc | gcaagattat | tctcgattgt | 600 |
| gatcccggga | tcgatgatgc | cgtggccatc | tttctcgccc | acggcaaccc | ggaggtcgag | 660 |
| ctgctggcca | ttacgacggt | ggtgggcaac | cagaccctgg | agaaggtgac | ccggaacgcg | 720 |
| cggctggtag | ctgacgtagc | cggcatcgtt | ggtgtgcccg | tcgcggctgg | ttgcaccaag | 780 |
| cccctcgtgc | gcggtgtgcg | gaatgcctct | cagattcatg | gcgaaaccgg | catgggtaac | 840 |
| gtctcctacc | accagagtt | caagacaaag | ttggacggcc | gtcatgcagt | gcagctgatc | 900 |
| atcgacctta | tcatgtcgca | cgagccgaag | acgatcacgc | ttgtgcctac | gggtggcctg | 960 |
| acgaacattg | cgatggctgt | ccgtcttgag | ccgcgcatcg | tggaccgtgt | gaaggaggtg | 1020 |
| gttctgatgg | gtggcggcta | ccatactggt | aatgcgtccc | ctgtagcgga | gttcaacgtc | 1080 |
| ttcgtcgacc | cggaggcggc | gcacattgtg | ttcaacgaga | gctggaacgt | aacgatggtg | 1140 |
| gggctggacc | taacgcacca | ggcactcgcc | acgccggcgg | tccagaagcg | agtgaaggag | 1200 |
| gtgggcacga | agccggctgc | cttcatgctg | cagattttgg | acttttacac | gaaggtgtac | 1260 |
| gaaaaggagc | gcaacacgta | cgcgacggtg | cacgatccct | gcgctgtggc | gtacgtgatt | 1320 |
| gaccccaccg | tgatgacgac | ggagcaagtg | ccagtggaca | tcgagctcaa | tggggcactg | 1380 |
| acgactggga | tgacggtcgc | ggacttccgc | tacccacggc | caaagcactg | ccacacgcag | 1440 |
| gtggctgtga | agctggactt | cgacaagttt | tggtgcctcg | tgattgacgc | actcaagcgc | 1500 |
| atcggcgatc | ctcaatccgc | cggtggccgt | gagaccgcgc | cgacgaacct | gattcgtcgc | 1560 |
| cgcaacaagg | acgagacaaa | cggggatgtc | agcgccgccg | ccgaccgctt | ccgcgaccgc | 1620 |
| ttcgagaagg | caaccctcga | ggagcgcaag | gccgccacca | cgacgatggt | caacgagtac | 1680 |
| tacgacctgg | tgacggactt | ctacgagtac | ggctggggcc | agaacttcca | tttcgcgccg | 1740 |
| cgctacgccg | gcgagacctt | cttcgagtcc | ctcgcgcgcc | acgagtactt | cctggccgct | 1800 |
| cgcggcggct | tcatggaggg | cgaccacatc | gtcgacgtgg | gctgcggcgt | cggcggtccg | 1860 |
| gcgcgcaaca | tggttcgcct | cacgcgctgc | aacgtcatcg | gcgtcaacaa | caacgattac | 1920 |
| cagatcagcc | gcgctcgccg | tcatgacgcg | ctcgccggta | tgagctccaa | gatcgactac | 1980 |

-continued

```
gtcaagaccg acttctgcaa catgagctta gccgacaaca ccttcgacgg cgcctacgcc    2040
atcgaggcca cctgccacgc aaaggacaag gtcaagtgct atagcgaggt cttccgtgtc    2100
atcaagcccg cacctgcttt tgtcctgtac gagtggtgca tgaccgacaa gtacaacccc    2160
aatgacgagt accaccgcac aatcaagcac cgcatcgagc tgggcgacgg cctgccggag    2220
atggagacgt gcaaacaggt gatcgagtac atgaagcagg ccggcttcgt ggtggaggag    2280
gccatagacg tcatcagtca gttcgagtcc agccccatca agagtatccc gtggtaccag    2340
ccgctggtcg gcgactattc gtccctgcag ggcctgcgct ctaccccgat ggccgcatc    2400 ctcacgaacg tcatgtgtcg cgtgctggag ttcgtgcgcc tagctccgaa gggcacgtac    2460
aaggcgacgg agattttgga ggaggctgcg gaaagcctgg tggtgggcgg tcagctcggc    2520
atcttcacgc cgtccttcta catccgcgct cgcaagccgt ccaagcaggc t              2571
```

<210> SEQ ID NO 20
<211> LENGTH: 857
<212> TYPE: PRT
<213> ORGANISM: Artificial Sequence
<220> FEATURE:
<223> OTHER INFORMATION: Synthetic Construct

<400> SEQUENCE: 20

```
Met Ser Ile Ile Lys Glu Asp Asp Ala Val Gly Cys Tyr Met Thr Val
1               5                   10                  15

Thr Leu Val Asp Asp Thr Lys Val Glu Gly Thr Ile Phe Thr Tyr Asn
            20                  25                  30

Pro Lys Glu Gly Ile Ile Val Leu Leu Ser Leu Arg Asp Asp Gln Thr
        35                  40                  45

Asn Met Lys Leu Ile Arg Thr Pro Tyr Ile Lys Glu Phe Ser Ile Ser
    50                  55                  60

His Ala Glu Glu Gly Thr His Leu Pro Pro Ala Leu Asp Ser Phe Asn
65                  70                  75                  80

Glu Leu Pro Ser Met His Ala Gly Arg Asp Lys Ser Ile Phe Lys His
                85                  90                  95

Ala Ser Thr Gln Leu Lys Asn Ala Glu Ala Asn Arg Glu Lys His Phe
            100                 105                 110

Asn Ser Val Thr Thr Asp Thr Pro Ile Ala Thr Leu Asp Ala Tyr Leu
        115                 120                 125

Lys Leu Leu Arg Leu Tyr Pro Phe Ile Glu Trp Asn Ser Asp Glu Gly
    130                 135                 140

Val Ile Gln Val Ser Asp Thr Val Ile Val Gly Asp Pro Asp Trp
145                 150                 155                 160

Arg Thr Pro Lys Ala Met Leu Val Asp Gly Ala Pro Glu Lys Asp Arg
                165                 170                 175

Pro Leu Val Asp Arg Leu Gln Val Ala Leu Gly Asn Gly Lys Lys Met
            180                 185                 190

Pro Arg Lys Ile Ile Leu Asp Cys Asp Pro Gly Ile Asp Ala Val
        195                 200                 205

Ala Ile Phe Leu Ala His Gly Asn Pro Glu Val Glu Leu Leu Ala Ile
    210                 215                 220

Thr Thr Val Val Gly Asn Gln Thr Leu Glu Lys Val Thr Arg Asn Ala
225                 230                 235                 240

Arg Leu Val Ala Asp Val Ala Gly Ile Val Gly Val Pro Val Ala Ala
                245                 250                 255

Gly Cys Thr Lys Pro Leu Val Arg Gly Val Arg Asn Ala Ser Gln Ile
```

-continued

```
                260                 265                 270
His Gly Glu Thr Gly Met Gly Asn Val Ser Tyr Pro Pro Glu Phe Lys
                275                 280                 285
Thr Lys Leu Asp Gly Arg His Ala Val Gln Leu Ile Ile Asp Leu Ile
                290                 295             300
Met Ser His Glu Pro Lys Thr Ile Thr Leu Val Pro Thr Gly Gly Leu
305                 310                 315                 320
Thr Asn Ile Ala Met Ala Val Arg Leu Glu Pro Arg Ile Val Asp Arg
                325                 330                 335
Val Lys Glu Val Val Leu Met Gly Gly Tyr His Thr Gly Asn Ala
                340                 345                 350
Ser Pro Val Ala Glu Phe Asn Val Phe Val Asp Pro Glu Ala Ala His
                355                 360                 365
Ile Val Phe Asn Glu Ser Trp Asn Val Thr Met Val Gly Leu Asp Leu
                370                 375             380
Thr His Gln Ala Leu Ala Thr Pro Ala Val Gln Lys Arg Val Lys Glu
385                 390                 395                 400
Val Gly Thr Lys Pro Ala Ala Phe Met Leu Gln Ile Leu Asp Phe Tyr
                405                 410                 415
Thr Lys Val Tyr Glu Lys Glu Arg Asn Thr Tyr Ala Thr Val His Asp
                420                 425                 430
Pro Cys Ala Val Ala Tyr Val Ile Asp Pro Thr Val Met Thr Thr Glu
                435                 440                 445
Gln Val Pro Val Asp Ile Glu Leu Asn Gly Ala Leu Thr Thr Gly Met
                450                 455             460
Thr Val Ala Asp Phe Arg Tyr Pro Arg Pro Lys His Cys His Thr Gln
465                 470                 475                 480
Val Ala Val Lys Leu Asp Phe Asp Lys Phe Trp Cys Leu Val Ile Asp
                485                 490                 495
Ala Leu Lys Arg Ile Gly Asp Pro Gln Ser Ala Gly Gly Arg Glu Thr
                500                 505                 510
Ala Pro Thr Asn Leu Ile Arg Arg Asn Lys Asp Glu Thr Asn Gly
                515                 520             525
Asp Val Ser Ala Ala Ala Asp Arg Phe Arg Asp Arg Phe Glu Lys Ala
                530                 535             540
Thr Leu Glu Glu Arg Lys Ala Ala Thr Thr Met Val Asn Glu Tyr
545                 550                 555                 560
Tyr Asp Leu Val Thr Asp Phe Tyr Glu Tyr Gly Trp Gly Gln Asn Phe
                565                 570                 575
His Phe Ala Pro Arg Tyr Ala Gly Glu Thr Phe Phe Glu Ser Leu Ala
                580                 585             590
Arg His Glu Tyr Phe Leu Ala Ala Arg Gly Gly Phe Met Glu Gly Asp
                595                 600                 605
His Ile Val Asp Val Gly Cys Gly Val Gly Gly Pro Ala Arg Asn Met
                610                 615             620
Val Arg Leu Thr Arg Cys Asn Val Ile Gly Val Asn Asn Asn Asp Tyr
625                 630                 635                 640
Gln Ile Ser Arg Ala Arg Arg His Asp Ala Leu Ala Gly Met Ser Ser
                645                 650                 655
Lys Ile Asp Tyr Val Lys Thr Asp Phe Cys Asn Met Ser Leu Ala Asp
                660                 665             670
Asn Thr Phe Asp Gly Ala Tyr Ala Ile Glu Ala Thr Cys His Ala Lys
                675                 680                 685
```

| Asp | Lys | Val | Lys | Cys | Tyr | Ser | Glu | Val | Phe | Arg | Val | Ile | Lys | Pro | Gly |
| | 690 | | | | 695 | | | | 700 | | | | | | |

| Thr | Cys | Phe | Val | Leu | Tyr | Glu | Trp | Cys | Met | Thr | Asp | Lys | Tyr | Asn | Pro |
| 705 | | | | | 710 | | | | | 715 | | | | | 720 |

| Asn | Asp | Glu | Tyr | His | Arg | Thr | Ile | Lys | His | Arg | Ile | Glu | Leu | Gly | Asp |
| | | | | 725 | | | | | 730 | | | | | 735 | |

| Gly | Leu | Pro | Glu | Met | Glu | Thr | Cys | Lys | Gln | Val | Ile | Glu | Tyr | Met | Lys |
| | | | 740 | | | | | 745 | | | | | 750 | | |

| Gln | Ala | Gly | Phe | Val | Val | Glu | Glu | Ala | Ile | Asp | Val | Ile | Ser | Gln | Phe |
| | | 755 | | | | | 760 | | | | | 765 | | | |

| Glu | Ser | Ser | Pro | Ile | Lys | Ser | Ile | Pro | Trp | Tyr | Gln | Pro | Leu | Val | Gly |
| 770 | | | | | 775 | | | | | 780 | | | | | |

| Asp | Tyr | Ser | Ser | Leu | Gln | Gly | Leu | Arg | Ser | Thr | Pro | Ile | Gly | Arg | Ile |
| 785 | | | | | 790 | | | | | 795 | | | | | 800 |

| Leu | Thr | Asn | Val | Met | Cys | Arg | Val | Leu | Glu | Phe | Val | Arg | Leu | Ala | Pro |
| | | | | 805 | | | | | 810 | | | | | 815 | |

| Lys | Gly | Thr | Tyr | Lys | Ala | Thr | Glu | Ile | Leu | Glu | Glu | Ala | Ala | Glu | Ser |
| | | | 820 | | | | | 825 | | | | | 830 | | |

| Leu | Val | Val | Gly | Gly | Gln | Leu | Gly | Ile | Phe | Thr | Pro | Ser | Phe | Tyr | Ile |
| | | 835 | | | | | 840 | | | | | 845 | | | |

| Arg | Ala | Arg | Lys | Pro | Ser | Lys | Gln | Ala |
| | 850 | | | | | 855 | | |

<210> SEQ ID NO 21
<211> LENGTH: 2499
<212> TYPE: DNA
<213> ORGANISM: Artificial Sequence
<220> FEATURE:
<223> OTHER INFORMATION: Synthetic Construct

<400> SEQUENCE: 21

```
atgagcatta tcaaggagga cgacgccgtg ggctgctaca tgacggtgac cctcgtggac      60
gacaccaagg tggagggtac catcttcacc tacaatccca aggaaggcat catagtactt     120
ctgtccctcc gcgacgatca gacgaacatg aagctgatcc gcactccata catcaaagag     180
ttcagtattt cacacgctga ggagggaacg cacctgcctc cggcactgga ctccttcaac     240
gagcttccgt ccatgcatgc cggccgcgac aagtccatct tcaagcacgc cagcacgcag     300
ctcaagaacg ccgaggcgaa ccgcgaaaag cacttcaact ctgtcacgac cgacacaccg     360
attgccacac tcgatgcgta cctcaagctc ctgcggctat acccttcat tgagtggaac     420
agcgacgagg gtgtcatcca ggtctcggat accgtcattg tcgtagggga ccccgactgg     480
cggacgccca aggcgatgct ggtagacggc gcccctgaga aggacagacc gctcgtagac     540
cgcctgcagg ttgcgctcgg aaacggcaag aagtccgccg gtggccgtga accgcgccg     600
acgaacctga ttcgtcgccg caacaaggac gagacaaacg gggatgtcag cgccgccgcc     660
gaccgcttcc gcgaccgctt cgagaaggca accctcgagg agcgcaaggc cgccaccacg     720
acgatggtca cgagtactac cgacctggtg acggacttct acgagtacgg ctggggccag     780
aacttccatt tcgcgccgcg ctacgccggc gagaccttct tcgagtccct cgcgcgccac     840
gagtacttcc tggccgctcg cggcggcttc atggagggcg accacatcgt cgacgtgggc     900
tgcggcgtcg gcggtccggc gcgcaacatg gttcgcctca cgcgctgcaa cgtcatcggc     960
gtcaacaaca acgattacca gatcagccgc gctcgccgtc atgacgcgct cgccggtatg    1020
agctccaaga tcgactacgt caagaccgac ttctgcaaca tgagcttagc cgacaacacc    1080
```

-continued

```
ttcgacggcg cctacgccat cgaggccacc tgccacgcaa aggacaaggt caagtgctat   1140
agcgaggtct tccgtgtcat caagcccggc acctgctttg tcctgtacga gtggtgcatg   1200
accgacaagt acaaccccaa tgacgagtac caccgcacaa tcaagcaccg catcgagctg   1260
ggcgacggcc tgccggagat ggagacgtgc aaacaggtga tcgagtacat gaagcaggcc   1320
ggcttcgtgg tggaggaggc catagacgtc atcagtcagt tcgagtccag ccccatcaag   1380
agtatcccgt ggtaccagcc gctggtcggc gactattcgt ccctgcaggg cctgcgctct   1440
accccgattg gccgcatcct cacgaacgtc atgtgtcgcg tgctggagtt cgtgcgccta   1500
gctccgaagg gcacgtacaa ggcgacggag attttggagg aggctgcgga aagcctggtg   1560
gtgggcggtc agctcggcat cttcacgccg tccttctaca tccgcgctcg caagccgtcc   1620
aagcaggctt cggcggtcgg caacatcgag tcgcagtggg cccgtgccgg ccacggcttg   1680
gtgagcctgt cggagcagca gctggtgagc tgcgatgaca agacaatggc tgcaacggc   1740
gggctgatgc tgcaggcgtt cgagtggctg ctgcgacaca tgtacgggat cgtgttcacg   1800
gagaagagct accccctacac gtccggcaac ggtgatgtgg ccgagtgctt gaacagcagt   1860
aaactcgttc ccggcgcgca aatcgacggc tacgtgatga tcccgagcaa cgaaacggtt   1920
atggctgcgt ggcttgcgga aatggcccc atcgcgattg cggtcgacgc cagctccttc   1980
atgtcttacc agagcggcgt gctgaccagc tgcgctggcg atgcactgaa ccacggcgtg   2040
ctgctcgtcg ggtacaacaa gaccggtggg gttccgtact gggtgatcaa gaactcgtgg   2100
ggtgaggact ggggcgagaa gggctacgtg cgcgtggtca tggggctgaa cgcgtgcctg   2160
ctcagtgaat accccgtgtc cgcgcatgtg ccgcggagtc tcacccctgg cccgggcacg   2220
gagagcgagg agcgcgcccc taaacgggtg acggtggagc agatgatgtg caccgatatg   2280
tactgcaggg aggggtgcaa gaagagtctt ctcaccgcga acgtgtgcta caagaacggg   2340
ggaggcggct cctctatgac gaagtgcggt ccgcagaagg tgctgatgtg ctcgtactcg   2400
aaccctcatt gctttggtcc tgggctgtgc ctcgagactc ctgatggcaa gtgcgcgccg   2460
tacttcttgg gctcgatcat gaacacctgc cagtacacg                         2499
```

<210> SEQ ID NO 22
<211> LENGTH: 833
<212> TYPE: PRT
<213> ORGANISM: Artificial Sequence
<220> FEATURE:
<223> OTHER INFORMATION: Synthetic Construct

<400> SEQUENCE: 22

```
Met Ser Ile Ile Lys Glu Asp Asp Ala Val Gly Cys Tyr Met Thr Val
1               5                   10                  15

Thr Leu Val Asp Asp Thr Lys Val Glu Gly Thr Ile Phe Thr Tyr Asn
                20                  25                  30

Pro Lys Glu Gly Ile Ile Val Leu Leu Ser Leu Arg Asp Asp Gln Thr
            35                  40                  45

Asn Met Lys Leu Ile Arg Thr Pro Tyr Ile Lys Glu Phe Ser Ile Ser
        50                  55                  60

His Ala Glu Glu Gly Thr His Leu Pro Ala Leu Asp Ser Phe Asn
65                  70                  75                  80

Glu Leu Pro Ser Met His Ala Gly Arg Asp Lys Ser Ile Phe Lys His
                85                  90                  95

Ala Ser Thr Gln Leu Lys Asn Ala Glu Ala Asn Arg Glu Lys His Phe
            100                 105                 110
```

```
Asn Ser Val Thr Thr Asp Thr Pro Ile Ala Thr Leu Asp Ala Tyr Leu
            115                 120                 125

Lys Leu Leu Arg Leu Tyr Pro Phe Ile Glu Trp Asn Ser Asp Glu Gly
        130                 135                 140

Val Ile Gln Val Ser Asp Thr Val Ile Val Gly Asp Pro Asp Trp
145                 150                 155                 160

Arg Thr Pro Lys Ala Met Leu Val Asp Gly Ala Pro Glu Lys Asp Arg
                165                 170                 175

Pro Leu Val Asp Arg Leu Gln Val Ala Leu Gly Asn Gly Lys Lys Ser
            180                 185                 190

Ala Gly Gly Arg Glu Thr Ala Pro Thr Asn Leu Ile Arg Arg Arg Asn
        195                 200                 205

Lys Asp Glu Thr Asn Gly Asp Val Ser Ala Ala Asp Arg Phe Arg
210                 215                 220

Asp Arg Phe Glu Lys Ala Thr Leu Glu Glu Arg Lys Ala Ala Thr Thr
225                 230                 235                 240

Thr Met Val Asn Glu Tyr Tyr Asp Leu Val Thr Asp Phe Tyr Glu Tyr
                245                 250                 255

Gly Trp Gly Gln Asn Phe His Phe Ala Pro Arg Tyr Ala Gly Glu Thr
            260                 265                 270

Phe Phe Glu Ser Leu Ala Arg His Glu Tyr Phe Leu Ala Ala Arg Gly
        275                 280                 285

Gly Phe Met Glu Gly Asp His Ile Val Asp Val Gly Cys Gly Val Gly
        290                 295                 300

Gly Pro Ala Arg Asn Met Val Arg Leu Thr Arg Cys Asn Val Ile Gly
305                 310                 315                 320

Val Asn Asn Asn Asp Tyr Gln Ile Ser Arg Ala Arg Arg His Asp Ala
                325                 330                 335

Leu Ala Gly Met Ser Ser Lys Ile Asp Tyr Val Lys Thr Asp Phe Cys
            340                 345                 350

Asn Met Ser Leu Ala Asp Asn Thr Phe Asp Gly Ala Tyr Ala Ile Glu
        355                 360                 365

Ala Thr Cys His Ala Lys Asp Lys Val Lys Cys Tyr Ser Glu Val Phe
    370                 375                 380

Arg Val Ile Lys Pro Gly Thr Cys Phe Val Leu Tyr Glu Trp Cys Met
385                 390                 395                 400

Thr Asp Lys Tyr Asn Pro Asn Asp Glu Tyr His Arg Thr Ile Lys His
                405                 410                 415

Arg Ile Glu Leu Gly Asp Gly Leu Pro Glu Met Glu Thr Cys Lys Gln
            420                 425                 430

Val Ile Glu Tyr Met Lys Gln Ala Gly Phe Val Val Glu Glu Ala Ile
        435                 440                 445

Asp Val Ile Ser Gln Phe Glu Ser Ser Pro Ile Lys Ser Ile Pro Trp
450                 455                 460

Tyr Gln Pro Leu Val Gly Asp Tyr Ser Ser Leu Gln Gly Leu Arg Ser
465                 470                 475                 480

Thr Pro Ile Gly Arg Ile Leu Thr Asn Val Met Cys Arg Val Leu Glu
                485                 490                 495

Phe Val Arg Leu Ala Pro Lys Gly Thr Tyr Lys Ala Thr Glu Ile Leu
            500                 505                 510

Glu Glu Ala Ala Glu Ser Leu Val Val Gly Gly Gln Leu Gly Ile Phe
        515                 520                 525
```

```
Thr Pro Ser Phe Tyr Ile Arg Ala Arg Lys Pro Ser Lys Gln Ala Ser
            530                 535                 540

Ala Val Gly Asn Ile Glu Ser Gln Trp Ala Arg Ala Gly His Gly Leu
545                 550                 555                 560

Val Ser Leu Ser Glu Gln Gln Leu Val Ser Cys Asp Asp Lys Asp Asn
                565                 570                 575

Gly Cys Asn Gly Gly Leu Met Leu Gln Ala Phe Glu Trp Leu Leu Arg
                580                 585                 590

His Met Tyr Gly Ile Val Phe Thr Glu Lys Ser Tyr Pro Tyr Thr Ser
            595                 600                 605

Gly Asn Gly Asp Val Ala Glu Cys Leu Asn Ser Lys Leu Val Pro
610                 615                 620

Gly Ala Gln Ile Asp Gly Tyr Val Met Ile Pro Ser Asn Glu Thr Val
625                 630                 635                 640

Met Ala Ala Trp Leu Ala Glu Asn Gly Pro Ile Ala Ile Ala Val Asp
                645                 650                 655

Ala Ser Ser Phe Met Ser Tyr Gln Ser Gly Val Leu Thr Ser Cys Ala
                660                 665                 670

Gly Asp Ala Leu Asn His Gly Val Leu Leu Val Gly Tyr Asn Lys Thr
                675                 680                 685

Gly Gly Val Pro Tyr Trp Val Ile Lys Asn Ser Trp Gly Glu Asp Trp
690                 695                 700

Gly Glu Lys Gly Tyr Val Arg Val Val Met Gly Leu Asn Ala Cys Leu
705                 710                 715                 720

Leu Ser Glu Tyr Pro Val Ser Ala His Val Pro Arg Ser Leu Thr Pro
                725                 730                 735

Gly Pro Gly Thr Glu Ser Glu Glu Arg Ala Pro Lys Arg Val Thr Val
                740                 745                 750

Glu Gln Met Met Cys Thr Asp Met Tyr Cys Arg Glu Gly Cys Lys Lys
                755                 760                 765

Ser Leu Leu Thr Ala Asn Val Cys Tyr Lys Asn Gly Gly Gly Ser
770                 775                 780

Ser Met Thr Lys Cys Gly Pro Gln Lys Val Leu Met Cys Ser Tyr Ser
785                 790                 795                 800

Asn Pro His Cys Phe Gly Pro Gly Leu Cys Leu Glu Thr Pro Asp Gly
                805                 810                 815

Lys Cys Ala Pro Tyr Phe Leu Gly Ser Ile Met Asn Thr Cys Gln Tyr
                820                 825                 830

Thr
```

<210> SEQ ID NO 23
<211> LENGTH: 2091
<212> TYPE: DNA
<213> ORGANISM: Artificial Sequence
<220> FEATURE:
<223> OTHER INFORMATION: Synthetic Construct

<400> SEQUENCE: 23

```
atgaaggaca aggcgacggg caagacgcag aacatcacga tcacggcgaa cggcgggctg      60
tcgaaggagc agatcgagca gatgatccgc gactcggagc agcacgcgga ggccgaccgc     120
gtgaagcgcg agcttgtgga ggtgcgcaac aacgcggaga cgcagctgac aacggcggag     180
aggcagctcg gcgagtggaa gtacgtgagc gatgcggaga aggagaacgt gaagacgctg     240
gtggcggagc tgcgcaaggc gatggagaac ccgaacgtcg cgaaggatga ccttgcggct     300
```

```
gcgacggaca agctgcagaa ggctgtgatg gagtgcggcc gcacagagta ccagcaggct    360
gccgcggcca actccggcag caccagcaac tccggtgagc agcagcagca gcagggccaa    420
ggtgagcagc agcagcagca gaacagcgaa gagaagaaga tgagcattat caaggaggac    480
gacgccgtgg gctgctacat gacggtgacc ctcgtggacg acaccaaggt ggagggtacc    540
atcttcacct acaatcccaa ggaaggcatc atagtacttc tgtccctccg cgacgatcag    600
acgaacatga agctgatccg cactccatac atcaaagagt tcagtatttc acacgctgag    660
gagggaacgc acctgcctcc ggcactggac tccttcaacg agcttccgtc catgcatgcc    720
ggccgcgaca agtccatctt caagcacgcc agcacgcagc tcaagaacgc cgaggcgaac    780
cgcgaaaagc acttcaactc tgtcacgacc gacacaccga ttgccacact cgatgcgtac    840
ctcaagctcc tgcggctata ccccttcatt gagtggaaca cgacgagggg tgtcatccag    900
gtctcggata ccgtcattgt cgtaggggac cccgactggc ggacgcccaa ggcgatgctg    960
gtagacggcg cccctgagaa ggacagaccg ctcgtagacc gcctgcaggt tgcgctcgga   1020
aacggcaaga agatgtccgc cggtggccgt gagaccgcgc cgacgaacct gattcgtcgc   1080
cgcaacaagg acgagacaaa cggggatgtc agcgccgccg ccgaccgctt ccgcgaccgc   1140
ttcgagaagg caaccctcga ggagcgcaag gccgccacca cgacgatggt caacgagtac   1200
tacgacctgg tgacggactt ctacgagtac ggctggggcc agaacttcca tttcgcgccg   1260
cgctacgccg cgcgagacct tcttcgagtcc ctcgcgcgcc acgagtactt cctgccgct   1320 cgcggcggct tcatggaggg cgaccacatc gtcgacgtgg gctgcggcgt cggcggtccg   1380
gcgcgcaaca tggttcgcct cacgcgctgc aacgtcatcg gcgtcaacaa caacgattac   1440
cagatcagcc gcgctcgccg tcatgacgcg ctcgccggta tgagctccaa gatcgactac   1500
gtcaagaccg acttctgcaa catgagctta gccgacaaca ccttcgacgg cgcctacgcc   1560
atcgaggcca cctgccacgc aaaggacaag gtcaagtgct atagcgaggt cttccgtgtc   1620
atcaagcccg gcacctgctt tgtcctgtac gagtggtgca tgaccgacaa gtacaacccc   1680
aatgacgagt accaccgcac aatcaagcac cgcatcgagc tgggcgacgg cctgccggag   1740
atggagacgt gcaaacaggt gatcgagtac atgaagcagg ccggcttcgt ggtggaggag   1800
gccatagacg tcatcagtca gttcgagtcc agccccatca agagtatccc gtggtaccag   1860
ccgctggtcg cgactattc gtccctgcag ggcctgcgct ctaccccgat tggccgcatc   1920
ctcacgaacg tcatgtgtcg cgtgctggag ttcgtgcgcc tagctccgaa gggcacgtac   1980
aaggcgacgg agattttgga ggaggctgcg gaaagcctgg tggtgggcgg tcagctcggc   2040
atcttcacgc cgtccttcta catccgcgct cgcaagccgt ccaagcaggc t            2091
```

<210> SEQ ID NO 24
<211> LENGTH: 697
<212> TYPE: PRT
<213> ORGANISM: Artificial Sequence
<220> FEATURE:
<223> OTHER INFORMATION: Synthetic Construct

<400> SEQUENCE: 24

```
Met Lys Asp Lys Ala Thr Gly Lys Thr Gln Asn Ile Thr Ile Thr Ala
 1               5                  10                  15

Asn Gly Gly Leu Ser Lys Glu Gln Ile Glu Gln Met Ile Arg Asp Ser
             20                  25                  30

Glu Gln His Ala Glu Ala Asp Arg Val Lys Arg Glu Leu Val Glu Val
         35                  40                  45
```

Arg Asn Asn Ala Glu Thr Gln Leu Thr Thr Ala Glu Arg Gln Leu Gly
 50                  55                  60

Glu Trp Lys Tyr Val Ser Asp Ala Glu Lys Asn Val Lys Thr Leu
 65                  70                  75                  80

Val Ala Glu Leu Arg Lys Ala Met Glu Asn Pro Asn Val Ala Lys Asp
                 85                  90                  95

Asp Leu Ala Ala Ala Thr Asp Lys Leu Gln Lys Ala Val Met Glu Cys
                100                 105                 110

Gly Arg Thr Glu Tyr Gln Gln Ala Ala Ala Asn Ser Gly Ser Thr
                115                 120                 125

Ser Asn Ser Gly Glu Gln Gln Gln Gln Gly Gln Gly Gln Gln
130                 135                 140

Gln Gln Gln Asn Ser Glu Glu Lys Lys Met Ser Ile Ile Lys Glu Asp
145                 150                 155                 160

Asp Ala Val Gly Cys Tyr Met Thr Val Thr Leu Val Asp Asp Thr Lys
                165                 170                 175

Val Glu Gly Thr Ile Phe Thr Tyr Asn Pro Lys Glu Gly Ile Ile Val
                180                 185                 190

Leu Leu Ser Leu Arg Asp Asp Gln Thr Asn Met Lys Leu Ile Arg Thr
                195                 200                 205

Pro Tyr Ile Lys Glu Phe Ser Ile Ser His Ala Glu Glu Gly Thr His
                210                 215                 220

Leu Pro Pro Ala Leu Asp Ser Phe Asn Glu Leu Pro Ser Met His Ala
225                 230                 235                 240

Gly Arg Asp Lys Ser Ile Phe Lys His Ala Ser Thr Gln Leu Lys Asn
                245                 250                 255

Ala Glu Ala Asn Arg Glu Lys His Phe Asn Ser Val Thr Thr Asp Thr
                260                 265                 270

Pro Ile Ala Thr Leu Asp Ala Tyr Leu Lys Leu Leu Arg Leu Tyr Pro
                275                 280                 285

Phe Ile Glu Trp Asn Ser Asp Glu Gly Val Ile Gln Val Ser Asp Thr
290                 295                 300

Val Ile Val Val Gly Asp Pro Asp Trp Arg Thr Pro Lys Ala Met Leu
305                 310                 315                 320

Val Asp Gly Ala Pro Glu Lys Asp Arg Pro Leu Val Asp Arg Leu Gln
                325                 330                 335

Val Ala Leu Gly Asn Gly Lys Lys Met Ser Ala Gly Arg Glu Thr
                340                 345                 350

Ala Pro Thr Asn Leu Ile Arg Arg Asn Lys Asp Glu Thr Asn Gly
                355                 360                 365

Asp Val Ser Ala Ala Asp Arg Phe Arg Asp Arg Phe Glu Lys Ala
370                 375                 380

Thr Leu Glu Glu Arg Lys Ala Ala Thr Thr Thr Met Val Asn Glu Tyr
385                 390                 395                 400

Tyr Asp Leu Val Thr Asp Phe Tyr Glu Tyr Gly Trp Gly Gln Asn Phe
                405                 410                 415

His Phe Ala Pro Arg Tyr Ala Gly Glu Thr Phe Phe Glu Ser Leu Ala
                420                 425                 430

Arg His Glu Tyr Phe Leu Ala Ala Arg Gly Gly Phe Met Glu Gly Asp
                435                 440                 445

His Ile Val Asp Val Gly Cys Gly Val Gly Gly Pro Ala Arg Asn Met
450                 455                 460

Val Arg Leu Thr Arg Cys Asn Val Ile Gly Val Asn Asn Asn Asp Tyr

```
                465              470              475              480
          Gln Ile Ser Arg Ala Arg Arg His Asp Ala Leu Ala Gly Met Ser Ser
                          485              490              495
          Lys Ile Asp Tyr Val Lys Thr Asp Phe Cys Asn Met Ser Leu Ala Asp
                      500              505              510
          Asn Thr Phe Asp Gly Ala Tyr Ala Ile Glu Ala Thr Cys His Ala Lys
                  515              520              525
          Asp Lys Val Lys Cys Tyr Ser Glu Val Phe Arg Val Ile Lys Pro Gly
              530              535              540
          Thr Cys Phe Val Leu Tyr Glu Trp Cys Met Thr Asp Lys Tyr Asn Pro
          545              550              555              560
          Asn Asp Glu Tyr His Arg Thr Ile Lys His Arg Ile Glu Leu Gly Asp
                          565              570              575
          Gly Leu Pro Glu Met Glu Thr Cys Lys Gln Val Ile Glu Tyr Met Lys
                      580              585              590
          Gln Ala Gly Phe Val Val Glu Glu Ala Ile Asp Val Ile Ser Gln Phe
                  595              600              605
          Glu Ser Ser Pro Ile Lys Ser Ile Pro Trp Tyr Gln Pro Leu Val Gly
              610              615              620
          Asp Tyr Ser Ser Leu Gln Gly Leu Arg Ser Thr Pro Ile Gly Arg Ile
          625              630              635              640
          Leu Thr Asn Val Met Cys Arg Val Leu Glu Phe Val Arg Leu Ala Pro
                          645              650              655
          Lys Gly Thr Tyr Lys Ala Thr Glu Ile Leu Glu Glu Ala Ala Glu Ser
                      660              665              670
          Leu Val Val Gly Gly Gln Leu Gly Ile Phe Thr Pro Ser Phe Tyr Ile
                  675              680              685
          Arg Ala Arg Lys Pro Ser Lys Gln Ala
              690              695

<210> SEQ ID NO 25
<211> LENGTH: 1653
<212> TYPE: DNA
<213> ORGANISM: Artificial Sequence
<220> FEATURE:
<223> OTHER INFORMATION: Synthetic Construct

<400> SEQUENCE: 25
atgaaggaca aggcgacggg caagacgcag aacatcacga tcacggcgaa cggcgggctg      60
tcgaaggagc agatcgagca gatgatccgc gactcggagc agcacgcgga ggccgaccgc     120
gtgaagcgcg agcttgtgga ggtgcgcaac aacgcggaga cgcagctgac aacggcggag     180
aggcagctcg cgagtggaa gtacgtgagc gatgcggaga aggagaacgt gaagacgctg      240
gtggcggagc tgcgcaaggc gatggagaac ccgaacgtcg cgaaggatga ccttgcggct     300
gcgacggaca agctgcagaa ggctgtgatg gagtgcggcc gcacagagta ccagcaggct     360
gccgcggcca actccggcag caccagcaac tccggtgagc agcagcagca gcagggccaa     420
ggtgagcagc agcagcagca gaacagcgaa gagaagaaga tggcctcttc tcgctctgct     480
ccccgcaagg cttcccacgc gcacaagtcg caccgcaagc cgaagcgctc gtggaacgtg     540
tacgtgggcc gctcgctgaa ggcgatcaac gcccagatgt cgatgtcgca ccgcacgtcc     600
gccggtggcc gtgagaccgc gccgacgaac ctgattcgtc gccgcaacaa ggacgagaca     660 aacgggatg tcagccgcc cgccgaccgc ttccgcgacc gcttcgagaa ggcaaccctc      720
gaggagcgca aggccgccac cacgacgatg gtcaacgagt actacgacct ggtgacggac     780
```

```
ttctacgagt acggctgggg ccagaacttc catttcgcgc cgcgctacgc cggcgagacc    840
ttcttcgagt ccctcgcgcg ccacgagtac ttcctggccg ctcgcggcgg cttcatggag    900
ggcgaccaca tcgtcgacgt gggctgcggc gtcggcggtc cggcgcgcaa catggttcgc    960
ctcacgcgct gcaacgtcat cggcgtcaac aacaacgatt accagatcag ccgcgctcgc   1020
cgtcatgacg cgctcgccgg tatgagctcc aagatcgact acgtcaagac cgacttctgc   1080
aacatgagct tagccgacaa caccttcgac ggcgcctacg ccatcgaggc cacctgccac   1140
gcaaaggaca aggtcaagtg ctatagcgag gtcttccgtg tcatcaagcc cggcacctgc   1200
tttgtcctgt acgagtggtg catgaccgac aagtacaacc ccaatgacga gtaccaccgc   1260
acaatcaagc accgcatcga gctgggcgac ggcctgccgg agatggagac gtgcaaacag   1320
gtgatcgagt acatgaagca ggccggcttc gtggtggagg aggccataga cgtcatcagt   1380
cagttcgagt ccagccccat caagagtatc ccgtggtacc agccgctggt cggcgactat   1440
tcgtccctgc agggcctgcg ctctaccccg attggccgca tcctcacgaa cgtcatgtgt   1500
cgcgtgctgg agttcgtgcg cctagctccg aagggcacgt acaaggcgac ggagattttg   1560
gaggaggctg cggaaaagcct ggtggtgggc ggtcagctcg gcatcttcac gccgtccttc   1620
tacatccgcg ctcgcaagcc gtccaagcag gct                                1653
```

<210> SEQ ID NO 26
<211> LENGTH: 550
<212> TYPE: PRT
<213> ORGANISM: Artificial Sequence
<220> FEATURE:
<223> OTHER INFORMATION: Synthetic Construct

<400> SEQUENCE: 26

```
Met Lys Asp Lys Ala Thr Gly Lys Thr Gln Asn Ile Thr Ile Thr Ala
  1               5                  10                  15

Asn Gly Gly Leu Ser Lys Glu Gln Ile Glu Gln Met Ile Arg Asp Ser
             20                  25                  30

Glu Gln His Ala Glu Ala Asp Arg Val Lys Arg Glu Leu Val Glu Val
         35                  40                  45

Arg Asn Asn Ala Glu Thr Gln Leu Thr Thr Ala Glu Arg Gln Leu Gly
     50                  55                  60

Glu Trp Lys Tyr Val Ser Asp Ala Glu Lys Glu Asn Val Lys Thr Leu
 65                  70                  75                  80

Val Ala Glu Leu Arg Lys Ala Met Glu Asn Pro Asn Val Ala Lys Asp
                 85                  90                  95

Asp Leu Ala Ala Ala Thr Asp Lys Leu Gln Lys Ala Val Met Glu Cys
            100                 105                 110

Gly Arg Thr Glu Tyr Gln Gln Ala Ala Ala Asn Ser Gly Ser Thr
        115                 120                 125

Ser Asn Ser Gly Glu Gln Gln Gln Gln Gly Gln Gly Glu Gln Gln
    130                 135                 140

Gln Gln Gln Asn Ser Glu Glu Lys Lys Met Ala Ser Ser Arg Ser Ala
145                 150                 155                 160

Pro Arg Lys Ala Ser His Ala His Lys Ser His Arg Lys Pro Lys Arg
                165                 170                 175

Ser Trp Asn Val Tyr Val Gly Arg Ser Leu Lys Ala Ile Asn Ala Gln
            180                 185                 190

Met Ser Met Ser His Arg Thr Ser Ala Gly Gly Arg Glu Thr Ala Pro
        195                 200                 205
```

```
Thr Asn Leu Ile Arg Arg Asn Lys Asp Glu Thr Asn Gly Asp Val
        210                 215                 220

Ser Ala Ala Ala Asp Arg Phe Arg Asp Arg Phe Glu Lys Ala Thr Leu
225                 230                 235                 240

Glu Glu Arg Lys Ala Ala Thr Thr Thr Met Val Asn Glu Tyr Tyr Asp
                245                 250                 255

Leu Val Thr Asp Phe Tyr Glu Tyr Gly Trp Gly Gln Asn Phe His Phe
                260                 265                 270

Ala Pro Arg Tyr Ala Gly Glu Thr Phe Phe Glu Ser Leu Ala Arg His
            275                 280                 285

Glu Tyr Phe Leu Ala Ala Arg Gly Gly Phe Met Glu Gly Asp His Ile
        290                 295                 300

Val Asp Val Gly Cys Gly Val Gly Gly Pro Ala Arg Asn Met Val Arg
305                 310                 315                 320

Leu Thr Arg Cys Asn Val Ile Gly Val Asn Asn Asn Asp Tyr Gln Ile
                325                 330                 335

Ser Arg Ala Arg Arg His Asp Ala Leu Ala Gly Met Ser Ser Lys Ile
            340                 345                 350

Asp Tyr Val Lys Thr Asp Phe Cys Asn Met Ser Leu Ala Asp Asn Thr
        355                 360                 365

Phe Asp Gly Ala Tyr Ala Ile Glu Ala Thr Cys His Ala Lys Asp Lys
    370                 375                 380

Val Lys Cys Tyr Ser Glu Val Phe Arg Val Ile Lys Pro Gly Thr Cys
385                 390                 395                 400

Phe Val Leu Tyr Glu Trp Cys Met Thr Asp Lys Tyr Asn Pro Asn Asp
                405                 410                 415

Glu Tyr His Arg Thr Ile Lys His Arg Ile Glu Leu Gly Asp Gly Leu
            420                 425                 430

Pro Glu Met Glu Thr Cys Lys Gln Val Ile Glu Tyr Met Lys Gln Ala
        435                 440                 445

Gly Phe Val Val Glu Glu Ala Ile Asp Val Ile Ser Gln Phe Glu Ser
    450                 455                 460

Ser Pro Ile Lys Ser Ile Pro Trp Tyr Gln Pro Leu Val Gly Asp Tyr
465                 470                 475                 480

Ser Ser Leu Gln Gly Leu Arg Ser Thr Pro Ile Gly Arg Ile Leu Thr
                485                 490                 495

Asn Val Met Cys Arg Val Leu Glu Phe Val Arg Leu Ala Pro Lys Gly
            500                 505                 510

Thr Tyr Lys Ala Thr Glu Ile Leu Glu Glu Ala Ala Glu Ser Leu Val
        515                 520                 525

Val Gly Gly Gln Leu Gly Ile Phe Thr Pro Ser Phe Tyr Ile Arg Ala
    530                 535                 540

Arg Lys Pro Ser Lys Gln
545                 550

<210> SEQ ID NO 27
<211> LENGTH: 152
<212> TYPE: PRT
<213> ORGANISM: Unknown
<220> FEATURE:
<223> OTHER INFORMATION: From Leishmania infantum or Leishmania donovani

<400> SEQUENCE: 27

Lys Asp Lys Ala Thr Gly Lys Thr Gln Asn Ile Thr Ile Thr Ala Asn
1               5                   10                  15
```

Gly Gly Leu Ser Lys Glu Gln Ile Glu Gln Met Ile Arg Asp Ser Glu
            20                  25                  30

Gln His Ala Glu Ala Asp Arg Val Lys Arg Glu Leu Val Glu Val Arg
        35                  40                  45

Asn Asn Ala Glu Thr Gln Leu Thr Thr Ala Glu Arg Gln Leu Gly Glu
    50                  55                  60

Trp Lys Tyr Val Ser Asp Ala Glu Lys Glu Asn Val Lys Thr Leu Val
65                  70                  75                  80

Ala Glu Leu Arg Lys Ala Met Glu Asn Pro Asn Val Ala Lys Asp Asp
                85                  90                  95

Leu Ala Ala Ala Thr Asp Lys Leu Gln Lys Ala Val Met Glu Cys Gly
            100                 105                 110

Arg Thr Glu Tyr Gln Gln Ala Ala Ala Asn Ser Gly Ser Thr Ser
        115                 120                 125

Asn Ser Gly Glu Gln Gln Gln Gln Gly Gln Gly Glu Gln Gln Gln
    130                 135                 140

Gln Gln Asn Ser Glu Glu Lys Lys
145                 150

<210> SEQ ID NO 28
<211> LENGTH: 152
<212> TYPE: PRT
<213> ORGANISM: Leishmania major

<400> SEQUENCE: 28

Lys Asp Lys Ala Thr Gly Lys Thr Gln Asn Ile Thr Ile Thr Ala Asn
1               5                   10                  15

Gly Gly Leu Ser Lys Glu Gln Ile Glu Gln Met Ile Arg Asp Ser Glu
            20                  25                  30

Gln His Ala Glu Ala Asp Arg Val Lys Arg Glu Leu Val Glu Val Arg
        35                  40                  45

Asn Asn Ala Glu Thr Gln Leu Thr Thr Ala Glu Arg Gln Leu Gly Glu
    50                  55                  60

Trp Lys Tyr Val Ser Asp Ala Glu Lys Glu Asn Val Lys Thr Leu Val
65                  70                  75                  80

Ala Glu Leu Arg Lys Ala Met Glu Asn Pro Asn Val Ala Lys Asp Asp
                85                  90                  95

Leu Ala Ala Ala Thr Asp Lys Leu Gln Lys Ala Val Met Glu Cys Gly
            100                 105                 110

Arg Thr Glu Tyr Gln Gln Ala Ala Ala Asn Ser Gly Ser Thr Ser
        115                 120                 125

Asn Ser Gly Glu Gln Gln Gln Gln Ser Gln Gly Glu Gln Gln Gln
    130                 135                 140

Gln Gln Asn Ser Glu Glu Lys Lys
145                 150

<210> SEQ ID NO 29
<211> LENGTH: 157
<212> TYPE: PRT
<213> ORGANISM: Leishmania mexicana

<400> SEQUENCE: 29

Lys Asp Lys Ala Thr Gly Lys Thr Gln Asn Ile Thr Ile Thr Ala Asn
1               5                   10                  15

Gly Gly Leu Ser Lys Glu Gln Ile Glu Gln Met Ile Arg Asp Ser Glu
            20                  25                  30

-continued

```
Gln His Ala Glu Ala Asp Arg Val Lys Arg Glu Leu Val Glu Val Arg
            35                  40                  45

Asn Asn Ala Glu Thr Gln Leu Thr Thr Ala Glu Arg Gln Leu Ser Glu
 50                  55                  60

Trp Lys Tyr Val Ser Asp Ala Glu Lys Glu Asn Val Arg Thr Leu Val
 65                  70                  75                  80

Ala Glu Leu Arg Lys Ala Met Glu Asn Pro Asn Val Ala Lys Asp Asp
                85                  90                  95

Leu Ser Ala Ala Thr Asp Lys Leu Gln Lys Ala Val Met Glu Cys Gly
            100                 105                 110

Arg Thr Glu Tyr Gln Gln Ala Ala Ala Asn Ser Gly Ser Thr Ser
            115                 120                 125

Asn Ser Gly Glu Gln Gln Gln Gln Gln Gln Ser Gln Gly Glu Gln
        130                 135                 140

Gln Gln Gln Gln Gln Gln Gln Gln Ala Glu Glu Arg
145                 150                 155

<210> SEQ ID NO 30
<211> LENGTH: 152
<212> TYPE: PRT
<213> ORGANISM: Leishmania braziliensis

<400> SEQUENCE: 30

Lys Asp Lys Ala Thr Gly Lys Thr Gln Asn Ile Thr Ile Thr Ala His
 1               5                  10                  15

Gly Gly Leu Ser Lys Glu Gln Ile Glu Gln Met Val Arg Asp Ser Glu
            20                  25                  30

Gln His Ala Glu Ala Asp Arg Val Lys Arg Glu Leu Val Glu Ala Arg
            35                  40                  45

Asn Asn Ala Glu Thr Gln Leu Thr Thr Ala Glu Arg Gln Leu Gly Glu
 50                  55                  60

Trp Lys Tyr Val Ser Asp Ala Glu Lys Glu Asn Val Lys Thr His Val
 65                  70                  75                  80

Ala Glu Leu Arg Lys Ala Met Glu Asn Pro Asn Val Ala Lys Asp Asp
                85                  90                  95

Leu Ala Ala Ala Thr Asp Lys Leu Gln Lys Ala Val Met Glu Cys Gly
            100                 105                 110

Arg Thr Glu Tyr Gln Gln Ala Ala Ala Ala Asn Ser Gly Ser Ser Ser
            115                 120                 125

Asn Ser Gly Glu Gln Gln Gln Gln Gln Gln Gly Asp Gln Gln
        130                 135                 140

Gln Gln Gln Ser Ser Glu Lys Asn
145                 150

<210> SEQ ID NO 31
<211> LENGTH: 290
<212> TYPE: PRT
<213> ORGANISM: Leishmania infantum

<400> SEQUENCE: 31

Ser Ala Val Gly Asn Ile Glu Ser Gln Trp Ala Arg Ala Gly His Gly
 1               5                  10                  15

Leu Val Ser Leu Ser Glu Gln Gln Leu Val Ser Cys Asp Asp Lys Asp
            20                  25                  30

Asn Gly Cys Asn Gly Gly Leu Met Leu Gln Ala Phe Glu Trp Leu Leu
            35                  40                  45
```

```
Arg His Met Tyr Gly Ile Val Phe Thr Glu Lys Ser Tyr Pro Tyr Thr
 50                  55                  60

Ser Gly Asn Gly Asp Val Ala Glu Cys Leu Asn Ser Ser Lys Leu Val
 65                  70                  75                  80

Pro Gly Ala Gln Ile Asp Gly Tyr Val Met Ile Pro Ser Asn Glu Thr
                 85                  90                  95

Val Met Ala Ala Trp Leu Ala Glu Asn Gly Pro Ile Ala Ile Ala Val
            100                 105                 110

Asp Ala Ser Ser Phe Met Ser Tyr Gln Ser Gly Val Leu Thr Ser Cys
            115                 120                 125

Ala Gly Asp Ala Leu Asn His Gly Val Leu Leu Val Gly Tyr Asn Lys
            130                 135                 140

Thr Gly Val Pro Tyr Trp Val Ile Lys Asn Ser Trp Gly Glu Asp
145                 150                 155                 160

Trp Gly Glu Lys Gly Tyr Val Arg Val Met Gly Leu Asn Ala Cys
                165                 170                 175

Leu Leu Ser Glu Tyr Pro Val Ser Ala His Val Pro Arg Ser Leu Thr
            180                 185                 190

Pro Gly Pro Gly Thr Glu Ser Glu Glu Arg Ala Pro Lys Arg Val Thr
            195                 200                 205

Val Glu Gln Met Met Cys Thr Asp Met Tyr Cys Arg Glu Gly Cys Lys
210                 215                 220

Lys Ser Leu Leu Thr Ala Asn Val Cys Tyr Lys Asn Gly Gly Gly
225                 230                 235                 240

Ser Ser Met Thr Lys Cys Gly Pro Gln Lys Val Leu Met Cys Ser Tyr
                245                 250                 255

Ser Asn Pro His Cys Phe Gly Pro Gly Leu Cys Leu Glu Thr Pro Asp
            260                 265                 270

Gly Lys Cys Ala Pro Tyr Phe Leu Gly Ser Ile Met Asn Thr Cys Gln
            275                 280                 285

Tyr Thr
    290

<210> SEQ ID NO 32
<211> LENGTH: 46
<212> TYPE: PRT
<213> ORGANISM: Leishmania infantum

<400> SEQUENCE: 32

Met Ala Ser Ser Arg Ser Ala Pro Arg Lys Ala Ser His Ala His Lys
  1               5                  10                  15

Ser His Arg Lys Pro Lys Arg Ser Trp Asn Val Tyr Val Gly Arg Ser
                 20                  25                  30

Leu Lys Ala Ile Asn Ala Gln Met Ser Met Ser His Arg Thr
            35                  40                  45

<210> SEQ ID NO 33
<211> LENGTH: 214
<212> TYPE: PRT
<213> ORGANISM: Leishmania donovani

<400> SEQUENCE: 33

Ser Ala Ser Ala Glu Pro His Lys Ala Ala Val Asp Val Gly Pro Leu
  1               5                  10                  15

Ser Val Gly Pro Gln Ser Val Gly Pro Leu Ser Val Gly Pro Gln Ala
                 20                  25                  30
```

Val Gly Pro Leu Ser Val Gly Pro Gln Ser Val Gly Pro Leu Ser Val
            35                  40                  45

Gly Pro Gln Ala Val Gly Pro Leu Ser Val Gly Pro Gln Ser Val Gly
        50                  55                  60

Pro Leu Ser Val Gly Pro Leu Ser Val Gly Pro Gln Ser Val Gly Pro
65                  70                  75                  80

Leu Ser Val Gly Ser Gln Ser Val Gly Pro Leu Ser Val Gly Pro Gln
                85                  90                  95

Ser Val Gly Pro Leu Ser Val Gly Pro Gln Ala Val Gly Pro Leu Ser
            100                 105                 110

Val Gly Pro Gln Ser Val Gly Pro Leu Ser Val Gly Pro Gln Ala Val
        115                 120                 125

Gly Pro Leu Ser Val Gly Pro Gln Ser Val Gly Pro Leu Ser Val Gly
    130                 135                 140

Pro Gln Ser Val Gly Pro Leu Ser Val Gly Ser Gln Ser Val Gly Pro
145                 150                 155                 160

Leu Ser Val Gly Pro Gln Ser Val Gly Pro Leu Ser Val Gly Pro Gln
                165                 170                 175

Ser Val Gly Pro Leu Ser Val Gly Pro Gln Ser Val Gly Pro Leu Ser
            180                 185                 190

Val Gly Pro Gln Ser Val Gly Pro Leu Ser Val Gly Pro Gln Ser Val
        195                 200                 205

Asp Val Ser Pro Val Ser
    210

<210> SEQ ID NO 34
<211> LENGTH: 190
<212> TYPE: PRT
<213> ORGANISM: Leishmania infantum

<400> SEQUENCE: 34

Ser Ile Ile Lys Glu Asp Asp Ala Val Gly Cys Tyr Met Thr Val Thr
1               5                   10                  15

Leu Val Asp Asp Thr Lys Val Glu Gly Thr Ile Phe Thr Tyr Asn Pro
            20                  25                  30

Lys Glu Gly Ile Ile Val Leu Leu Ser Leu Arg Asp Asp Gln Thr Asn
        35                  40                  45

Met Lys Leu Ile Arg Thr Pro Tyr Ile Lys Glu Phe Ser Ile Ser His
    50                  55                  60

Ala Glu Glu Gly Thr His Leu Pro Pro Ala Leu Asp Ser Phe Asn Glu
65                  70                  75                  80

Leu Pro Ser Met His Ala Gly Arg Asp Lys Ser Ile Phe Lys His Ala
                85                  90                  95

Ser Thr Gln Leu Lys Asn Ala Glu Ala Asn Arg Glu Lys His Phe Asn
            100                 105                 110

Ser Val Thr Thr Asp Thr Pro Ile Ala Thr Leu Asp Ala Tyr Leu Lys
        115                 120                 125

Leu Leu Arg Leu Tyr Pro Phe Ile Glu Trp Asn Ser Asp Glu Gly Val
    130                 135                 140

Ile Gln Val Ser Asp Thr Val Ile Val Gly Asp Pro Asp Trp Arg
145                 150                 155                 160

Thr Pro Lys Ala Met Leu Val Asp Gly Ala Pro Glu Lys Asp Arg Pro
                165                 170                 175

Leu Val Asp Arg Leu Gln Val Ala Leu Gly Asn Gly Lys Lys 180             185             190

<210> SEQ ID NO 35
<211> LENGTH: 314
<212> TYPE: PRT
<213> ORGANISM: Unknown
<220> FEATURE:
<223> OTHER INFORMATION: From Leishmania infantum or Leishmania donovani

<400> SEQUENCE: 35

Met Pro Arg Lys Ile Ile Leu Asp Cys Asp Pro Gly Ile Asp Asp Ala
1               5                   10                  15

Val Ala Ile Phe Leu Ala His Gly Asn Pro Glu Val Glu Leu Leu Ala
            20                  25                  30

Ile Thr Thr Val Val Gly Asn Gln Thr Leu Glu Lys Val Thr Arg Asn
        35                  40                  45

Ala Arg Leu Val Ala Asp Val Ala Gly Ile Val Gly Val Pro Val Ala
    50                  55                  60

Ala Gly Cys Thr Lys Pro Leu Val Arg Gly Val Arg Asn Ala Ser Gln
65                  70                  75                  80

Ile His Gly Glu Thr Gly Met Gly Asn Val Ser Tyr Pro Pro Glu Phe
                85                  90                  95

Lys Thr Lys Leu Asp Gly Arg His Ala Val Gln Leu Ile Ile Asp Leu
            100                 105                 110

Ile Met Ser His Glu Pro Lys Thr Ile Thr Leu Val Pro Thr Gly Gly
        115                 120                 125

Leu Thr Asn Ile Ala Met Ala Val Arg Leu Glu Pro Arg Ile Val Asp
130                 135                 140

Arg Val Lys Glu Val Val Leu Met Gly Gly Gly Tyr His Thr Gly Asn
145                 150                 155                 160

Ala Ser Pro Val Ala Glu Phe Asn Val Phe Val Asp Pro Glu Ala Ala
                165                 170                 175

His Ile Val Phe Asn Glu Ser Trp Asn Val Thr Met Val Gly Leu Asp
            180                 185                 190

Leu Thr His Gln Ala Leu Ala Thr Pro Ala Val Gln Lys Arg Val Lys
        195                 200                 205

Glu Val Gly Thr Lys Pro Ala Ala Phe Met Leu Gln Ile Leu Asp Phe
    210                 215                 220

Tyr Thr Lys Val Tyr Glu Lys Glu Arg Asn Thr Tyr Ala Thr Val His
225                 230                 235                 240

Asp Pro Cys Ala Val Ala Tyr Val Ile Asp Pro Thr Val Met Thr Thr
                245                 250                 255

Glu Gln Val Pro Val Asp Ile Glu Leu Asn Gly Ala Leu Thr Thr Gly
            260                 265                 270

Met Thr Val Ala Asp Phe Arg Tyr Pro Arg Pro Lys His Cys His Thr
        275                 280                 285

Gln Val Ala Val Lys Leu Asp Phe Asp Lys Phe Trp Cys Leu Val Ile
    290                 295                 300

Asp Ala Leu Lys Arg Ile Gly Asp Pro Gln
305                 310

<210> SEQ ID NO 36
<211> LENGTH: 352
<212> TYPE: PRT
<213> ORGANISM: Leishmania infantum

<400> SEQUENCE: 36

```
Ser Ala Gly Gly Arg Glu Thr Ala Pro Thr Asn Leu Ile Arg Arg Arg
1               5                   10                  15

Asn Lys Asp Glu Thr Asn Gly Asp Val Ser Ala Ala Asp Arg Phe
            20                  25                  30

Arg Asp Arg Phe Glu Lys Ala Thr Leu Glu Glu Arg Lys Ala Ala Thr
        35                  40                  45

Thr Thr Met Val Asn Glu Tyr Tyr Asp Leu Val Thr Asp Phe Tyr Glu
    50                  55                  60

Tyr Gly Trp Gly Gln Asn Phe His Phe Ala Pro Arg Tyr Ala Gly Glu
65                  70                  75                  80

Thr Phe Phe Glu Ser Leu Ala Arg His Glu Tyr Phe Leu Ala Ala Arg
                85                  90                  95

Gly Gly Phe Met Glu Gly Asp His Ile Val Asp Val Gly Cys Gly Val
                100                 105                 110

Gly Gly Pro Ala Arg Asn Met Val Arg Leu Thr Arg Cys Asn Val Ile
            115                 120                 125

Gly Val Asn Asn Asn Asp Tyr Gln Ile Ser Arg Ala Arg Arg His Asp
        130                 135                 140

Ala Leu Ala Gly Met Ser Ser Lys Ile Asp Tyr Val Lys Thr Asp Phe
145                 150                 155                 160

Cys Asn Met Ser Leu Ala Asp Asn Thr Phe Asp Gly Ala Tyr Ala Ile
                165                 170                 175

Glu Ala Thr Cys His Ala Lys Asp Lys Val Lys Cys Tyr Ser Glu Val
                180                 185                 190

Phe Arg Val Ile Lys Pro Gly Thr Cys Phe Val Leu Tyr Glu Trp Cys
                195                 200                 205

Met Thr Asp Lys Tyr Asn Pro Asn Asp Glu Tyr His Arg Thr Ile Lys
210                 215                 220

His Arg Ile Glu Leu Gly Asp Gly Leu Pro Glu Met Glu Thr Cys Lys
225                 230                 235                 240

Gln Val Ile Glu Tyr Met Lys Gln Ala Gly Phe Val Glu Glu Ala
                245                 250                 255

Ile Asp Val Ile Ser Gln Phe Glu Ser Ser Pro Ile Lys Ser Ile Pro
            260                 265                 270

Trp Tyr Gln Pro Leu Val Gly Asp Tyr Ser Ser Leu Gln Gly Leu Arg
    275                 280                 285

Ser Thr Pro Ile Gly Arg Ile Leu Thr Asn Val Met Cys Arg Val Leu
    290                 295                 300

Glu Phe Val Arg Leu Ala Pro Lys Gly Thr Tyr Lys Ala Thr Glu Ile
305                 310                 315                 320

Leu Glu Glu Ala Ala Glu Ser Leu Val Val Gly Gly Gln Leu Gly Ile
                325                 330                 335

Phe Thr Pro Ser Phe Tyr Ile Arg Ala Arg Lys Pro Ser Lys Gln Ala
                340                 345                 350

<210> SEQ ID NO 37
<211> LENGTH: 236
<212> TYPE: PRT
<213> ORGANISM: Leishmania donovani

<400> SEQUENCE: 37

Met Lys Ile Arg Ser Val Arg Pro Leu Val Val Leu Leu Val Ser Val
1               5                   10                  15

Ala Ala Val Leu Ala Leu Ser Ala Ser Ala Glu Pro His Lys Ala Ala
```

```
                20              25              30
Val Asp Val Gly Pro Leu Ser Val Gly Pro Gln Ser Val Gly Pro Leu
            35                  40                  45

Ser Val Gly Pro Gln Ala Val Gly Pro Leu Ser Val Gly Pro Gln Ser
        50                  55                  60

Val Gly Pro Leu Ser Val Gly Pro Gln Ala Val Gly Pro Leu Ser Val
65                  70                  75                  80

Gly Pro Gln Ser Val Gly Pro Leu Ser Val Gly Pro Leu Ser Val Gly
                85                  90                  95

Pro Gln Ser Val Gly Pro Leu Ser Val Gly Ser Gln Ser Val Gly Pro
            100                 105                 110

Leu Ser Val Gly Pro Gln Ser Val Gly Pro Leu Ser Val Gly Pro Gln
        115                 120                 125

Ala Val Gly Pro Leu Ser Val Gly Pro Gln Ser Val Gly Pro Leu Ser
    130                 135                 140

Val Gly Pro Gln Ala Val Gly Pro Leu Ser Val Gly Pro Gln Ser Val
145                 150                 155                 160

Gly Pro Leu Ser Val Gly Pro Gln Ser Val Gly Pro Leu Ser Val Gly
                165                 170                 175

Ser Gln Ser Val Gly Pro Leu Ser Val Gly Pro Gln Ser Val Gly Pro
            180                 185                 190

Leu Ser Val Gly Pro Gln Ser Val Gly Pro Leu Ser Val Gly Pro Gln
        195                 200                 205

Ser Val Gly Pro Leu Ser Val Gly Pro Gln Ser Val Gly Pro Leu Ser
    210                 215                 220

Val Gly Pro Gln Ser Val Asp Val Ser Pro Val Ser
225                 230                 235

<210> SEQ ID NO 38
<211> LENGTH: 2591
<212> TYPE: DNA
<213> ORGANISM: Artificial Sequence
<220> FEATURE:
<223> OTHER INFORMATION: Synthetic Construct

<400> SEQUENCE: 38
atgaaggaca aggcgacggg caagacgcag aacatcacga tcacggcgaa cggcgggctg      60
tcgaaggagc agatcgagca gatgatccgc gactcggagc agcacgcgga ggccgaccgc     120
gtgaagcgcg agcttgtgga ggtgcgcaac aacgcggaga cgcagctgac aacggcggag     180
aggcagctcg gcgagtggaa gtacgtgagc gatgcggaga aggagaacgt gaagacgctg     240
gtggcggagc tgcgcaaggc gatggagaac ccgaacgtcg cgaaggatga ccttgcggct     300
gcgacggaca agctgcagaa ggctgtgatg gagtgcggcc gcacagagta ccagcaggct     360
gccgcggcca actccggcag caccagcaac tccggtgagc agcagcagca gagggccaa      420 ggtgagcagc agcagcagca gaacagcgaa gagaagaagc ctcttctcgc tctgctcccc     480
gcaaggcttc ccacgcgcac aagtcgcacc gcaagccgaa gcgctcgtgg aacgtgtacg     540
tgggccgctc gctgaaggcg atcaacgccc agatgtcgat gtcgcaccgc acgatgccgc     600
gcaagattat tctcgattgt gatcccggga tcgatgatgc cgtggccatc tttctcgccc     660
acggcaaccc ggaggtcgag ctgctggcca ttacgacggt ggtgggcaac cagaccctgg     720
agaaggtgac ccggaacgcg cggctggtag ctgacgtagc cggcatcgtt ggtgtgcccg     780
tcgcggctgg ttgcaccaag ccctcgtgc gcggtgtgcg gaatgcctct cagattcatg     840
```

```
gcgaaaccgg catgggtaac gtctcctacc caccagagtt caagacaaag ttggacggcc    900
gtcatgcagt gcagctgatc atcgacctta tcatgtcgca cgagccgaag acgatcacgc    960
ttgtgcctac gggtggcctg acgaacattg cgatggctgt ccgtcttgag ccgcgcatcg   1020
tggaccgtgt gaaggaggtg gttctgatgg gtggcggcta ccatactggt aatgcgtccc   1080
ctgtagcgga gttcaacgtc ttcgtcgacc cggaggcggc gcacattgtg ttcaacgaga   1140
gctggaacgt aacgatggtg gggctggacc taacgcacca ggcactcgcc acgcggcgg    1200
tccagaagcg agtgaaggag gtgggcacga agccggctgc cttcatgctg cagattttgg   1260
acttttacac gaaggtgtac gaaaaggagc gcaacacgta cgcgacggtg cacgatccct   1320
gcgctgtggc gtacgtgatt gaccccaccg tgatgacgac ggagcaagtg ccagtggaca   1380
tcgagctcaa tggggcactg acgactggga tgacggtcgc ggacttccgc tacccacggc   1440
caaagcactg ccacacgcag gtggctgtga agctggactt cgacaagttt tggtgcctcg   1500
tgattgacgc actcaagcgc atcggcgatc ctcaatccgc cggtggccgt gagaccgcgc   1560
cgacgaacct gattcgtcgc cgcaacaagg acgagacaaa cggggatgtc agcgccgccg   1620
ccgaccgctt ccgcgaccgc ttcgagaagg caaccctcga ggagcgcaag gccgccacca   1680
cgacgatggt caacgagtac tacgacctgg tgacggactt ctacgagtac ggctggggcc   1740
agaacttcca tttcgcgccg cgctacgccg cgagaccttt cttcgagtcc ctcgcgcgcc   1800
acgagtactt cctggccgct cgcggcggct tcatggaggg cgaccacatc gtcgacgtgg   1860
gctgcggcgt cggcggtccg gcgcgcaaca tggttcgcct cacgcgctgc aacgtcatcg   1920
gcgtcaacaa caacgattac cagatcagcc gcgctcgccg tcatgacgcg ctcgccggta   1980
tgagctccaa gatcgactac gtcaagaccg acttctgcaa catgagctta gccgacaaca   2040
ccttcgacgg cgcctacgcc atcgaggcca cctgccacgc aaaggacaag gtcaagtgct   2100
atagcgaggt cttccgtgtc atcaagcccg gcacctgctt tgtcctgtac gagtggtgca   2160
tgaccgacaa gtacaacccc aatgacgagt accaccgcac aatcaagcac cgcatcgagc   2220
tgggcgacgg cctgccggag atggagacgt gcaaacaggt gatcgagtac atgaagcagg   2280
ccggcttcgt ggtggaggag gccatagacg tcatcagtca gttcgagtcc agccccatca   2340
agagtatccc gtggtaccag ccgctggtcg gcgactattc gtccctgcag ggcctgcgct   2400
ctaccccgat tggccgcatc ctcacgaacg tcatgtgtcg cgtgctggag ttcgtgcgcc   2460
tagctccgaa gggcacgtac aaggcgacgg agattttgga ggaggctgcg gaaagcctgg   2520
tggtgggcgg tcagctcggc atcttcacgc cgtccttcta catccgcgct cgcaagccgt   2580
ccaagcaggc t                                                        2591
```

<210> SEQ ID NO 39
<211> LENGTH: 863
<212> TYPE: PRT
<213> ORGANISM: Artificial Sequence
<220> FEATURE:
<223> OTHER INFORMATION: Synthetic Construct

<400> SEQUENCE: 39

Met Lys Asp Lys Ala Thr Gly Lys Thr Gln Asn Ile Thr Ile Thr Ala
  1               5                  10                  15

Asn Gly Gly Leu Ser Lys Glu Gln Ile Glu Gln Met Ile Arg Asp Ser
                 20                  25                  30

Glu Gln His Ala Glu Ala Asp Arg Val Lys Arg Glu Leu Val Glu Val
             35                  40                  45

```
Arg Asn Asn Ala Glu Thr Gln Leu Thr Thr Ala Glu Arg Gln Leu Gly
 50                  55                  60

Glu Trp Lys Tyr Val Ser Asp Ala Glu Lys Glu Asn Val Lys Thr Leu
 65                  70                  75                  80

Val Ala Glu Leu Arg Lys Ala Met Glu Asn Pro Asn Val Ala Lys Asp
                 85                  90                  95

Asp Leu Ala Ala Ala Thr Asp Lys Leu Gln Lys Ala Val Met Glu Cys
                100                 105                 110

Gly Arg Thr Glu Tyr Gln Gln Ala Ala Ala Asn Ser Gly Ser Thr
                115                 120                 125

Ser Asn Ser Gly Glu Gln Gln Gln Gln Gly Gln Gly Gln Gln
130                 135                 140

Gln Gln Gln Asn Ser Glu Glu Lys Lys Ala Ser Ser Arg Ser Ala Pro
145                 150                 155                 160

Arg Lys Ala Ser His Ala His Lys Ser His Arg Lys Pro Lys Arg Ser
                165                 170                 175

Trp Asn Val Tyr Val Gly Arg Ser Leu Lys Ala Ile Asn Ala Gln Met
                180                 185                 190

Ser Met Ser His Arg Thr Met Pro Arg Lys Ile Ile Leu Asp Cys Asp
                195                 200                 205

Pro Gly Ile Asp Asp Ala Val Ala Ile Phe Leu Ala His Gly Asn Pro
                210                 215                 220

Glu Val Glu Leu Leu Ala Ile Thr Thr Val Val Gly Asn Gln Thr Leu
225                 230                 235                 240

Glu Lys Val Thr Arg Asn Ala Arg Leu Val Ala Asp Val Ala Gly Ile
                245                 250                 255

Val Gly Val Pro Val Ala Ala Gly Cys Thr Lys Pro Leu Val Arg Gly
                260                 265                 270

Val Arg Asn Ala Ser Gln Ile His Gly Glu Thr Gly Met Gly Asn Val
                275                 280                 285

Ser Tyr Pro Pro Glu Phe Lys Thr Lys Leu Asp Gly Arg His Ala Val
                290                 295                 300

Gln Leu Ile Ile Asp Leu Ile Met Ser His Glu Pro Lys Thr Ile Thr
305                 310                 315                 320

Leu Val Pro Thr Gly Gly Leu Thr Asn Ile Ala Met Ala Val Arg Leu
                325                 330                 335

Glu Pro Arg Ile Val Asp Arg Val Lys Glu Val Val Leu Met Gly Gly
                340                 345                 350

Gly Tyr His Thr Gly Asn Ala Ser Pro Val Ala Glu Phe Asn Val Phe
                355                 360                 365

Val Asp Pro Glu Ala Ala His Ile Val Phe Asn Glu Ser Trp Asn Val
                370                 375                 380

Thr Met Val Gly Leu Asp Leu Thr His Gln Ala Leu Ala Thr Pro Ala
385                 390                 395                 400

Val Gln Lys Arg Val Lys Glu Val Gly Thr Lys Pro Ala Ala Phe Met
                405                 410                 415

Leu Gln Ile Leu Asp Phe Tyr Thr Lys Val Tyr Glu Lys Glu Arg Asn
                420                 425                 430

Thr Tyr Ala Thr Val His Asp Pro Cys Ala Val Ala Tyr Val Ile Asp
                435                 440                 445

Pro Thr Val Met Thr Thr Glu Gln Val Pro Val Asp Ile Glu Leu Asn
                450                 455                 460

Gly Ala Leu Thr Thr Gly Met Thr Val Ala Asp Phe Arg Tyr Pro Arg
```

```
            465                 470                 475                 480
        Pro Lys His Cys His Thr Gln Val Ala Val Lys Leu Asp Phe Asp Lys
                        485                 490                 495
        Phe Trp Cys Leu Val Ile Asp Ala Leu Lys Arg Ile Gly Asp Pro Gln
                    500                 505                 510
        Ser Ala Gly Gly Arg Glu Thr Ala Pro Thr Asn Leu Ile Arg Arg Arg
                    515                 520                 525
        Asn Lys Asp Glu Thr Asn Gly Asp Val Ser Ala Ala Ala Asp Arg Phe
                    530                 535                 540
        Arg Asp Arg Phe Glu Lys Ala Thr Leu Glu Glu Arg Lys Ala Ala Thr
        545                 550                 555                 560
        Thr Thr Met Val Asn Glu Tyr Tyr Asp Leu Val Thr Asp Phe Tyr Glu
                            565                 570                 575
        Tyr Gly Trp Gly Gln Asn Phe His Phe Ala Pro Arg Tyr Ala Gly Glu
                        580                 585                 590
        Thr Phe Phe Glu Ser Leu Ala Arg His Glu Tyr Phe Leu Ala Ala Arg
                    595                 600                 605
        Gly Gly Phe Met Glu Gly Asp His Ile Val Asp Val Gly Cys Gly Val
                610                 615                 620
        Gly Gly Pro Ala Arg Asn Met Val Arg Leu Thr Arg Cys Asn Val Ile
        625                 630                 635                 640
        Gly Val Asn Asn Asn Asp Tyr Gln Ile Ser Arg Ala Arg Arg His Asp
                            645                 650                 655
        Ala Leu Ala Gly Met Ser Ser Lys Ile Asp Tyr Val Lys Thr Asp Phe
                        660                 665                 670
        Cys Asn Met Ser Leu Ala Asp Asn Thr Phe Asp Gly Ala Tyr Ala Ile
                    675                 680                 685
        Glu Ala Thr Cys His Ala Lys Asp Lys Val Lys Cys Tyr Ser Glu Val
                    690                 695                 700
        Phe Arg Val Ile Lys Pro Gly Thr Cys Phe Val Leu Tyr Glu Trp Cys
        705                 710                 715                 720
        Met Thr Asp Lys Tyr Asn Pro Asn Asp Glu Tyr His Arg Thr Ile Lys
                            725                 730                 735
        His Arg Ile Glu Leu Gly Asp Gly Leu Pro Glu Met Glu Thr Cys Lys
                        740                 745                 750
        Gln Val Ile Glu Tyr Met Gln Ala Gly Phe Val Glu Glu Ala Ile
                    755                 760                 765
        Asp Val Ile Ser Gln Phe Glu Ser Ser Pro Ile Lys Ser Ile Pro Trp
                    770                 775                 780
        Tyr Gln Pro Leu Val Gly Asp Tyr Ser Ser Leu Gln Gly Leu Arg Ser
        785                 790                 795                 800
        Thr Pro Ile Gly Arg Ile Leu Thr Asn Val Met Cys Arg Val Leu Glu
                            805                 810                 815
        Phe Val Arg Leu Ala Pro Lys Gly Thr Tyr Lys Ala Thr Glu Ile Leu
                        820                 825                 830
        Glu Glu Ala Ala Glu Ser Leu Val Val Gly Gly Gln Leu Gly Ile Phe
                    835                 840                 845
        Thr Pro Ser Phe Tyr Ile Arg Ala Arg Lys Pro Ser Lys Gln Ala
                    850                 855                 860

<210> SEQ ID NO 40
<211> LENGTH: 2706
<212> TYPE: DNA
<213> ORGANISM: Artificial Sequence
```

<220> FEATURE:
<223> OTHER INFORMATION: Synthetic Construct

<400> SEQUENCE: 40

| | | | | | |
|---|---|---|---|---|---:|
| atggcctctt | ctcgctctgc | tccccgcaag | gcttcccacg | cgcacaagtc | gcaccgcaag | 60 |
| ccgaagcgct | cgtggaacgt | gtacgtgggc | cgctcgctga | aggcgatcaa | cgcccagatg | 120 |
| tcgatgtcgc | accgcacgag | cattatcaag | gaggacgacg | ccgtgggctg | ctacatgacg | 180 |
| gtgaccctcg | tggacgacac | caaggtggag | ggtaccatct | tcacctacaa | tcccaaggaa | 240 |
| ggcatcatag | tacttctgtc | cctccgcgac | gatcagacga | catgaagct | gatccgcact | 300 |
| ccatacatca | aagagttcag | tatttcacac | gctgaggagg | gaacgcacct | gcctccggca | 360 |
| ctggactcct | tcaacgagct | tccgtccatg | catgccggcc | gcgacaagtc | catcttcaag | 420 |
| cacgccagca | cgcagctcaa | gaacgccgag | gcgaaccgcg | aaaagcactt | caactctgtc | 480 |
| acgaccgaca | caccgattgc | cacactcgat | gcgtacctca | agctcctgcg | gctataccc | 540 |
| ttcattgagt | ggaacagcga | cgagggtgtc | atccaggtct | cggataccgt | cattgtcgta | 600 |
| ggggaccccg | actggcggac | gcccaaggcg | atgctggtag | acggcgcccc | tgagaaggac | 660 |
| agaccgctcg | tagaccgcct | gcaggttgcg | ctcggaaacg | gcaagaagat | gccgcgcaag | 720 |
| attattctcg | attgtgatcc | cgggatcgat | gatgccgtgg | ccatctttct | cgcccacggc | 780 |
| aacccggagg | tcgagctgct | ggccattacg | acggtggtgg | gcaaccagac | cctggagaag | 840 |
| gtgacccgga | acgcgcggct | ggtagctgac | gtagccggca | tcgttggtgt | gcccgtcgcg | 900 |
| gctggttgca | ccaagcccct | cgtgcgcggt | gtgcggaatg | cctctcagat | tcatggcgaa | 960 |
| accggcatgg | gtaacgtctc | ctacccacca | gagttcaaga | caaagttgga | cggccgtcat | 1020 |
| gcagtgcagc | tgatcatcga | ccttatcatg | tcgcacgagc | cgaagacgat | cacgcttgtg | 1080 |
| cctacgggtg | gcctgacgaa | cattgcgatg | gctgtccgtc | ttgagccgcg | catcgtggac | 1140 |
| cgtgtgaagg | aggtggttct | gatgggtggc | ggctaccata | ctggtaatgc | gtcccctgta | 1200 |
| gcggagttca | acgtcttcgt | cgacccggag | gcggcgcaca | ttgtgttcaa | cgagagctgg | 1260 |
| aacgtaacga | tggtggggct | ggacctaacg | caccaggcac | tcgccacgcc | ggcggtccag | 1320 |
| aagcgagtga | aggaggtggg | cacgaagccg | gctgccttca | tgctgcagat | tttggacttt | 1380 |
| tacacgaagg | tgtacgaaaa | ggagcgcaac | acgtacgcga | cggtgcacga | tccctgcgct | 1440 |
| gtggcgtacg | tgattgaccc | caccgtgatg | acgacggagc | aagtgccagt | ggacatcgag | 1500 |
| ctcaatgggg | cactgacgac | tgggatgacg | gtcgcggact | tccgctaccc | acggccaaag | 1560 |
| cactgccaca | cgcaggtggc | tgtgaagctg | gacttcgaca | gtttttggtg | cctcgtgatt | 1620 |
| gacgcactca | agcgcatcgg | cgatcctcaa | tccgccggtg | gccgtgagac | cgcgccgacg | 1680 |
| aacctgattc | gtcgccgcaa | caaggacgag | acaaacgggg | atgtcagcgc | cgccgccgac | 1740 |
| cgcttccgcg | accgcttcga | gaaggcaacc | ctcgaggagc | gcaaggccgc | caccacgacg | 1800 |
| atggtcaacg | agtactacga | cctggtgacg | gacttctacg | agtacggctg | gggccagaac | 1860 |
| ttccatttcg | cgccgcgcta | cgccggcgag | accttcttcg | agtccctcgc | gcgccacgag | 1920 |
| tacttcctgg | ccgctcgcgg | cggcttcatg | gagggcgacc | acatcgtcga | cgtgggctgc | 1980 |
| ggcgtcggcg | gtccggcgcg | caacatggtt | cgcctcacgc | gctgcaacgt | catcggcgtc | 2040 |
| aacaacaacg | attaccagat | cagccgcgct | cgccgtcatg | acgcgctcgc | cggtatgagc | 2100 |
| tccaagatcg | actacgtcaa | gaccgacttc | tgcaacatga | gcttagccga | caacaccttc | 2160 |
| gacggcgcct | acgccatcga | ggccacctgc | cacgcaaagg | acaaggtcaa | gtgctatagc | 2220 |

-continued

```
gaggtcttcc gtgtcatcaa gcccggcacc tgctttgtcc tgtacgagtg gtgcatgacc      2280
gacaagtaca accccaatga cgagtaccac cgcacaatca agcaccgcat cgagctgggc      2340
gacggcctgc cggagatgga cgtgcaaa caggtgatcg agtacatgaa gcaggccggc       2400
ttcgtggtgg aggaggccat agacgtcatc agtcagttcg agtccagccc catcaagagt      2460
atcccgtggt accagccgct ggtcggcgac tattcgtccc tgcagggcct gcgctctacc      2520
ccgattggcc gcatcctcac gaacgtcatg tgtcgcgtgc tggagttcgt gcgcctagct      2580
ccgaagggca cgtacaaggc gacggagatt ttggaggagg ctgcggaaag cctggtggtg      2640
ggcggtcagc tcggcatctt cacgccgtcc ttctacatcc gcgctcgcaa gccgtccaag      2700
caggct                                                                 2706
```

<210> SEQ ID NO 41
<211> LENGTH: 902
<212> TYPE: PRT
<213> ORGANISM: Artificial Sequence
<220> FEATURE:
<223> OTHER INFORMATION: Synthetic Construct

<400> SEQUENCE: 41

```
Met Ala Ser Ser Arg Ser Ala Pro Arg Lys Ala Ser His Ala His Lys
 1               5                  10                  15

Ser His Arg Lys Pro Lys Arg Ser Trp Asn Val Tyr Val Gly Arg Ser
             20                  25                  30

Leu Lys Ala Ile Asn Ala Gln Met Ser Met Ser His Arg Thr Ser Ile
         35                  40                  45

Ile Lys Glu Asp Asp Ala Val Gly Cys Tyr Met Thr Val Thr Leu Val
     50                  55                  60

Asp Asp Thr Lys Val Glu Gly Thr Ile Phe Thr Tyr Asn Pro Lys Glu
 65                  70                  75                  80

Gly Ile Ile Val Leu Leu Ser Leu Arg Asp Asp Gln Thr Asn Met Lys
                 85                  90                  95

Leu Ile Arg Thr Pro Tyr Ile Lys Glu Phe Ser Ile Ser His Ala Glu
            100                 105                 110

Glu Gly Thr His Leu Pro Pro Ala Leu Asp Ser Phe Asn Glu Leu Pro
        115                 120                 125

Ser Met His Ala Gly Arg Asp Lys Ser Ile Phe Lys His Ala Ser Thr
    130                 135                 140

Gln Leu Lys Asn Ala Glu Ala Asn Arg Glu Lys His Phe Asn Ser Val
145                 150                 155                 160

Thr Thr Asp Thr Pro Ile Ala Thr Leu Asp Ala Tyr Leu Lys Leu Leu
                165                 170                 175

Arg Leu Tyr Pro Phe Ile Glu Trp Asn Ser Asp Glu Gly Val Ile Gln
            180                 185                 190

Val Ser Asp Thr Val Ile Val Val Gly Asp Pro Asp Trp Arg Thr Pro
        195                 200                 205

Lys Ala Met Leu Val Asp Gly Ala Pro Glu Lys Asp Arg Pro Leu Val
    210                 215                 220

Asp Arg Leu Gln Val Ala Leu Gly Asn Gly Lys Lys Met Pro Arg Lys
225                 230                 235                 240

Ile Ile Leu Asp Cys Asp Pro Gly Ile Asp Asp Ala Val Ala Ile Phe
                245                 250                 255

Leu Ala His Gly Asn Pro Glu Val Glu Leu Leu Ala Ile Thr Thr Val
            260                 265                 270
```

```
Val Gly Asn Gln Thr Leu Glu Lys Val Thr Arg Asn Ala Arg Leu Val
            275                 280                 285
Ala Asp Val Ala Gly Ile Val Gly Val Pro Val Ala Ala Gly Cys Thr
290                 295                 300
Lys Pro Leu Val Arg Gly Val Arg Asn Ala Ser Gln Ile His Gly Glu
305                 310                 315                 320
Thr Gly Met Gly Asn Val Ser Tyr Pro Pro Glu Phe Lys Thr Lys Leu
                325                 330                 335
Asp Gly Arg His Ala Val Gln Leu Ile Ile Asp Leu Ile Met Ser His
            340                 345                 350
Glu Pro Lys Thr Ile Thr Leu Val Pro Thr Gly Gly Leu Thr Asn Ile
        355                 360                 365
Ala Met Ala Val Arg Leu Glu Pro Arg Ile Val Asp Arg Val Lys Glu
    370                 375                 380
Val Val Leu Met Gly Gly Gly Tyr His Thr Gly Asn Ala Ser Pro Val
385                 390                 395                 400
Ala Glu Phe Asn Val Phe Val Asp Pro Glu Ala Ala His Ile Val Phe
                405                 410                 415
Asn Glu Ser Trp Asn Val Thr Met Val Gly Leu Asp Leu Thr His Gln
            420                 425                 430
Ala Leu Ala Thr Pro Ala Val Gln Lys Arg Val Lys Glu Val Gly Thr
        435                 440                 445
Lys Pro Ala Ala Phe Met Leu Gln Ile Leu Asp Phe Tyr Thr Lys Val
    450                 455                 460
Tyr Glu Lys Glu Arg Asn Thr Tyr Ala Thr Val His Asp Pro Cys Ala
465                 470                 475                 480
Val Ala Tyr Val Ile Asp Pro Thr Val Met Thr Thr Glu Gln Val Pro
                485                 490                 495
Val Asp Ile Glu Leu Asn Gly Ala Leu Thr Thr Gly Met Thr Val Ala
            500                 505                 510
Asp Phe Arg Tyr Pro Arg Pro Lys His Cys His Thr Gln Val Ala Val
        515                 520                 525
Lys Leu Asp Phe Asp Lys Phe Trp Cys Leu Val Ile Asp Ala Leu Lys
    530                 535                 540
Arg Ile Gly Asp Pro Gln Ser Ala Gly Gly Arg Glu Thr Ala Pro Thr
545                 550                 555                 560
Asn Leu Ile Arg Arg Asn Lys Asp Glu Thr Asn Gly Asp Val Ser
                565                 570                 575
Ala Ala Ala Asp Arg Phe Arg Asp Arg Phe Glu Lys Ala Thr Leu Glu
            580                 585                 590
Glu Arg Lys Ala Ala Thr Thr Thr Met Val Asn Glu Tyr Tyr Asp Leu
        595                 600                 605
Val Thr Asp Phe Tyr Glu Tyr Gly Trp Gly Gln Asn Phe His Phe Ala
    610                 615                 620
Pro Arg Tyr Ala Gly Glu Thr Phe Phe Glu Ser Leu Ala Arg His Glu
625                 630                 635                 640
Tyr Phe Leu Ala Ala Arg Gly Gly Phe Met Glu Gly Asp His Ile Val
                645                 650                 655
Asp Val Gly Cys Gly Val Gly Gly Pro Ala Arg Asn Met Val Arg Leu
            660                 665                 670
Thr Arg Cys Asn Val Ile Gly Val Asn Asn Asn Asp Tyr Gln Ile Ser
        675                 680                 685
Arg Ala Arg Arg His Asp Ala Leu Ala Gly Met Ser Ser Lys Ile Asp
```

-continued

```
                      690                 695                 700
Tyr Val Lys Thr Asp Phe Cys Asn Met Ser Leu Ala Asp Asn Thr Phe
705                 710                 715                 720

Asp Gly Ala Tyr Ala Ile Glu Ala Thr Cys His Ala Lys Asp Lys Val
                    725                 730                 735

Lys Cys Tyr Ser Glu Val Phe Arg Val Ile Lys Pro Gly Thr Cys Phe
                740                 745                 750

Val Leu Tyr Glu Trp Cys Met Thr Asp Lys Tyr Asn Pro Asn Asp Glu
            755                 760                 765

Tyr His Arg Thr Ile Lys His Arg Ile Glu Leu Gly Asp Gly Leu Pro
            770                 775                 780

Glu Met Glu Thr Cys Lys Gln Val Ile Glu Tyr Met Lys Gln Ala Gly
785                 790                 795                 800

Phe Val Val Glu Glu Ala Ile Asp Val Ile Ser Gln Phe Glu Ser Ser
                    805                 810                 815

Pro Ile Lys Ser Ile Pro Trp Tyr Gln Pro Leu Val Gly Asp Tyr Ser
                820                 825                 830

Ser Leu Gln Gly Leu Arg Ser Thr Pro Ile Gly Arg Ile Leu Thr Asn
            835                 840                 845

Val Met Cys Arg Val Leu Glu Phe Val Arg Leu Ala Pro Lys Gly Thr
850                 855                 860

Tyr Lys Ala Thr Glu Ile Leu Glu Glu Ala Ala Glu Ser Leu Val Val
865                 870                 875                 880

Gly Gly Gln Leu Gly Ile Phe Thr Pro Ser Phe Tyr Ile Arg Ala Arg
                    885                 890                 895

Lys Pro Ser Lys Gln Ala
                900
```

<210> SEQ ID NO 42
<211> LENGTH: 226
<212> TYPE: PRT
<213> ORGANISM: Leishmania major

<400> SEQUENCE: 42

```
Met Ala Gln Asn Asp Lys Ile Ala Pro Gln Asp Gln Asp Ser Phe Leu
1               5                   10                  15

Asp Asp Gln Pro Gly Val Arg Pro Ile Pro Ser Phe Asp Met Pro
            20                  25                  30

Leu His Gln Asn Leu Leu Arg Gly Ile Tyr Ser Tyr Gly Phe Glu Lys
            35                  40                  45

Pro Ser Ser Ile Gln Gln Arg Ala Ile Ala Pro Phe Thr Arg Gly Gly
        50                  55                  60

Asp Ile Ile Ala Gln Ala Gln Ser Gly Thr Gly Lys Thr Gly Ala Phe
65                  70                  75                  80

Ser Ile Gly Leu Leu Gln Arg Leu Asp Phe Arg His Asn Leu Ile Gln
                85                  90                  95

Gly Leu Val Leu Ser Pro Thr Arg Glu Leu Ala Leu Gln Thr Ala Glu
            100                 105                 110

Val Ile Ser Arg Ile Gly Glu Phe Leu Ser Asn Ser Ser Lys Phe Cys
        115                 120                 125

Glu Thr Phe Val Gly Gly Thr Arg Val Gln Asp Asp Leu Arg Lys Leu
    130                 135                 140

Gln Ala Gly Val Ile Val Ala Val Gly Thr Pro Gly Arg Val Ser Asp
145                 150                 155                 160
```

```
Val Ile Lys Arg Gly Ala Leu Arg Thr Glu Ser Leu Arg Val Leu Val
                165                 170                 175

Leu Asp Glu Ala Asp Glu Met Leu Ser Gln Gly Phe Ala Asp Gln Ile
            180                 185                 190

Tyr Glu Ile Phe Arg Phe Leu Pro Lys Asp Ile Gln Val Ala Leu Phe
        195                 200                 205

Ser Ala Thr Met Pro Glu Glu Val Leu Glu Leu Thr Lys Lys Phe Met
210                 215                 220

Arg Asp
225

<210> SEQ ID NO 43
<211> LENGTH: 892
<212> TYPE: PRT
<213> ORGANISM: Artificial Sequence
<220> FEATURE:
<223> OTHER INFORMATION: Synthetic Construct

<400> SEQUENCE: 43

Met Pro Arg Lys Ile Ile Leu Asp Cys Asp Pro Gly Ile Asp Asp Ala
1               5                   10                  15

Val Ala Ile Phe Leu Ala His Gly Asn Pro Glu Val Glu Leu Leu Ala
            20                  25                  30

Ile Thr Thr Val Val Gly Asn Gln Thr Leu Glu Lys Val Thr Arg Asn
        35                  40                  45

Ala Arg Leu Val Ala Asp Val Ala Gly Ile Val Gly Val Pro Val Ala
    50                  55                  60

Ala Gly Cys Thr Lys Pro Leu Val Arg Gly Val Arg Asn Ala Ser Gln
65                  70                  75                  80

Ile His Gly Glu Thr Gly Met Gly Asn Val Ser Tyr Pro Pro Glu Phe
                85                  90                  95

Lys Thr Lys Leu Asp Gly Arg His Ala Val Gln Leu Ile Ile Asp Leu
            100                 105                 110

Ile Met Ser His Glu Pro Lys Thr Ile Thr Leu Val Pro Thr Gly Gly
        115                 120                 125

Leu Thr Asn Ile Ala Met Ala Val Arg Leu Glu Pro Arg Ile Val Asp
    130                 135                 140

Arg Val Lys Glu Val Val Leu Met Gly Gly Gly Tyr His Thr Gly Asn
145                 150                 155                 160

Ala Ser Pro Val Ala Glu Phe Asn Val Phe Val Asp Pro Glu Ala Ala
                165                 170                 175

His Ile Val Phe Asn Glu Ser Trp Asn Val Thr Met Val Gly Leu Asp
            180                 185                 190

Leu Thr His Gln Ala Leu Ala Thr Pro Ala Val Gln Lys Arg Val Lys
        195                 200                 205

Glu Val Gly Thr Lys Pro Ala Ala Phe Met Leu Gln Ile Leu Asp Phe
    210                 215                 220

Tyr Thr Lys Val Tyr Glu Lys Glu Arg Asn Thr Tyr Ala Thr Val His
225                 230                 235                 240

Asp Pro Cys Ala Val Ala Tyr Val Ile Asp Pro Thr Val Met Thr Thr
                245                 250                 255

Glu Gln Val Pro Val Asp Ile Glu Leu Asn Gly Ala Leu Thr Thr Gly
            260                 265                 270

Met Thr Val Ala Asp Phe Arg Tyr Pro Arg Pro Lys His Cys His Thr
        275                 280                 285
```

```
Gln Val Ala Val Lys Leu Asp Phe Asp Lys Phe Trp Cys Leu Val Ile
    290                 295                 300

Asp Ala Leu Lys Arg Ile Gly Asp Pro Gln Ser Ala Gly Gly Arg Glu
305                 310                 315                 320

Thr Ala Pro Thr Asn Leu Ile Arg Arg Asn Lys Asp Glu Thr Asn
                325                 330                 335

Gly Asp Val Ser Ala Ala Asp Arg Phe Arg Asp Arg Phe Glu Lys
            340                 345                 350

Ala Thr Leu Glu Glu Arg Lys Ala Thr Thr Met Val Asn Glu
                355                 360                 365

Tyr Tyr Asp Leu Val Thr Asp Phe Tyr Glu Tyr Gly Trp Gly Gln Asn
    370                 375                 380

Phe His Phe Ala Pro Arg Tyr Ala Gly Glu Thr Phe Phe Glu Ser Leu
385                 390                 395                 400

Ala Arg His Glu Tyr Phe Leu Ala Ala Arg Gly Gly Phe Met Glu Gly
                405                 410                 415

Asp His Ile Val Asp Val Gly Cys Gly Val Gly Gly Pro Ala Arg Asn
                420                 425                 430

Met Val Arg Leu Thr Arg Cys Asn Val Ile Gly Val Asn Asn Asn Asp
                435                 440                 445

Tyr Gln Ile Ser Arg Ala Arg Arg His Asp Ala Leu Ala Gly Met Ser
    450                 455                 460

Ser Lys Ile Asp Tyr Val Lys Thr Asp Phe Cys Asn Met Ser Leu Ala
465                 470                 475                 480

Asp Asn Thr Phe Asp Gly Ala Tyr Ala Ile Glu Ala Thr Cys His Ala
                485                 490                 495

Lys Asp Lys Val Lys Cys Tyr Ser Glu Val Phe Arg Val Ile Lys Pro
                500                 505                 510

Gly Thr Cys Phe Val Leu Tyr Glu Trp Cys Met Thr Asp Lys Tyr Asn
    515                 520                 525

Pro Asn Asp Glu Tyr His Arg Thr Ile Lys His Arg Ile Glu Leu Gly
    530                 535                 540

Asp Gly Leu Pro Glu Met Glu Thr Cys Lys Gln Val Ile Glu Tyr Met
545                 550                 555                 560

Lys Gln Ala Gly Phe Val Val Glu Glu Ala Ile Asp Val Ile Ser Gln
                565                 570                 575

Phe Glu Ser Ser Pro Ile Lys Ser Ile Pro Trp Tyr Gln Pro Leu Val
            580                 585                 590

Gly Asp Tyr Ser Ser Leu Gln Gly Leu Arg Ser Thr Pro Ile Gly Arg
    595                 600                 605

Ile Leu Thr Asn Val Met Cys Arg Val Leu Glu Phe Val Arg Leu Ala
    610                 615                 620

Pro Lys Gly Thr Tyr Lys Ala Thr Glu Ile Leu Glu Glu Ala Ala Glu
625                 630                 635                 640

Ser Leu Val Val Gly Gly Gln Leu Gly Ile Phe Thr Pro Ser Phe Tyr
                645                 650                 655

Ile Arg Ala Arg Lys Pro Ser Lys Gln Ala Met Ala Gln Asn Asp Lys
                660                 665                 670

Ile Ala Pro Gln Asp Gln Asp Ser Phe Leu Asp Gln Pro Gly Val
                675                 680                 685

Arg Pro Ile Pro Ser Phe Asp Asp Met Pro Leu His Gln Asn Leu Leu
    690                 695                 700

Arg Gly Ile Tyr Ser Tyr Gly Phe Glu Lys Pro Ser Ser Ile Gln Gln
```

```
            705                 710                 715                 720
        Arg Ala Ile Ala Pro Phe Thr Arg Gly Gly Asp Ile Ile Ala Gln Ala
                        725                 730                 735

Gln Ser Gly Thr Gly Lys Thr Gly Ala Phe Ser Ile Gly Leu Leu Gln
                        740                 745                 750

Arg Leu Asp Phe Arg His Asn Leu Ile Gln Gly Leu Val Leu Ser Pro
                        755                 760                 765

Thr Arg Glu Leu Ala Leu Gln Thr Ala Glu Val Ile Ser Arg Ile Gly
                        770                 775                 780

Glu Phe Leu Ser Asn Ser Ser Lys Phe Cys Glu Thr Phe Val Gly Gly
        785                 790                 795                 800

Thr Arg Val Gln Asp Asp Leu Arg Lys Leu Gln Ala Gly Val Ile Val
                        805                 810                 815

Ala Val Gly Thr Pro Gly Arg Val Ser Asp Val Ile Lys Arg Gly Ala
                        820                 825                 830

Leu Arg Thr Glu Ser Leu Arg Val Leu Val Leu Asp Glu Ala Asp Glu
                        835                 840                 845

Met Leu Ser Gln Gly Phe Ala Asp Gln Ile Tyr Glu Ile Phe Arg Phe
                        850                 855                 860

Leu Pro Lys Asp Ile Gln Val Ala Leu Phe Ser Ala Thr Met Pro Glu
        865                 870                 875                 880

Glu Val Leu Glu Leu Thr Lys Lys Phe Met Arg Asp
                        885                 890

<210> SEQ ID NO 44
<211> LENGTH: 1001
<212> TYPE: PRT
<213> ORGANISM: Artificial Sequence
<220> FEATURE:
<223> OTHER INFORMATION: Synthetic Construct

<400> SEQUENCE: 44

Met Ala Ser Ser Arg Ser Ala Pro Arg Lys Ala Ser His Ala His Lys
        1               5                   10                  15

Ser His Arg Lys Pro Lys Arg Ser Trp Asn Val Tyr Val Gly Arg Ser
                        20                  25                  30

Leu Lys Ala Ile Asn Ala Gln Met Ser Met Ser His Arg Thr Pro Arg
                        35                  40                  45

Lys Ile Ile Leu Asp Cys Asp Pro Gly Ile Asp Asp Ala Val Ala Ile
                        50                  55                  60

Phe Leu Ala His Gly Asn Pro Glu Val Glu Leu Leu Ala Ile Thr Thr
        65                  70                  75                  80

Val Val Gly Asn Gln Thr Leu Glu Lys Val Thr Arg Asn Ala Arg Leu
                        85                  90                  95

Val Ala Asp Val Ala Gly Ile Val Gly Val Pro Val Ala Ala Gly Cys
                        100                 105                 110

Thr Lys Pro Leu Val Arg Gly Val Arg Asn Ala Ser Gln Ile His Gly
                        115                 120                 125

Glu Thr Gly Met Gly Asn Val Ser Tyr Pro Pro Glu Phe Lys Thr Lys
                        130                 135                 140

Leu Asp Gly Arg His Ala Val Gln Leu Ile Ile Asp Leu Ile Met Ser
        145                 150                 155                 160

His Glu Pro Lys Thr Ile Thr Leu Val Pro Thr Gly Gly Leu Thr Asn
                        165                 170                 175

Ile Ala Met Ala Val Arg Leu Glu Pro Arg Ile Val Asp Arg Val Lys
```

```
                180                 185                 190
Glu Val Val Leu Met Gly Gly Gly Tyr His Thr Gly Asn Ala Ser Pro
                195                 200                 205

Val Ala Glu Phe Asn Val Phe Val Asp Pro Glu Ala Ala His Ile Val
        210                 215                 220

Phe Asn Glu Ser Trp Asn Val Thr Met Val Gly Leu Asp Leu Thr His
225                 230                 235                 240

Gln Ala Leu Ala Thr Pro Ala Val Gln Lys Arg Val Lys Glu Val Gly
                245                 250                 255

Thr Lys Pro Ala Ala Phe Met Leu Gln Ile Leu Asp Phe Tyr Thr Lys
            260                 265                 270

Val Tyr Glu Lys Glu Arg Asn Thr Tyr Ala Thr Val His Asp Pro Cys
        275                 280                 285

Ala Val Ala Tyr Val Ile Asp Pro Thr Val Met Thr Thr Glu Gln Val
    290                 295                 300

Pro Val Asp Ile Glu Leu Asn Gly Ala Leu Thr Thr Gly Met Thr Val
305                 310                 315                 320

Ala Asp Phe Arg Tyr Pro Arg Pro Lys His Cys His Thr Gln Val Ala
                325                 330                 335

Val Lys Leu Asp Phe Asp Lys Phe Trp Cys Leu Val Ile Asp Ala Leu
            340                 345                 350

Lys Arg Ile Gly Asp Pro Gln Ser Ala Gly Arg Glu Thr Ala Pro
        355                 360                 365

Thr Asn Leu Ile Arg Arg Asn Lys Asp Glu Thr Asn Gly Asp Val
    370                 375                 380

Ser Ala Ala Ala Asp Arg Phe Arg Asp Arg Phe Glu Lys Ala Thr Leu
385                 390                 395                 400

Glu Glu Arg Lys Ala Ala Thr Thr Thr Met Val Asn Glu Tyr Tyr Asp
                405                 410                 415

Leu Val Thr Asp Phe Tyr Glu Tyr Gly Trp Gly Gln Asn Phe His Phe
            420                 425                 430

Ala Pro Arg Tyr Ala Gly Glu Thr Phe Phe Glu Ser Leu Ala Arg His
        435                 440                 445

Glu Tyr Phe Leu Ala Ala Arg Gly Gly Phe Met Glu Gly Asp His Ile
    450                 455                 460

Val Asp Val Gly Cys Gly Val Gly Gly Pro Ala Arg Asn Met Val Arg
465                 470                 475                 480

Leu Thr Arg Cys Asn Val Ile Gly Val Asn Asn Asp Tyr Gln Ile
            485                 490                 495

Ser Arg Ala Arg Arg His Asp Ala Leu Ala Gly Met Ser Ser Lys Ile
                500                 505                 510

Asp Tyr Val Lys Thr Asp Phe Cys Asn Met Ser Leu Ala Asp Asn Thr
            515                 520                 525

Phe Asp Gly Ala Tyr Ala Ile Glu Ala Thr Cys His Ala Lys Asp Lys
        530                 535                 540

Val Lys Cys Tyr Ser Glu Val Phe Arg Val Ile Lys Pro Gly Thr Cys
545                 550                 555                 560

Phe Val Leu Tyr Glu Trp Cys Met Thr Asp Lys Tyr Asn Pro Asn Asp
                565                 570                 575

Glu Tyr His Arg Thr Ile Lys His Arg Ile Glu Leu Gly Asp Gly Leu
            580                 585                 590

Pro Glu Met Glu Thr Cys Lys Gln Val Ile Glu Tyr Met Lys Gln Ala
        595                 600                 605
```

| | | | | | | | | | | |
|---|---|---|---|---|---|---|---|---|---|---|
|Gly|Phe|Val|Val|Glu|Ala|Ile|Asp|Val|Ile|Ser|Gln|Phe|Glu|Ser|
| |610| | | |615| | | |620| | | | | |

Gly Phe Val Val Glu Ala Ile Asp Val Ile Ser Gln Phe Glu Ser
    610             615             620

Ser Pro Ile Lys Ser Ile Pro Trp Tyr Gln Pro Leu Val Gly Asp Tyr
625             630             635             640

Ser Ser Leu Gln Gly Leu Arg Ser Thr Pro Ile Gly Arg Ile Leu Thr
                645             650             655

Asn Val Met Cys Arg Val Leu Glu Phe Val Arg Leu Ala Pro Lys Gly
                660             665             670

Thr Tyr Lys Ala Thr Glu Ile Leu Glu Glu Ala Ala Glu Ser Leu Val
        675             680             685

Val Gly Gly Gln Leu Gly Ile Phe Thr Pro Ser Phe Tyr Ile Arg Ala
690             695             700

Arg Lys Pro Ser Lys Gln Ala Ser Ala Val Gly Asn Ile Glu Ser Gln
705             710             715             720

Trp Ala Arg Ala Gly His Gly Leu Val Ser Leu Ser Glu Gln Gln Leu
                725             730             735

Val Ser Cys Asp Asp Lys Asp Asn Gly Cys Asn Gly Leu Met Leu
                740             745             750

Gln Ala Phe Glu Trp Leu Leu Arg His Met Tyr Gly Ile Val Phe Thr
        755             760             765

Glu Lys Ser Tyr Pro Tyr Thr Ser Gly Asn Gly Asp Val Ala Glu Cys
770             775             780

Leu Asn Ser Ser Lys Leu Val Pro Gly Ala Gln Ile Asp Gly Tyr Val
785             790             795             800

Met Ile Pro Ser Asn Glu Thr Val Met Ala Ala Trp Leu Ala Glu Asn
                805             810             815

Gly Pro Ile Ala Ile Ala Val Asp Ala Ser Ser Phe Met Ser Tyr Gln
                820             825             830

Ser Gly Val Leu Thr Ser Cys Ala Gly Asp Ala Leu Asn His Gly Val
        835             840             845

Leu Leu Val Gly Tyr Asn Lys Thr Gly Gly Val Pro Tyr Trp Val Ile
850             855             860

Lys Asn Ser Trp Gly Glu Asp Trp Gly Glu Lys Gly Tyr Val Arg Val
865             870             875             880

Val Met Gly Leu Asn Ala Cys Leu Leu Ser Glu Tyr Pro Val Ser Ala
                885             890             895

His Val Pro Arg Ser Leu Thr Pro Gly Pro Gly Thr Glu Ser Glu Glu
                900             905             910

Arg Ala Pro Lys Arg Val Thr Val Glu Gln Met Met Cys Thr Asp Met
        915             920             925

Tyr Cys Arg Glu Gly Cys Lys Lys Ser Leu Leu Thr Ala Asn Val Cys
930             935             940

Tyr Lys Asn Gly Gly Gly Gly Ser Ser Met Thr Lys Cys Gly Pro Gln
945             950             955             960

Lys Val Leu Met Cys Ser Tyr Ser Asn Pro His Cys Phe Gly Pro Gly
                965             970             975

Leu Cys Leu Glu Thr Pro Asp Gly Lys Cys Ala Pro Tyr Phe Leu Gly
                980             985             990

Ser Ile Met Asn Thr Cys Gln Tyr Thr
        995             1000

<210> SEQ ID NO 45
<211> LENGTH: 21

```
<212> TYPE: DNA
<213> ORGANISM: Artificial Sequence
<220> FEATURE:
<223> OTHER INFORMATION: Synthetic Construct

<400> SEQUENCE: 45
atgcatcacc atcaccatca c                                              21
```

We claim:

1. A fusion polypeptide comprising a *Leishmania* non-specific nucleoside hydrolase (NH) polypeptide, a *Leishmania* sterol 24-c-methyltransferase (SMT) polypeptide, and a portion of a *Leishmania* cysteine polypeptidease B (CpB) polypeptide, wherein the NH polypeptide comprises the amino acid sequence set forth in SEQ ID NO:35, or a sequence having at least a 90% sequence identity to the amino acid sequence set forth in SEQ ID NO:35, wherein the SMT polypeptide comprises the amino acid sequence set forth in SEQ ID NO:36 or a sequence having at least a 90% sequence identity to the amino acid sequence set forth in SEQ ID NO:36, and wherein the portion of the CpB polypeptide comprises the amino acid sequence set forth in SEQ ID No:31 or a sequence having at least a 90% sequence identity to the amino acid sequence set forth in SEQ ID NO:31.

2. The fusion polypeptide of claim 1, wherein the NH polypeptide is from a *L. infantum*, a *L. donovani*, a *L. major*, or a *L. Mexicana*.

3. The fusion polypeptide of claim 1, wherein the SMT polypeptide, is from a *L. infantum*, a *L. donovani*, a *L. major*, or a *L. mexicana*.

4. The fusion polypeptide of claim 1, wherein the fusion polypeptide comprises sequences from at least two different *Leishmania* strains.

5. The fusion polypeptide of claim 1, wherein the fusion polypeptide comprises the amino acid sequence set forth in SEQ ID NO:2 or a sequence having at least 90% sequence identity to the amino acid sequence set forth in SEQ ID NO:2.

6. A composition comprising the polypeptide of claim 1 and an immunostimulant.

7. The composition of claim 6, wherein the immunostimulant is selected from the group consisting of a CpG-containing oligonucleotide, synthetic lipid A, MPLTM, 3D-MPLTM, saponins, saponin mimetics, AGPs, Toll-like receptor agonists, or a combination thereof.

8. The composition of claim 6, wherein the immunostimulant is selected from the group consisting of a TLR4 agonist, a TLR7/8 agonist and a TLR9 agonist.

9. The composition of claim 6, wherein the immunostimulant is selected from the group consisting of GLA, CpG-containing oligonucleotide, imiquimod, gardiquimod and resiquimod.

10. The composition of claim 6, wherein the immunostimulant has the formula:

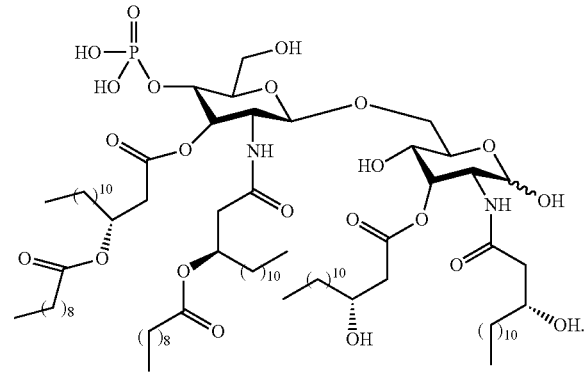

11. A method for stimulating an immune response against *Leishmania* in a mammal comprising administering to a mammal in need thereof a composition of claim 6.

12. A method for detecting *Leishmania* infection in a biological sample, comprising: (a) contacting a biological sample with the polypeptide of claim 1; and (b) detecting in the biological sample the presence of antibodies that bind to the polypeptide, thereby detecting *Leishmania* infection in a biological sample.

13. The method of claim 12, wherein the biological sample is selected from the group consisting of sera, blood and saliva.

14. The method of claim 12, wherein the fusion polypeptide is bound to a solid support.

15. A diagnostic reagent comprising the fusion polypeptide of claim 1, wherein the polypeptide is immobilized on a solid support.

16. A diagnostic kit for detecting *Leishmania* infection in a biological sample comprising (i) the fusion polypeptide of claim 1; and (ii) a detection reagent.

17. The kit of claim 16, wherein the kit comprises an assay format selected from the group consisting of a lateral flow test strip assay, a dual path platform assay and an ELISA assay.

18. A point of care diagnostic kit for detecting *Leishmania* infection in a biological sample comprising the fusion polypeptide of claim 1, wherein the fusion polypeptide is immobilized on a solid support in a lateral flow test strip format.

19. The fusion polypeptide of claim 1, wherein the CpB polypeptide is from a *L. infantum* or a *L. donovani*.

20. The fusion polypeptide of claim 1, consisting essentially of a Leishmania non-specific nucleoside hydrolase (NH) polypeptide comprising the amino acid sequence set forth in SEQ ID NO:35 or a sequence having at least a 90% sequence identity to the amino acid sequence set forth in SEQ ID NO:35, a Leishmania sterol 24-c-methyltransferase (SMT) polypeptide comprising the amino acid sequence set forth in SEQ ID NO:36 or a sequence having at least a 90% sequence identity to the amino acid sequence set forth in SEQ ID NO:36, and a portion of a CpB polypeptide comprising the amino acid sequence set forth in SEQ ID NO:31 or a sequence having at least a 90% sequence identity to the amino acid sequence set forth in SEQ ID NO:31.

21. The fusion polypeptide of claim 16, wherein the fusion polypeptide comprises the amino acid sequence set forth in SEQ ID NO:2 or a sequence having at least 95% sequence identity to the amino acid sequence set forth in SEQ ID NO:2.

22. The fusion polypeptide of claim 16, wherein the fusion polypeptide comprises the amino acid sequence set forth in SEQ ID NO:2 or a sequence having at least 98% sequence identity to the amino acid sequence set forth in SEQ ID NO:2.

23. The fusion polypeptide of claim 16, wherein the fusion polypeptide consists essentially of the amino acid sequence set forth in SEQ ID NO:2 or a sequence having at least 98% sequence identity to the amino acid sequence set forth in SEQ ID NO:2.

* * * * *